United States Patent
Li et al.

(10) Patent No.: US 9,481,654 B2
(45) Date of Patent: *Nov. 1, 2016

(54) COMPOSITIONS AND METHODS FOR INHIBITION OF THE JAK PATHWAY

(71) Applicant: Rigel Pharmaceuticals, Inc., South San Francisco, CA (US)

(72) Inventors: Hui Li, Santa Clara, CA (US); Ankush Argade, Foster City, CA (US); Kin Tso, San Francisco, CA (US); Sambaiah Thota, Fremont, CA (US); David Carroll, San Francisco, CA (US); Arvinder Sran, Fremont, CA (US); Robin Cooper, St. George Island, FL (US); Rajinder Singh, Belmont, CA (US); Somasekhar Bhamidipati, Foster City, CA (US); Vanessa Taylor, San Francisco, CA (US); Esteban Masuda, Menlo Park, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/624,301

(22) Filed: Feb. 17, 2015

(65) Prior Publication Data
US 2015/0158824 A1 Jun. 11, 2015

Related U.S. Application Data

(63) Continuation of application No. 11/678,488, filed on Feb. 23, 2007, now Pat. No. 8,962,643.

(60) Provisional application No. 60/862,166, filed on Oct. 19, 2006, provisional application No. 60/776,636, filed on Feb. 24, 2006.

(51) Int. Cl.
| | | |
|---|---|---|
| *C07D 239/48* | (2006.01) | |
| *A61K 31/505* | (2006.01) | |
| *C07D 239/50* | (2006.01) | |
| *C07D 401/12* | (2006.01) | |
| *C07D 403/12* | (2006.01) | |
| *C07D 409/12* | (2006.01) | |
| *C07D 417/12* | (2006.01) | |
| *A61K 31/506* | (2006.01) | |
| *A61K 45/06* | (2006.01) | |

(52) U.S. Cl.
CPC .......... *C07D 239/50* (2013.01); *A61K 31/505* (2013.01); *A61K 31/506* (2013.01); *A61K 45/06* (2013.01); *C07D 239/48* (2013.01); *C07D 401/12* (2013.01); *C07D 403/12* (2013.01); *C07D 409/12* (2013.01); *C07D 417/12* (2013.01)

(58) Field of Classification Search
CPC  C07D 239/42; C07D 239/48; C07D 513/04; A61K 31/505; A61K 31/506; A61K 31/5415
USPC .......................... 544/12, 324; 514/223.2, 275
See application file for complete search history.

(56) References Cited

U.S. PATENT DOCUMENTS

| | | | | |
|---|---|---|---|---|
| 8,268,851 B2 * | 9/2012 | Bhamidipati | ........ | C07D 239/48 514/275 |
| 8,399,472 B2 * | 3/2013 | Li | ........ | C07D 239/42 514/275 |
| 8,415,365 B2 * | 4/2013 | Li | ........ | C07D 239/42 514/275 |
| 8,420,659 B2 * | 4/2013 | Bhamidipati | ........ | C07D 239/48 514/275 |
| 8,815,848 B2 * | 8/2014 | Li | ........ | C07D 239/42 514/223.2 |
| 8,962,643 B2 * | 2/2015 | Li | ........ | C07D 239/48 514/275 |
| 9,248,190 B2 * | 2/2016 | Li | ........ | C07D 239/42 |

OTHER PUBLICATIONS

Versotovsek, "Therapeutic potential of JAK2 inhibitors," Hematology, American Society of Hematology Education Program Book, pp. 636-642, 2009.*
Simone, "Oncology: Introduction," Cecil Textbook of Medicine, 20th ed., 1:1004-1010, 1996.*
Pearce et al., "Failure modes in anticancer drug discovery and development," Cancer Drug Design and Discovery, edited by Stephen Neidle, Chapter 18, pp. 424-435, 2008.*
Levine et al., "Myeloproliferative Disorders," Blood 112(6):2190-2198, 2008.*
Getts et al., "Current landscape for T-cell targeting in autoimmunity and transplantation," Immunotherapy 3(7):853-870, 2011.*
Harkiolaki et al., "T Cell-Mediated Autoimmune Disease Due to Low-Affinity Crossreactivity to Common Microbial Peptides," Immunity 30:348-357, 2009.*
Johnson et al., "Relationships between drug activity in NCI preclinical in vitro and in vivo models and early clinical trials," British Journal of Cancer 84(10):1424-1431, 2001.*
Borie et al., "JAK3 inhibition, a viable new modality of immunosuppression of solid organ transplants," Trends in Molecular Medicine 10(11):532-541, 2004.*

* cited by examiner

*Primary Examiner* — Deepak Rao
(74) *Attorney, Agent, or Firm* — Travis Young; Klarquist Sparkman, LLP

(57) ABSTRACT

The invention encompasses compounds having formula I and the compositions and methods using these compounds in the treatment of conditions in which modulation of the JAK pathway or inhibition of JAK kinases, particularly JAK3, are therapeutically useful.

19 Claims, No Drawings

COMPOSITIONS AND METHODS FOR INHIBITION OF THE JAK PATHWAY

I. CROSS REFERENCE TO RELATED APPLICATIONS

This application is a continuation of U.S. patent application Ser. No. 11/678,488, filed Feb. 23, 2007, which claims the benefit of U.S. provisional application Ser. No. 60/862,166, filed Oct. 19, 2006 and U.S. Provisional application Ser. No. 60/776,636, filed Feb. 24, 2006. These prior applications are incorporated herein by reference.

II. INTRODUCTION

A. Field

The present invention relates to compounds, prodrugs, and methods of using these compounds and prodrugs thereof in the treatment of conditions in which modulation of the JAK pathway or inhibition of JAK kinases, particularly JAK3, are therapeutically useful.

B. Background

Protein kinases constitute a large family of structurally related enzymes that are responsible for the control of a variety of signal transduction processes within cells (see, e.g., Hardie and Hanks, *The Protein Kinase Facts Book*, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases can be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), *FASEB J.* 9:576-596; Knighton et al., (1991), *Science* 253:407-414; Hiles et al., (1992), *Cell* 70:419-429; Kunz et al., (1993), *Cell* 73:585-596; Garcia-Bustos et al., (1994), *EMBO J.* 13:2352-2361).

JAK kinases (JAnus Kinases) are a family of cytoplasmic protein tyrosine kinases including JAK1, JAK2, JAK3 and TYK2. Each of the JAK kinases is selective for the receptors of certain cytokines, though multiple JAK kinases can be affected by particular cytokine or signaling pathways. Studies suggest that JAK3 associates with the common gamma (γc) chain of the various cytokine receptors. JAK3 in particular selectively binds to receptors and is part of the cytokine signaling pathway for IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-α. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes (Leonard et al., (2000), *J. Allergy Clin. Immunol.* 105:877-888). JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), *Mol. Med.* 5:432:456 and Seidel et al., (2000), *Oncogene* 19:2645-2656.

JAK3 in particular has been implicated in a variety of biological processes. For example, the proliferation and survival of murine mast cells induced by IL-4 and IL-9 have been shown to be dependent on JAK3- and gamma chain-signaling (Suzuki et al., (2000), *Blood* 96:2172-2180). JAK3 also plays a crucial role in IgE receptor-mediated mast cell degranulation responses (Malaviya et al., (1999), *Biochem. Biophys. Res. Commun.* 257:807-813), and inhibition of JAK3 kinase has been shown to prevent type I hypersensitivity reactions, including anaphylaxis (Malaviya et al., (1999), *J. Biol. Chem.* 274:27028-27038). JAK3 inhibition has also been shown to result in immune suppression for allograft rejection (Kirken, (2001), *Transpl. Proc.* 33:3268-3270). JAK3 kinases have also been implicated in the mechanism involved in early and late stages of rheumatoid arthritis (Muller-Ladner et al., (2000), *J. Immunal.* 164:3894-3901); familial amyotrophic lateral sclerosis (Trieu et al., (2000), *Biochem Biophys. Res. Commun.* 267:22-25); leukemia (Sudbeck et al., (1999), *Clin. Cancer Res.* 5:1569-1582); mycosis fungoides, a form of T-cell lymphoma (Nielsen et al., (1997), *Prac. Natl. Acad. Sci. USA* 94:6764-6769); and abnormal cell growth (Yu et al., (1997), *J. Immunol.* 159:5206-5210; Catlett-Falcone et al., (1999), *Immunity* 10:105-115).

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), *Mol. Cell. Biol.* 16:4710-6; Jurlander et al., (1997), *Blood.* 89:4146-52; Kaneko et al., (1997), *Clin. Exp. Immun.* 109:185-193; and Nakamura et al., (1996), *J. Biol. Chem.* 271:19483-8). They are also known to be important to lymphocyte differentiation, function and survival. JAK-3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) *Am. J. Transplant* 4:51-57; Changelian (2003) *Science* 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes), and inflammation (e.g., asthma, allergic reactions). Conditions which can benefit for inhibition of JAK3 are discussed in greater detail below.

In view of the numerous conditions that are contemplated to benefit by treatment involving modulation of the JAK pathway it is immediately apparent that new compounds that modulate JAK pathways and methods of using these compounds should provide substantial therapeutic benefits to a wide variety of patients. Provided herein are novel 2,4-pyrimidinediamine compounds for use in the treatment of conditions in which targeting of the JAK pathway or inhibition of JAK kinases, particularly JAK3, are therapeutically useful.

Patents and patent applications related to modulation of the JAK pathway include: U.S. Pat. Nos. 5,728,536; 6,080,747; 6,080,748; 6,133,305; 6,177,433; 6,210,654; 6,313,130; 6,316,635; 6,433,018; 6,486,185; 6,506,763; 6,528,509; 6,593,357; 6,608,048; 6,610,688; 6,635,651; 6,677,368; 6,683,082; 6,696,448; 6,699,865; 6,777,417; 6,784,195; 6,825,190; 6,506,763; 6,784,195; 6,528,509; 6,608,048; 7,105,529; 6,699,865; 6,825,190; 6,815,439; 6,949,580; 7,056,944; 6,998,391; 7074,793; 6,969,760; U.S. Pat. App. Pub. No. 2001/0007033 A1; 2002/0115173 A1; 2002/0137141 A1; 2003/0236244 A1; 2004/0102455 A1; 2004/0142404 A1; 2004/0147507 A1; and 2004/0214817 A1; and International patent applications WO 95/03701A1; WO 99/15500A1; WO 00/00202A1; WO 00/10981A1; WO 00/47583A1; WO 00/51587A2; WO 00/55159A2; WO 01/42246A2; WO 01/45641A2; WO 01/52892A2; WO 01/56993A2; WO 01/57022A2; WO 01/72758A1; WO 02/00661A1; WO 02/43735A1; WO 02/48336A2; WO 02/060492A1; WO 02/060927A1; WO 02/096909A1; WO 02/102800A1; WO 03/020698A2; WO 03/048162A1; WO 03/101989A1; WO 2004/016597A2; WO 2004/041789A1; WO 2004/041810A1; WO 2004/041814A1; WO 2004/046112A2; WO 2004/046120A2; WO 2004/047843A1; WO 2004/058749A1; WO 2004/058753A1; WO 2004/085388A2; WO 2004/092154A1; WO 2005/009957A1; WO 2005/016344A1; WO 2005/028475A2; and WO 2005/033107A1.

Patents and patent applications describing substituted pyrimidinediamine compounds include: U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO 04/014382), U.S. application Ser. No. 10/903,263 filed Jul. 30, 2004, and international application Serial No. PCT/US2004/24716 (WO 05/016893), the disclosures of which are incorporated herein by reference. Substituted pyrimidinediamine compounds are also described in international patent application publication numbers: WO 02/059110, WO 03/074515, WO 03/106416, WO 03/066601, WO 03/063794, WO 04/046118, WO 05/016894, WO 05/122294, WO 05/066156, WO 03/002542, WO 03/030909, WO 00/39101, WO 05/037800 and U.S. Pat. Pub. No. 2003/0149064.

All of the above publications are herein incorporated by reference in their entirety to the same extent as if each individual publication was specifically and individually indicated to be incorporated by reference in its entirety.

III. SUMMARY OF THE INVENTION

This invention is directed to compounds, prodrugs, and methods of using these compounds and prodrugs thereof in the treatment of conditions in which modulation of the JAK pathway or inhibition of JAK kinases, particularly JAK3, will be therapeutically useful.

In one embodiment, the present invention provides a compound of formula I, a solvate, prodrug or pharmaceutically acceptable salt thereof:

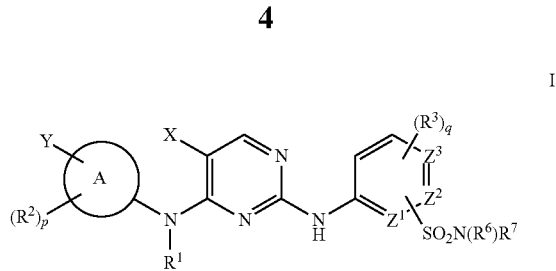

wherein:
ring A is aryl or heteroaryl;
p is 0, 1, 2, or 3 when ring A is monocyclic or p is 0, 1, 2, 3, 4, or 5 when ring A is bi- or tricyclic;
q is 0, 1, 2, or 3;
X is selected from the group consisting of hydrogen, alkyl, substituted alkyl, hydroxy, alkoxy, substituted alkoxy, amino, substituted amino, carboxyl, carboxyl ester, cyano, halo, nitro, alkenyl, substituted alkenyl, alkynyl, substituted alkynyl, cycloalkynyl, and substituted cycloalkynyl;
Y is alk-$SO_2N(R^4)R^5$ or alk-$N(R^4)SO_2R^5$;
alk is selected from the group consisting of straight or branched chain $C_{1-6}$ alkylene group, cycloalkylene, and substituted cycloalkylene;
$R^1$ is selected from the group consisting of hydrogen, alkyl, substituted alkyl, alkenyl, substituted alkenyl, alkynyl, substituted alkynyl, cycloalkynyl, substituted cycloalkynyl, cycloalkyl, and substituted cycloalkyl;
each $R^2$ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, halo and oxo;
wherein if $R^2$ is oxo then the oxo substituent is attached to a nonaromatic portion of ring A; or
$R^4$ and one of $R^2$ together with the intervening atoms bound thereto form a heterocyclic or substituted heterocyclic fused to ring A; or
$R^5$ and one of $R^2$ together with the intervening atoms bound thereto form a heterocyclic or substituted heterocyclic fused to ring A;
$Z^1$, $Z^2$, and $Z^3$ each independently is carbon or nitrogen, wherein no more than one of $Z^1$, $Z^2$, and $Z^3$ is N;
each $R^3$ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, halo, and aminosulfonyl; or
$R^6$ and one of $R^3$ together with the intervening atoms bound thereto form a heterocyclic or substituted heterocyclic fused to the ring containing $Z^1$, $Z^2$ and $Z^3$; or R⁷ and one of R³ together with the intervening atoms bound thereto form a heterocyclic or substituted heterocyclic fused to the ring containing Z¹, Z² and Z³; or R⁴ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, acyl, and M⁺, wherein M⁺ is a counterion selected from the group consisting of K⁺, Na⁺, Li⁺, and ⁺N(R⁸)₄, wherein R⁸ is hydrogen or alkyl, and the nitrogen of —SO₂N(R⁴)R⁵ or —N(R⁴)SO₂R⁵ is N⁻;

R⁵ is selected from the group consisting of hydrogen, alkyl, substituted alkyl, amino, cycloalkyl, substituted cycloalkyl, heterocyclic, substituted heterocyclic, aryl, substituted aryl, heteroaryl, substituted heteroaryl, and acyl; or R⁴ and R⁵ together with the intervening atom or atoms bound thereto form a heterocyclic or substituted heterocyclic group;

R⁶ is selected from the group consisting of hydrogen, alkyl, substituted alkyl, cycloalkyl, substituted cycloalkyl, heterocyclic, substituted heterocyclic, carboxyl, carboxyl ester, aryl, substituted aryl, heteroaryl, substituted heteroaryl, acyl, and M⁺, wherein M⁺ is a counterion selected from the group consisting of K⁺, Na⁺, Li⁺, or ⁺N(R⁸)₄, wherein R⁸ is hydrogen or alkyl, and the nitrogen of —SO₂N(R⁶)R⁷ or —N(R⁶)SO₂R⁷ is N⁻; or R⁶ and R⁷ together with the intervening atom or atoms bound thereto, form a heterocyclic or substituted heterocyclic group;

R⁷ is selected from the group consisting of hydrogen, alkyl, substituted alkyl, amino, cycloalkyl, substituted cycloalkyl, heterocyclic, substituted heterocyclic, aryl, substituted aryl, heteroaryl, substituted heteroaryl, carboxyl, carboxyl ester, and acyl;

provided:
when X is hydrogen, ring A is not benzimidazolyl or indazolyl.

Although M⁺ is preferably a monovalent cation, it can also be a divalent cation with appropriate counterions, for example, two of the parent drug anion, one of parent/one of other counter anion, etc.

In another embodiment, the present invention provides a compound of formula III, prodrugs, solvates, or pharmaceutically acceptable salts thereof:

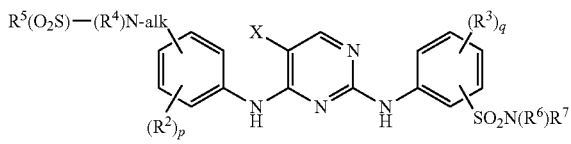

III wherein:
p is 0, 1, 2 or 3 when ring A is monocyclic or p is 0, 1, 2, 3, 4, or 5 when ring A is bi- or tricyclic;
q is 0, 1, 2, or 3;
X is selected from the group consisting of hydrogen, alkyl, substituted alkyl, hydroxy, alkoxy, substituted alkoxy, amino, substituted amino, carboxyl, carboxyl ester, cyano, halo, nitro, alkenyl, substituted alkenyl, alkynyl, substituted alkynyl, cycloalkynyl, and substituted cycloalkynyl;

alk is selected from the group consisting of straight or branched chain C₁₋₆ alkylene group, cycloalkylene, and substituted cycloalkylene;

each R² independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, and halo; or R⁴ and one of R² together with the intervening atoms bound thereto form a heterocyclic or substituted heterocyclic fused to ring A; or R⁵ and one of R² together with the intervening atoms bound thereto form a heterocyclic or substituted heterocyclic fused to ring A;

each R³ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, halo, and aminosulfonyl; or R⁶ and one of R³ together with the intervening atoms bound thereto form a heterocyclic or substituted heterocyclic fused to the ring containing Z¹, Z², and Z³; or R⁷ and one of R³ together with the intervening atoms bound thereto form a heterocyclic or substituted heterocyclic fused to the ring containing Z¹, Z², and Z³; or R⁴ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, acyl, and M⁺, wherein M⁺ is a counterion selected from the group consisting of K⁺, Na⁺, Li⁺, and ⁺N(R⁸)₄, wherein R⁸ is hydrogen or alkyl, and the nitrogen of —SO₂N(R⁴)R⁵ or —N(R⁴)SO₂R⁵ is N⁻;

R⁵ is selected from the group consisting of hydrogen, alkyl, substituted alkyl, amino, cycloalkyl, substituted cycloalkyl, heterocyclic, substituted heterocyclic, aryl, substituted aryl, heteroaryl, substituted heteroaryl, and acyl; or R⁴ and R⁵ together with the intervening atom or atoms bound thereto form a heterocyclic or substituted heterocyclic group;

R⁶ is selected from the group consisting of hydrogen, alkyl, substituted alkyl, cycloalkyl, substituted cycloalkyl, heterocyclic, substituted heterocyclic, carboxyl, carboxyl ester, aryl, substituted aryl, heteroaryl, substituted heteroaryl, acyl, and M⁺, wherein M⁺ is a counterion selected from the group consisting of K⁺, Na$^+$, Li$^+$, or $^+$N(R$^8$)$_4$, wherein R$^8$ is hydrogen or alkyl, and the nitrogen of —SO$_2$N(R$^6$)R$^7$ or —N(R$^6$)SO$_2$R$^7$ is N$^-$; or R$^6$ and R$^7$ together with the intervening atom or atoms bound thereto, form a heterocyclic or substituted heterocyclic group; and R$^7$ is selected from the group consisting of hydrogen, alkyl, substituted alkyl, amino, cycloalkyl, substituted cycloalkyl, heterocyclic, substituted heterocyclic, aryl, substituted aryl, heteroaryl, substituted heteroaryl, carboxyl, carboxyl ester, and acyl.

Although M$^+$ is preferably a monovalent cation, it can also be a divalent cation with appropriate counterions, for example, two of the parent drug anion, one of parent/one of other counter anion, etc.

In another embodiment, this invention provides a compound represented by formula V:

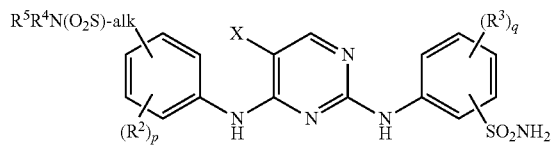

V wherein:
p is 0, 1, 2, or 3;
q is 0, 1, 2, or 3;
X is selected from the group consisting of hydrogen, alkyl, substituted alkyl, hydroxy, alkoxy, substituted alkoxy, amino, substituted amino, carboxyl, carboxyl ester, cyano, halo, nitro, alkenyl, substituted alkenyl, alkynyl, substituted alkynyl, cycloalkynyl, and substituted cycloalkynyl;
alk is selected from the group consisting of straight or branched chain C$_{1-6}$ alkylene group, cycloalkylene, and substituted cycloalkylene;
each R$^2$ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, and halo; or
R$^4$ and one of R$^2$ together with the intervening atoms bound thereto form a heterocyclic or substituted heterocyclic fused to ring A; or
R$^5$ and one of R$^2$ together with the intervening atoms bound thereto form a heterocyclic or substituted heterocyclic fused to ring A;
each R$^3$ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, halo, and aminosulfonyl;

R$^4$ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, acyl, and M$^+$, wherein M$^+$ is a counterion selected from the group consisting of K$^+$, Na$^+$, Li$^+$, and $^+$N(R$^8$)$_4$, wherein R$^8$ is hydrogen or alkyl, and the nitrogen of —SO$_2$N(R$^4$)R$^5$ or —N(R$^4$)SO$_2$R$^5$ is N$^-$;

R$^5$ is selected from the group consisting of hydrogen, alkyl, substituted alkyl, amino, cycloalkyl, substituted cycloalkyl, heterocyclic, substituted heterocyclic, aryl, substituted aryl, heteroaryl, substituted heteroaryl, and acyl; or R$^4$ and R$^5$ together with the intervening atom or atoms bound thereto form a heterocyclic or substituted heterocyclic group.

Although M$^+$ is preferably a monovalent cation, it can also be a divalent cation with appropriate counterions, for example, two of the parent drug anion, one of parent/one of other counter anion, etc.

In another embodiment, this invention provides a method of inhibiting an activity of a JAK kinase, comprising contacting the JAK kinase with an amount of a compound of this invention effective to inhibit an activity of the JAK kinase.

In another embodiment, this invention provides a method of inhibiting an activity of a JAK kinase, comprising contacting in vitro a JAK3 kinase with an amount of a compound of this invention to inhibit an activity of the JAK kinase.

In another embodiment, this invention provides a method of inhibiting an activity of a JAK kinase, comprising contacting in a cell a JAK3 kinase with an amount of a compound effective to inhibit an activity of the JAK kinase wherein the compound is selected from the compounds of this invention, as described above.

In another embodiment, this invention provides a method of treating a T-cell mediated autoimmune disease, comprising administering to a patient suffering from such an autoimmune disease an amount of a compound of this invention effective to treat the autoimmune disease.

In another embodiment, this invention provides a method of treating or preventing allograft transplant rejection in a transplant recipient, comprising administering to the transplant recipient an amount of a compound of this invention effective to treat or prevent the rejection.

In another embodiment, this invention provides a method of treating or preventing a Type IV hypersensitivity reaction, comprising administering to a subject an amount of a compound of this invention effective to treat or prevent the hypersensitivity reaction.

In another embodiment, this invention provides a method of inhibiting a signal transduction cascade in which JAK3 kinase plays a role, comprising contacting a cell expressing a receptor involved in such a signaling cascade with a compound of this invention, as described above.

In another embodiment, this invention provides a method of treating or preventing a JAK kinase-mediated disease, comprising administering to a subject an amount of a compound of this invention effective to treat or prevent the JAK kinase-mediated disease.

In another embodiment, this invention provides a pharmaceutical formulation comprising a compound selected from the compounds of this invention, as described above.

In another embodiment, this invention provides a kit comprising a compound selected from the compounds of this invention or a prodrug thereof, packaging, and instructions for use.

It will be appreciated by one of skill in the art that the implementations summarized above may be used together in any suitable combination to generate implementations not expressly recited above and that such implementations are considered to be part of the present invention.

IV. DETAILED DESCRIPTION

A. Overview

The invention encompasses compounds having formula I and the compositions and methods using these compounds in the treatment of conditions in which modulation of the JAK pathway or inhibition of JAK kinases, particularly JAK3, are therapeutically useful.

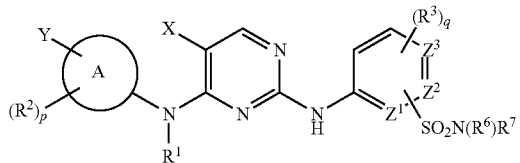

B. Definitions

As used herein, the following definitions shall apply unless otherwise indicated.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Substituted alkyl" refers to an alkyl group having from 1 to 5 hydrogens replaced with substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, alkynyl, substituted alkynyl, cycloalkynyl, substituted cycloalkynyl guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, sulfonyl, sulfonyloxy, thioacyl, thiol, alkylthio, and substituted alkylthio, wherein said substituents are defined herein. In some embodiments, the alkyl has 1 to 3 of the aforementioned groups. In other embodiments, the alkyl has 1 to 2 of the aforementioned groups.

"Alkylene" refers to divalent saturated aliphatic hydrocarbyl groups preferably having from 1 to 6 and more preferably 1 to 3 carbon atoms that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$—) or (—$CH(CH_3)CH_2$—), and the like.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein. In some embodiments, the alkylene has 1 to 2 of the aforementioned groups. It is to be noted that when the alkylene is substituted by an oxo group, 2 hydrogens attached to the same carbon of the alkylene group are replaced by "=O".

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like.

"Substituted alkoxy" refers to the group —O-(substituted alkyl), wherein substituted alkyl is as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{20}C(O)$alkyl, —$NR^{20}C(O)$substituted alkyl, —$NR^{20}C(O)$cycloalkyl, —$NR^{20}C(O)$substituted cycloalkyl, —$NR^{20}C(O)$cycloalkenyl, —$NR^{20}C(O)$substituted cycloalkenyl, —$NR^{20}C(O)$alkenyl, —$NR^{20}C(O)$substituted alkenyl, —$NR^{20}C(O)$alkynyl, —$NR^{20}C(O)$substituted alkynyl, —$NR^{20}C(O)$aryl, —$NR^{20}C(O)$substituted aryl, —$NR^{20}C(O)$heteroaryl, —$NR^{20}C(O)$substituted heteroaryl, —$NR^{20}C(O)$heterocyclic, and —$NR^{20}C(O)$substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —NH$_2$.

"Substituted amino" refers to the group —NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, where one of R$^{21}$ and R$^{22}$ is sulfonyl, and wherein R$^{21}$ and R$^{22}$ are optionally joined together with the nitrogen bound thereto to form a heterocyclic or substituted heterocyclic group, provided that R$^{21}$ and R$^{22}$ are not both hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, sulfonyl, substituted heteroaryl, heterocyclic, and substituted heterocyclic are as defined herein. When R$^{21}$ is hydrogen and R$^{22}$ is alkyl, the substituted amino group is sometimes referred to herein as "alkylamino." When R$^{21}$ and R$^{22}$ are alkyl, the substituted amino group is sometimes referred to herein as "dialkylamino." When referring to a monosubstituted amino, it is meant that either R$^{21}$ or R$^{22}$ is hydrogen, but not both. When referring to a disubstituted amino, it is meant that neither R$^{21}$ nor R$^{22}$ is hydrogen.

"Aminoacyl" or "Aminocarbonyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{20}$C(O)NR$^{21}$R$^{22}$, wherein R$^{20}$ is hydrogen or alkyl and R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NR$^{20}$C(S)NR$^{21}$R$^{22}$, wherein R$^{20}$ is hydrogen or alkyl and R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminoacyloxy" or "Aminocarbonyloxy" refers to the group —O—C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic; R$^{21}$ and R$^{22}$ are optionally joined together with the nitrogen bound thereto to form a heterocyclic or substituted heterocyclic group; and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —NR$^{20}$—SO$_2$NR$^{21}$R$^{22}$, wherein R$^{20}$ is hydrogen or alkyl and R$^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —$NR^{21}SO_2R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —$C(=NR^{30})NR^{31}R^{32}$, wherein $R^{31}$ and $R^{32}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{31}$ and $R^{32}$ are optionally joined together with the nitrogen bound thereto to form a heterocyclic or substituted heterocyclic group. $R^{30}$ is selected from the group consisting of hydrogen, alkyl, substituted alkyl, alkenyl, substituted alkenyl, alkynyl, substituted alkynyl, cycloalkynyl, substituted cycloalkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, nitro, nitroso, hydroxy, alkoxy, cyano, —N=N—N-alkyl, —N=N—N-substituted alkyl, —N(alkyl)SO$_2$-alkyl, —N(alkyl)SO$_2$-substituted alkyl, —N=N-N-alkyl, —N=N—N— substituted alkyl, acyl, —SO$_2$-alkyl and —SO$_2$-substituted alkyl, wherein alkyl, substituted alkyl, alkenyl, substituted alkenyl, alkynyl, substituted alkynyl, cycloalkynyl, substituted cycloalkynyl, cycloalkyl, substituted cycloalkyl, cycloalkenyl, substituted cycloalkenyl, aryl, substituted aryl, heteroaryl, substituted heteroaryl, heterocyclic, substituted heterocyclic, nitro, nitroso, hydroxy, alkoxy, and cyano are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like), provided that the point of attachment is through an atom of the aromatic aryl group. Preferred aryl groups include phenyl and naphthyl.

"Substituted aryl" refers to aryl groups having 1 to 5 hydrogens replaced with substituents independently selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, sulfonyl, sulfonyloxy, thioacyl, thiol, alkylthio, and substituted alkylthio, wherein said substituents are as defined herein. In some embodiments, the aryl has 1 to 3 of the aforementioned groups. In other embodiments, the aryl has 1 to 2 of the aforementioned groups.

"Aryloxy" refers to the group —O-aryl, wherein aryl is as defined herein, including, by way of example, phenoxy, naphthoxy, and the like.

"Substituted aryloxy" refers to the group —O-(substituted aryl), wherein substituted aryl is as defined herein.

"Arylthio" refers to the group —S-aryl, wherein aryl is as defined herein. In other embodiments, sulfur may be oxidized to —S(O)— or —SO$_2$— moieties. The sulfoxide may exist as one or more stereoisomers.

"Substituted arylthio" refers to the group —S-(substituted aryl), wherein substituted aryl is as defined herein. In other embodiments, sulfur may be oxidized to —S(O)— or —SO$_2$— moieties. The sulfoxide may exist as one or more stereoisomers.

"Alkenyl" refers to monovalent unsaturated hydrocarbyl groups having from 2 to 6 carbon atoms and preferably 2 to 4 carbon atoms and having at least 1 and preferably from 1 to 2 sites of unsaturation. Such groups are exemplified by vinyl, allyl, but-3-en-1-yl, and the like.

"Substituted alkenyl" refers to alkenyl groups having from 1 to 3 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, sulfonyl, sulfonyloxy, thioacyl, thiol, alkylthio, and substituted alkylthio, wherein said substituents are as defined herein and with the proviso that any hydroxy substitution is not attached to a vinyl (unsaturated) carbon atom. In some embodiments, the alkenyl has 1 to 2 of the aforementioned groups.

"Alkenylene" refers to divalent unsaturated straight chain or branched chain hydrocarbyl groups having from 2 to 10 carbon atoms and preferably 2 to 6 carbon atoms and having at least 1 and preferably from 1-2 sites of double bond unsaturation. The term "alkenylene" encompasses any and all combinations of cis and trans isomers arising from the presence of unsaturation. "Substituted alkenylene" refers to divalent alkenylene groups having from 1 to 3 substituents selected from the group consisting of alkyl, substituted alkyl, alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic, provided that any hydroxy or thiol substitution is not on a double bond carbon. In some embodiments, the alkenylene has 1 to 2 of the aforementioned groups.

"Alkynyl" refers to monovalent unsaturated hydrocarbyl groups having from 2 to 6 carbon atoms and preferably 2 to 3 carbon atoms and having at least 1 and preferably from 1 to 2 sites of triple bond unsaturation.

"Substituted alkynyl" refers to alkynyl groups having from 1 to 3 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, sulfonyl, sulfonyloxy, thioacyl, thiol, alkylthio, and substituted alkylthio, wherein said substituents are as defined herein and with the proviso that any hydroxy or thiol substitution is not attached to an acetylenic carbon atom. In some embodiments, the alkynyl has 1 to 2 of the aforementioned groups.

"Alkynyloxy" refers to the group —O-alkynyl, wherein alkynyl is as defined herein. Alkynyloxy includes, by way of example, ethynyloxy, propynyloxy, and the like.

"Carboxyl" or "carboxy" refers to —COOH or salts thereof.

"Carboxyl ester" or "carboxy ester" refers to the groups —C(O)O-alkyl, —C(O)O— substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the groups —NR—C(O)O-alkyl, —NR—C(O)O— substituted alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic, wherein R is alkyl or hydrogen and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "Carbonate ester" refers to the groups —O—C(O)O-alkyl, —O—C(O)O— substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like.

"Cycloalkenyl" refers to non-aromatic cyclic alkyl groups of from 3 to 10 carbon atoms having single or multiple rings and having at least one double bond and preferably from 1 to 2 double bonds.

"Cycloalkynyl" refers to non-aromatic cycloalkyl groups of from 5 to 10 carbon atoms having single or multiple rings and having at least one triple bond.

"Cycloalkylene" refers to divalent cycloalkyl groups, wherein cycloalkyl is as defined herein.

"Substituted cycloalkylene" refers to cycloalkylene group having from 1 to 3 hydrogens replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are as defined herein. In some embodiments, the alkylene has 1 to 2 of the aforementioned groups. It is to be noted that when the cycloalkylene is substituted by an oxo group, 2 hydrogens attached to the same carbon of the cycloalkylene group are replaced by "=O".

"Substituted cycloalkyl," "substituted cycloalkenyl," and "substituted cycloalkynyl" refer to a cycloalkyl, cycloalkenyl, or cycloalkynyl group having from 1 to 5 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, sulfonyl, sulfonyloxy, thioacyl, thiol, alkylthio, and substituted alkylthio, wherein said substituents are as defined herein, provides that any hydroxy or thiol substitution is not attached to an unsaturated carbon atom. In some embodiments, the cycloalkyl or cycloalkenyl has 1 to 3 of the aforementioned groups. In some embodiments, the cycloalkyl group may have multiple condensed rings (e.g. tetrahydronaphthyl or tetrahydroanthacenyl), provided that the point of attachment is through an atom of the nonaromatic ring.

"Cycloalkoxy" refers to —O-cycloalkyl.

"Substituted cycloalkoxy" refers to —O-(substituted cycloalkyl).

"Cycloalkylthio" refers to —S-cycloalkyl. In other embodiments, sulfur may be oxidized to —S(O)— or —$SO_2$— moieties. The sulfoxide may exist as one or more stereoisomers.

"Substituted cycloalkylthio" refers to —S-(substituted cycloalkyl). In other embodiments, sulfur may be oxidized to —S(O)—, or —$SO_2$— moieties. The sulfoxide may exist as one or more stereoisomers.

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl. In other embodiments, sulfur may be oxidized to sulfinyl or sulfonyl moieties. The sulfoxide may exist as one or more stereoisomers.

"Substituted cycloalkenylthio" refers to —S-(substituted cycloalkenyl). In other embodiments, sulfur may be oxidized to —S(O)— or —$SO_2$— moieties. The sulfoxide may exist as one or more stereoisomers.

"Guanidino" refers to the group —NHC(=NH)$NH_2$.

"Substituted guanidino" refers to the group —$NR^{33}$C(=$NR^{33}$)N($R^{33}$)$_2$, wherein each $R^{33}$ independently is selected from the group consisting of hydrogen, alkyl, substituted alkyl, aryl, substituted aryl, heteroaryl, substituted heteroaryl, heterocyclic, and substituted heterocyclic; two R groups attached to a common guanidino nitrogen atom are optionally joined together with the nitrogen bound thereto to form a heterocyclic or substituted heterocyclic group, provided that at least one R is not hydrogen; and said substituents are as defined herein.

"Halo" or "halogen" refers to fluoro, chloro, bromo, and iodo and is preferably fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl or furyl) or multiple condensed rings (e.g., indolizinyl or benzothienyl), wherein the condensed rings may or may not be aromatic and/or contain a heteroatom, provided that the point of attachment is through an atom of the aromatic heteroaryl group. In one embodiment, the nitrogen and/or sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5 substituents selected from the group consisting of the same group of substituents defined for substituted aryl. In some embodiments, the heteroaryl has 1 to 3 of the aforementioned groups. In other embodiments, the heteroaryl has 1 to 2 of the aforementioned groups.

"Heteroaryloxy" refers to —O-heteroaryl.

"Substituted heteroaryloxy" refers to the group —O-(substituted heteroaryl).

"Heteroarylthio" refers to the group —S-heteroaryl. In other embodiments, sulfur may be oxidized to —S(O)— or —$SO_2$— moieties. The sulfoxide may exist as one or more stereoisomers.

"Substituted heteroarylthio" refers to the group —S-(substituted heteroaryl). In other embodiments, sulfur may be oxidized to —S(O)— or —$SO_2$— moieties. The sulfoxide may exist as one or more stereoisomers.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In one embodiment, the nitrogen and/or sulfur atom(s) of the heterocyclic group are optionally oxidized to provide for the N-oxide, —S(O)—, or —$SO_2$— moieties.

"Substituted heterocyclic," "substituted heterocycloalkyl," and"substituted heterocyclyl" refer to heterocyclyl groups that are substituted with from 1 to 5 of the same substituents as defined for substituted cycloalkyl. In some embodiments, the heterocyclyl has 1 to 3 of the aforementioned groups.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl. In other embodiments, sulfur may be oxidized to —S(O)— or —$SO_2$— moieties. The sulfoxide may exist as one or more stereoisomers.

"Substituted heterocyclylthio" refers to the group —S-(substituted heterocycyl). In other embodiments, sulfur may be oxidized to —S(O)— or —$SO_2$— moieties. The sulfoxide may exist as one or more stereoisomers.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Nitro" refers to the group —NO$_2$.

"Nitroso" refers to the group —NO.

"Oxo" refers to the atom (=O).

"Sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, and —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thioxo" refers to the atom (=S).

"Alkylthio" refers to the group —S-alkyl, wherein alkyl is as defined herein. In other embodiments, sulfur may be oxidized to —S(O)—. The sulfoxide may exist as one or more stereoisomers.

"Substituted alkylthio" refers to the group —S-(substituted alkyl), wherein substituted alkyl is as defined herein. In other embodiments, sulfur may be oxidized to —S(O)—. The sulfoxide may exist as one or more stereoisomers.

"Stereoisomer" and "stereoisomers" refer to compounds that differ in the chirality of one or more stereocenters. Stereoisomers include enantiomers and diastereomers.

"Tautomer" refers to alternate forms of a molecule that differ in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

"Patient" refers to human and non-human animals, especially mammals.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, choline, arginine and the like; and when the molecule contains a basic functionality, salts of organic or inorganic acids, such as hydrochloride, hydrobromide, tartrate, mesylate, acetate, maleate, oxalate, and the like.

"Prodrug" refers to a derivative of an active 4-pyrimidineamine compound (drug) that may require a transformation under the conditions of use, such as within the body, to release the active 2,4-pyrimidinediamine drug. Prodrugs are frequently, but not necessarily, pharmacologically inactive until converted into the active drug. Prodrugs are typically obtained by masking one or more functional groups in an active 2,4-pyrimidinediamine drug believed to be in part required for activity with a progroup (defined below) to form a promoiety which undergoes a transformation, such as cleavage, under the specified conditions of use to release the functional group, and hence the active 2,4-pyrimidinediamine drug. The cleavage of the promoiety may proceed spontaneously, such as by way of a hydrolysis reaction, or it can be catalyzed or induced by another agent, such as an enzyme, light, an acid or base, or a change of or exposure to a physical or environmental parameter, such as temperature. The agent can be endogenous to the conditions of use, such as an enzyme present in the cells to which the prodrug is administered or the acidic conditions of the stomach, or it can be supplied exogenously.

"Progroup" refers to a type of protecting group that, when used to mask a functional group within an active 2,4-pyrimidinediamine drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are easily recognized by a person having ordinary skill in the art.

C. Compounds of the Invention

This invention provides novel 2,4-pyrimidinediamine compounds, prodrugs of the compounds, methods of making the compounds, and methods of using these compounds in the treatment of conditions in which targeting of the JAK pathway or inhibition of JAK kinases, particularly JAK3, are therapeutically useful. These conditions include, but are not limited to, debilitating and fatal diseases and disorders that affect both children and adults. Examples of these conditions include oncological diseases such as leukemia, including childhood leukemia and lymphoma; autoimmune conditions, such as transplant rejection; and the other conditions described herein. Given the severity of and suffering caused by these conditions, it is vital that new treatments are developed to treat these conditions.

In one embodiment, the present invention provides a compound of formula I, prodrugs, solvates, or pharmaceutically acceptable salts thereof:

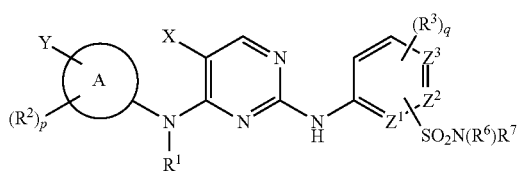

wherein:
ring A is aryl or heteroaryl;
p is 0, 1, 2 or 3 when ring A is monocyclic or p is 0, 1, 2, 3, 4, or 5 when ring A is bi- or tricyclic;
q is 0, 1, 2 or 3;
X is selected from the group consisting of hydrogen, alkyl, substituted alkyl, hydroxy, alkoxy, substituted alkoxy, amino, substituted amino, carboxyl, carboxyl ester, cyano, halo, nitro, alkenyl, substituted alkenyl, alkynyl, substituted alkynyl, cycloalkynyl and substituted cycloalkynyl;
Y is alk-$SO_2N(R^4)R^5$ or alk-$N(R^4)SO_2R^5$;
alk is selected from the group consisting of straight or branched chain $C_{1-6}$ alkylene group, cycloalkylene and substituted cycloalkylene;
$R^1$ is selected from the group consisting of hydrogen, alkyl, substituted alkyl, alkenyl, substituted alkenyl, alkynyl, substituted alkynyl, cycloalkynyl, substituted cycloalkynyl, cycloalkyl and substituted cycloalkyl;
each $R^2$ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, nitro, halo, and oxo; or $R^4$ and one of $R^2$ together with the intervening atoms bound thereto form a heterocyclic or a substituted heterocyclic fused to ring A; or
$R^5$ and one of $R^2$ together with the intervening atoms bound thereto form a heterocyclic or a substituted heterocyclic fused to ring A;
$Z^1$, $Z^2$, and $Z^3$ each independently is carbon or nitrogen, wherein no more than one of $Z^1$, $Z^2$, and $Z^3$ is N;
each $R^3$ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, halo, and aminosulfonyl; or
$R^6$ and one of $R^3$, together with the intervening atoms bound thereto form a heterocyclic or a substituted heterocyclic fused to the ring containing $Z^1$, $Z^2$ and $Z^3$; or
$R^7$ and one of $R^3$, together with the intervening atoms bound thereto form a heterocyclic or a substituted heterocyclic fused to the ring containing $Z^1$, $Z^2$ and $Z^3$; or
$R^4$ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, acyl and $M^+$, wherein $M^+$ is a counterion selected from the group consisting of $K^+$, $Na^+$, $Li^+$ and $^+N(R^8)_4$, wherein $R^8$ is hydrogen or alkyl, and the nitrogen of —$SO_2N(R^4)R^5$ or —$N(R^4)SO_2R^5$ is $N^-$; or
$R^5$ is selected from the group consisting of hydrogen, alkyl, substituted alkyl, amino, cycloalkyl, substituted cycloalkyl, heterocyclic, substituted heterocyclic, aryl, substituted aryl, heteroaryl, substituted heteroaryl, and acyl; or
$R^4$ and $R^5$ together with the intervening atom or atoms bound thereto form a heterocyclic or a substituted heterocyclic group;
$R^6$ is selected from the group consisting of hydrogen, alkyl, substituted alkyl, cycloalkyl, substituted cycloalkyl, heterocyclic, substituted heterocyclic, carboxyl, carboxyl ester, aryl, substituted aryl, heteroaryl, substituted heteroaryl, acyl and $M^+$, wherein $M^+$ is a counterion selected from the group consisting of $K^+$, $Na^+$, $Li^+$ or $^+N(R^8)_4$, wherein $R^8$ is hydrogen or alkyl, and the nitrogen of —$SO_2N(R^6)R^7$ or —$N(R^6)SO_2R^7$ is $N^-$; or
$R^6$ and $R^7$ together with the intervening atom or atoms bound thereto, form a heterocyclic or a substituted heterocyclic group;
$R^7$ is selected from the group consisting of hydrogen, alkyl, substituted alkyl, amino, cycloalkyl, substituted cycloalkyl, heterocyclic, substituted heterocyclic, aryl, substituted aryl, heteroaryl, substituted heteroaryl, carboxyl, carboxyl ester and acyl;
provided:
when X is hydrogen, ring A is not benzimidazolyl or indazolyl.

Although M+ is preferably a monovalent cation it can also be a divalent cation with appropriate counterions, for example, two of the parent drug anion, one of parent/one of other counter anion, etc.

In another embodiment, the present invention provides a compound of formula II, prodrugs, solvates, or pharmaceutically acceptable salts thereof:

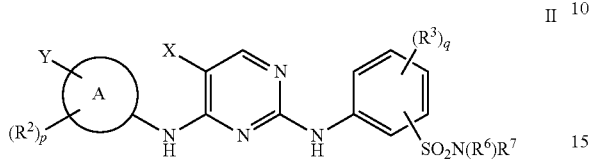

II wherein:
ring A is aryl or heteroaryl;
p is 0, 1, 2 or 3 when ring A is monocyclic or p is 0, 1, 2, 3, 4, or 5 when ring A is bi- or tricyclic;
q is 0, 1, 2 or 3;
X is selected from the group consisting of hydrogen, alkyl, substituted alkyl, hydroxy, alkoxy, substituted alkoxy, amino, substituted amino, carboxyl, carboxyl ester, cyano, halo, nitro, alkenyl, substituted alkenyl, alkynyl, substituted alkynyl, cycloalkynyl, substituted cycloalkynyl;
Y is alk-$SO_2N(R^4)R^5$ or alk-$N(R^4)SO_2R^5$;
alk is selected from the group consisting of straight or branched chain $C_{1-6}$ alkylene group, cycloalkylene and substituted cycloalkylene;
$R^1$ is selected from the group consisting of hydrogen, alkyl, substituted alkyl, alkenyl, substituted alkenyl, alkynyl, substituted alkynyl, cycloalkynyl, substituted cycloalkynyl, cycloalkyl and substituted cycloalkyl;
each $R^2$ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, halo, and oxo; or
$R^4$ and one of $R^2$ together with the intervening atoms bound thereto form a heterocyclic or a substituted heterocyclic fused to ring A; or
$R^5$ and one of $R^2$ together with the intervening atoms bound thereto form a heterocyclic or a substituted heterocyclic fused to ring A;
$Z^1$, $Z^2$, and $Z^3$ each independently is carbon or nitrogen, wherein no more than one of $Z^1$, $Z^2$, and $Z^3$ is N;
each $R^3$ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, halo, and aminosulfonyl; or
$R^6$ and one of $R^3$, together with the intervening atoms bound thereto form a heterocyclic or a substituted heterocyclic fused to the ring containing $Z^1$, $Z^2$ and $Z^3$; or
$R^7$ and one of $R^3$, together with the intervening atoms bound thereto form a heterocyclic or a substituted heterocyclic fused to the ring containing $Z^1$, $Z^2$ and $Z^3$; or
$R^4$ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, acyl and M+, wherein M+ is a counterion selected from the group consisting of K+, Na+, Li+ and +$N(R^8)_4$, wherein $R^8$ is hydrogen or alkyl, and the nitrogen of —$SO_2N(R^4)R^5$ or —$N(R^4)SO_2R^5$ is N−; or
$R^4$ and $R^5$ together with the intervening atom or atoms bound thereto form a heterocyclic or substituted heterocyclic group; or
$R^5$ is selected from the group consisting of hydrogen, alkyl, substituted alkyl, amino, cycloalkyl, substituted cycloalkyl, heterocyclic, substituted heterocyclic, aryl, substituted aryl, heteroaryl, substituted heteroaryl, and acyl; or
$R^4$ and $R^5$ together with the intervening atom or atoms bound thereto form a heterocyclic or a substituted heterocyclic group;
$R^6$ is selected from the group consisting of hydrogen, alkyl, substituted alkyl, cycloalkyl, substituted cycloalkyl, heterocyclic, substituted heterocyclic, carboxyl, carboxyl ester, aryl, substituted aryl, heteroaryl, substituted heteroaryl, acyl and M+, wherein M+ is a counterion selected from the group consisting of K+, Na+, Li+ or +$N(R^8)_4$, wherein $R^8$ is hydrogen or alkyl, and the nitrogen of —$SO_2N(R^6)R^7$ or —$N(R^6)SO_2R^7$ is N−; or
$R^6$ and $R^7$ together with the intervening atom or atoms bound thereto, form a heterocyclic or a substituted heterocyclic group;
$R^7$ is selected from the group consisting of hydrogen, alkyl, substituted alkyl, amino, cycloalkyl, substituted cycloalkyl, heterocyclic, substituted heterocyclic, aryl, substituted aryl, heteroaryl, substituted heteroaryl, carboxyl, carboxyl ester, and acyl;
provided:
when X is hydrogen, ring A is not benzimidazolyl or indazolyl.

Although M+ is preferably a monovalent cation it can also be a divalent cation with appropriate counterions, for example, two of the parent drug anion, one of parent/one of other counter anion, etc.

In another embodiment, the present invention provides a compound of formula III, prodrugs, solvates, or pharmaceutically acceptable salts thereof:

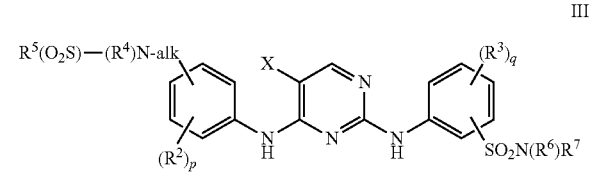

III wherein:
p is 0, 1, 2 or 3 when ring A is monocyclic or p is 0, 1, 2, 3, 4, or 5 when ring A is bi- or tricyclic;
q is 0, 1, 2 or 3;
X is selected from the group consisting of hydrogen, alkyl, substituted alkyl, hydroxy, alkoxy, substituted alkoxy, amino, substituted amino, carboxyl, carboxyl ester, cyano, halo, nitro, alkenyl, substituted alkenyl, alkynyl, substituted alkynyl, cycloalkynyl, substituted cycloalkynyl;
alk is selected from the group consisting of straight or branched chain $C_{1-6}$ alkylene group, cycloalkylene and substituted cycloalkylene;
each $R^2$ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, and halo; or
$R^4$ and one of $R^2$ together with the intervening atoms bound thereto form a heterocyclic or a substituted heterocyclic fused to ring A; or
$R^5$ and one of $R^2$ together with the intervening atoms bound thereto form a heterocyclic or a substituted heterocyclic fused to ring A;
each $R^3$ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, halo, and aminosulfonyl; or
$R^6$ and one of $R^3$, together with the intervening atoms bound thereto form a heterocyclic or a substituted heterocyclic fused to the ring containing $Z^1$, $Z^2$ and $Z^3$; or
$R^7$ and one of $R^3$ together with the intervening atoms bound thereto form a heterocyclic or a substituted heterocyclic fused to the ring containing $Z^1$, $Z^2$, and $Z^3$; or
$R^4$ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, acyl and $M^+$, wherein $M^+$ is a counterion selected from the group consisting of $K^+$, $Na^+$, $Li^+$ and $^+N(R^8)_4$, wherein $R^8$ is hydrogen or alkyl, and the nitrogen of —$SO_2N(R^4)R^5$ or —$N(R^4)SO_2R^5$ is $N^-$;
$R^5$ is selected from the group consisting of hydrogen, alkyl, substituted alkyl, amino, cycloalkyl, substituted cycloalkyl, heterocyclic, substituted heterocyclic, aryl, substituted aryl, heteroaryl, substituted heteroaryl, and acyl; or
$R^4$ and $R^5$ together with the intervening atom or atoms bound thereto form a heterocyclic or a substituted heterocyclic group;

$R^6$ is selected from the group consisting of hydrogen, alkyl, substituted alkyl, cycloalkyl, substituted cycloalkyl, heterocyclic, substituted heterocyclic, carboxyl, carboxyl ester, aryl, substituted aryl, heteroaryl, substituted heteroaryl, acyl and $M^+$, wherein $M^+$ is a counterion selected from the group consisting of $K^+$, $Na^+$, $Li^+$ or $^+N(R^8)_4$, wherein $R^8$ is hydrogen or alkyl, and the nitrogen of —$SO_2N(R^6)R^7$ or —$N(R^6)SO_2R^7$ is $N^-$; or
$R^6$ and $R^7$ together with the intervening atom or atoms bound thereto, form a heterocyclic or a substituted heterocyclic group; and
$R^7$ is selected from the group consisting of hydrogen, alkyl, substituted alkyl, amino, cycloalkyl, substituted cycloalkyl, heterocyclic, substituted heterocyclic, aryl, substituted aryl, heteroaryl, substituted heteroaryl, carboxyl, carboxyl ester and acyl.

Although $M^+$ is preferably a monovalent cation it can also be a divalent cation with appropriate counterions, for example, two of the parent drug anion, one of parent/one of other counter anion, etc.

In one embodiment, alk is $C_{1-2}$ alkyl. In a preferred embodiment, X is halo, alkyl or haloalkyl. In another preferred embodiment, p is 0, 1 or 2 and $R^2$ is halo. In another preferred embodiment, q is 0, 1 or 2 and $R^3$ is alkyl. In another preferred embodiment, each of $R^6$ and $R^7$ independently is selected from the group consisting of hydrogen, alkyl, substituted alkyl, alkynyl, substituted alkynyl, substituted alkynyl, cycloalkynyl, substituted cycloalkynyl, acyl, and carboxyl ester; or $R^6$ and $R^7$ together with the nitrogen atom bound thereto optionally form —N=C(OR$^9$)$_2$ wherein each $R^9$ independently is an alkyl group. In another preferred embodiment, each of $R^6$ and $R^7$ independently is selected from the group consisting of hydrogen and acyl.

In one embodiment, the compound is represented by formula III, wherein $R^4$ and one of $R^2$ together with the intervening atoms bound thereto form a heterocyclic or a substituted heterocyclic. In a preferred embodiment, the compound is represented by formula IVa:

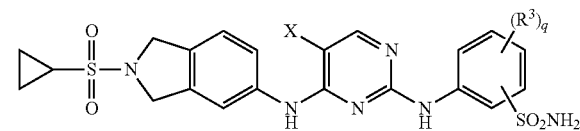

IVa

In another preferred embodiment, the compound is represented by formula IVb:

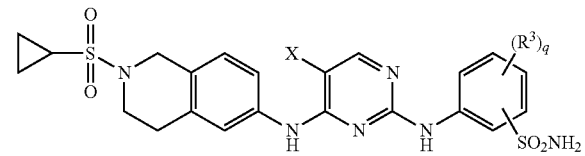

IVb

In another embodiment, the compound is selected from the group consisting of:
I-7 5-Fluoro-N4-[4-(cyclopropylsulfonylaminomethyl)phenyl]-N2-[3-(prop-2-ynylaminosulfonyl)phenyl]-2,4-pyrimidinediamine;

I-8 (N2-(4-aminosulfonyl)phenyl-N4-(4-ethylsulfonylaminomethyl)phenyl-5-fluoro-2,4-pyrimidinediamine; I-9 N2-(3-aminosulfonyl)phenyl-N4-(4-ethylsulfonylaminomethyl)phenyl-5-fluoro-2,4-pyrimidinediamine;

I-10 N2-(3-aminosulfonyl-4-methyl)phenyl-N4-(4-ethylsulfonylaminomethyl)phenyl-5-fluoro-2,4-pyrimidinediamine; I-11 N2-(4-aminosulfonyl)phenyl-N4-(3-ethylsulfonylaminomethyl)phenyl-5-fluoro-2,4-pyrimidinediamine;

I-12 N2-(3-aminosulfonyl)phenyl-N4-(3-ethylsulfonylaminomethyl)phenyl-5-fluoro-2,4-pyrimidinediamine;

I-13 N2-(3-aminosulfonyl-4-methyl)phenyl-N4-(3-ethylsulfonylaminomethyl)phenyl-5-fluoro-2,4-pyrimidinediamine;

I-14 N2-(4-aminosulfonyl)phenyl-N4-[4-(2-ethylsulfonylamino)ethyl]phenyl-5-fluoro-2,4-pyrimidinediamine;

I-15 N2-(3-aminosulfonyl)phenyl-N4-[4-(2-ethylsulfonylamino)ethyl]phenyl-5-fluoro-2,4-pyrimidinediamine;

I-16 N2-(3-aminosulfonyl-4-methyl)phenyl-N4-[4-(2-ethylsulfonylamino)ethyl]phenyl-5-fluoro-2,4-pyrimidinediamine;

I-17 N2-(4-aminosulfonyl)phenyl-N4-[4-(N-ethylsulfonyl-N-propylamino)methyl]phenyl-5-fluoro-2,4-pyrimidinediamine;

I-18 N2-(3-aminosulfonyl)phenyl-N4-[4-(N-ethylsulfonyl-N-propylamino)methyl]phenyl-5-fluoro-2,4-pyrimidinediamine;

I-19 N2-(3-aminosulfonyl-4-methyl)phenyl-N4-[4-(N-ethylsulfonyl-N-propylamino)methyl]phenyl-5-fluoro-2,4-pyrimidinediamine;

I-20 N2-(4-aminosulfonyl)phenyl-N4-(4-ethylsulfonylaminomethyl)phenyl-5-methyl-2,4-pyrimidinediamine;

I-21 N2-(3-aminosulfonyl)phenyl-N4-(4-ethylsulfonylaminomethyl)phenyl-5-methyl-2,4-pyrimidinediamine;

I-22 N2-(3-aminosulfonyl-4-methyl)phenyl-N4-(4-ethylsulfonylaminomethyl)phenyl-5-methyl-2,4-pyrimidinediamine;

I-23 N2-(4-aminosulfonyl)phenyl-N4-(4-cyclopropylsulfonylaminomethyl)phenyl-5-fluoro-2,4-pyrimidinediamine;

I-24 N2-(3-aminosulfonyl)phenyl-N4-(4-cyclopropylsulfonylaminomethyl)phenyl-5-fluoro-2,4-pyrimidinediamine;

I-25 N2-(3-aminosulfonyl-4-methyl)phenyl-N4-(4-cyclopropylsulfonylaminomethyl)phenyl-5-fluoro-2,4-pyrimidinediamine;

I-26 N2-(4-aminosulfonyl)phenyl-N4-[4-(1S-ethylsulfonylamino)ethyl]phenyl-5-fluoro-2,4-pyrimidinediamine;

I-27 N2-(3-aminosulfonyl)phenyl-N4-[4-(1S-ethylsulfonylamino)ethyl]phenyl-5-fluoro-2,4-pyrimidinediamine;

I-28 N2-(3-aminosulfonyl-4-methyl)phenyl-N4-[4-(1S-ethylsulfonylamino)ethyl]phenyl-5-fluoro-2,4-pyrimidinediamine;

I-29 N2-(4-aminosulfonyl)phenyl-N4-[4-(1R-ethylsulfonylamino)ethyl]phenyl-5-fluoro-2,4-pyrimidinediamine;

I-30 N2-(3-aminosulfonyl)phenyl-N4-[4-(1R-ethylsulfonylamino)ethyl]phenyl-5-fluoro-2,4-pyrimidinediamine;

I-31 N2-(3-aminosulfonyl-4-methyl)phenyl-N4-[4-(1R-ethylsulfonylamino)ethyl]phenyl-5-fluoro-2,4-pyrimidinediamine;

I-32 N2-(4-aminosulfonyl)phenyl-N4-(3-cyclopropylsulfonylaminomethyl)phenyl-5-fluoro-2,4-pyrimidinediamine;

I-33 N2-(3-aminosulfonyl)phenyl-N4-(3-cyclopropylsulfonylaminomethyl)phenyl-5-fluoro-2,4-pyrimidinediamine;

I-34 N2-(3-aminosulfonyl-4-methyl)phenyl-N4-(3-cyclopropylsulfonylaminomethyl)phenyl-5-fluoro-2,4-pyrimidinediamine;

I-35 N2-(4-aminosulfonyl)phenyl-5-fluoro-N4-[4-(thiophen-2-yl)sulfonylaminomethyl]phenyl-2,4-pyrimidinediamine;

I-36 N2-(3-aminosulfonyl)phenyl-5-fluoro-N4-[4-(thiophen-2-yl)sulfonylaminomethyl]phenyl-2,4-pyrimidinediamine;

I-37 N2-(3-aminosulfonyl-4-methyl)phenyl-5-fluoro-N4-[4-(thiophen-2-yl)sulfonylaminomethyl]phenyl-2,4-pyrimidinediamine;

I-38 N2-(4-aminosulfonyl)phenyl-N4-[4-(2-ethylsulfonylamino)ethyl]phenyl-5-methyl-2,4-pyrimidinediamine;

I-39 N2-(3-aminosulfonyl)phenyl-N4-[4-(2-ethylsulfonylamino)ethyl]phenyl-5-methyl-2,4-pyrimidinediamine;

I-40 N2-(3-aminosulfonyl-4-methyl)phenyl-N4-[4-(2-ethylsulfonylamino)ethyl]phenyl-5-methyl-2,4-pyrimidinediamine;

I-41 N4-[4-(2-amino-4-methylthiazol-5-yl)sulfonylaminomethyl]phenyl-N2-(3-aminosulfonyl)phenyl-5-fluoro-2,4-pyrimidinediamine;

I-42 N4-[4-(2-acetylamino-4-methylthiazol-5-yl)sulfonylaminomethyl]phenyl-N2-(3-aminosulfonyl)phenyl-5-fluoro-2,4-pyrimidinediamine;

I-43 N4-[4-(2-amino-4-methylthiazol-5-yl)sulfonylaminomethyl]phenyl-N2-(3-aminosulfonyl-4-methyl)phenyl-5-fluoro-2,4-pyrimidinediamine;

I-44 N4-[4-(2-acetylamino-4-methylthiazol-5-yl)sulfonylaminomethyl]phenyl-N2-(3-aminosulfonyl-4-methyl)phenyl-5-fluoro-2,4-pyrimidinediamine;

I-45 N2-(4-aminosulfonyl)phenyl-N4-(4-cyclopropylsulfonylaminomethyl)phenyl-5-methyl-2,4-pyrimidinediamine;

I-46 N2-(3-aminosulfonyl)phenyl-N4-(4-cyclopropylsulfonylaminomethyl)phenyl-5-methyl-2,4-pyrimidinediamine;

I-47 N2-(3-aminosulfonyl-4-methyl)phenyl-N4-(4-cyclopropylsulfonylaminomethyl)phenyl-5-methyl-2,4-pyrimidinediamine;

I-48 N2-(4-aminosulfonyl)phenyl-5-fluoro-N4-(4-trifluoroethylsulfonylaminomethyl)phenyl-2,4-pyrimidinediamine;

I-49 N2-(3-aminosulfonyl)phenyl-5-fluoro-N4-(4-trifluoroethylsulfonylaminomethyl)phenyl-2,4-pyrimidinediamine;

I-50 N2-(3-aminosulfonyl-4-methyl)phenyl-5-fluoro-N4-(4-trifluoroethylsulfonylaminomethyl)phenyl-2,4-pyrimidinediamine;

I-51 N2-(3-aminosulfonyl)phenyl-N4-(3-cyclopropylsulfonylaminomethyl)phenyl-5-methyl-2,4-pyrimidinediamine;

I-52 N2-(3-aminosulfonyl-4-methyl)phenyl-N4-(3-cyclopropylsulfonylaminomethyl)phenyl-5-methyl-2,4-pyrimidinediamine;

I-53 N2-(4-aminosulfonyl)phenyl-N4-[4-(2-cyclopropylsulfonylamino)ethyl]phenyl-5-methyl-2,4-pyrimidinediamine;

I-54 N2-(3-aminosulfonyl)phenyl-N4-[4-(2-cyclopropylsulfonylamino)ethyl]phenyl-5-methyl-2,4-pyrimidinediamine;

I-55 N2-(3-aminosulfonyl-4-methyl)phenyl-N4-[4-(2-cyclopropylsulfonylamino)ethyl]phenyl-5-methyl-2,4-pyrimidinediamine;

I-56 N2-(4-aminosulfonyl)phenyl-N4-(3-cyclopropylsulfonylaminomethyl)phenyl-5-methyl-2,4-pyrimidinediamine;

I-57 N4-(4-cyclopropylsulfonylaminomethyl)phenyl-5-fluoro-N2-(3-propionylaminosulfonyl)phenyl-2,4-pyrimidinediamine;

I-58 N4-[4-(N-cyclopropylsulfonyl-N-propionyl)aminomethyl]phenyl-5-fluoro-N2-(3-propionylaminosulfonyl)phenyl-2,4-pyrimidinediamine;
I-59 N4-(4-cyclopropylsulfonylaminomethyl)phenyl-5-fluoro-N2-(4-methyl-3-propionylaminosulfonyl)phenyl-2,4-pyrimidinediamine;
I-60 N4-[4-(N-cyclopropylsulfonyl-N-propionyl)aminomethyl]phenyl-5-fluoro-N2-(4-methyl-3-propionylaminosulfonyl)phenyl-2,4-pyrimidinediamine;
I-61 N4-(4-cyclopropylsulfonylaminomethyl)phenyl-5-fluoro-N2-(3-propionylaminosulfonyl)phenyl-2,4-pyrimidinediamine sodium salt;
I-62 N4-[4-(N-cyclopropylsulfonyl-N-propionyl)aminomethyl]phenyl-5-fluoro-N2-(3-propionylaminosulfonyl)phenyl-2,4-pyrimidinediamine sodium salt;
I-63 N4-(4-cyclopropylsulfonylaminomethyl)phenyl-5-fluoro-N2-(4-methyl-3-propionylaminosulfonyl)phenyl-2,4-pyrimidinediamine sodium salt;
I-64 N4-[4-(N-cyclopropylsulfonyl-N-propionyl)aminomethyl]phenyl-5-fluoro-N2-(4-methyl-3-propionylaminosulfonyl)phenyl-2,4-pyrimidinediamine sodium salt;
I-65 N2-(4-aminosulfonyl)phenyl-5-fluoro-N4-(4-isopropylsulfonylaminomethyl)phenyl-2,4-pyrimidinediamine;
I-66 N2-(3-aminosulfonyl)phenyl-5-fluoro-N4-(4-isopropylsulfonylaminomethyl)phenyl-2,4-pyrimidinediamine;
I-67 N2-(3-aminosulfonyl-4-methyl)phenyl-5-fluoro-N4-(4-isopropylsulfonylaminomethyl)phenyl-2,4-pyrimidinediamine;
I-68 N2-(4-aminosulfonyl)phenyl-N4-(4-cyclopentylsulfonylaminomethyl)phenyl-5-fluoro-2,4-pyrimidinediamine;
I-69 N2-(3-aminosulfonyl)phenyl-N4-(4-cyclopentylsulfonylaminomethyl)phenyl-5-fluoro-2,4-pyrimidinediamine;
I-70 N2-(3-aminosulfonyl-4-methyl)phenyl-N4-(4-cyclopentylsulfonylaminomethyl)phenyl-5-fluoro-2,4-pyrimidinediamine;
I-71 N2-(4-aminosulfonyl)phenyl-N4-(4-cyclohexylsulfonylaminomethyl)phenyl-5-fluoro-2,4-pyrimidinediamine;
I-72 N2-(3-aminosulfonyl)phenyl-N4-(4-cyclohexylsulfonylaminomethyl)phenyl-5-fluoro-2,4-pyrimidinediamine;
I-73 N2-(3-aminosulfonyl-4-methyl)phenyl-N4-(4-cyclohexylsulfonylaminomethyl)phenyl-5-fluoro-2,4-pyrimidinediamine;
I-74 N2-(4-aminosulfonyl)phenyl-N4-(3-chloro-4-ethylsulfonylaminomethyl)phenyl-5-fluoro-2,4-pyrimidinediamine;
I-75 N2-(3-aminosulfonyl)phenyl-N4-(3-chloro-4-ethylsulfonylaminomethyl)phenyl-5-fluoro-2,4-pyrimidinediamine;
I-76 N2-(3-aminosulfonyl-4-methyl)phenyl-N4-(3-chloro-4-ethylsulfonylaminomethyl)phenyl-5-fluoro-2,4-pyrimidinediamine;
I-77 N4-[4-(N-cyclopropylsulfonyl-N-propionyl)aminomethyl]phenyl-5-methyl-N2-(4-propionylaminosulfonyl)phenyl-2,4-pyrimidinediamine;
I-78 N4-[4-(N-cyclopropylsulfonyl-N-propionyl)aminomethyl]phenyl-5-methyl-N2-(4-propionylaminosulfonyl)phenyl-2,4-pyrimidinediamine sodium salt;
I-79 N2-(4-aminosulfonyl)phenyl-N4-[4-(N-cyclopropylsulfonyl-N-propylamino)methyl]phenyl-5-methyl-2,4-pyrimidinediamine;
I-80 N2-(3-aminosulfonyl)phenyl-N4-[4-(N-cyclopropylsulfonyl-N-propylamino)methyl]phenyl-5-methyl-2,4-pyrimidinediamine;
I-81 N2-(3-aminosulfonyl-4-methyl)phenyl-N4-[4-(N-cyclopropylsulfonyl-N-propylamino)methyl]phenyl-5-methyl-2,4-pyrimidinediamine;
I-82 N4-(4-cyclopropylsulfonylaminomethyl)phenyl-N2-(3,5-diaminosulfonyl)phenyl-5-fluoro-2,4-pyrimidinediamine;
I-83 N4-(4-cyclopropylsulfonylaminomethyl)phenyl-5-methyl-N2-(4-propionylaminosulfonyl)phenyl-2,4-pyrimidinediamine;
I-84 N4-(4-cyclopropylsulfonylaminomethyl)phenyl-N2-(3,5-diaminosulfonyl)phenyl-5-methyl-2,4-pyrimidinediamine;
I-85 N2-(4-aminosulfonyl)phenyl-5-fluoro-N4-[4-(methylsulfonylmethylsulfonylamino)methyl]phenyl-2,4-pyrimidinediamine;
I-86 N2-(3-aminosulfonyl)phenyl-5-fluoro-N4-[4-(methylsulfonylmethylsulfonylamino)methyl]phenyl-2,4-pyrimidinediamine;
I-87 N2-(3-aminosulfonyl-4-methyl)phenyl-5-fluoro-N4-[4-(methylsulfonylmethylsulfonylamino)methyl]phenyl-2,4-pyrimidinediamine;
I-88 N4-(4-cyclopropylsulfonylaminomethyl)phenyl-5-methyl-N2-(4-propionylaminosulfonyl)phenyl-2,4-pyrimidinediamine sodium salt; I-89 N2-(4-aminosulfonyl)phenyl-5-fluoro-N4-[4-(pyrid-3-yl)sulfonylaminomethyl]phenyl-2,4-pyrimidinediamine;
I-90 N2-(3-aminosulfonyl-4-methyl)phenyl-5-fluoro-N4-[4-(pyrid-3-yl)sulfonylaminomethyl]phenyl-2,4-pyrimidinediamine;
I-91 N4-[4-(N-ethylsulfonyl-N-propionyl)aminomethyl]phenyl-5-methyl-N2-(4-propionylaminosulfonyl)phenyl-2,4-pyrimidinediamine;
I-92 N4-[4-(N-ethylsulfonyl-N-propionyl)aminomethyl]phenyl-5-methyl-N2-(4-propionylaminosulfonyl)phenyl-2,4-pyrimidinediamine sodium salt;
I-93 N4-[3-(N-cyclopropylsulfonyl-N-propionyl)aminomethyl]phenyl-5-methyl-N2-(3-propionylaminosulfonyl)phenyl-2,4-pyrimidinediamine;
I-94 N4-[3-(N-cyclopropylsulfonyl-N-propionyl)aminomethyl]phenyl-5-methyl-N2-(3-propionylaminosulfonyl)phenyl-2,4-pyrimidinediamine sodium salt;
I-95 N2-(3-aminosulfonyl)phenyl-5-fluoro-N4-[4-(pyrid-3-yl)sulfonylaminomethyl]phenyl-2,4-pyrimidinediamine;
I-96 N2-(4-aminosulfonyl)phenyl-5-methyl-N4-(4-trifluoroethylsulfonylaminomethyl)phenyl-2,4-pyrimidinediamine;
I-97 N2-(3-aminosulfonyl)phenyl-5-methyl-N4-(4-trifluoroethylsulfonylaminomethyl)phenyl-2,4-pyrimidinediamine;
I-98 N2-(3-aminosulfonyl-4-methyl)phenyl-5-methyl-N4-(4-trifluoroethylsulfonylaminomethyl)phenyl-2,4-pyrimidinediamine;
I-99 N2-(4-aminosulfonyl)phenyl-5-methyl-N4-[4-(pyrid-3-yl)sulfonylaminomethyl]phenyl-2,4-pyrimidinediamine;
I-100 N2-(3-aminosulfonyl)phenyl-5-methyl-N4-[4-(pyrid-3-yl)sulfonylaminomethyl]phenyl-2,4-pyrimidinediamine;
I-101 N2-(3-aminosulfonyl-4-methyl)phenyl-5-methyl-N4-[4-(pyrid-3-yl)sulfonylaminomethyl]phenyl-2,4-pyrimidinediamine;
I-140 N2-{3-N-[2-(t-butoxycarbonylamino)-1-oxoethyl]aminosulfonyl}phenyl-N4-(3-cyclopropylsulfonylaminomethyl)phenyl-5-methyl-2,4-pyrimidinediamine;
I-141 N2-{3-N-[2-(t-butoxycarbonylamino)-1-oxoethyl]aminosulfonyl}phenyl-N4-(3-cyclopropylsulfonylaminomethyl)phenyl-5-methyl-2,4-pyrimidinediamine sodium salt;

I-142  N2-{3-N-[2-(benzoxycarbonylamino)-1-oxoethyl]aminosulfonyl}phenyl-N4-(3-cyclopropylsulfonylaminomethyl)phenyl-5-methyl-2,4-pyrimidinediamine;

I-143  N2-{3-N-[2-(benzoxycarbonylamino)-1-oxoethyl]aminosulfonyl}phenyl-N4-(3-cyclopropylsulfonylaminomethyl)phenyl-5-methyl-2,4-pyrimidinediamine sodium salt;

I-136  N4-(3-cyclopropylsulfonylaminomethyl)phenyl-5-methyl-N2-(3-propionylaminosulfonyl)phenyl-2,4-pyrimidinediamine;

I-116  N2-(3-aminosulfonyl)phenyl-N4-[3-(N-cyclopropylsulfonyl-N-propionyl)aminomethyl]phenyl-5-methyl-2,4-pyrimidinediamine;

I-137  N4-(3-cyclopropylsulfonylaminomethyl)phenyl-5-methyl-N2-(3-propionylaminosulfonyl)phenyl-2,4-pyrimidinediamine sodium salt;

I-123  N2-(4-aminosulfonyl)phenyl-N4-(4-isopropylsulfonylaminomethyl)phenyl-5-methyl-2,4-pyrimidinediamine;

I-118  N2-(3-aminosulfonyl)phenyl-N4-(4-isopropylsulfonylaminomethyl)phenyl-5-methyl-2,4-pyrimidinediamine;

I-117  N2-(3-aminosulfonyl-4-methyl)phenyl-N4-(4-isopropylsulfonylaminomethyl)phenyl-5-methyl-2,4-pyrimidinediamine;

I-131  N2-[3-N-(2-amino-1-oxoethyl)aminosulfonyl]phenyl-N4-(3-cyclopropylsulfonylaminomethyl)phenyl-5-methyl-2,4-pyrimidinediamine;

I-133  N2-[3-N-(2-amino-1-oxoethyl)aminosulfonyl]phenyl-N4-(3-cyclopropylsulfonylaminomethyl)phenyl-5-methyl-2,4-pyrimidinediamine hydrogen chloride salt;

I-129  N2-(4-aminosulfonyl)phenyl-N4-(3-chloro-4-cyclopropylsulfonylaminomethyl)phenyl-5-methyl-2,4-pyrimidinediamine;

I-119  N2-(3-aminosulfonyl)phenyl-N4-(3-chloro-4-cyclopropylsulfonylaminomethyl)phenyl-5-methyl-2,4-pyrimidinediamine;

I-125  N2-(3-aminosulfonyl-4-methyl)phenyl-N4-(3-chloro-4-cyclopropylsulfonylaminomethyl)phenyl-5-methyl-2,4-pyrimidinediamine;

I-127  N2-(4-aminosulfonyl)phenyl-N4-[4-(N-cyclopropylsulfonyl-N-methyl)aminomethyl]phenyl-5-methyl-2,4-pyrimidinediamine;

I-121  N2-(3-aminosulfonyl)phenyl-N4-[4-(N-cyclopropylsulfonyl-N-methyl)aminomethyl]phenyl-5-methyl-2,4-pyrimidinediamine;

I-126  N2-(3-aminosulfonyl-4-methyl)phenyl-N4-[4-(N-cyclopropylsulfonyl-N-methyl)aminomethyl]phenyl-5-methyl-2,4-pyrimidinediamine;

I-124  N2-(4-aminosulfonyl)phenyl-N4-[3-(N-cyclopropylsulfonyl-N-methyl)aminomethyl]phenyl-5-methyl-2,4-pyrimidinediamine;

I-120  N2-(3-aminosulfonyl)phenyl-N4-[3-(N-cyclopropylsulfonyl-N-methyl)aminomethyl]phenyl-5-methyl-2,4-pyrimidinediamine;

I-122  N2-(3-aminosulfonyl-4-methyl)phenyl-N4-[3-(N-cyclopropylsulfonyl-N-methyl)aminomethyl]phenyl-5-methyl-2,4-pyrimidinediamine;

I-139  N2-[3-N-(Cbz-L-Phe)aminosulfonyl]phenyl-N4-(3-cyclopropylsulfonylaminomethyl)phenyl-5-methyl-2,4-pyrimidinediamine;

I-144  N2-[3-N-(Cbz-L-Val)aminosulfonyl]phenyl-N4-(3-cyclopropylsulfonylaminomethyl)phenyl-5-methyl-2,4-pyrimidinediamine;

I-135  N2-[3-N-(Cbz-L-Phe)aminosulfonyl]phenyl-N4-(3-cyclopropylsulfonylaminomethyl)phenyl-5-methyl-2,4-pyrimidinediamine sodium salt;

I-134  N2-[3-N-(L-Phe)aminosulfonyl]phenyl-N4-(3-cyclopropylsulfonylaminomethyl)phenyl-5-methyl-2,4-pyrimidinediamine;

I-132  N2-[3-N-(L-Phe)aminosulfonyl]phenyl-N4-(3-cyclopropylsulfonylaminomethyl)phenyl-5-methyl-2,4-pyrimidinediamine hydrogen chloride salt;

I-138  N2-[3-N-(L-Val)aminosulfonyl]phenyl-N4-(3-cyclopropylsulfonylaminomethyl)phenyl-5-methyl-2,4-pyrimidinediamine;

I-148  N2-[3-N-(Boc-cycloleucine)aminosulfonyl]phenyl-N4-(3-cyclopropylsulfonylaminomethyl)phenyl-5-methyl-2,4-pyrimidinediamine;

I-146  N2-[3-N-(L-Val)aminosulfonyl]phenyl-N4-(3-cyclopropylsulfonylaminomethyl)phenyl-5-methyl-2,4-pyrimidinediamine hydrogen chloride salt;

I-145  N2-[3-N-(cycloleucine)aminosulfonyl]phenyl-N4-(3-cyclopropylsulfonylaminomethyl)phenyl-5-methyl-2,4-pyrimidinediamine hydrogen chloride salt;

I-147  N2-[3-N-(Cbz-L-Val)aminosulfonyl]phenyl-N4-(3-cyclopropylsulfonylaminomethyl)phenyl-5-methyl-2,4-pyrimidinediamine sodium salt;

I-130  N4-(3-cyclopropylsulfonylaminomethyl)phenyl-N2-[3-(N-ethoxycarbonyl-N-ethyl)aminosulfonyl]phenyl-5-methyl-2,4-pyrimidinediamine;

I-128  N4-(3-cyclopropylsulfonylaminomethyl)phenyl-N2-[3-(diethoxy)carbonimidylsulfonyl]phenyl-5-methyl-2,4-pyrimidinediamine;

II-1  N2-(4-aminosulfonyl)phenyl-N4-[(N-cyclopropylsulfonyl)-1,2,3,4-tetrahydroisoquinolin-6-yl]-5-methyl-2,4-pyrimidinediamine;

II-2  N2-(3-aminosulfonyl)phenyl-N4-[(N-cyclopropylsulfonyl)-1,2,3,4-tetrahydroisoquinolin-6-yl]-5-methyl-2,4-pyrimidinediamine;

II-3  N2-(3-aminosulfonyl-4-methyl)phenyl-N4-[(N-cyclopropylsulfonyl)-1,2,3,4-tetrahydroisoquinolin-6-yl]-5-methyl-2,4-pyrimidinediamine;

I-115  N2-(4-aminosulfonyl)phenyl-5-chloro-N4-(4-cyclopropylsulfonylaminomethyl)phenyl-2,4-pyrimidinediamine;

I-114  N2-(3-aminosulfonyl)phenyl-5-chloro-N4-(4-cyclopropylsulfonylaminomethyl)phenyl-2,4-pyrimidinediamine;

I-113  N2-(3-aminosulfonyl-4-methyl)phenyl-5-chloro-N4-(4-cyclopropylsulfonylaminomethyl)phenyl-2,4-pyrimidinediamine;

II-4  N2-(3-Aminosulfonyl-4-methylphenyl)-N4-[(2-cyclopropylsulfonyl)-isoindolin-5-yl]-5-fluoro-2,4-pyrimidinediamine;

II-5  N2-(3-Aminosulfonyl-phenyl)-N4-[(2-cyclopropylsulfonyl)-isoindolin-5-yl]-5-fluoro-2,4-pyrimidinediamine;

II-6  N2-(4-Aminosulfonyl-phenyl)-N4-[(2-cyclopropylsulfonyl)-isoindolin-5-yl]-5-fluoro-2,4-pyrimidinediamine;

II-7  N2-(3-Aminosulfonyl-4-methylphenyl)-N4-[(2-cyclopropylsulfonyl)-isoindolin-5-yl]-5-methyl-2,4-pyrimidinediamine;

II-8  N2-(3-Aminosulfonyl-phenyl)-N4-[(2-cyclopropylsulfonyl)-isoindolin-5-yl]-5-methyl-2,4-pyrimidinediamine;

II-9  N2-(4-Aminosulfonyl-phenyl)-N4-[(2-cyclopropylsulfonyl)-isoindolin-5-yl]-5-methyl-2,4-pyrimidinediamine;

I-149  N4-(4-cyclopropylsulfonylaminomethyl)phenyl-5-methyl-N2-(4-phenylaminosulfonyl)phenyl-2,4-pyrimidinediamine;

I-150  N4-(4-cyclopropylsulfonylaminomethyl)phenyl-5-methyl-N2-(3-phenylaminosulfonyl)phenyl-2,4-pyrimidinediamine;

I-151 N4-(4-cyclopropylsulfonylaminomethyl)phenyl-5-methyl-N2-[4-(1-methylpiperidin-4-yl)aminosulfonyl]phenyl-2,4-pyrimidinediamine;

I-152 N4-(4-cyclopropylsulfonylaminomethyl)phenyl-5-methyl-N2-[3-(1-methylpiperidin-4-yl)aminosulfonyl]phenyl-2,4-pyrimidinediamine;

I-153 N2-(4-benzylaminosulfonyl)phenyl-N4-(4-cyclopropylsulfonylaminomethyl)phenyl-5-methyl-2,4-pyrimidinediamine;

I-154 N2-(3-benzylaminosulfonyl)phenyl-N4-(4-cyclopropylsulfonylaminomethyl)phenyl-5-methyl-2,4-pyrimidinediamine;

I-155 N4-(3-cyclopropylsulfonylaminomethyl)phenyl-5-methyl-N2-(4-phenylaminosulfonyl)phenyl-2,4-pyrimidinediamine;

I-156 N4-(3-cyclopropylsulfonylaminomethyl)phenyl-5-methyl-N2-(3-phenylaminosulfonyl)phenyl-2,4-pyrimidinediamine;

I-157 N2-(4-benzylaminosulfonyl)phenyl-N4-(3-cyclopropylsulfonylaminomethyl)phenyl-5-methyl-2,4-pyrimidinediamine;

I-158 N2-(3-benzylaminosulfonyl)phenyl-N4-(3-cyclopropylsulfonylaminomethyl)phenyl-5-methyl-2,4-pyrimidinediamine;

I-159 N4-(3-cyclopropylsulfonylaminomethyl)phenyl-5-methyl-N2-[4-(1-methylpiperidin-4-yl)aminosulfonyl]phenyl-2,4-pyrimidinediamine;

I-160 N4-(3-cyclopropylsulfonylaminomethyl)phenyl-5-methyl-N2-[3-(1-methylpiperidin-4-yl)aminosulfonyl]phenyl-2,4-pyrimidinediamine;

I-161 N4-(4-cyclopropylsulfonylaminomethyl)phenyl-5-methyl-N2-(3-methylaminosulfonyl)phenyl-2,4-pyrimidinediamine;

I-162 N4-(3-cyclopropylsulfonylaminomethyl)phenyl-5-methyl-N2-(3-methylaminosulfonyl)phenyl-2,4-pyrimidinediamine;

I-163 N4-(4-cyclopropylsulfonylaminomethyl)phenyl-5-methyl-N2-(4-methylaminosulfonyl)phenyl-2,4-pyrimidinediamine;

I-164 N4-(4-cyclopropylsulfonylaminomethyl)phenyl-5-methyl-N2-(4-propargylaminosulfonyl)phenyl-2,4-pyrimidinediamine;

I-165 N4-(4-cyclopropylsulfonylaminomethyl)phenyl-5-methyl-N2-(3-propargylaminosulfonyl)phenyl-2,4-pyrimidinediamine;

I-166 N2-(4-cyclopentylaminosulfonyl)phenyl-N4-(4-cyclopropylsulfonylaminomethyl)phenyl-5-methyl-2,4-pyrimidinediamine I-167 N2-(4-aminosulfonyl)phenyl-N4-[4-(N-cyclopropylsulfonyl-N-propionyl)aminomethyl]phenyl-5-methyl-2,4-pyrimidinediamine;

I-168 N4-(4-cyclopropylsulfonylaminomethyl)phenyl-5-methyl-N2-[4-(4-pyridylmethyl)aminosulfonyl]phenyl-2,4-pyrimidinediamine;

I-169 N4-(4-cyclopropylsulfonylaminomethyl)phenyl-5-methyl-N2-[3-(4-pyridylmethyl)aminosulfonyl]phenyl-2,4-pyrimidinediamine;

I-170 N2-(3-cyclopentylaminosulfonyl)phenyl-N4-(4-cyclopropylsulfonylaminomethyl)phenyl-5-methyl-2,4-pyrimidinediamine;

I-171 N4-(4-cyclopropylsulfonylaminomethyl)phenyl-5-methyl-N2-[4-(3-pyridyl)aminosulfonyl]phenyl-2,4-pyrimidinediamine;

I-172 N4-(4-cyclopropylsulfonylaminomethyl)phenyl-N2-(4-isopropylaminosulfonyl)phenyl-5-methyl-2,4-pyrimidinediamine;

I-173 N4-(4-cyclopropylsulfonylaminomethyl)phenyl-N2-(3-isopropylaminosulfonyl)phenyl-5-methyl-2,4-pyrimidinediamine;

I-174 N4-(4-cyclopropylsulfonylaminomethyl)phenyl-5-methyl-N2-[3-(3-pyridyl)aminosulfonyl]phenyl-2,4-pyrimidinediamine;

I-175 N4-(4-cyclopropylsulfonylaminomethyl)phenyl-N2-(4-ethylaminosulfonyl)phenyl-5-methyl-2,4-pyrimidinediamine;

I-176 N4-(4-cyclopropylsulfonylaminomethyl)phenyl-N2-(3-ethylaminosulfonyl)phenyl-5-methyl-2,4-pyrimidinediamine;

I-177 N4-(4-cyclopropylsulfonylaminomethyl)phenyl-5-methyl-N2-(4-propylaminosulfonyl)phenyl-2,4-pyrimidinediamine;

I-178 N4-(4-cyclopropylsulfonylaminomethyl)phenyl-5-methyl-N2-(3-propylaminosulfonyl)phenyl-2,4-pyrimidinediamine;

I-179 N2-(4-cyclopropylmethylaminosulfonyl)phenyl-N4-(4-cyclopropylsulfonylaminomethyl)phenyl-5-methyl-2,4-pyrimidinediamine;

I-180 N2-(3-cyclopropylmethylaminosulfonyl)phenyl-N4-(4-cyclopropylsulfonylaminomethyl)phenyl-5-methyl-2,4-pyrimidinediamine;

I-181 N4-(4-cyclopropylsulfonylaminomethyl)phenyl-N2-[4-(3-methoxypropyl)aminosulfonyl]phenyl-5-methyl-2,4-pyrimidinediamine;

I-182 N4-(4-cyclopropylsulfonylaminomethyl)phenyl-N2-[3-(3-methoxypropyl)aminosulfonyl]phenyl-5-methyl-2,4-pyrimidinediamine;

I-183 N4-(4-cyclopropylsulfonylaminomethyl)phenyl-N2-[4-(2-methoxyethyl)aminosulfonyl]phenyl-5-methyl-2,4-pyrimidinediamine;

I-184 N4-(4-cyclopropylsulfonylaminomethyl)phenyl-N2-[3-(2-methoxyethyl)aminosulfonyl]phenyl-5-methyl-2,4-pyrimidinediamine;

I-185 N4-(4-cyclopropylsulfonylaminomethyl)phenyl-5-methyl-N2-(4-methyl-3-methylaminosulfonyl)phenyl-2,4-pyrimidinediamine;

I-186 N4-(4-cyclopropylsulfonylaminomethyl)phenyl-N2-(3-ethylaminosulfonyl-4-methyl)phenyl-5-methyl-2,4-pyrimidinediamine;

I-187 N4-(4-cyclopropylsulfonylaminomethyl)phenyl-5-methyl-N2-(4-methyl-3-propylaminosulfonyl)phenyl-2,4-pyrimidinediamine;

I-188 N4-(4-cyclopropylsulfonylaminomethyl)phenyl-5-methyl-N2-(4-methyl-3-propargylaminosulfonyl)phenyl-2,4-pyrimidinediamine;

I-189 N4-(4-cyclopropylsulfonylaminomethyl)phenyl-N2-(3-isopropylaminosulfonyl-4-methyl)phenyl-5-methyl-2,4-pyrimidinediamine;

I-190 N4-(4-cyclopropylsulfonylaminomethyl)phenyl-N2-[3-(2-methoxyethyl)aminosulfonyl-4-methyl]phenyl-5-methyl-2,4-pyrimidinediamine;

I-191 N4-(4-cyclopropylsulfonylaminomethyl)phenyl-N2-[3-(3-methoxypropyl)aminosulfonyl-4-methyl]phenyl-5-methyl-2,4-pyrimidinediamine;

I-192 N2-(3-cyclopropylmethylaminosulfonyl-4-methyl)phenyl-N4-(4-cyclopropylsulfonylaminomethyl)phenyl-5-methyl-2,4-pyrimidinediamine;

I-193 N2-(3-acetamidosulfonyl)phenyl-N4-[3-(N-acetyl-N-cyclopropylsulfonyl)aminomethyl]phenyl-5-methyl-2,4-pyrimidinediamine;

I-194 N2-(4-acetamidosulfonyl)phenyl-N4-[4-(N-acetyl-N-cyclopropylsulfonyl)aminomethyl]phenyl-5-methyl-2,4-pyrimidinediamine;

I-195 N2-(3-benzylaminosulfonyl-4-methyl)phenyl-N4-(4-cyclopropylsulfonylaminomethyl)phenyl-5-methyl-2,4-pyrimidinediamine;

I-196 N2-(3-acetamidosulfonyl)phenyl-N4-[3-(N-acetyl-N-cyclopropylsulfonyl)aminomethyl]phenyl-5-methyl-2,4-pyrimidinediamine sodium salt;

I-197 N2-(4-acetamidosulfonyl)phenyl-N4-[4-(N-acetyl-N-cyclopropylsulfonyl)aminomethyl]phenyl-5-methyl-2,4-pyrimidinediamine sodium salt;

I-198 N4-[3-(N-cyclopropylsulfonyl-N-isobutyryl)aminomethyl]phenyl-N2-(3-isobutyrylaminosulfonyl)phenyl-5-methyl-2,4-pyrimidinediamine;

I-199 N4-[4-(N-cyclopropylsulfonyl-N-isobutyryl)aminomethyl]phenyl-N2-(4-isobutyrylaminosulfonyl)phenyl-5-methyl-2,4-pyrimidinediamine;

I-200 N4-[3-(N-cyclopropylsulfonyl-N-isobutyryl)aminomethyl]phenyl-N2-(3-isobutyrylaminosulfonyl)phenyl-5-methyl-2,4-pyrimidinediamine sodium salt;

I-201 N4-[4-(N-cyclopropylsulfonyl-N-isobutyryl)aminomethyl]phenyl-N2-(4-isobutyrylaminosulfonyl)phenyl-5-methyl-2,4-pyrimidinediamine sodium salt;

I-202 N4-(4-cyclopropylsulfonylaminomethyl)phenyl-5-methyl-N2-(4-methyl-3-phenylaminosulfonyl)phenyl-2,4-pyrimidinediamine;

I-203 N2-(3-butyrylaminosulfonyl)phenyl-N4-[3-(N-butyryl-N-cyclopropylsulfonyl)aminomethyl]phenyl-5-methyl-2,4-pyrimidinediamine;

I-204 N2-(4-butyrylaminosulfonyl)phenyl-N4-[4-(N-butyryl-N-cyclopropylsulfonyl)aminomethyl]phenyl-5-methyl-2,4-pyrimidinediamine;

I-205 N2-(3-butyrylaminosulfonyl)phenyl-N4-[3-(N-butyryl-N-cyclopropylsulfonyl)aminomethyl]phenyl-5-methyl-2,4-pyrimidinediamine sodium salt;

I-206 N2-(4-butyrylaminosulfonyl)phenyl-N4-[4-(N-butyryl-N-cyclopropylsulfonyl)aminomethyl]phenyl-5-methyl-2,4-pyrimidinediamine sodium salt;

I-207 N4-(3-cyclopropylsulfonylaminomethyl)phenyl-5-methyl-N2-(4-methylaminosulfonyl)phenyl-2,4-pyrimidinediamine;

I-208 N4-(3-cyclopropylsulfonylaminomethyl)phenyl-N2-(3-ethylaminosulfonyl)phenyl-5-methyl-2,4-pyrimidinediamine;

I-209 N4-(3-cyclopropylsulfonylaminomethyl)phenyl-N2-(3-isopropylaminosulfonyl-4-methyl)phenyl-5-methyl-2,4-pyrimidinediamine;

I-210 N4-(3-cyclopropylsulfonylaminomethyl)phenyl-N2-[3-(2-methoxyethyl)aminosulfonyl-4-methyl]phenyl-5-methyl-2,4-pyrimidinediamine;

I-211 N4-(3-cyclopropylsulfonylaminomethyl)phenyl-5-methyl-N2-(4-methyl-3-methylaminosulfonyl)phenyl-2,4-pyrimidinediamine;

I-212 N4-(3-cyclopropylsulfonylaminomethyl)phenyl-N2-(4-ethylaminosulfonyl)phenyl-5-methyl-2,4-pyrimidinediamine;

I-213 N4-(3-cyclopropylsulfonylaminomethyl)phenyl-N2-(3-ethylaminosulfonyl-4-methyl)phenyl-5-methyl-2,4-pyrimidinediamine;

(I-214) N4-(3-cyclopropylsulfonylaminomethyl)phenyl-5-methyl-N2-(4-methyl-3-propargylaminosulfonyl)phenyl-2,4-pyrimidinediamine;

I-215 N4-(3-cyclopropylsulfonylaminomethyl)phenyl-5-methyl-N2-(4-methyl-3-propylaminosulfonyl)phenyl-2,4-pyrimidinediamine;

I-216 N2-(3-cyclopropylmethylaminosulfonyl-4-methyl)phenyl-N4-(3-cyclopropylsulfonylaminomethyl)phenyl-5-methyl-2,4-pyrimidinediamine;

I-217 N4-(3-cyclopropylsulfonylaminomethyl)phenyl-N2-[3-(3-methoxypropyl)aminosulfonyl-4-methyl]phenyl-5-methyl-2,4-pyrimidinediamine;

I-218 N4-[3-(N-cyclopropylsulfonyl-N-hexanoyl)aminomethyl]phenyl-N2-(3-hexanoylaminosulfonyl)phenyl-5-methyl-2,4-pyrimidinediamine;

I-219 N4-[3-(N-cyclopropylsulfonyl-N-hexanoyl)aminomethyl]phenyl-N2-(3-hexanoylaminosulfonyl)phenyl-5-methyl-2,4-pyrimidinediamine sodium salt;

I-220 N4-[3-(N-cyclopropylsulfonyl-N-valeryl)aminomethyl]phenyl-5-methyl-N2-(3-valerylaminosulfonyl)phenyl-2,4-pyrimidinediamine; and I-221 N4-[3-(N-cyclopropylsulfonyl-N-valeryl)aminomethyl]phenyl-5-methyl-N2-(3-valerylaminosulfonyl)phenyl-2,4-pyrimidinediamine sodium salt.

I-222 N2-(3-butyrylaminosulfonyl)phenyl-N4-[3-(N-butyryl-N-cyclopropylsulfonyl)aminomethyl]phenyl-5-methyl-2,4-pyrimidinediamine Choline salt I-223 N2-(3-butyrylaminosulfonyl)phenyl-N4-(3-cyclopropylsulfonylaminomethyl)phenyl-5-methyl-2,4-pyrimidinediamine I-224 N2-(3-aminosulfonyl)phenyl-N4-[3-(N-butyryl-N-cyclopropylsulfonyl)aminomethyl]phenyl-5-methyl-2,4-pyrimidinediamine I-225 N2-[3-(N-acetoxymethyl-N-butyryl)aminosulfonyl]phenyl-N4-(3-cyclopropylsulfonylaminomethyl)phenyl-5-methyl-2,4-pyrimidinediamine I-226 N4-[3-(N-cyclopropylsulfonyl-N-propionyl)aminomethyl]phenyl-5-methyl-N2-(3-propionylaminosulfonyl)phenyl-2,4-pyrimidinediamine Choline salt In one embodiment, this invention provides a compound represented by formula V:

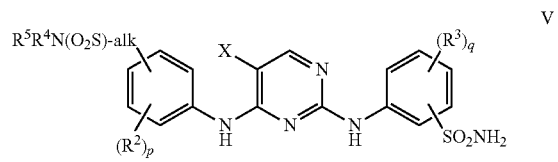

wherein:
p is 0, 1, 2 or 3;
q is 0, 1, 2 or 3;
X is selected from the group consisting of hydrogen, alkyl, substituted alkyl, hydroxy, alkoxy, substituted alkoxy, amino, substituted amino, carboxyl, carboxyl ester, cyano, halo, nitro, alkenyl, substituted alkenyl, alkynyl, substituted alkynyl, cycloalkynyl, substituted cycloalkynyl;
alk is selected from the group consisting of straight or branched chain $C_{1-6}$ alkylene group, cycloalkylene and substituted cycloalkylene;
each $R^2$ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, and halo; or R⁴ and one of R² together with the intervening atoms bound thereto form a heterocyclic or a substituted heterocyclic fused to ring A; or R⁵ and one of R² together with the intervening atoms bound thereto form a heterocyclic or a substituted heterocyclic fused to ring A;

each R³ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, halo, and aminosulfonyl;

R⁴ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, acyl and M⁺, wherein M⁺ is a counterion selected from the group consisting of K⁺, Na⁺, Li⁺ and ⁺N(R⁸)₄, wherein R⁸ is hydrogen or alkyl, and the nitrogen of —SO₂N(R⁴)R⁵ or —N(R⁴)SO₂R⁵ is N⁻;

R⁵ is selected from the group consisting of hydrogen, alkyl, substituted alkyl, amino, cycloalkyl, substituted cycloalkyl, heterocyclic, substituted heterocyclic, aryl, substituted aryl, heteroaryl, substituted heteroaryl, and acyl; or R⁴ and R⁵ together with the intervening atom or atoms bound thereto form a heterocyclic or a substituted heterocyclic group.

In a preferred embodiment, X is halo. In another preferred embodiment, X is fluoro. In another preferred embodiment, p is 0 and q is 0 or 1. In another preferred embodiment, q is 1 or 2 and R³ is alkyl.

In another embodiment, X is fluoro, alk is —CH₂— and each of R⁴ and R⁵ independently is selected from the group consisting of hydrogen, alkyl, alkynyl, cycloalkyl and heterocyclic.

In another embodiment, wherein the compound is selected from the group consisting of:

I-1 N4-(4-Aminosulfonylmethylenephenyl)-N2-(3-aminosulfonyl-4-methyl-phenyl)-5-fluoro-2,4-pyrimidinediamine;

I-2 N2-(4-Aminosulfonylphenyl)-5-fluoro-N4-[3-(prop-2-ynylaminosulfonylmethyl)phenyl]-2,4-pyrimidinediamine;

I-3 N2-(3-Aminosulfonylphenyl)-5-fluoro-N4-[3-(prop-2-ynylaminosulfonylmethyl)phenyl]-2,4-pyrimidinediamine;

I-4 N2-(3-Aminosulfonylphenyl)-5-fluoro-N4-[4-(prop-2-ynylaminosulfonylmethyl)phenyl]-2,4-pyrimidinediamine, I-5 N2-(3-Aminosulfonyl-4-methylphenyl)-5-fluoro-N4-[4-(prop-2-ynylaminosulfonylmethyl)phenyl]-2,4-pyrimidinediamine;

I-6 N2-(4-Aminosulfonylphenyl)-5-fluoro-N4-[4-(prop-2-ynylaminosulfonylmethyl)phenyl]-2,4-pyrimidinediamine;

I-102 N2-(3-Aminosulfonylphenyl)-5-fluoro-N4-[3-(N-methylaminosulfonylmethylene)phenyl]-2,4-pyrimidinediamine;

I-103 N2-(3-Aminosulfonyl-4-methylphenyl)-5-fluoro-N4-[3-(N-methylaminosulfonylmethylene)phenyl]-2,4-pyrimidinediamine;

I-104 N2-(3-Aminosulfonylphenyl)-5-fluoro-N4-[3-(N,N-dimethylaminosulfonylmethylene)phenyl]-2,4-pyrimidinediamine;

I-105 N2-(3-Aminosulfonyl-4-methylphenyl)-5-fluoro-N4-[3-(N,N-dimethylaminosulfonylmethylene)phenyl]-2,4-pyrimidinediamine;

I-106 N2-(3-Aminosulfonylphenyl)-5-fluoro-N4-[4-(N-methylaminosulfonylmethylene)phenyl]-2,4-pyrimidinediamine;

I-107 N2-(3-Aminosulfonyl-4-methylphenyl)-5-fluoro-N4-[3-(1-methylpiperdin-4-ylaminosulfonylmethylene)phenyl]-2,4-pyrimidinediamine;

I-108 N2-(3-Aminosulfonylphenyl)-5-fluoro-N4-[3-(1-methylpiperdin-4-ylaminosulfonylmethylene)phenyl]-2,4-pyrimidinediamine;

I-109 N2-(3-Aminosulfonyl-4-methylphenyl)-5-fluoro-N4-[4-(N-methylaminosulfonylmethylene)phenyl]-2,4-pyrimidinediamine;

I-110 N2-(3-Aminosulfonyl-4-methylphenyl)-5-fluoro-N4-[4-(N,N-dimethylaminosulfonylmethylene)phenyl]-2,4-pyrimidinediamine;

I-111 N2-(3-Aminosulfonylphenyl)-5-fluoro-N4-[3-(N-cyclopropylaminosulfonylmethylene)phenyl]-2,4-pyrimidinediamine; and I-112 N2-(3-Aminosulfonyl-4-methylphenyl)-5-fluoro-N4-[3-(N-cyclopropylaminosulfonylmethylene)phenyl]-2,4-pyrimidinediamine.

Those of skill in the art will appreciate that the 2,4-pyrimidinediamine compounds described herein may include functional groups that can be masked with progroups to create prodrugs. Such prodrugs are usually, but need not be, pharmacologically inactive until converted into their active drug form. Indeed, many of the 2,4-pyrimidinediamine compounds described in this invention include promoieties that are hydrolyzable or otherwise cleavable under conditions of use. For example, ester groups commonly undergo acid-catalyzed hydrolysis to yield the parent carboxylic acid when exposed to the acidic conditions of the stomach or base-catalyzed hydrolysis when exposed to the basic conditions of the intestine or blood. Thus, when administered to a subject orally, 2,4-pyrimidinediamine compounds that include ester moieties can be considered prodrugs of their corresponding carboxylic acid, regardless of whether the ester form is pharmacologically active.

The mechanism by which the progroup(s) metabolizes is not critical and can be caused, for example, by hydrolysis under the acidic conditions of the stomach, as described above, and/or by enzymes present in the digestive tract and/or tissues or organs of the body. Indeed, the progroup(s) can be selected to metabolize at a particular site within the body. For example, many esters are cleaved under the acidic conditions found in the stomach. Prodrugs designed to cleave chemically in the stomach to the active 2,4-pyrimidinediamine can employ progroups including such esters. Alternatively, the progroups can be designed to metabolize in the presence of enzymes such as esterases, amidases, lipolases, and phosphatases, including ATPases and kinase, etc. Progroups including linkages capable of metabolizing in vivo are well known and include, by way of example and not limitation, ethers, thioethers, silylethers, silylthioethers, esters, thioesters, carbonates, thiocarbonates, carbamates, thiocarbamates, ureas, thioureas, and carboxamides. In some instances, a "precursor" group that is oxidized by oxidative enzymes such as, for example, cytochrome P450 of the liver, to a metabolizable group, can be selected.

In the prodrugs, any available functional moiety can be masked with a progroup to yield a prodrug. Functional groups within the 2,4-pyrimidinediamine compounds that can be masked with progroups for inclusion in a promoiety include, but are not limited to, amines (primary and secondary), hydroxyls, sulfanyls (thiols), and carboxyls. A wide variety of progroups, as well as the resultant promoieties, suitable for masking functional groups in active 2,4-pyrimidinediamine compounds to yield prodrugs are well-known in the art. For example, a hydroxyl functional group can be masked as a sulfonate, ester, or carbonate promoiety, which can be hydrolyzed in vivo to provide the hydroxyl group. An amino functional group can be masked as an amide, carbamate, imine, urea, phosphenyl, phosphoryl, or sulfenyl promoiety, which can be hydrolyzed in vivo to provide the amino group. A carboxyl group can be masked as an ester (including silyl esters and thioesters), amide, or hydrazide promoiety, which can be hydrolyzed in vivo to provide the carboxyl group. Other specific examples of suitable progroups and their respective promoieties will be apparent to those of skill in the art. All of these progroups, alone or in combinations, can be included in the prodrugs.

In some embodiments of the 2,4-pyrimidinediamine compounds and methods of using the compounds, the progroup(s) can be attached to any available primary or secondary amine, including, for example, the N2 nitrogen atom of the 2,4-pyrimidinediamine moiety, the N4 nitrogen atom of the 2,4-pyrimidinediamine moiety, and/or a primary or secondary nitrogen atom included in a substituent on the 2,4-pyrimidinediamine compound.

In particular embodiments of the 2,4-pyrimidinediamine compounds and methods of using the compounds, the prodrugs described herein are 2,4-pyrimidinediamine compounds that are substituted at the N4 nitrogen of the 2,4-pyrimidinediamine moiety with a substituted or unsubstituted nitrogen-containing bicyclic ring that includes at least one progroup at one or more of the following: the nitrogen atom(s) of the bicyclic ring, the N2 nitrogen of the 2,4-pyrimidinediamine moiety, and the N4 nitrogen of the 2,4-pyrimidinediamine moiety.

As noted above, the identity of the progroup is not critical, provided that it can be metabolized under the desired conditions of use, for example, under the acidic conditions found in the stomach and/or by enzymes found in vivo, to yield a biologically active group, e.g., the 2,4-pyrimidinediamines as described herein. Thus, skilled artisans will appreciate that the progroup can comprise virtually any known or later-discovered hydroxyl, amine or thiol protecting group. Non-limiting examples of suitable protecting groups can be found, for example, in *Protective Groups in Organic Synthesis*, Greene & Wuts, 2nd Ed., John Wiley & Sons, New York, 1991 (especially pages 10-142 (alcohols, 277-308 (thiols) and 309-405 (amines) the disclosure of which is incorporated herein by reference).

Additionally, the identity of the progroup(s) can also be selected so as to impart the prodrug with desirable characteristics. For example, lipophilic groups can be used to decrease water solubility and hydrophilic groups can be used to increase water solubility. In this way, prodrugs specifically tailored for selected modes of administration can be obtained. The progroup can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, and targeting-specific transporters. Groups capable of imparting prodrugs with these characteristics are well-known and are described, for example, in Ettmayer et al., 2004, J. Med. Chem. 47(10):2393-2404, the disclosure of which is incorporated by reference. All of the various groups described in these references can be utilized in the prodrugs described herein.

As noted above, progroup(s) may also be selected to increase the water solubility of the prodrug as compared to the active drug. Thus, the progroup(s) may include or can be a group(s) suitable for imparting drug molecules with improved water solubility. Such groups are well-known and include, by way of example and not limitation, hydrophilic groups such as alkyl, aryl, and arylalkyl, or cycloheteroalkyl groups substituted with one or more of an amine, alcohol, a carboxylic acid, a phosphorous acid, a sulfoxide, a sugar, an amino acid, a thiol, a polyol, an ether, a thioether, and a quaternary amine salt.

The suitability of any particular progroup for a desired mode of administration can be confirmed in biochemical assays. For example, if a prodrug is to be administered by injection into a particular tissue or organ and the identities of the various enzyme(s) expressed in the tissue or organ are known, the particular prodrug can be tested for metabolism in biochemical assays with the isolated enzyme(s). Alternatively, the particular prodrug can be tested for metabolism to the active 2,4-pyrimidinediamine compound with tissue and/or organ extracts. Using tissue and/or organ extracts can be of particular convenience when the identity(ies) of the enzymes expressed in the target tissues or organs are unknown or in instances when the isolated enzymes are not conveniently available. Skilled artisans will be able to readily select progroups having metabolic properties (such as kinetics) suitable for particular applications using such in vitro tests. Of course, specific prodrugs could also be tested for suitable metabolism in in vitro animal models.

Numerous references teach the use and synthesis of prodrugs, including, for example, Ettmayer et al., supra and Bungaard et al., (1989) *J. Med. Chem.* 32(12): 2503-2507. Additionally, the preparation and use of prodrugs of 2,4-pyrimidinediamines is specifically taught in U.S. Provisional Patent Application 60/654,620, filed Feb. 18, 2005, entitled "Pyrimidinediamine Prodrugs and Their Uses," the disclosure of which is hereby incorporated by reference in its entirety.

One of ordinary skill in the art will appreciate that many of the compounds and prodrugs thereof, as well as the various compound species specifically described and/or illustrated herein, may exhibit the phenomena of tautomerism, conformational isomerism, geometric isomerism, and/or optical isomerism. For example, the compounds and prodrugs of the invention may include one or more chiral centers and/or double bonds and as a consequence may exist as stereoisomers, such as double-bond isomers (i.e., geometric isomers), enantiomers, diastereomers, and mixtures thereof, such as racemic mixtures. As another example, the compounds and prodrugs of the invention may exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, it should be understood that the invention encompasses any tautomeric, conformational isomeric, optical isomeric, and/or geometric isomeric forms of the compounds or prodrugs having one or more of the utilities described herein, as well as mixtures of these various different isomeric forms. In cases of limited rotation around the 2,4-pryimidinediamine core structure, atropisomers are also possible and are also specifically included in the compounds of the invention. It is intended that the compounds encompassed herein are, with the exception of forms of isomerism, chemically stable and able to be isolated.

Depending upon the nature of the various substituents, the 2,4-pyrimidinediamine compounds and prodrugs of the invention can be in the form of salts. Such salts include salts suitable for pharmaceutical uses ("pharmaceutically-acceptable salts"), salts suitable for veterinary uses, etc. Such salts can be derived from acids or bases, as is well-known in the art.

In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion) or coordinates with an organic base (e.g., ethanolamine, diethanolamine, triethanolamine, N-methylglucamine, morpholine, piperidine, dimethylamine, diethylamine, triethylamine, and ammonia).

The 2,4-pyrimidinediamine compounds and prodrugs thereof, as well as the salts thereof, may also be in the form of hydrates, solvates, and N-oxides, as is well-known in the art.

In another embodiment, this invention provides a compound, or stereoisomer, tautomer, prodrug, solvate, or pharmaceutically acceptable salt thereof, selected from Tables I and II.

TABLE I

| # | Y— | —(R$^2$)$_p$ | —X | —(R$^3$)$_q$ | —SO$_2$N(R$^4$)R$^5$ |
|---|---|---|---|---|---|
| I-1 | 4-(sulfamoylmethyl)- | p = 0 | F | 4-Me | 3-SO$_2$NH$_2$ |
| I-2 | 3-((N-prop-2-ynyl)sulfamoylmethyl)- | p = 0 | F | q = 0 | 4-SO$_2$NH$_2$ |
| I-3 | 3-((N-prop-2-ynyl)sulfamoylmethyl)- | p = 0 | F | q = 0 | 3-SO$_2$NH$_2$ |
| I-4 | 4-((N-prop-2-ynyl)sulfamoylmethyl)- | p = 0 | F | q = 0 | 3-SO$_2$NH$_2$ |
| I-5 | 4-((N-prop-2-ynyl)sulfamoylmethyl)- | p = 0 | F | 4-Me | 3-SO$_2$NH$_2$ |
| I-6 | 4-((N-prop-2-ynyl)sulfamoylmethyl)- | p = 0 | F | q = 0 | 4-SO$_2$NH$_2$ |
| I-7 | 4-(cyclopropylsulfonamidomethyl)- | p = 0 | F | q = 0 | 3-SO$_2$N(H)CH$_2$C≡CH |
| I-8 | 4-(ethylsulfonamidomethyl)- | p = 0 | F | q = 0 | 4-SO$_2$NH$_2$ |
| I-9 | 4-(ethylsulfonamidomethyl)- | p = 0 | F | q = 0 | 3-SO$_2$NH$_2$ |
| I-10 | 4-(ethylsulfonamidomethyl)- | p = 0 | F | 4-Me | 3-SO$_2$NH$_2$ |
| I-11 | 3-(ethylsulfonamidomethyl)- | p = 0 | F | q = 0 | 4-SO$_2$NH$_2$ |
| I-12 | 3-(ethylsulfonamidomethyl)- | p = 0 | F | q = 0 | 3-SO$_2$NH$_2$ |
| I-13 | 3-(ethylsulfonamidomethyl)- | p = 0 | F | 4-Me | 3-SO$_2$NH$_2$ |
| I-14 | 4-(ethylsulfonamidoethyl)- | p = 0 | F | q = 0 | 4-SO$_2$NH$_2$ |
| I-15 | 4-(ethylsulfonamidoethyl)- | p = 0 | F | q = 0 | 3-SO$_2$NH$_2$ |
| I-16 | 4-(ethylsulfonamidoethyl)- | p = 0 | F | 4-Me | 3-SO$_2$NH$_2$ |
| I-17 | 4-(((N-n-propyl)ethylsulfonamido)methyl)- | p = 0 | F | q = 0 | 4-SO$_2$NH$_2$ |
| I-18 | 4-(((N-n-propyl)ethylsulfonamido)methyl)- | p = 0 | F | q =0 | 3-SO$_2$NH$_2$ |
| I-19 | 4-(((N-n-propyl)ethylsulfonamido)methyl)- | p = 0 | F | 4-Me | 3-SO$_2$NH$_2$ |
| I-20 | 4-(ethylsulfonamidomethyl)- | p = 0 | Me | q = 0 | 4-SO$_2$NH$_2$ |
| I-21 | 4-(ethylsulfonamidomethyl)- | p = 0 | Me | q = 0 | 3-SO$_2$NH$_2$ |
| I-22 | 4-(ethylsulfonamidomethyl)- | p = 0 | Me | 4-Me | 3-SO$_2$NH$_2$ |
| I-23 | 4-(cyclopropylsulfonamidomethyl)- | p = 0 | F | q = 0 | 4-SO$_2$NH$_2$ |
| I-24 | 4-(cyclopropylsulfonamidomethyl)- | p = 0 | F | q = 0 | 3-SO$_2$NH$_2$ |
| I-25 | 4-(cyclopropylsulfonamidomethyl)- | p = 0 | F | 4-Me | 3-SO$_2$NH$_2$ |
| I-26 | (S)-4-((1-ethylsulfonamido)ethyl)- | p = 0 | F | q = 0 | 4-SO$_2$NH$_2$ |
| I-27 | (S)-4-((1-ethylsulfonamido)ethyl)- | p = 0 | F | q = 0 | 3-SO$_2$NH$_2$ |
| I-28 | (S)-4-((1-ethylsulfonamido)ethyl)- | p = 0 | F | 4-Me | 3-SO$_2$NH$_2$ |
| I-29 | (R)-4-((1-ethylsulfonamido)ethyl)- | p = 0 | F | q = 0 | 4-SO$_2$NH$_2$ |
| I-30 | (R)-4-((1-ethylsulfonamido)ethyl)- | p = 0 | F | q = 0 | 3-SO$_2$NH$_2$ |
| I-31 | (R)-4-((1-ethylsulfonamido)ethyl)- | p = 0 | F | 4-Me | 3-SO$_2$NH$_2$ |
| I-32 | 3-(cyclopropylsulfonamidomethyl)- | p = 0 | F | q = 0 | 4-SO$_2$NH$_2$ |

TABLE I-continued

| # | Y— | —(R²)ₚ | —X | —(R³)_q | —SO₂N(R⁴)R⁵ |
|---|---|---|---|---|---|
| I-33 | 3-(cyclopropylsulfonamidomethyl)- | p = 0 | F | q = 0 | 3-SO₂NH₂ |
| I-34 | 3-(cyclopropylsulfonamidomethyl)- | p = 0 | F | 4-Me | 3-SO₂NH₂ |
| I-35 | 4-((thiophene-2-sulfonamido)methyl)- | p = 0 | F | q = 0 | 4-SO₂NH₂ |
| I-36 | 4-((thiophene-2-sulfonamido)methyl)- | p = 0 | F | q = 0 | 3-SO₂NH₂ |
| I-37 | 4-((thiophene-2-sulfonamido)methyl)- | p = 0 | F | 4-Me | 3-SO₂NH₂ |
| I-38 | 4-(ethylsulfonamidoethyl)- | p = 0 | Me | q = 0 | 4-SO₂NH₂ |
| I-39 | 4-(ethylsulfonamidoethyl)- | p = 0 | Me | q = 0 | 3-SO₂NH₂ |
| I-40 | 4-(ethylsulfonamidoethyl)- | p = 0 | Me | 4-Me | 3-SO₂NH₂ |
| I-41 | 4-((2-amino-4-methylthiazole-5-sulfonamido)methyl)- | p = 0 | F | q = 0 | 3-SO₂NH₂ |
| I-42 | 4-((2-acetamido-4-methylthiazole-5-sulfonamido)methyl)- | p = 0 | F | q = 0 | 3-SO₂NH₂ |
| I-43 | 4-((2-amino-4-methylthiazole-5-sulfonamido)methyl)- | p = 0 | F | 4-Me | 3-SO₂NH₂ |
| I-44 | 4-((2-acetamido-4-methylthiazole-5-sulfonamido)methyl)- | p = 0 | F | 4-Me | 3-SO₂NH₂ |
| I-45 | 4-(cyclopropylsulfonamidomethyl)- | p = 0 | Me | q = 0 | 4-SO₂NH₂ |
| I-46 | 4-(cyclopropylsulfonamidomethyl)- | p = 0 | Me | q = 0 | 3-SO₂NH₂ |
| I-47 | 4-(cyclopropylsulfonamidomethyl)- | p = 0 | Me | 4-Me | 3-SO₂NH₂ |
| I-48 | 4-((2,2,2-trifluoroethylsulfonamido)methyl)- | p = 0 | F | q = 0 | 4-SO₂NH₂ |
| I-49 | 4-((2,2,2-trifluoroethylsulfonamido)methyl)- | p = 0 | F | q = 0 | 3-SO₂NH₂ |
| I-50 | 4-((2,2,2-trifluoroethylsulfonamido)methyl)- | p = 0 | F | 4-Me | 3-SO₂NH₂ |
| I-51 | 3-(cyclopropylsulfonamidomethyl)- | p = 0 | Me | q = 0 | 3-SO₂NH₂ |
| I-52 | 3-(cyclopropylsulfonamidomethyl)- | p = 0 | Me | 4-Me | 3-SO₂NH₂ |
| I-53 | 4-(cyclopropylsulfonamidomethyl)- | p = 0 | Me | q = 0 | 4-SO₂NH₂ |
| I-54 | 4-(cyclopropylsulfonamidomethyl)- | p = 0 | Me | q = 0 | 3-SO₂NH₂ |
| I-55 | 4-(cyclopropylsulfonamidomethyl)- | p = 0 | Me | 4-Me | 3-SO₂NH₂ |
| I-56 | 3-(cyclopropylsulfonamidomethyl)- | p = 0 | Me | q = 0 | 4-SO₂NH₂ |
| I-57 | 4-(cyclopropylsulfonamidomethyl)- | p = 0 | F | q = 0 | 3-SO₂NHC(O)Et |
| I-58 | 4-((N-propaonyl)-cyclopropylsulfonamidomethyl)- | p = 0 | F | q = 0 | 3-SO₂NHC(O)Et |
| I-59 | 4-(cyclopropylsulfonamidomethyl)- | p = 0 | F | 4-Me | 3-SO₂NHC(O)Et |
| I-60 | 4-((N-propaonyl)-cyclopropylsulfonamidomethyl)- | p = 0 | F | 4-Me | 3-SO₂NHC(O)Et |
| I-61 Na salt | 4-(cyclopropylsulfonamidomethyl)- | p = 0 | F | q = 0 | 3-SO₂N⁻(⁺Na)C(O)Et |
| I-62 Na salt | 4-((N-propaonyl)-cyclopropylsulfonamidomethyl)- | p = 0 | F | q = 0 | 3-SO₂NHC(O)Et |
| I-63 Na salt | 4-(cyclopropylsulfonamidomethyl)- | p = 0 | F | 4-Me | 3-SO₂NHC(O)Et |
| I-64 Na salt | 4-((N-propaonyl)-cyclopropylsulfonamidomethyl)- | p = 0 | F | 4-Me | 3-SO₂NHC(O)Et |
| I-65 | 4-(isopropylsulfonamidomethyl)- | p = 0 | F | q = 0 | 4-SO₂NH₂ |
| I-66 | 4-(isopropylsulfonamidomethyl)- | p = 0 | F | q = 0 | 3-SO₂NH₂ |
| I-67 | 4-(isopropylsulfonamidomethyl)- | p = 0 | F | 4-Me | 3-SO₂NH₂ |
| I-68 | 4-(cyclopentylsulfonamidomethyl)- | p = 0 | F | q = 0 | 4-SO₂NH₂ |
| I-69 | 4-(cyclopentylsulfonamidomethyl)- | p = 0 | F | q = 0 | 3-SO₂NH₂ |
| I-70 | 4-(cyclopentylsulfonamidomethyl)- | p = 0 | F | 4-Me | 3-SO₂NH₂ |
| I-71 | 4-(cyclohexylsulfonamidomethyl)- | p = 0 | F | q = 0 | 4-SO₂NH₂ |
| I-72 | 4-(cyclohexylsulfonamidomethyl)- | p = 0 | F | q = 0 | 3-SO₂NH₂ |
| I-73 | 4-(cyclohexylsulfonamidomethyl)- | p = 0 | F | 4-Me | 3-SO₂NH₂ |
| I-74 | 4-(ethylsulfonamidomethyl)- | 3-Cl | F | q = 0 | 4-SO₂NH₂ |
| I-75 | 4-(ethylsulfonamidomethyl)- | 3-Cl | F | q = 0 | 3-SO₂NH₂ |
| I-76 | 4-(ethylsulfonamidomethyl)- | 3-Cl | F | 4-Me | 3-SO₂NH₂ |
| I-77 | 4-((N-propaonyl)-cyclopropylsulfonamidomethyl)- | p = 0 | Me | q = 0 | 4-SO₂NHC(O)Et |
| I-78 Na salt | 4-((N-propaonyl)-cyclopropylsulfonamidomethyl)- | p = 0 | Me | q = 0 | 4-SO₂NHC(O)Et |
| I-79 | 4-((N-propylcyclopropylsulfonamido)methyl)- | p = 0 | Me | q = 0 | 4-SO₂NH₂ |
| I-80 | 4-((N-propylcyclopropylsulfonamido)methyl)- | p = 0 | Me | q = 0 | 3-SO₂NH₂ |
| I-81 | 4-((N-propylcyclopropylsulfonamido)methyl)- | p = 0 | Me | 4-Me | 3-SO₂NH₂ |
| I-82 | 4-(cyclopropylsulfonamidomethyl)- | p = 0 | F | 5-SO₂NH₂ | 3-SO₂NH₂ |
| I-83 | 4-(cyclopropylsulfonamidomethyl)- | p = 0 | Me | q = 0 | 4-SO₂NHC(O)Et |
| I-84 | 4-(cyclopropylsulfonamidomethyl)- | p = 0 | Me | 5-SO₂NH₂ | 3-SO₂NH₂ |
| I-85 | 4-((methylsulfonylmethylsulfonamido)methyl)- | p = 0 | F | q = 0 | 4-SO₂NH₂ |
| I-86 | 4-((methylsulfonylmethylsulfonamido)methyl)- | p = 0 | F | q = 0 | 3-SO₂NH₂ |
| I-87 | 4-((methylsulfonylmethylsulfonamido)methyl)- | p = 0 | F | 4-Me | 3-SO₂NH₂ |
| I-88 Na salt | 4-(cyclopropylsulfonamidomethyl)- | p = 0 | Me | q = 0 | 4-SO₂NHC(O)Et |
| I-89 | 4-((pyridine-3-sulfonamido)methyl)- | p = 0 | F | q = 0 | 4-SO₂NH₂ |
| I-90 | 4-((pyridine-3-sulfonamido)methyl)- | p = 0 | F | 4-Me | 3-SO₂NH₂ |

TABLE I-continued

| # | Y— | —(R²)ₚ | —X | —(R³)_q | —SO₂N(R⁴)R⁵ |
|---|---|---|---|---|---|
| I-91 | 4-((N-propanoyl)-ethylsulfonamidomethyl)- | p = 0 | Me | q = 0 | 4-SO₂NHC(O)Et |
| I-92 Na salt | 4-((N-propanoyl)-ethylsulfonamidomethyl)- | p = 0 | Me | q = 0 | 4-SO₂NHC(O)Et |
| I-93 | 3-((N-propanoyl)-cyclopropylsulfonamidomethyl)- | p = 0 | Me | q = 0 | 3-SO₂NHC(O)Et |
| I-94 Na salt | 3-((N-propanoyl)-cyclopropylsulfonamidomethyl)- | p = 0 | Me | q = 0 | 3-SO₂NHC(O)Et |
| I-95 | 4-((pyridine-3-sulfonamido)methyl)- | p = 0 | F | q = 0 | 3-SO₂NH₂ |
| I-96 | 4-((2,2,2-trifluoroethylsulfonamido)methyl)- | p = 0 | Me | q = 0 | 4-SO₂NH₂ |
| I-97 | 4-((2,2,2-trifluoroethylsulfonamido)methyl)- | p = 0 | Me | q = 0 | 3-SO₂NH₂ |
| I-98 | 4-((2,2,2-trifluoroethylsulfonamido)methyl)- | p = 0 | Me | 4-Me | 3-SO₂NH₂ |
| I-99 | 4-((pyriidne-3-sulfonamido)methyl)- | p = 0 | Me | q = 0 | 4-SO₂NH₂ |
| I-100 | 4-((pyridine-3-sulfonamido)methyl)- | p = 0 | Me | q = 0 | 3-SO₂NH₂ |
| I-101 | 4-((pyridine-3-sulfonamido)methyl)- | p = 0 | Me | 4-Me | 3-SO₂NH₂ |
| I-102 | 3-(N-methylsulfomoylmethyl)- | p = 0 | F | q = 0 | 3-SO₂NH₂ |
| I-103 | 3-(N-methylsulfamoylmethyl)- | p = 0 | F | 4-Me | 3-SO₂NH₂ |
| I-104 | 3-(N,N-dimethylsulfamoylmethyl)- | p = 0 | F | q = 0 | 3-SO₂NH₂ |
| I-105 | 3-(N,N-dimethylsulfamoylmethyl)- | p = 0 | F | q = 0 | 3-SO₂NH₂ |
| I-106 | 4-(N-methylsulfamoylmethyl)- | p = 0 | F | q = 0 | 3-SO₂NH₂ |
| I-107 | 4-((N-(1-methylpiperidin-4-yl)sulfamoyl)methyl)- | p = 0 | F | 4-Me | 3-SO₂NH₂ |
| I-108 | 4-((N-(1-methylpiperidin-4-yl)sulfamoyl)methyl)- | p = 0 | F | q = 0 | 3-SO₂NH₂ |
| I-109 | 4-(N-methylsulfamoylmethyl)- | p = 0 | F | 4-Me | 3-SO₂NH₂ |
| I-110 | 4-(N,N-dimethylsulfamoylmethyl) | p = 0 | F | 4-Me | 3-SO₂NH₂ |
| I-111 | 4-N-cyclopropylsulfamoylmethyl)- | p = 0 | F | q = 0 | 3-SO₂NH₂ |
| I-112 | 4-N-cyclopropylsulfamoylmethyl)- | p = 0 | F | 4-Me | 3-SO₂NH₂ |
| I-113 | 4-(cyclopropylsulfonamidomethyl)- | p = 0 | Cl | 4-Me | 3-SO₂NH₂ |
| I-114 | 4-(cyclopropylsulfonamidomethyl)- | p = 0 | Cl | q = 0 | 3-SO₂NH₂ |
| I-115 | 4-(cyclopropylsulfonamidomethyl)- | p = 0 | Cl | q = 0 | 4-SO₂NH₂ |
| I-116 | 3-((N-propanoyl)-cyclopropylsulfonamidomethyl)- | p = 0 | Me | q = 0 | 3-SO₂NH₂ |
| I-117 | 4-(isopropylsulfonamidomethyl)- | p = 0 | Me | 4-Me | 3-SO₂NH₂ |
| I-118 | 4-(isopropylsulfonamidomethyl)- | p = 0 | Me | q = 0 | 3-SO₂NH₂ |
| I-119 | 4-(cyclopropylsulfonamidomethyl)- | 3-Cl | Me | q = 0 | 3-SO₂NH₂ |
| I-120 | 3-((N-methyl)-cyclopropylsulfonamidomethyl)- | p = 0 | Me | q = 0 | 3-SO₂NH₂ |
| I-121 | 4-((N-methyl)-cyclopropylsulfonamidomethyl)- | p = 0 | Me | q = 0 | 3-SO₂NH₂ |
| I-122 | 3-((N-methyl)-cyclopropylsulfonamidomethyl)- | p = 0 | Me | 4-Me | 3-SO₂NH₂ |
| I-123 | 4-(isopropylsulfonamidomethyl)- | p = 0 | Me | q = 0 | 4-SO₂NH₂ |
| I-124 | 3-((N-methyl)-cyclopropylsulfonamidomethyl)- | p = 0 | Me | q = 0 | 4-SO₂NH₂ |
| I-125 | 4-(cyclopropylsulfonamidomethyl)- | 3-Cl | Me | 4-Me | 3-SO₂NH₂ |
| I-126 | 4-((N-methyl)-cyclopropylsulfonamidomethyl)- | p = 0 | Me | 4-Me | 3-SO₂NH₂ |
| I-127 | 4-((N-methyl)-cyclopropylsulfonamidomethyl)- | p = 0 | Me | q = 0 | 4-SO₂NH₂ |
| I-128 | 3-(cyclopropylsulfonamidomethyl)- | p = 0 | Me | q = 0 | 3-SO₂N=C(OMe)₂ |
| I-129 | 4-(cyclopropylsulfonamidomethyl)- | 3-Cl | Me | q = 0 | 4-SO₂NH₂ |
| I-130 | 3-(cyclopropylsulfonamidomethyl)- | p = 0 | Me | q = 0 | 3-SO₂N(Et)C(O)OEt |
| I-131 | 3-(cyclopropylsulfonamidomethyl)- | p = 0 | Me | q = 0 | 3-SO₂NHC(O)CH₂NH₂ |
| I-132 HCl salt | 3-(cyclopropylsulfonamidomethyl)- | p = 0 | Me | q = 0 | 3-SO₂NHC(O)CH(CH₂Ph)NH₂ |
| I-133 | 3-(cyclopropylsulfonamidomethyl)- | p = 0 | Me | q = 0 | 3-SO₂NHC(O)CH₂NH₂ |
| I-134 | 3-(cyclopropylsulfonamidomethyl)- | p = 0 | Me | q = 0 | 3-SO₂NHC(O)CH(CH₂Ph)NH₂ |
| I-135 Na salt | 3-(cyclopropylsulfonamidomethyl)- | p = 0 | Me | q = 0 | 3-SO₂NHC(O)CH(CH₂Ph)NHC(O)OCH₂Ph |
| I-136 | 3-(cyclopropylsulfonamidomethyl)- | p = 0 | Me | q = 0 | 3-SO₂NHC(O)Et |
| I-137 Na salt | 3-(cyclopropylsulfonamidomethyl)- | p = 0 | Me | q = 0 | 3-SO₂NHC(O)Et |
| I-138 | 3-(cyclopropylsulfonamidomethyl)- | p = 0 | Me | q = 0 | 3-SO₂NHC(O)CH(i-pr)NH₂ |
| I-139 | 3-(cyclopropylsulfonamidomethyl)- | p = 0 | Me | q = 0 | 3-SO₂NHC(O)CH(CH₂Ph)NHC(O)OCH₂Ph |
| I-140 | 3-(cyclopropylsulfonamidomethyl)- | p = 0 | Me | q = 0 | 3-SO₂NHC(O)CH₂NHC(O)O-ᵗBu |
| I-141 Na salt | 3-(cyclopropylsulfonamidomethyl)- | p = 0 | Me | q = 0 | 3-SO₂NHC(O)CH₂NHC(O)O-ᵗBu |
| I-142 | 3-(cyclopropylsulfonamidomethyl)- | p = 0 | Me | q = 0 | 3-SO₂NHC(O)CH₂NHC(O)OCH₂Ph |
| I-143 Na salt | 3-(cyclopropylsulfonamidomethyl)- | p = 0 | Me | q = 0 | 3-SO₂NHC(O)CH₂NHC(O)OCH₂Ph |
| I-144 | 3-(cyclopropylsulfonamidomethyl)- | p = 0 | Me | q = 0 | 3-SO₂NHC(O)CH(i-pr)NHC(O)OCH₂Ph |
| I-145 | 3-(cyclopropylsulfonamidomethyl)- | p = 0 | Me | q = 0 | 3-SO₂NHC(O)(1-aminocyclopent-1-yl) |
| I-146 Na salt | 3-(cyclopropylsulfonamidomethyl)- | p = 0 | Me | q = 0 | 3-SO₂NHC(O)CH(i-pr)NH₂ |
| I-147 Na salt | 3-(cyclopropylsulfonamidomethyl)- | p = 0 | Me | q = 0 | 3-SO₂NHC(O)CH(i-Pr)NHC(O)OCH₂Ph |
| I-148 | 3-(cyclopropylsulfonamidomethyl)- | p = 0 | Me | q = 0 | 3-SO₂NHC(O)(1-NH(Boc)-cyclopent-1-yl) |
| I-149 | 4-(cyclopropylsulfonamidomethyl)- | p = 0 | Me | q = 0 | 4-SO₂NHPh |
| I-150 | 4-(cyclopropylsulfonamidomethyl)- | p = 0 | Me | q = 0 | 3-SO₂NHPh |
| I-151 | 4-(cyclopropylsulfonamidomethyl)- | p = 0 | Me | q = 0 | 4-((N-methylpiperidin-4-yl)sulfamoyl) |

TABLE I-continued

| # | Y— | —(R²)ₚ | —X | —(R³)_q | —SO₂N(R⁴)R⁵ |
|---|---|---|---|---|---|
| I-152 | 4-(cyclopropylsulfonamidomethyl)- | p = 0 | Me | q = 0 | 3-((N-methylpiperidin-4-yl)sulfamoyl) |
| I-153 | 4-(cyclopropylsulfonamidomethyl)- | p = 0 | Me | q = 0 | 4-SO₂NHCH₂Ph |
| I-154 | 4-(cyclopropylsulfonamidomethyl)- | p = 0 | Me | q = 0 | 3-SO₂NHCH₂Ph |
| I-155 | 3-(cyclopropylsulfonamidomethyl)- | p = 0 | Me | q = 0 | 4-SO₂NHPh |
| I-156 | 3-(cyclopropylsulfonamidomethyl)- | p = 0 | Me | q = 0 | 3-SO₂NHPh |
| I-157 | 3-(cyclopropylsulfonamidomethyl)- | p = 0 | Me | q = 0 | 4-SO₂NHCH₂Ph |
| I-158 | 3-(cyclopropylsulfonamidomethyl)- | p = 0 | Me | q = 0 | 3-SO₂NHCH₂Ph |
| I-159 | 3-(cyclopropylsulfonamidomethyl)- | p = 0 | Me | q = 0 | 4-((N-methylpiperidin-4-yl)sulfamoyl) |
| I-160 | 3-(cyclopropylsulfonamidomethyl)- | p = 0 | Me | q = 0 | 3-((N-methylpiperidin-4-yl)sulfamoyl) |
| I-161 | 4-(cyclopropylsulfonamidomethyl)- | p = 0 | Me | q = 0 | 3-SO₂NHMe |
| I-162 | 3-(cyclopropylsulfonamidomethyl)- | p = 0 | Me | q = 0 | 3-SO₂NHMe |
| I-163 | 4-(cyclopropylsulfonamiodmethyl)- | p = 0 | Me | q = 0 | 4-SO₂NHMe |
| I-164 | 4-(cyclopropylsulfonamidomethyl)- | p = 0 | Me | q = 0 | 4-SO₂NHCH₂C≡CH |
| I-165 | 4-(cyclopropylsulfonamidomethyl)- | p = 0 | Me | q = 0 | 3-SO₂NHCH₂C≡CH |
| I-166 | 4-(cyclopropylsulfonamidomethyl)- | p = 0 | Me | q = 0 | 4-((N-cyclopentyl)sulfamoyl) |
| I-167 | 4-((N-(cyclopropylsulfonyl)propionamido)methyl)- | p = 0 | Me | q = 0 | 4-SO₂NH₂ |
| I-168 | 4-(cyclopropylsulfonamidomethyl)- | p = 0 | Me | q = 0 | 4-((pyridin-4-ylmethyl)sulfamoyl) |
| I-169 | 4-(cyclopropylsulfonamidomethyl)- | p = 0 | Me | q = 0 | 3-((pyridin-4-ylmethyl)sulfamoyl) |
| I-170 | 4-(cyclopropylsulfonamidomethyl)- | p = 0 | Me | q = 0 | 4-((N-cyclopentyl)sulfamoyl) |
| I-171 | 4-(cyclopropylsulfonamidomethyl)- | p = 0 | Me | q = 0 | 4-((pyridin-3-yl)sulfamoyl) |
| I-172 | 4-(cyclopropylsulfonamidomethyl)- | p = 0 | Me | q = 0 | 4-SO₂NH(i-Pr) |
| I-173 | 4-(cyclopropylsulfonamidomethyl)- | p = 0 | Me | q = 0 | 3-SO₂NH(i-Pr) |
| I-174 | 4-(cyclopropylsulfonamidomethyl)- | p = 0 | Me | q = 0 | 3-((pyridin-3-yl)sulfamoyl) |
| I-175 | 4-(cyclopropylsulfonamidomethyl)- | p = 0 | Me | q = 0 | 4-SO₂NHEt |
| I-176 | 4-(cyclopropylsulfonamidomethyl)- | p = 0 | Me | q = 0 | 3-SO₂NHEt |
| I-177 | 4-(cyclopropylsulfonamidomethyl)- | p = 0 | Me | q = 0 | 4-SO₂NHPr |
| I-178 | 4-(cyclopropylsulfonamidomethyl)- | p = 0 | Me | q = 0 | 3-SO₂NHPr |
| I-179 | 4-(cyclopropylsulfonamidomethyl)- | p = 0 | Me | q = 0 | 4-((N-cyclopropylmethyl)sulfamoyl) |
| I-180 | 4-(cyclopropylsulfonamidomethyl)- | p = 0 | Me | q = 0 | 4-((N-cyclopropylmethyl)sulfamoyl) |
| I-181 | 4-(cyclopropylsulfonamidomethyl)- | p = 0 | Me | q = 0 | 4-(N-(3-methoxypropyl)sulfamoyl) |
| I-182 | 4-(cyclopropylsulfonamidomethyl)- | p = 0 | Me | q = 0 | 3-(N-(3-methoxypropyl)sulfamoyl) |
| I-183 | 4-(cyclopropylsulfonamidomethyl)- | p = 0 | Me | q = 0 | 4-(N-(2-methoxyethyl)sulfamoyl) |
| I-184 | 4-(cyclopropylsulfonamidomethyl)- | p = 0 | Me | q = 0 | 3-(N-(2-methoxyethyl)sulfamoyl) |
| I-185 | 4-(cyclopropylsulfonamidomethyl)- | p = 0 | Me | 4-Me | 3-SO₂NHMe |
| I-186 | 4-(cyclopropylsulfonamidomethyl)- | p = 0 | Me | 4-Me | 3-SO₂NHEt |
| I-187 | 4-(cyclopropylsulfonamidomethyl)- | p = 0 | Me | 4-Me | 3-SO₂NHPr |
| I-188 | 4-(cyclopropylsulfonamidomethyl)- | p = 0 | Me | 4-Me | 3-SO₂NHCH₂C≡CH |
| I-189 | 4-(cyclopropylsulfonamidomethyl)- | p = 0 | Me | 4-Me | 3-SO₂NH(i-Pr) |
| I-190 | 4-(cyclopropylsulfonamiodmethyl)- | p = 0 | Me | 4-Me | 3-(N-(2-methoxyethyl)sulfamoyl) |
| I-191 | 4-(cyclopropylsulfonamiodmethyl)- | p = 0 | Me | 4-Me | 3-(N-(3-methoxypropyl)sulfamoyl) |
| I-192 | 4-(cyclopropylsulfonamidomethyl)- | p = 0 | Me | 4-Me | 3-((N-cyclopropylmethyl)sulfamoyl) |
| I-193 | 3-((N-(cyclopropylsulfonyl)acetamido)methyl)- | p = 0 | Me | q = 0 | 3-SO₂NHC(O)CH₂ |
| I-194 | 4-((N-(cyclopropylsulfonyl)acetamido)methyl)- | p = 0 | Me | q = 0 | 4-SO₂NHC(O)CH₂ |
| I-195 | 4-(cyclopropylsulfonamidomethyl)- | p = 0 | Me | 4-Me | 3-SO₂NHCH₂Ph |
| I-196 | 3-((N-(cyclopropylsulfonyl)acetamido)methyl)- | p = 0 | Me | q = 0 | 3-SO₂NHC(O)CH₂ |
| I-197 | 4-((N-(cyclopropylsulfonyl)acetamido)methyl)- | p = 0 | Me | q = 0 | 4-SO₂NHC(O)CH₂ |
| I-198 | 3-((N-(cylcopropylsulfonyl)isobutyramido)methyl)- | p = 0 | Me | q = 0 | 3-(N-isobutyrylsulfamoyl) |
| I-199 | 4-((N-(cyclopropylsulfonyl)isobutyramido)methyl)- | p = 0 | Me | q = 0 | 4-(N-isobutyrylsulfamoyl) |
| I-200 Na salt | 3-((N-(cyclopropylsulfonyl)isobutyramido)methyl)- | p = 0 | Me | q = 0 | 3-(N-isobutyrylsulfamoyl) |
| I-201 Na salt | 4-((N-(cyclopropylsulfonyl)isobutyramido)methyl)- | p = 0 | Me | q = 0 | 4-(N-isobutyrylsulfamoyl) |
| I-202 | 4-(cyclopropylsulfonamidomethyl)- | p = 0 | Me | 4-Me | 3-SO₂NHPh |
| I-203 | 3-((N-(cyclopropylsulfonyl)butyramido)methyl)- | p = 0 | Me | q = 0 | 3-(N-butyrylsulfamoyl) |
| I-204 | 4-((N-(cyclopropylsulfonyl)butyramido)methyl)- | p = 0 | Me | q = 0 | 4-(N-butyrylsulfamoyl) |
| I-205 Na salt | 3-((N-(cyclopropylsulfonyl)butyramido)methyl)- | p = 0 | Me | q = 0 | 3-(N-butyrylsulfamoyl) |
| I-206 Na salt | 4-((N-(cyclopropylsulfonyl)butyramido)methyl)- | p = 0 | Me | q = 0 | 4-(N-butyrylsulfamoyl) |
| I-207 | 3-(cyclopropylsulfonamidomethyl)- | p = 0 | Me | q = 0 | 4-SO₂NHMe |
| I-208 | 3-(cyclopropylsulfonamidomethyl)- | p = 0 | Me | q = 0 | 3-SO₂NHEt |
| I-209 | 3-(cylcopropylsulfonamidomethyl)- | p = 0 | Me | 4-Me | 3-SO₂NH(i-Pr) |
| I-210 | 3-(cyclopropylsulfonamidomethyl)- | p = 0 | Me | 4-Me | 3-(N-(2-methoxyethyl)sulfamoyl) |
| I-211 | 3-(cyclopropylsulfonamidomethyl)- | p = 0 | Me | 4-Me | 3-SO₂NHMe |
| I-212 | 3-(cyclopropylsulfonamidomethyl)- | p = 0 | Me | q = 0 | 4-SO₂NHEt |
| I-213 | 3-(cyclopropylsulfonamidomethyl)- | p = 0 | Me | 4-Me | 3-SO₂NHEt |
| I-214 | 3-(cyclopropylsulfonamidomethyl)- | p = 0 | Me | 4-Me | 3-SO₂NHCH₂C≡CH |
| I-215 | 3-(cyclopropylsulfonamiodmethyl)- | p = 0 | Me | 4-Me | 3-SO₂NHPr |
| I-216 | 3-(cyclopropylsulfonamidomethyl)- | p = 0 | Me | 4-Me | 3-(N-cyclopropylmethyl)sulfamoyl) |
| I-217 | 3-(cyclopropylsulfonamidomethyl)- | p = 0 | Me | 4-Me | 3-(N-(3-methoxypropyl)sulfamoyl) |

TABLE I-continued

| # | Y— | —(R²)ₚ | —X | —(R³)_q | —SO₂N(R⁴)R⁵ |
|---|---|---|---|---|---|
| I-218 | 3-((N-hexanoyl)-cyclopropylsulfonamidomethyl)- | p = 0 | Me | q = 0 | 3-SO₂NHC(O)(CH₂)₄Me |
| I-219 Na salt | 3-((N-hexanoyl)-cyclopropylsulfonamidomethyl)- | p = 0 | Me | q = 0 | 3-SO₂NHC(O)(CH₂)₄Me |
| I-220 | 3-((N-pentanoyl)-cyclopropylsulfonamidomethyl)- | p = 0 | Me | q = 0 | 3-SO₂NHC(O)(CH₂)₃Me |
| I-221 Na salt | 3-((N-pentanoyl)-cyclopropylsulfonamidomethyl)- | p = 0 | Me | q = 0 | 3-SO₂NHC(O)(CH₂)₃Me |
| I-222 choline salt | 3-((N-butanoyl)-cyclopropylsulfonamidomethyl)- | p = 0 | Me | q = 0 | 3-SO₂NHC(O)(CH₂)₂Me |
| I-223 | 3-cylcopropylsulfonamidomethyl | p = 0 | Me | q = 0 | 3-SO₂NHC(O)(CH₂)₂Me |
| I-224 | 3-((N-butanoyl)-cyclopropylsulfonamidomethyl)- | p = 0 | Me | q = 0 | 3-SO₂NH₂ |
| I-225 | 3-cyclopropylsulfonamidomethyl | p = 0 | Me | q = 0 | 3-SO₂N(CH₂OC(O)Me)C(O)(CH₂)₂Me |
| I-226 choline salt | 3-((N-propanoyl)-cyclopropylsulfonamidomethyl)- | p = 0 | Me | q = 0 | 3-SO₂NHC(O)Et |

TABLE II

| # | Y | X | (R³)_q | Position of SO₂NH₂ |
|---|---|---|---|---|
| II-1 | cyclopropylsulfonyl-tetrahydroisoquinoline | Me | q = 0 | 4 |
| II-2 | cyclopropylsulfonyl-tetrahydroisoquinoline | Me | q = 0 | 3 |
| II-3 | cyclopropylsulfonyl-tetrahydroisoquinoline | Me | 4-Me | 3 |
| II-4 | cyclopropylsulfonyl-isoindoline | F | 4-Me | 3 |
| II-5 | cyclopropylsulfonyl-isoindoline | F | q = 0 | 3 |
| II-6 | cyclopropylsulfonyl-isoindoline | F | q = 0 | 4 |
| II-7 | cyclopropylsulfonyl-isoindoline | Me | 4-Me | 3 |
| II-8 | cyclopropylsulfonyl-isoindoline | Me | q = 0 | 3 |

TABLE II-continued

| # | (R²)ₚ-[ring]-Y- substituent | X | (R³)_q | Position of SO₂NH₂ |
|---|---|---|---|---|
| II-9 | cyclopropyl-S(O)₂-N-isoindoline | Me | q = 0 | 4 |

D. Methods of the Invention

The present invention provides 2,4-pyrimidinediamine compounds and prodrugs thereof, as described herein, for use in therapy for the conditions described herein. The present invention further provides use of the compounds of the present invention in the manufacture of a medicament for the treatment of conditions in which targeting of the JAK pathway or inhibition of JAK kinases, particularly JAK3, are therapeutically useful. These include conditions where the function of lymphocytes, macrophages, or mast cells is involved. Conditions in which targeting of the JAK pathway or inhibition of the JAK kinases, particularly JAK3, are therapeutically useful include leukemia, lymphoma, transplant rejection (e.g., pancreas islet transplant rejection), bone marrow transplant applications (e.g., graft-versus-host disease)), autoimmune diseases (e.g., rheumatoid arthritis, etc.), inflammation (e.g., asthma, etc.) and other conditions as described in greater detail herein.

As noted previously, numerous conditions can be treated using the 2,4-substituted pyrimidinediamine compounds, prodrugs thereof, and methods of treatment as described herein. As used herein, "Treating" or "treatment" of a disease in a patient refers to (1) preventing the disease from occurring in a patient that is predisposed or does not yet display symptoms of the disease; (2) inhibiting the disease or arresting its development; or (3) ameliorating or causing regression of the disease. As well understood in the art, "treatment" is an approach for obtaining beneficial or desired results, including clinical results. For the purposes of this invention, beneficial or desired results can include one or more, but are not limited to, alleviation or amelioration of one or more symptoms, diminishment of extent of a condition, including a disease, stabilized (i.e., not worsening) state of a condition, including diseases, preventing spread of disease, delay or slowing of condition, including disease, progression, amelioration or palliation of the condition, including disease, state, and remission (whether partial or total), whether detectable or undetectable. Preferred are compounds that are potent and can be administered locally at very low doses, thus minimizing systemic adverse effects.

The compounds described herein are potent and selective inhibitors of JAK kinases and are particularly selective for cytokine signaling pathways containing JAK3. As a consequence of this activity, the compounds can be used in a variety of in vitro, in vivo, and ex vivo contexts to regulate or inhibit JAK kinase activity, signaling cascades in which JAK kinases play a role, and the biological responses effected by such signaling cascades. For example, in one embodiment, the compounds can be used to inhibit JAK kinase, either in vitro or in vivo, in virtually any cell type expressing the JAK kinase, such as in hematopoietic cells in which, for example, JAK3 is predominantly expressed. They may also be used to regulate signal transduction cascades in which JAK kinases, particularly JAK3, play a role. Such JAK-dependent signal transduction cascades include, but are not limited to, the signaling cascades of cytokine receptors that involve the common gamma chain, such as, for example, the IL-4, IL-7, IL-5, IL-9, IL-15 and IL-21, or IL-2, IL-4, IL-7, IL-9, IL-15, and IL-21 receptor signaling cascades. The compounds may also be used in vitro or in vivo to regulate, and in particular to inhibit, cellular or biological responses affected by such JAK-dependent signal transduction cascades. Such cellular or biological responses include, but are not limited to, IL-4/ramos CD23 upregulation and IL-2 mediated T-cell proliferation. Importantly, the compounds can be used to inhibit JAK kinases in vivo as a therapeutic approach towards the treatment or prevention of diseases mediated, either wholly or in part, by a JAK kinase activity (referred to herein as "JAK kinase mediated diseases"). Non-limiting examples of JAK kinase mediated diseases that can be treated or prevented with the compounds include, but are not limited to, the following: allergies; asthma; autoimmune diseases such as transplant rejection (e.g., kidney, heart, lung, liver, pancreas, skin, small intestine, large intestine, host versus graft reaction (HVGR), and graft versus host reaction (GVHR)), rheumatoid arthritis, and amyotrophic lateral sclerosis; T-cell mediated autoimmune diseases such as multiple sclerosis, psoraiasis, and Sjogren's syndrome; Type II inflammatory diseases such as vascular inflammation (including vasculitis, arteritis, atherosclerosis, and coronary artery disease); diseases of the central nervous system such as stroke; pulmonary diseases such as bronchitis obliteraus and primary pulmonary hypertension; solid, delayed Type IV hypersensitivity reactions; and hematologic malignancies such as leukemia and lymphomas.

Examples of diseases that are mediated, at least in part, by JAK kinases that can be treated or prevented according to the methods include, but are not limited to, allergies, asthma, autoimmune diseases such as transplant rejection (e.g., kidney, heart, lung, liver, pancreas, skin, host versus graft reaction (HVGR), etc.), rheumatoid arthritis, and amyotrophic lateral sclerosis, multiple sclerosis, psoraiasis and Sjogren's syndrome, Type II inflammatory disease such as vascular inflammation (including vasculitis, ateritis, atherosclerosis and coronary artery disease) or other inflammatory diseases such as osteoarthritis, inflammatory bowel disease, ulcerative colitis, Crohn's disease, idiopathic inflammatory bowel disease, irritable bowel syndrome, spastic colon, low grade scarring (e.g., scleroderma, increased fibrosis, keloids, post-surgical scars, pulmonary fibrosis, vascular spasms, migraine, reperfusion injury and post myocardial infarction), and sicca complex or syndrome, diseases of the central nervous system such as stroke, pulmonary diseases such as bronchitis obliterous and primary and primary pulmonary hypertension, delayed or cell-mediated, Type IV hypersensitivity and solid and hematologic malignancies such as leukemias and lyphomas.

In another embodiment, this invention provides a method of inhibiting an activity of a JAK kinase, comprising contacting the JAK kinase with an amount of a compound effective to inhibit an activity of the JAK kinase, wherein the compound is selected from the compounds of this invention.

In certain embodiments of the methods described herein, the method is carried out in vivo.

In another embodiment, this invention provides a method of inhibiting an activity of a JAK kinase, comprising contacting in vitro a JAK3 kinase with an amount of a compound effective to inhibit an activity of the JAK kinase, wherein the compound is selected from the compounds of this invention.

In a specific embodiment, the compounds can be used to treat and/or prevent rejection in organ and/or tissue transplant recipients (i.e., treat and/or prevent allorgraft rejection). Allografts can be rejected through either a cell-mediated or humoral immune reaction of the recipient against transplant (histocompatibility) antigens present on the membranes of the donor's cells. The strongest antigens are governed by a complex of genetic loci termed human leukocyte group A (HLA) antigens. Together with the ABO blood groups antigens, they are the chief transplantation antigens detectable in humans.

Rejection following transplantation can generally be broken into three categories: hyperacute, occurring hours to days following transplantation; acute, occurring days to months following transplantation; and chronic, occurring months to years following transplantation.

Hyperacute rejection is caused mainly by the production of host antibodies that attack the graft tissue. In a hyperacute rejection reaction, antibodies are observed in the transplant vascular very soon after transplantation. Shortly thereafter, vascular clotting occurs, leading to ischemia, eventual necrosis and death. The graft infarction is unresponsive to known immunosuppressive therapies. Because HLA antigens can be identified in vitro, pre-transplant screening is used to significantly reduce hyperacute rejection. As a consequence of this screening, hyperacute rejection is relatively uncommon today.

Acute rejection is thought to be mediated by the accumulation of antigen specific cells in the graft tissue. The T-cell-mediated immune reaction against these antigens (i.e., HVGR or GVHR) is the principle mechanism of acute rejection. Accumulation of these cells leads to damage of the graft tissue. It is believed that both CD4+ helper T-cells and CD8+ cytotoxic T-cells are involved in the process and that the antigen is presented by donor and host dendritic cells. The CD4+ helper T-cells help recruit other effector cells, such as macrophapges and eosinophils, to the graft. Accessing T-cell activation signal transduction cascades (for example, CD28, CD40L, and CD2 cascades) are also involved.

The cell-mediated acute rejection can be reversed in many cases by intensifying immunotherapy. After successful reversal, severely damaged elements of the graft heal by fibrosis and the remainder of the graft appears normal. After resolution of acute rejection, dosages of immunosuppressive drugs can be reduced to very low levels.

Chronic rejection, which is a particular problem in renal transplants, often progresses insidiously despite increased immunosuppressive therapy. It is thought to be due, in large part, to cell-mediated Type IV hypersensitivity. The pathologic profile differs from that of acute rejection. The arterial endothelium is primarily involved with extensive proliferation that may gradually occlude the vessel lumen, leading to ischemia, fibrosis, a thickened intima, and atherosclerotic changes. Chronic rejection is mainly due to a progressive obliteration of graft vasculature and resembles a slow, vasculitic process.

In Type IV hypersensitivity, CD8 cytotoxic T-cells and CD4 helper T cells recognize either intracellular or extracellular synthesized antigen when it is complexed, respectively, with either Class I or Class II MHC molecules. Macrophages function as antigen-presenting cells and release IL-1, which promotes proliferation of helper T-cells. Helper T-cells release interferon gamma and IL-2, which together regulate delayed hyperactivity reactions mediated by macrophage activation and immunity mediated by T cells. In the case of organ transplant, the cytotoxic T-cells destroy the graft cells on contact.

Since JAK kinases play a critical role in the activation of T-cells, the 2,4-pyrimidinediamine compounds described herein can be used to treat and/or prevent many aspects of transplant rejection, and are particularly useful in the treatment and/or prevention of rejection reactions that are mediated, at least in part, by T-cells, such as HVGR or GVHR. The 2,4-pyrimidinediamine compounds can also be used to treat and/or prevent chronic rejection in transplant recipients and, in particular, in renal transplant recipients. The compound can also be administered to a tissue or an organ prior to transplanting the tissue or organ in the transplant recipient.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention. In certain embodiments of the methods the autoimmune disease is multiple sclerosis (MS), psoraisis, or Sjogran's syndrome. Such autoimmune disease include, but are not limited to, those autoimmune diseases that are frequently designated as single organ or single cell-type autoimmune disorders and those autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid. Additional autoimmune diseases, which can be β-cell (humoral) based or T-cell based, include Cogan's syndrome, ankylosing spondylitis, Wegener's granulomatosis, autoimmune alopecia, Type I or juvenile onset diabetes, and thyroiditis.

The types of autoimmune diseases that may be treated or prevented with such prodrugs generally include those disorders involving tissue injury that occurs as a result of a humoral and/or cell-mediated response to immunogens or antigens of endogenous and/or exogenous origin. Such diseases are frequently referred to as diseases involving the nonanaphylactic (i.e., Type II, Type III and/or Type IV) hypersensitivity reactions.

Type I hypersensitivity reactions generally result from the release of pharmacologically active substances, such as histamine, from mast and/or basophil cells following contact with a specific exogenous antigen. As mentioned above, such Type I reactions play a role in numerous diseases, including allergic asthma, allergic rhinitis, etc.

Type II hypersensitivity reactions (also referred to as cytotoxic, cytolytic complement-dependent or cell-stimulating hypersensitivity reactions) result when immunoglobulins react with antigenic components of cells or tissue, or with an antigen or hapten that has become intimately coupled to cells or tissue. Diseases that are commonly associated with Type II hypersensitivity reactions include, but are not limited, to autoimmune hemolytic anemia, erythroblastosis fetalis and Goodpasture's disease.

Type III hypersensitivity reactions, (also referred to as toxic complex, soluble complex, or immune complex hypersensitivity reactions) result from the deposition of soluble circulating antigen-immunoglobulin complexes in vessels or in tissues, with accompanying acute inflammatory reactions at the site of immune complex deposition. Non-limiting examples of prototypical Type III reaction diseases include the Arthus reaction, rheumatoid arthritis, serum sickness, systemic lupus erythematosis, certain types of glomerulonephritis, multiple sclerosis and bullous pemphingoid.

Type IV hypersensitivity reactions (frequently called cellular, cell-mediated, delayed, or tuberculin-type hypersensitivity reactions) are caused by sensitized T-lymphocytes which result from contact with a specific antigen. Non-limiting examples of diseases cited as involving Type IV reactions are contact dermatitis and allograft rejection.

Autoimmune diseases associated with any of the above nonanaphylactic hypersensitivity reactions may be treated or prevented with the prodrugs according to structural formulae (I) and (Ia). In particular, the methods may be used to treat or prevent those autoimmune diseases frequently characterized as single organ or single cell-type autoimmune disorders including, but not limited to: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, as well as those autoimmune diseases frequently characterized as involving systemic autoimmune disorder, which include but are not limited to: systemic lupus erythematosis (SLE), rheumatoid arthritis, Sjogren's syndrome, Reiter's syndrome, polymyositis-dermatomyositis, systemic sclerosis, polyarteritis nodosa, multiple sclerosis and bullous pemphigoid.

It will be appreciated by skilled artisans that many of the above-listed autoimmune diseases are associated with severe symptoms, the amelioration of which provides significant therapeutic benefit even in instances where the underlying autoimmune disease may not be ameliorated.

Therapy using the 2,4-pyrimidinediamine compounds described herein can be applied alone, or it can be applied in combination with or adjunctive to other common immunosuppressive therapies, such as, for example, the following: mercaptopurine; corticosteroids such as prednisone; methylprednisolone and prednisolone; alkylating agents such as cyclophosphamide; calcineurin inhibitors such as cyclosporine, sirolimus, and tacrolimus; inhibitors of inosine monophosphate dehydrogenase (IMPDH) such as mycophenolate, mycophenolate mofetil, and azathioprine; and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also: the prescribing information in the 2006 Edition of *The Physician's Desk Reference*), the disclosures of which are incorporated herein by reference. Azathioprine is currently available from Salix Pharmaceuticals, Inc., under the brand name AZASAN; mercaptopurine is currently available from Gate Pharmaceuticals, Inc., under the brand name PURINETHOL; prednisone and prednisolone are currently available from Roxane Laboratories, Inc.; Methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand dame SANDIMMUNE and from Abbott under the brand name GENGRAF; IMPDH inhibitors such as mycophenolate mofetil and mycophenolic acid are currently available from Roche under the brand name CELLCEPT and from Novartis under the brand name MYFORTIC; azathioprine is currently available from Glaxo Smith Kline under the brand name IMURAN; and antibodies are currently available from Ortho Biotech under the brand name ORTHOCLONE, from Novartis under the brand name SIMULECT (basiliximab), and from Roche under the brand name ZENAPAX (daclizumab).

In another embodiment, the 2,4-pyrimidinediamine compounds could be administered either in combination or adjunctively with an inhibitor of a Syk kinase. Syk kinase is a tyrosine kinase known to play a critical role in Fcγ receptor signaling, as well as in other signaling cascades, such as those involving B-Cell receptor signaling (Tumer et al., (2000), *Immunology Today* 21:148-154) and integrins beta (1), beta (2), and beta (3) in neutrophils (Mocsavi et al., (2002), *Immunity* 16:547-558). For example, Syk kinase plays a pivotal role in high affinity IgE receptor signaling in mast cells that leads to activation and subsequent release of multiple chemical mediators that trigger allergic attacks. However, unlike the JAK kinases, which help regulate the pathways involved in delayed or cell-mediated Type IV hypersensitivity reactions, Syk kinase helps regulate the pathways involved in immediate IgE-mediated, Type I hypersensitivity reactions. Certain compounds that affect the Syk pathway may or may not also affect the JAK pathways.

Suitable Syk inhibitory compounds are described, for example, in Ser. No. 10/355,543 filed Jan. 31, 2003 (publication no. 2004/0029902); WO 03/063794; Ser. No. 10/631,029 filed Jul. 29, 2003; WO 2004/014382; Ser. No. 10/903,263 filed Jul. 30, 2004; PCT/US2004/24716 filed Jul. 30, 2004 (WO05/016893); Ser. No. 10/903,870 filed Jul. 30, 2004; PCT/US2004/24920 filed Jul. 30, 2004; Ser. No. 60/630,808 filed Nov. 24, 2004; Ser. No. 60/645,424 filed Jan. 19, 2005; and Ser. No. 60/654,620, filed Feb. 18, 2005, the disclosures of which are incorporated herein by reference. The 2,4-pyrimidinediamine described herein and Syk inhibitory compounds could be used alone or in combination with one or more conventional transplant rejection treatments, as described above.

In a specific embodiment, the 2,4-pyrimidinediamine compounds can be used to treat or prevent these diseases in patients that are either initially non-responsive (resistant) to or that become non-responsive to treatment with a Syk inhibitory compound or one of the other current treatments for the particular disease. The 2,4-pyrimidinediamine compounds could also be used in combination with Syk inhibitory compounds in patients that are Syk-compound resistant or non-responsive. Suitable Syk-inhibitory compounds with which the 2,4-pyrimidinediamine compounds can be administered are provided supra.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention, as described herein, and the compound is administered in combination with or adjunctively to a compound that inhibits Syk kinase with an $IC_{50}$ in the range of at least 10 μM.

In another embodiment, this invention provides a method of treating or preventing allograft transplant rejection in a transplant recipient, comprising administering to the transplant recipient an amount of a compound effective to treat or prevent the rejection wherein the compound is selected from the compounds of the invention, as described herein. In a further embodiment, the compound is administered to a tissue or an organ prior to transplanting the tissue or organ in the transplant recipient.

In another embodiment, this invention provides a method of treating or preventing allograft transplant rejection in a transplant recipient, in which the rejection is acute rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is chronic rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is mediated by HVGR or GVHR, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection wherein the compound is selected from the compounds of the invention, as described herein, in which the compound is administered in combination with or adjunctively to another immunosuppressant.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of the invention, as described herein, in which the compound is administered in combination with or adjunctively to another immunosuppressant, in which the immunosuppressant is selected from cyclosporine, tacrolimus, sirolimus, an inhibitor of IMPDH, mycophenolate, mycophanolate mofetil, an anti-T-Cell antibody, and OKT3.

The 2,4-pyrimidinediamine compounds described herein are cytokine moderators of IL-4 signaling. As a consequence, the 2,4-pyrimidinediamine compounds could slow the response of Type I hypersensitivity reactions. Thus, in a specific embodiment, the 2,4-pyrimidinediamine compounds could be used to treat such reactions and, therefore, the diseases associated with, mediated by, or caused by such hypersensitivity reactions (for example, allergies), prophylactically. For example, an allergy sufferer could take one or more of the JAK selective compounds described herein prior to expected exposure to allergens to delay the onset or progress of, or eliminate altogether, an allergic response.

When used to treat or prevent such diseases, the 2,4-pyrimidinediamine compounds can be administered singly, as mixtures of one or more 2,4-pyrimidinediamine compounds, or in mixture or combination with other agents useful for treating such diseases and/or the symptoms associated with such diseases. The 2,4-pyrimidinediamine compounds may also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, β-agonists, tryptase inhibitors, aspirin, cyclooxygenase (COX) inhibitors, methotrexate, anti-TNF drugs, retuxin, PD4 inhibitors, p38 inhibitors, PDE4 inhibitors, and antihistamines, to name a few. The 2,4-pyrimidinediamine compounds can be administered per se in the form of prodrugs or as pharmaceutical compositions, comprising an active compound or prodrug.

In another embodiment, this invention provides a method of treating or preventing a Type IV hypersensitivity reaction, comprising administering to a subject an amount of a compound effective to treat or prevent the hypersensitivity reaction, wherein the compound is selected from the compounds of this invention, as described herein.

In another embodiment, this invention provides a method of treating or preventing a Type IV hypersensitivity reaction, which is practical prophylactically, comprising administering to a subject an amount of a compound effective to treat or prevent the hypersensitivity reaction, wherein the compound is selected from the compounds of this invention, as described herein, and is administered prior to exposure to an allergen.

In another embodiment, this invention provides a method of inhibiting a signal transduction cascade in which JAK3 kinase plays a role, comprising contacting a cell expressing a receptor involved in such a signaling cascade with a compound, wherein the compound is selected from the compounds of this invention, as described herein.

In another embodiment, this invention provides a method of treating or preventing a JAK kinase-mediated disease, comprising administering to a subject an amount of compound effective to treat or prevent the JAK kinase-mediated disease, wherein the compound is selected from the compounds of this invention, as described herein.

In another embodiment, this invention provides a method of treating or preventing a JAK kinase-mediated disease, in which the JAK-mediated disease is HVGR or GVHR, comprising administering to a subject an amount of compound effective to treat or prevent the JAK kinase-mediated disease, wherein the compound is selected from the compounds of the invention, as described herein.

In another embodiment, this invention provides a method of treating or preventing a JAK kinase-mediated disease, in which the JAK-mediated disease is acute allograft rejection, comprising administering to a subject an amount of compound effective to treat or prevent the JAK kinase-mediated disease, wherein the compound is selected from the compounds of the invention, as described herein.

In another embodiment, this invention provides a method of treating or preventing a JAK kinase-mediated disease, in which the JAK-mediated disease is chronic allograft rejection, comprising administering to a subject an amount of compound effective to treat or prevent the JAK kinase-mediated disease, wherein the compound is selected from the compounds of the invention, as described herein.

Active compounds of the invention typically inhibit the JAK/Stat pathway. The activity of a specified compound as an inhibitor of a JAK kinase can be assessed in vitro or in vivo. In some embodiments, the activity of a specified compound can be tested in a cellular assay. Suitable assays include assays that determine inhibition of either the phosphorylation activity or ATPase activity of a JAK kinase. Thus, a compound is said to inhibit an activity of a JAK kinase if it inhibits the phosphorylation or ATPase activity of a JAK kinase with an $IC_{50}$ of about 20 µM or less.

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

"Hematopoietic neoplasm" refers to a cell proliferative disorder arising from cells of the hematopoietic lineage. Generally, hematopoiesis is the physiological process whereby undifferentiated cells or stem cells develop into various cells found in the peripheral blood. In the initial phase of development, hematopoietic stem cells, typically found in the bone marrow, undergo a series of cell divisions to form multipotent progenitor cells that commit to two main developmental pathways: the lymphoid lineage and the myeloid lineage. The committed progenitor cells of the myeloid lineage differentiate into three major sub-branches comprised of the erythroid, megakaryocyte, and granulocyte/monocyte developmental pathways. An additional pathway leads to formation of dendritic cells, which are involved in antigen presentation. The erythroid lineage gives rise to red blood cells while the megakaryocytic lineage gives rise to blood platelets. Committed cells of the granulocyte/monocyte lineage split into granulocyte or monocyte developmental pathways, the former pathway leading to formation of neutrophils, eosinophils, and basophils and the latter pathway giving rise to blood monocytes and macrophages.

Committed progenitor cells of the lymphoid lineage develop into the B cell pathway, T cell pathway, or the non-T/B cell pathway. Similar to the myeloid lineage, an additional lymphoid pathway appears to give rise to dendritic cells involved in antigen presentation. The B cell progenitor cell develops into a precursor B cell (pre-B), which differentiates into B cells responsible for producing immunoglobulins. Progenitor cells of the T cell lineage differentiate into precursor T cells (pre-T) that, based on the influence of certain cytokines, develop into cytotoxic or helper/suppressor T cells involved in cell mediated immunity. Non-T/B cell pathway leads to generation of natural killer (NK) cells. Neoplasms of hematopoietic cells can involve cells of any phase of hematopoiesis, including hematopoietic stem cells, multipotent progenitor cells, oligopotent committed progenitor cells, precursor cells, and mature differentiated cells. The categories of hematopoietic neoplasms can generally follow the descriptions and diagnostic criteria employed by those of skill in the art (see, e.g., International Classification of Disease and Related Health Problems (ICD 10), World Health Organization (2003)). Hematopoietic neoplasms can also be characterized based on the molecular features, such as cell surface markers and gene expression profiles, cell phenotype exhibited by the aberrant cells, and/or chromosomal aberrations (e.g., deletions, translocations, insertions, etc.) characteristic of certain hematopoietic neoplasms, such as the Philadelphia chromosome found in chronic myelogenous leukemia. Other classifications include National Cancer Institute Working Formulation (Cancer, 1982, 49:2112-2135) and Revised European-American Lymphoma Classification (REAL).

"Lymphoid neoplasm" refers a proliferative disorder involving cells of the lymphoid lineage of hematopoiesis. Lymphoid neoplasms can arise from hematopoietic stem cells as well as lymphoid committed progenitor cells, precursor cells, and terminally differentiated cells. These neoplasms can be subdivided based on the phenotypic attributes of the aberrant cells or the differentiated state from which the abnormal cells arise. Subdivisions include, among others, B cell neoplasms, T cell neoplasms, NK cell neoplasms, and Hodgkin's lymphoma.

"Myeloid neoplasm" refers to proliferative disorder of cells of the myeloid lineage of hematopoiesis. Neoplasms can arise from hematopoietic stem cells, myeloid committed progenitor cells, precursor cells, and terminally differentiated cells. Myeloid neoplasms can be subdivided based on the phenotypic attributes of the aberrant cells or the differentiated state from which the abnormal cells arise. Subdivisions include, among others, myeloproliferative diseases, myelodysplastic/myeloproliferative diseases, myelodysplastic syndromes, acute myeloid leukemia, and acute biphenotypic leukemia.

Generally, cell proliferative disorders treatable with the compounds disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, *Blood* 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, *Blood* 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., *Proc. Natl. Acad. Sci. USA*, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant JAK activity can be treated with the JAK inhibitory compounds.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9;22)(qq34;q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various embodiments, any of the myeloid neoplasms that are associated with aberrant JAK activity can be treated with the JAK inhibitory compounds.

In some embodiments, the JAK inhibitory compounds can be used to treat Acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1(CBF-alpha)/ETO, Acute promyelocytic leukemia (AML with t(15;17)(q22;q11-12) and variants, PML/RAR-alpha), AML with abnormal bone marrow eosinophils (inv(16)(p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

One means of assaying for such inhibition is detection of the effect of the 2,4-pyrimidinediamine compounds on the upregulation of downstream gene products. In the Ramos/

IL4 assay, B-cells are stimulated with the cytokine Interleukin-4 (IL-4) leading to the activation of the JAK/Stat pathway through phosphorylation of the JAK family kinases, JAK1 and JAK3, which in turn phosphorylate and activate the transcription factor Stat-6. One of the genes upregulated by activated Stat-6 is the low affinity IgE receptor, CD23. To study the effect of inhibitors (e.g., the 2,4-substituted pyrimindinediamine compounds described herein) on the JAK1 and JAK3 kinases, human Ramos B cells are stimulated with human IL-4. 20 to 24 hours post stimulation, cells are stained for upregulation of CD23 and analyzed using flow cytometry (FACS). A reduction of the amount of CD23 present compared to control conditions indicates the test compound actively inhibits the JAK kinase pathway. An exemplary assay of this type is described in greater detail in Example 3.

The activity of the active compounds of the invention may further be characterized by assaying the effect of the 2,4-pyrimidinediamine compounds described herein on the proliferative response of primary human T-cells. In this assay, primary human T-cells derived from peripheral blood and pre-activated through stimulation of the T-cell receptor and CD28, proliferate in culture in response to the cytokine Interleukin-2 (IL-2). This proliferative response is dependent on the activation of JAK1 and JAK3 tyrosine kinases, which phosphorylate and activate the transcription factor Stat-5. The primary human T-cells are incubated with the 2,4-pyrimidinediamine compounds in the presence of IL-2 for 72 hours, and at the assay endpoint intracellular ATP concentrations are measured to assess cell viability. A reduction in cell proliferation compared to control conditions is indicative of inhibition of the JAK kinase pathway. An exemplary assay of this type is described in greater detail in Example 4.

The activity of the compounds of the invention may additionally be characterized by assaying the effect of the 2,4-pyrimidinediamine compounds described herein on A549 lung epithelial cells and U937 cells. A549 lung epithelial cells and U937 cells up-regulate ICAM-1 (CD54) surface expression in response to a variety of different stimuli. Therefore, using ICAM-1 expression as readout, test compound effects on different signaling pathways can be assessed in the same cell type. Stimulation with IL-1β through the IL-1β receptor activates the TRAF6/NFκB pathway resulting in up-regulation of ICAM-1. IFNγ induces ICAM-1 up-regulation through activation of the JAK1/JAK2 pathway. The up-regulation of ICAM-1 can be quantified by flow cytometry across a compound dose curve and $EC_{50}$ values are calculated. Exemplary assays of this type are described in greater detail in Examples 5 and 6.

Active compounds as described herein generally inhibit the JAK kinase pathway with an $IC_{50}$ in the range of about 1 mM or less, as measured in the assays described herein. Of course, skilled artisans will appreciate that compounds which exhibit lower $IC_{50}$s, (on the order, for example, of 100 µM, 75 µM, 50 µM, 40 µM, 30 µM, 20 µM, 15 µM, 10 µM, 5 µM, 1 µM, 500 nM, 100 nM, 10 nM, 1 nM, or even lower) can be particularly useful in therapeutic applications. In instances where activity specific to a particular cell type is desired, the compound can be assayed for activity with the desired cell type and counter-screened for a lack of activity against other cell types. The desired degree of "inactivity" in such counter screens, or the desired ratio of activity vs. inactivity, may vary for different situations and can be selected by the user.

The 2,4-pyrimidinediamine active compounds also typically inhibit IL-4 stimulated expression of CD23 in B-cells with an $IC_{50}$ in the range of about 20 µM or less, typically in the range of about 10 µM, 500 nM, 100 nM, 10 nM, 1 nM, or even lower. A suitable assay that can be used is the assay described in Example 3, "Assay for Ramos B-Cell Line Stimulated with IL-4." In certain embodiments, the active 2,4-pyrimidinediamine compounds have an $IC_{50}$ of less than or equal to 5 µM, greater than 5 µM but less than 20 µM, greater than 20 µM, or greater than 20 µM but less than 50 µM in the assay described in Example 3.

Additionally, the 2,4-pyrimidinediamine active compounds typically inhibit an activity of human primary T-cells with an $IC_{50}$ in the range of about 20 µM or less, typically in the range of about 10 µM, 500 nM, 100 nM, 10 nM, 1 nM, or even lower. The $IC_{50}$ against human primary T-cells can be determined in a standard in vitro assay with isolated human primary T-cells. A suitable assay that can be used is the assay described in Example 4, "Primary Human T-cell Proliferation Assay Stimulated with IL-2." In certain embodiments, the active 2,4-pyrimidinediamine compounds have an $IC_{50}$ of less than or equal to 5 µM, greater than 5 µM but less than 20 µM, greater than 20 µM, or greater than 20 µM but less than 50 µM in the assay described in Example 4.

The 2,4-pyrimidinediamine active compounds also typically inhibit expression of ICAM1 (CD54) induced by IFNγ exposure in U937 or A549 cells with an $IC_{50}$ in the range of about 20 µM or less, typically in the range of about 10 µM, 500 nM, 100 nM, 10 nM, 1 nM, or even lower. The $IC_{50}$ against expression of ICAM (CD54) in IFNγ stimulated cells can be determined in a functional cellular assay with an isolated A549 or U937 cell line. Suitable assays that can be used are the assays described in Examples 5 and 6, "A549 Epithelial Line Stimulated with IFNγ" and "U937 IFNγ ICAM1 FACS Assay," respectively. In certain embodiments, the active 2,4-pyrimidinediamine compounds have an $IC_{50}$ of less than or equal to 20 µM, greater than 20 µM, or greater than 20 µM but less than 50 µM in the assays described in Example 5 and 6.

E. Pharmaceutical Compositions of the Invention

Pharmaceutical compositions comprising the 2,4-pyrimidinediamine compounds described herein (or prodrugs thereof) can be manufactured by means of conventional mixing, dissolving, granulating, dragee-making levigating, emulsifying, encapsulating, entrapping, or lyophilization processes. The compositions can be formulated in conventional manner using one or more physiologically acceptable carriers, diluents, excipients, or auxiliaries which facilitate processing of the active compounds into preparations which can be used pharmaceutically.

The 2,4-pyrimidinediamine compound or prodrug can be formulated in the pharmaceutical compositions per se, or in the form of a hydrate, solvate, N-oxide, or pharmaceutically acceptable salt, as described herein. Typically, such salts are more soluble in aqueous solutions than the corresponding free acids and bases, but salts having lower solubility than the corresponding free acids and bases may also be formed.

In one embodiment, this invention provides a pharmaceutical formulation comprising a compound selected from the compounds of the invention, as described herein, or a prodrug thereof, and at least one pharmaceutically acceptable excipient, diluent, preservative, stabilizer, or mixture thereof.

In another embodiment, the methods can be practiced as a therapeutic approach towards the treatment of the conditions described herein. Thus, in a specific embodiment, the 2,4-pyrimidinediamine compounds (and the various forms described herein, including pharmaceutical formulations comprising the compounds (in the various forms)) can be used to treat the conditions described herein in animal subjects, including humans. The methods generally comprise administering to the subject an amount of a compound of the invention, or a salt, prodrug, hydrate, or N-oxide thereof, effective to treat the condition. In one embodiment, the subject is a non-human mammal, including, but not limited to, bovine, horse, feline, canine, rodent, or primate. In another embodiment, the subject is a human.

The compounds can be provided in a variety of formulations and dosages. The compounds can be provided in a pharmaceutically acceptable form, including where the compound or prodrug can be formulated in the pharmaceutical compositions per se, or in the form of a hydrate, solvate, N-oxide, or pharmaceutically acceptable salt, as described herein. Typically, such salts are more soluble in aqueous solutions than the corresponding free acids and bases, but salts having lower solubility than the corresponding free acids and bases may also be formed. It is to be understood that reference to the compound, 2,4-pyrimidinediamine compound, or "active" in discussions of formulations is also intended to include, where appropriate as known to those of skill in the art, formulation of the prodrugs of the 2,4-pyrimidinediamine compounds.

In one embodiment, the compounds are provided as non-toxic pharmaceutically acceptable salts, as noted previously. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid, or phosphoric acid. Salts of amine groups may also comprise quaternary ammonium salts in which the amino nitrogen atom carries a suitable organic group such as an alkyl, alkenyl, alkynyl, or substituted alkyl moiety. Furthermore, where the compounds of the invention carry an acidic moiety, suitable pharmaceutically acceptable salts thereof may include metal salts such as alkali metal salts, e.g., sodium or potassium salts; and alkaline earth metal salts, e.g., calcium or magnesium salts.

The pharmaceutically acceptable salts of the present invention can be formed by conventional means, such as by reacting the free base form of the product with one or more equivalents of the appropriate acid in a solvent or medium in which the salt is insoluble or in a solvent such as water which is removed in vacuo, by freeze drying, or by exchanging the anions of an existing salt for another anion on a suitable ion exchange resin.

The present invention includes within its scope solvates of the 2,4-pyrimidinediamine compounds and salts thereof, for example, hydrates.

The 2,4-pyrimidinediamine compounds may have one or more asymmetric centers and may accordingly exist both as enantiomers and as diastereoisomers. It is to be understood that all such isomers and mixtures thereof are encompassed within the scope of the present invention.

The 2,4-pyrimidinediamine compounds can be administered by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. In addition to the treatment of warm-blooded animals such as mice, rats, horses, cattle, sheep, dogs, cats, and monkeys, the compounds of the invention can be effective in humans.

The pharmaceutical compositions for the administration of the 2,4-pyrimidinediamine compounds can be conveniently presented in dosage unit form and can be prepared by any of the methods well known in the art of pharmacy. The pharmaceutical compositions can be, for example, prepared by uniformly and intimately bringing the active ingredient into association with a liquid carrier, a finely divided solid carrier or both, and then, if necessary, shaping the product into the desired formulation. In the pharmaceutical composition the active object compound is included in an amount sufficient to produce the desired therapeutic effect. For example, pharmaceutical compositions of the invention may take a form suitable for virtually any mode of administration, including, for example, topical, ocular, oral, buccal, systemic, nasal, injection, transdermal, rectal, and vaginal, or a form suitable for administration by inhalation or insufflation.

For topical administration, the JAK-selective compound(s) or prodrug(s) can be formulated as solutions, gels, ointments, creams, suspensions, etc., as is well-known in the art.

Systemic formulations include those designed for administration by injection (e.g., subcutaneous, intravenous, intramuscular, intrathecal, or intraperitoneal injection) as well as those designed for transdermal, transmucosal, oral, or pulmonary administration.

Useful injectable preparations include sterile suspensions, solutions, or emulsions of the active compound(s) in aqueous or oily vehicles. The compositions may also contain formulating agents, such as suspending, stabilizing, and/or dispersing agents. The formulations for injection can be presented in unit dosage form, e.g., in ampules or in multidose containers, and may contain added preservatives.

Alternatively, the injectable formulation can be provided in powder form for reconstitution with a suitable vehicle, including but not limited to sterile pyrogen free water, buffer, and dextrose solution, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets, or capsules prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulfate). The tablets can be coated by methods well known in the art with, for example, sugars, films, or enteric coatings. Additionally, the pharmaceutical compositions containing the 2,4-substituted pyrmidinediamine as active ingredient or prodrug thereof in a form suitable for oral use may also include, for example, troches, lozenges, aqueous, or oily suspensions, dispersible powders or granules, emulsions, hard or soft capsules, or syrups or elixirs. Compositions intended for oral use can be prepared according to any method known to the art for the manufacture of pharmaceutical compositions, and such compositions may contain one or more agents selected from the group consisting of sweetening agents, flavoring agents, coloring agents, and preserving agents in order to provide pharmaceutically elegant and palatable preparations. Tablets contain the active ingredient (including drug and/or prodrug) in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (e.g., corn starch or alginic acid); binding agents (e.g. starch, gelatin, or acacia); and lubricating agents (e.g., magnesium stearate, stearic acid, or talc). The tablets can be left uncoated or they can be coated by known techniques to delay disintegration and absorption in the gastrointestinal tract and thereby provide a sustained action over a longer period. For example, a time delay material such as glyceryl monostearate or glyceryl distearate can be employed. They may also be coated by the techniques described in the U.S. Pat. Nos. 4,256,108; 4,166,452; and 4,265,874 to form osmotic therapeutic tablets for control release. The pharmaceutical compositions of the invention may also be in the form of oil-in-water emulsions.

Liquid preparations for oral administration may take the form of, for example, elixirs, solutions, syrups, or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives, or hydrogenated edible fats); emulsifying agents (e.g., lecithin, or acacia); non-aqueous vehicles (e.g., almond oil, oily esters, ethyl alcohol, Cremophore™, or fractionated vegetable oils); and preservatives (e.g., methyl or propyl-p-hydroxybenzoates or sorbic acid). The preparations may also contain buffer salts, preservatives, flavoring, coloring, and sweetening agents as appropriate.

Preparations for oral administration can be suitably formulated to give controlled release of the active compound or prodrug, as is well known.

For buccal administration, the compositions may take the form of tablets or lozenges formulated in the conventional manner.

For rectal and vaginal routes of administration, the active compound(s) can be formulated as solutions (for retention enemas), suppositories, or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant(e.g., dichlorodifluoromethane, trichlorofluoromethane, dichlorotetrafluoroethane, fluorocarbons, carbon dioxide, or other suitable gas). In the case of a pressurized aerosol, the dosage unit can be determined by providing a valve to deliver a metered amount. Capsules and cartridges for use in an inhaler or insufflator (for example, capsules and cartridges comprised of gelatin) can be formulated containing a powder mix of the compound and a suitable powder base such as lactose or starch.

The pharmaceutical compositions can be in the form of a sterile injectable aqueous or oleaginous suspension. This suspension can be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that can be employed are water, Ringer's solution, and isotonic sodium chloride solution. The 2,4-pyrimidinediamine compounds may also be administered in the form of suppositories for rectal or urethral administration of the drug. In particular embodiments, the compounds can be formulated as urethral suppositories, for example, for use in the treatment of fertility conditions, particularly in males (e.g., for the treatment of testicular dysfunction).

According to the invention, 2,4-pyrimidinediamine compounds can be used for manufacturing a composition or medicament, including medicaments suitable for rectal or urethral administration. The invention also relates to methods for manufacturing compositions including 2,4-pyrimidinediamine compounds in a form that is suitable for urethral or rectal administration, including suppositories.

For topical use, creams, ointments, jellies, gels, solutions, suspensions, etc., containing the 2,4-pyrimidinediamine compounds can be employed. In certain embodiments, the 2,4-pyrimidinediamine compounds can be formulated for topical administration with polyethylene glycol (PEG). These formulations may optionally comprise additional pharmaceutically acceptable ingredients such as diluents, stabilizers, and/or adjuvants. In particular embodiments, the topical formulations are formulated for the treatment of allergic conditions and/or skin conditions including psoriasis, contact dermatitis, and atopic dermatitis, among others described herein.

According to the invention, 2,4-pyrimidinediamine compounds can be used for manufacturing a composition or medicament, including medicaments suitable for topical administration. The invention also relates to methods for manufacturing compositions including 2,4-pyrimidinediamine compounds in a form that is suitable for topical administration.

According to the present invention, 2,4-pyrimidinediamine compounds can also be delivered by any of a variety of inhalation devices and methods known in the art, including, for example: U.S. Pat. Nos. 6,241,969; 6,060,069; 6,238,647; 6,335,316; 5,364,838; 5,672,581; WO96/32149; WO95/24183; U.S. Pat. Nos. 5,654,007; 5,404,871; 5,672,581; 5,743,250; 5,419,315; 5,558,085; WO98/33480; U.S. Pat. Nos. 5,364,833; 5,320,094; 5,780,014; 5,658,878; 5,518,998; 5,506,203; 5,661,130; 5,655,523; 5,645,051; 5,622,166; 5,577,497; 5,492,112; 5,327,883; 5,277,195; U.S. Pat. App. No. 20010041190; U.S. Pat. App. No. 20020006901; and U.S. Pat. App. No. 20020034477.

Included among the devices which can be used to administer particular examples of the 2,4-pyrimidinediamine compounds are those well-known in the art, such as metered dose inhalers, liquid nebulizers, dry powder inhalers, sprayers, thermal vaporizers, and the like. Other suitable technology for administration of particular 2,4-pyrimidinediamine compounds includes electrohydrodynamic aerosolizers.

In addition, the inhalation device is preferably practical, in the sense of being easy to use, small enough to carry conveniently, capable of providing multiple doses, and durable. Some specific examples of commercially available inhalation devices are Turbohaler (Astra, Wilmington, Del.), Rotahaler (Glaxo, Research Triangle Park, NC), Diskus (Glaxo, Research Triangle Park, NC), the Ultravent nebulizer (Mallinckrodt), the Acorn II nebulizer (Marquest Medical Products, Totowa, N.J.) the Ventolin metered dose inhaler (Glaxo, Research Triangle Park, NC), and the like. In one embodiment, 2,4-pyrimidinediamine compounds can be delivered by a dry powder inhaler or a sprayer.

As those skilled in the art will recognize, the formulation of 2,4-pyrimidinediamine compounds, the quantity of the formulation delivered, and the duration of administration of a single dose depend on the type of inhalation device employed as well as other factors. For some aerosol delivery systems, such as nebulizers, the frequency of administration and length of time for which the system is activated will depend mainly on the concentration of 2,4-pyrimidinediamine compounds in the aerosol. For example, shorter periods of administration can be used at higher concentrations of 2,4-pyrimidinediamine compounds in the nebulizer solution. Devices such as metered dose inhalers can produce higher aerosol concentrations and can be operated for shorter periods to deliver the desired amount of 2,4-pyrimidinediamine compounds in some embodiments. Devices such as dry powder inhalers deliver active agent until a given charge of agent is expelled from the device. In this type of inhaler, the amount of 2,4-pyrimidinediamine compounds in a given quantity of the powder determines the dose delivered in a single administration. The formulation of 2,4-pyrimidinediamine is selected to yield the desired particle size in the chosen inhalation device.

Formulations of 2,4-pyrimidinediamine compounds for administration from a dry powder inhaler may typically include a finely divided dry powder containing 2,4-pyrimidinediamine compounds, but the powder can also include a bulking agent, buffer, carrier, excipient, another additive, or the like. Additives can be included in a dry powder formulation of 2,4-pyrimidinediamine compounds, for example, to dilute the powder as required for delivery from the particular powder inhaler, to facilitate processing of the formulation, to provide advantageous powder properties to the formulation, to facilitate dispersion of the powder from the inhalation device, to stabilize to the formulation (e.g., antioxidants or buffers), to provide taste to the formulation, or the like. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; and the like.

The present invention also relates to a pharmaceutical composition including 2,4-pyrimidinediamine compounds suitable for administration by inhalation. According to the invention, 2,4-pyrimidinediamine compounds can be used for manufacturing a composition or medicament, including medicaments suitable for administration by inhalation. The invention also relates to methods for manufacturing compositions including 2,4-pyrimidinediamine compounds in a form that is suitable for administration, including administration by inhalation. For example, a dry powder formulation can be manufactured in several ways, using conventional techniques, such as described in any of the publications mentioned above and incorporated expressly herein by reference, and, for example, Baker, et al., U.S. Pat. No. 5,700,904, the entire disclosure of which is incorporated expressly herein by reference. Particles in the size range appropriate for maximal deposition in the lower respiratory tract can be made by micronizing, milling, or the like. And a liquid formulation can be manufactured by dissolving the 2,4-pyrimidinediamine compounds in a suitable solvent, such as water, at an appropriate pH, including buffers or other excipients.

Pharmaceutical compositions comprising the 2,4-pyrimidinediamine compounds described herein (or prodrugs thereof) can be manufactured by means of conventional mixing, dissolving, granulating, dragee-making levigating, emulsifying, encapsulating, entrapping, or lyophilization processes. The compositions can be formulated in conventional manner using one or more physiologically acceptable carriers, diluents, excipients, or auxiliaries which facilitate processing of the active compounds into preparations which can be used pharmaceutically.

For ocular administration, the 2,4-pyrimidinediamine compound(s) or prodrug(s) can be formulated as a solution, emulsion, suspension, etc., suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

For prolonged delivery, the 2,4-pyrimidinediamine compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives (e.g., as a sparingly soluble salt). Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in, for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device can be accompanied by instructions for administration.

The 2,4-pyrimidinediamine compound(s) or prodrug(s) described herein, or compositions thereof, will generally be used in an amount effective to achieve the intended result, for example, in an amount effective to treat or prevent the particular condition being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack or a reduction in the frequency or severity of asthmatic episodes. As another specific example, therapeutic benefit in the context of transplantation rejection includes the ability to alleviate an acute rejection episode, such as, for example, HVGR or GVHR, or the ability to prolong the time period between onset of acute rejection episodes and/or onset of chronic rejection. Therapeutic benefit also includes halting or slowing the progression of the disease, regardless of whether improvement is realized.

The amount of compound administered will depend upon a variety of factors, including, for example, the particular condition being treated, the mode of administration, the severity of the condition being treated, the age and weight of the patient, the bioavailability of the particular active compound. Determination of an effective dosage is well within the capabilities of those skilled in the art.

As known by those of skill in the art, the preferred dosage of 2,4-pyrimidinediamine compounds will also depend on the age, weight, general health, and severity of the condition of the individual being treated. Dosage may also need to be tailored to the sex of the individual and/or the lung capacity of the individual, where administered by inhalation. Dosage may also be tailored to individuals suffering from more than one condition or those individuals who have additional conditions which affect lung capacity and the ability to breathe normally, for example, emphysema, bronchitis, pneumonia, and respiratory infections. Dosage, and frequency of administration of the compounds or prodrugs thereof, will also depend on whether the compounds are formulated for treatment of acute episodes of a condition or for the prophylactic treatment of a disorder. For example, acute episodes of allergic conditions, including allergy-related asthma, transplant rejection, etc. A skilled practitioner will be able to determine the optimal dose for a particular individual.

For prophylactic administration, the compound can be administered to a patient at risk of developing one of the previously described conditions. For example, if it is unknown whether a patient is allergic to a particular drug, the compound can be administered prior to administration of the drug to avoid or ameliorate an allergic response to the drug. Alternatively, prophylactic administration can be applied to avoid the onset of symptoms in a patient diagnosed with the underlying disorder. For example, a compound can be administered to an allergy sufferer prior to expected exposure to the allergen. Compounds may also be administered prophylactically to healthy individuals who are repeatedly exposed to agents known to one of the above-described maladies to prevent the onset of the disorder. For example, a compound can be administered to a healthy individual who is repeatedly exposed to an allergen known to induce allergies, such as latex, in an effort to prevent the individual from developing an allergy. Alternatively, a compound can be administered to a patient suffering from asthma prior to partaking in activities which trigger asthma attacks to lessen the severity of, or avoid altogether, an asthmatic episode.

In the context of transplant rejection, the compound can be administered while the patient is not having an acute rejection reaction to avoid the onset of rejection and/or prior to the appearance of clinical indications of chronic rejection. The compound can be administered systemically to the patient as well as administered to the tissue or organ prior to transplanting the tissue or organ in the patient.

The amount of compound administered will depend upon a variety of factors, including, for example, the particular indication being treated, the mode of administration, whether the desired benefit is prophylactic or therapeutic, the severity of the indication being treated and the age and weight of the patient, and the bioavailability of the particular active compound. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an $IC_{50}$ of the particular compound as measured in as in vitro assay. Calculating dosages to achieve such circulating blood or serum concentrations taking into account the bioavailability of the particular compound is well within the capabilities of skilled artisans. For guidance, the reader is referred to Fingl & Woodbury, "General Principles," In: *Goodman and Gilman's The Pharmaceutical Basis of Therapeutics*, Chapter 1, pp. 1-46, latest edition, Pergamagon Press, and the references cited therein.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) *Allergy* 50(21Suppl):6-9, discussion 34-38 and Tumas et al., (2001), *J. Allergy Clin. Immunol.* 107(6):1025-1033. Suitable animal models of allergic rhinitis are described in Szelenyi et al., (2000), *Arzneimittelforschung* 50(11):1037-42; Kawaguchi et al., (1994), *Clin. Exp. Allergy* 24(3):238-244 and Sugimoto et al., (2000), *Immunopharmacology* 48(1):1-7. Suitable animal models of allergic conjunctivitis are described in Carreras et al., (1993), *Br. J. Ophthalmol.* 77(8):509-514; Saiga et al., (1992), *Ophthalmic Res.* 24(1):45-50; and Kunert et al., (2001), *Invest. Ophthalmol. Vis. Sci.* 42(11):2483-2489. Suitable animal models of systemic mastocytosis are described in O'Keefe et al., (1987), *J. Vet. Intern. Med.* 1(2):75-80 and Bean-Knudsen et al., (1989), *Vet. Pathol.* 26(1):90-92. Suitable animal models of hyper IgE syndrome are described in Claman et al., (1990), *Clin. Immunol. Immunopathol.* 56(1):46-53. Suitable animal models of B-cell lymphoma are described in Hough et al., (1998), *Proc. Natl. Acad. Sci. USA* 95:13853-13858 and Hakim et al., (1996), *J. Immunol.* 157(12):5503-5511. Suitable animal models of atopic disorders such as atopic dermatitis, atopic eczema, and atopic asthma are described in Chan et al., (2001), *J. Invest. Dermatol.* 117(4):977-983 and Suto et al., (1999), *Int. Arch. Allergy Immunol.* 120(Suppl 1):70-75. Suitable animal models of transplant rejection, such as models of HVGR, are described in O'Shea et al., (2004), *Nature Reviews Drug Discovery* 3:555-564; Cetkovic-Curlje & Tibbles, (2004), *Current Pharmaceutical Design* 10:1767-1784; and Chengelian et al., (2003), *Science* 302: 875-878. Ordinarily skilled artisans can routinely adapt such information to determine dosages suitable for human administration.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. For example, the compounds can be administered once per week, several times per week (e.g., every other day), once per day, or multiple times per day, depending upon, among other things, the mode of administration, the specific indication being treated, and the judgment of the prescribing physician. In cases of local administration or selective uptake, such as local topical administration, the effective local concentration of active compound(s) may not be related to plasma concentration.

Skilled artisans will be able to optimize effective local dosages without undue experimentation.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The foregoing disclosure pertaining to the dosage requirements for the 2,4-substituted pyrimidinediamine compounds is pertinent to dosages required for prodrugs, with the realization, apparent to the skilled artisan, that the amount of prodrug(s) administered will also depend upon a variety of factors, including, for example, the bioavailability of the particular prodrug(s) and the conversation rate and efficiency into active drug compound under the selected route of administration. Determination of an effective dosage of prodrug(s) for a particular use and mode of administration is well within the capabilities of those skilled in the art.

Effective dosages can be estimated initially from in vitro activity and metabolism assays. For example, an initial dosage of prodrug for use in animals can be formulated to achieve a circulating blood or serum concentration of the metabolite active compound that is at or above an $IC_{50}$ of the particular compound as measured in as in vitro assay, such as the in vitro CHMC or BMMC and other in vitro assays described in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004, and international application Serial No. PCT/US2004/24716 (WO005/016893). Calculating dosages to achieve such circulating blood or serum concentrations, taking into account the bioavailability of the particular prodrug via the desired route of administration, is well within the capabilities of skilled artisans. For guidance, the reader is referred to Fingl & Woodbury, "General Principles," In: *Goodman and Gilman's The Pharmaceutical Basis of Therapeutics*, Chapter 1, pp. 1-46, latest edition, Pagamonon Press, and the references cited therein.

Also provided are kits for administration of the 2,4-pyrimidinediamine, prodrug thereof, or pharmaceutical formulations comprising the compound that may include a dosage amount of at least one 2,4-pyrimidinediamine or a composition comprising at least one 2,4-pyrimidinediamine, as disclosed herein. Kits may further comprise suitable packaging and/or instructions for use of the compound. Kits may also comprise a means for the delivery of the at least one 2,4-pyrimidinediamine or compositions comprising at least one 2,4-pyrimidinediamine, such as an inhaler, spray dispenser (e.g., nasal spray), syringe for injection, or pressure pack for capsules, tables, suppositories, or other device as described herein.

Additionally, the compounds of the present invention can be assembled in the form of kits. The kit provides the compound and reagents to prepare a composition for administration. The composition can be in a dry or lyophilized form or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to, syringe, pipette, transdermal patch, or inhalant.

The kits may include other therapeutic compounds for use in conjunction with the compounds described herein. In one embodiment, the therapeutic agents are immunosuppressant or anti-allergan compounds. These compounds can be provided in a separate form or mixed with the compounds of the present invention.

The kits will include appropriate instructions for preparation and administration of the composition, side effects of the compositions, and any other relevant information. The instructions can be in any suitable format, including, but not limited to, printed matter, videotape, computer readable disk, or optical disc.

In one embodiment, this invention provides a kit comprising a compound selected from the compounds of the invention or a prodrug thereof, packaging, and instructions for use.

In another embodiment, this invention provides a kit comprising the pharmaceutical formulation comprising a compound selected from the compounds of the invention or a prodrug thereof and at least one pharmaceutically acceptable excipient, diluent, preservative, stabilizer, or mixture thereof, packaging, and instructions for use.

In another aspect of the invention, kits for treating an individual who suffers from or is susceptible to the conditions described herein are provided, comprising a container comprising a dosage amount of an 2,4-pyrimidinediamine or composition, as disclosed herein, and instructions for use. The container can be any of those known in the art and appropriate for storage and delivery of oral, intravenous, topical, rectal, urethral, or inhaled formulations.

Kits may also be provided that contain sufficient dosages of the 2,4-pyrimidinediamine or composition to provide effective treatment for an individual for an extended period, such as a week, 2 weeks, 3, weeks, 4 weeks, 6 weeks, or 8 weeks or more.

It will be appreciated by one of skill in the art that the embodiments summarized above may be used together in any suitable combination to generate additional embodiments not expressly recited above, and that such embodiments are considered to be part of the present invention.

F. General Synthesis of the Compounds of the Invention

The 2,4-pyrimidinediamine compounds and prodrugs of the invention can be synthesized via a variety of different synthetic routes using commercially available starting materials and/or starting materials prepared by conventional synthetic methods. Suitable exemplary methods that can be routinely adapted to synthesize the 2,4-pyrimidinediamine compounds and prodrugs of the invention are found in U.S. Pat. No. 5,958,935, the disclosure of which is incorporated herein by reference. Specific examples describing the synthesis of numerous 2,4-pyrimidinediamine compounds and prodrugs, as well as intermediates thereof, are described in copending U.S. application Ser. No. 10/355,543, filed Jan. 31, 2003 (US2004/0029902A1), the contents of which are incorporated herein by reference. Suitable exemplary methods that can be routinely used and/or adapted to synthesize active 2,4-pyrimidinediamine compounds can also be found in international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004, and international application Serial No. PCT/US2004/24716 (WO005/016893), the disclosures of which are incorporated herein by reference. All of the compounds described herein (including prodrugs) can be prepared by routine adaptation of these methods.

Specific exemplary synthetic methods for the 2,4-pyrimidinediamines described herein are also described in Examples 1 and 2 below. Those of skill in the art will also be able to readily adapt these examples for the synthesis of additional 2,4-pyrimidinediamines as described herein.

A variety of exemplary synthetic routes that can be used to synthesize the 2,4-pyrimidinediamine compounds of the invention are described in Schemes (I)-(VII), below. These methods can be routinely adapted to synthesize the 2,4-pyrimidinediamine compounds and prodrugs described herein.

In one exemplary embodiment, the compounds can be synthesized from substituted or unsubstituted uracils as illustrated in Scheme (I), below:

trifluoromethyl, a 50:50 mixture of 4N-substituted-4-pyrimidineamine A-4 and the corresponding 2N-substituted-2-pyrimidineamine is obtained. The regioselectivity of the reaction can also be controlled by adjusting the solvent and other synthetic conditions (such as temperature), as is well-known in the art.

The reactions depicted in Scheme (I) may proceed more quickly when the reaction mixtures are heated via microwave. When heating in this fashion, the following conditions can be used: heat to 175° C. in ethanol for 5-20 min. in a Smith Reactor (Personal Chemistry, Uppsala, Sweden) in a sealed tube (at 20 bar pressure).

The uracil A-1 starting materials can be purchased from commercial sources or prepared using standard techniques

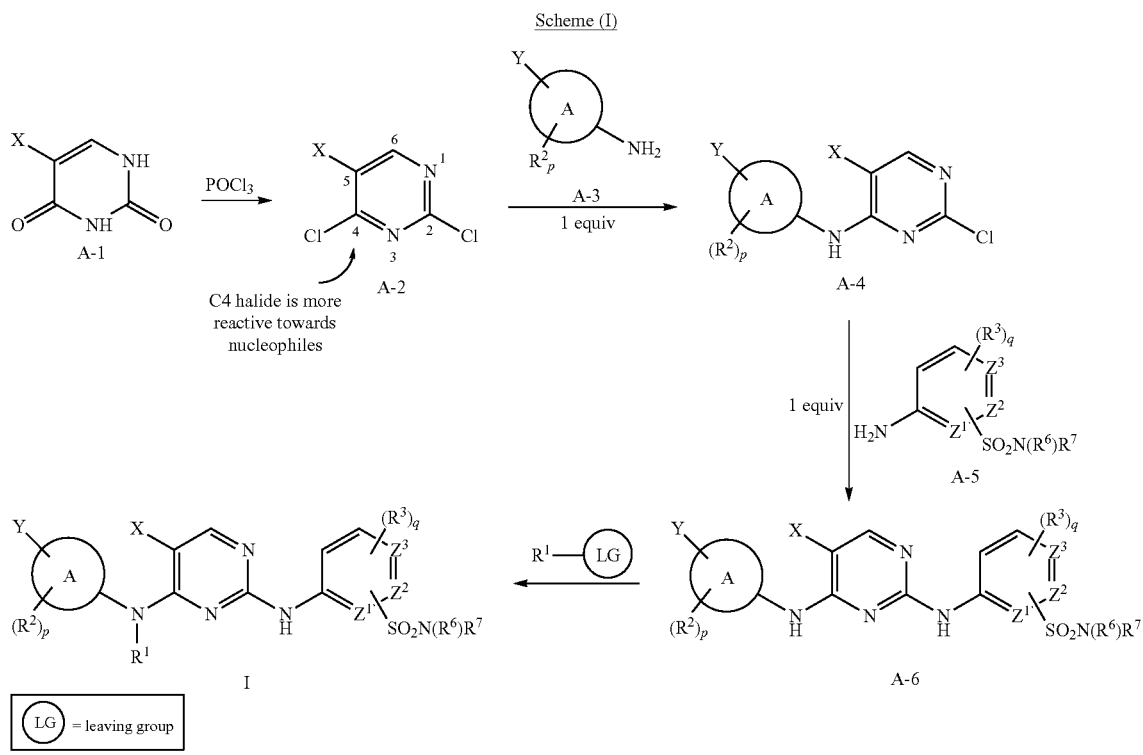

In Scheme (I), ring A, $R^1$, $(R^2)_p$, $(R^3)_q$, $R^6$, $R^7$, X, Y, $Z^1$, $Z^2$, and $Z^3$ are as defined herein.

According to Scheme (I), uracil A-1 is dihalogenated at the 2- and 4-positions using a standard halogenating agent such as $POCl_3$ (or other standard halogenating agent) under standard conditions to yield 2,4-dichloropyrimidine A-2. Depending upon the X substituent, in pyrimidinediamine A-2, the chloride at the C4 position is more reactive towards nucleophiles than the chloride at the C2 position. This differential reactivity can be exploited to synthesize 2,4-pyrimidinediamines I by reacting 2,4-dichloropyrimidine A-2 first with one equivalent of amine A-3, yielding 4N-substituted-2-chloro-4-pyrimidineamine A-4, and then with amine A-5, yielding a 2,4-pyrimidinediamine derivative A-6, where N4 nitrogen can be selectively alkylated to give compounds of formula I.

Typically, the C4 halide is more reactive towards nucleophiles, as illustrated in Scheme (I). However, as will be recognized by skilled artisans, the identity of the X substituent may alter this reactivity. For example, when X is of organic chemistry. Commercially available uracils that can be used as starting materials in Scheme (I) include, by way of example and not limitation, uracil (Aldrich #13,078-8; CAS Registry 66-22-8); 5-bromouracil (Aldrich #85,247-3; CAS Registry 51-20-7; 5-fluorouracil (Aldrich #85,847-1; CAS Registry 51-21-8); 5-iodouracil (Aldrich #85,785-8; CAS Registry 696-07-1); 5-nitrouracil (Aldrich #85,276-7; CAS Registry 611-08-5); and 5-(trifluoromethyl)-uracil (Aldrich #22,327-1; CAS Registry 54-20-6). Additional 5-substituted uracils are available from General Intermediates of Canada, Inc., Edmonton, CA, and/or Interchim, Cedex, France, or can be prepared using standard techniques. Myriad textbook references teaching suitable synthetic methods are provided infra.

Amines A-3 and A-5 can be purchased from commercial sources or, alternatively, can be synthesized using standard techniques. For example, suitable amines can be synthesized from nitro precursors using standard chemistry. Specific exemplary reactions are provided in the Examples section. See also Vogel, 1989, *Practical Organic Chemistry*, Addison Wesley Longman, Ltd. and John Wiley & Sons, Inc.

Skilled artisans will recognize that in some instances, amines A-3 and A-5 and/or substituent X on uracil A-1 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts, *Protective Groups in Organic Synthesis*, 3d Edition, John Wiley & Sons, Inc., New York (1999) and the references cited therein (hereinafter "Greene & Wuts").

Thus, "protecting group" refers to a group of atoms that, when attached to a reactive functional group in a molecule, mask, reduce or prevent the reactivity of the functional group. Typically, a protecting group can be selectively removed as desired during the course of a synthesis. Examples of protecting groups can be found in Greene and Wuts, as mentioned above, and, additionally, in Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC"), and the like. Representative hydroxyl protecting groups include, but are not limited to, those where the hydroxyl group is either acylated to form acetate and benzoate esters or alkylated to form benzyl and trityl ethers, as well as alkyl ethers, tetrahydropyranyl ethers, trialkylsilyl ethers (e.g., TMS or TIPPS groups), aryl silyl ethers (e.g., triphenylsilyl ether), mixed alkyl and aryl substituted silyl ethers, and allyl ethers.

A specific embodiment of Scheme (I) utilizing 5-fluorouracil (Aldrich #32,937-1) as a starting material is illustrated in Scheme (Ia), below:

Scheme (Ia)

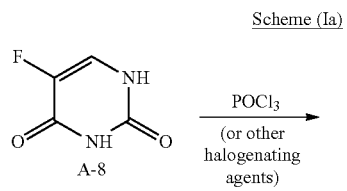

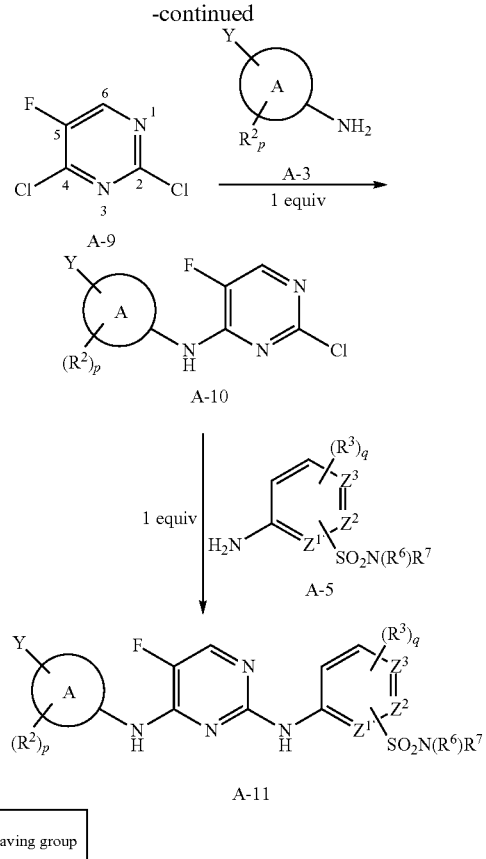

In Scheme (Ia), ring A, $(R^2)_p$, $(R^3)_q$, $R^6$, $R^7$, Y, $Z^1$, $Z^2$, and $Z^3$ are as previously defined for Scheme (I). Asymmetric 2N,4N-disubstituted-5-fluoro-2,4-pyrimidinediamine A-11 can be obtained by reacting 2,4-dichloro-5-fluoropyrimidine A-9 with one equivalent of amine A-3 (to yield 2-chloro-N4-substituted-5-fluoro-4-pyrimidineamine A-10) followed by one or more equivalents of amine A-5.

In another exemplary embodiment, the 2,4-pyrimidinediamine compounds of the invention can be synthesized from substituted or unsubstituted cytosines as illustrated in Schemes (IIa) and (IIb), below:

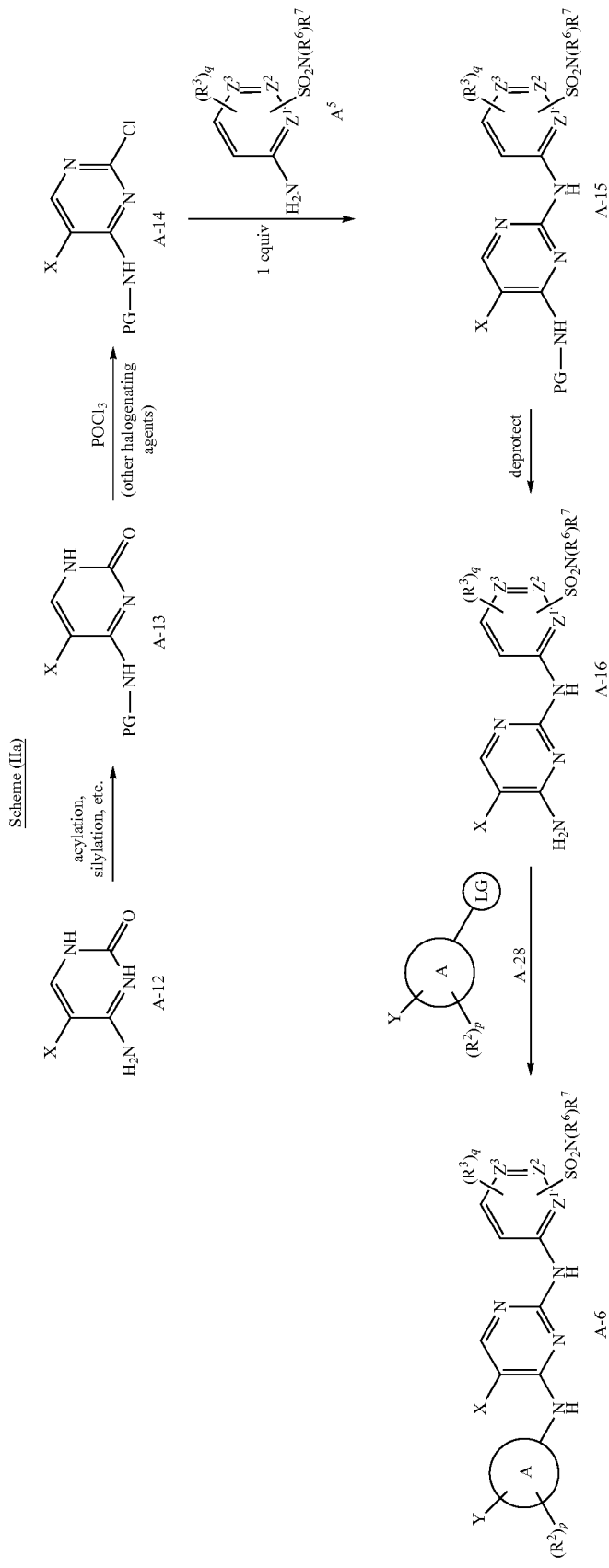

Scheme (IIb)

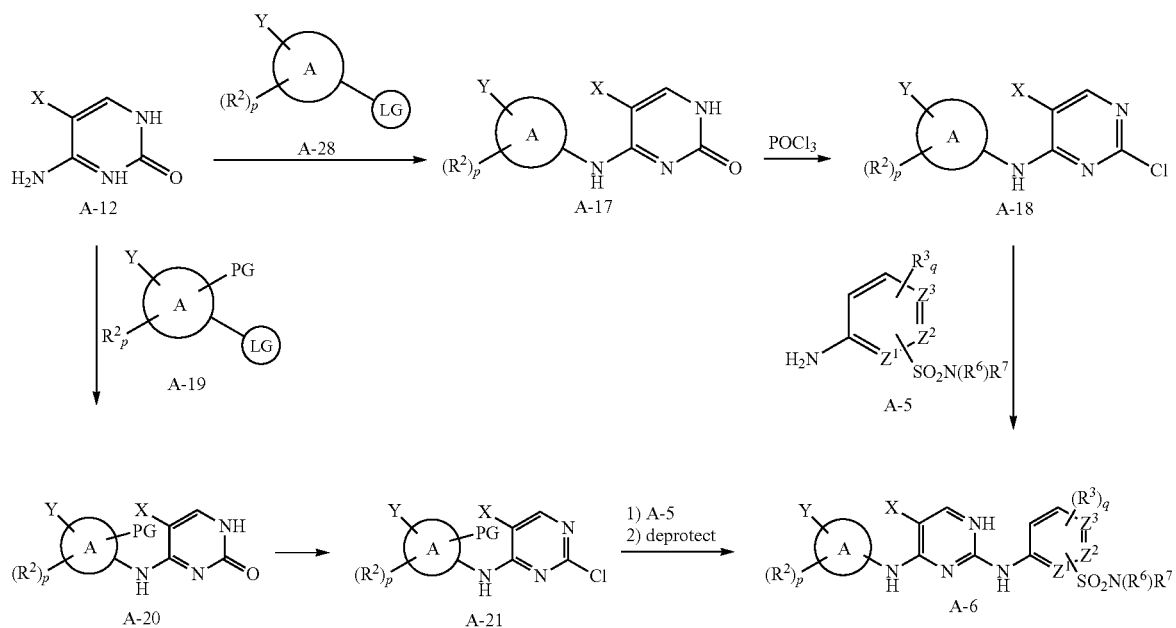

In Schemes (IIa) and (IIb), ring A, $(R^2)_p$, $(R^3)_q$, $R^6$, $R^7$, X, Y, $Z^1$, $Z^2$, and $Z^3$ are as previously defined for Scheme (I) and PG represents a protecting group. Referring to Scheme (IIa), the C4 exocyclic amine of cytosine A-12 is first protected with a suitable protecting group PG to yield N4-protected cytosine A-13. For specific guidance regarding protecting groups useful in this context, see Vorbrüggen and Ruh-Pohlenz, 2001, *Handbook of Nucleoside Synthesis*, John Wiley & Sons, NY, pp. 1-631 ("Vorbrüggen"). Protected cytosine A-13 is halogenated at the C2 position using a standard halogenation reagent under standard conditions to yield 2-chloro-4N-protected-4-pyrimidineamine A-14. Reaction with amine A-5 gives A-15, which, on deprotection of the C4 exocyclic amine, gives A-16. Reaction of A-16 with electrophile A-28 yields 2,4-pyrimidinediamine derivative A-6.

Alternatively, referring to Scheme (IIb), cytosine A-12 can be reacted with electrophile A-28 or A-19 to yield N4-substituted cytosine A-17 or A-20, respectively. These substituted cytosines may then be halogenated as previously described, deprotected (in the case of N4-substituted cytosine A-20) and reacted with amine A-5 to yield a 2,4-pyrimidinediamine A-6.

Commercially-available cytosines that can be used as starting materials in Schemes (IIa) and (IIb) include, but are not limited to, cytosine (Aldrich #14,201-8; CAS Registry 71-30-7); $N^4$-acetylcytosine (Aldrich #37,791-0; CAS Registry 14631-20-0); 5-fluorocytosine (Aldrich #27,159-4; CAS Registry 2022-85-7); and 5-(trifluoromethyl)-cytosine. Other suitable cytosines useful as starting materials in Schemes (IIa) are available from General Intermediates of Canada, Inc., Edmonton, CA, and/or Interchim, Cedex, France, or can be prepared using standard techniques. Myriad textbook references teaching suitable synthetic methods are provided infra.

In still another exemplary embodiment, the 2,4-pyrimidinediamine compounds of the invention can be synthesized from substituted or unsubstituted 2-amino-4-pyrimidinols as illustrated in Scheme (III), below:

Scheme (III)

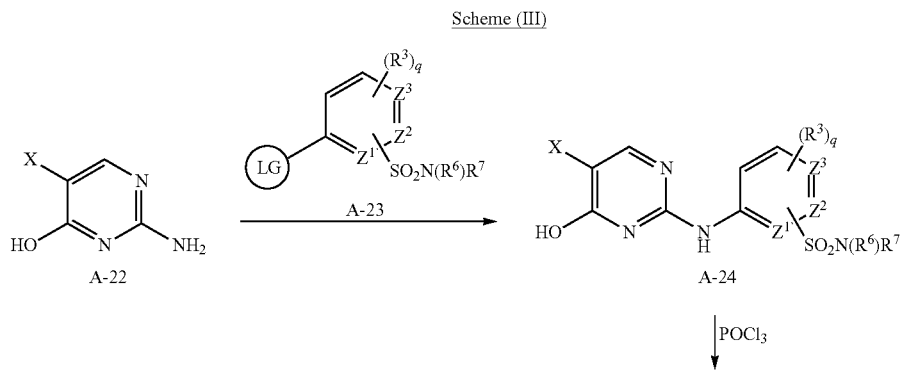

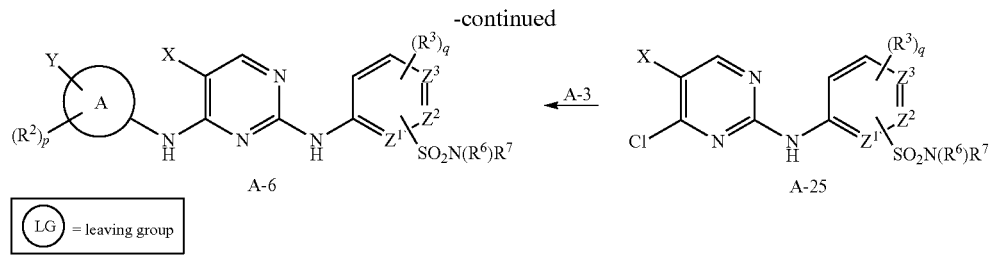

A-6

LG = leaving group

In Scheme (III), ring A, $(R^2)_p$, $(R^3)_q$, $R^6$, $R^7$, X, Y, $Z^1$, $Z^2$, and $Z^3$ are as previously defined for Scheme (I) and LG is a leaving group as discussed in more detail in connection with Scheme IV, infra. Referring to Scheme (III), 2-amino-4-pyrimidinol A-22 is reacted with arylating agent A-23 to yield N2-substituted-4-pyrimidinol A-24, which is then halogenated as previously described to yield N2-substituted-4-halo-2-pyrimidineamine A-25. Further reaction with amine A-3 affords a 2,4-pyrimidinediamine derivative A-6.

Suitable commercially-available 2-amino-4-pyrimidinols A-22 that can be used as starting materials in Scheme (III) are available from General Intermediates of Canada, Inc., Edmonton, CA, and/or Interchim, Cedex, France, or can be prepared using standard techniques. Myriad textbook references teaching suitable synthetic methods are provided infra.

Alternatively, the 2,4-pyrimidinediamine compounds of the invention can be prepared from substituted or unsubstituted 4-amino-2-pyrimidinols as illustrated in Scheme (IV), below:

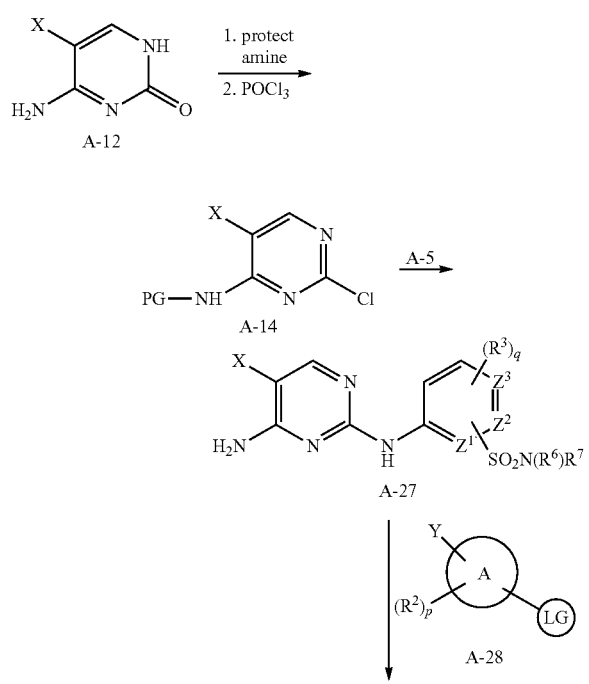

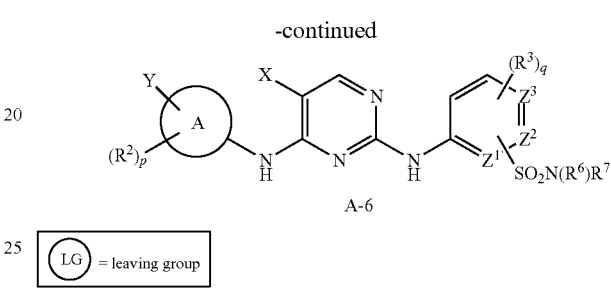

A-6

LG = leaving group

In Scheme (IV), ring A, $(R^2)_p$, $(R^3)_q$, $R^6$, $R^7$, X, Y, $Z^1$, $Z^2$, and $Z^3$ are as previously defined for Scheme (I). Referring to Scheme (IV), the C4 exocyclic amine of cytosine A-12 is first protected with a suitable protecting group PG and the resultant 2-hydroxy cytosine is halogenated at the C2 position using a standard halogenation reagent under standard conditions to yield 2-chloro-4N-protected-4-pyrimidineamine A-14. Reaction of A-14 with amine A-5 yields N2-substituted-2,4-pyrimidinediamine A-27. Subsequent reaction with compound A-28, which includes a suitable leaving group, yields a 2,4-pyrimidinediamine derivative A-6. Compound A-28 may include virtually any leaving group that can be displaced by the C4-amino of N2-substituted-2,4-pyrimidinediamine A-27. Suitable leaving groups include, but are not limited to, halogens, methanesulfonyloxy (mesyloxy; "OMs"), trifluoromethanesulfonyloxy ("OTf") and p-toluenesulfonyloxy (tosyloxy; "OTs"), benzene sulfonyloxy ("besylate"), and m-nitro benzene sulfonyloxy ("nosylate"). Other suitable leaving groups will be apparent to those of skill in the art.

Substituted 4-amino-2-pyrimidinol starting materials can be obtained commercially or synthesized using standard techniques. Myriad textbook references teaching suitable synthetic methods are provided infra.

In still another exemplary embodiment, the 2,4-pyrimidinediamine compounds of the invention can be prepared from 2-chloro-4-aminopyrimidines or 2-amino-4-chloropyrimidines as illustrated in Scheme (V), below:

Scheme (V)

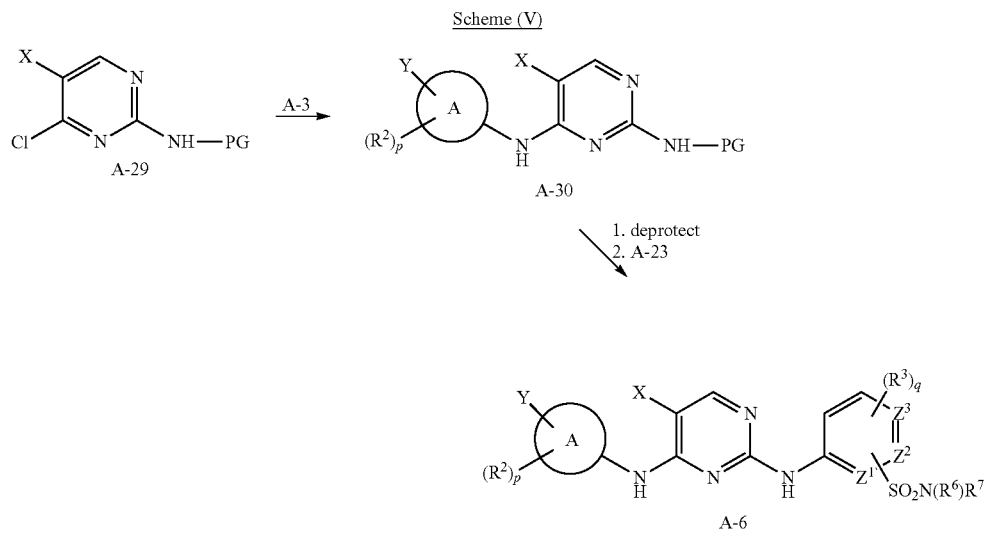

In Scheme (V), ring A, $(R^2)_p$, $(R^3)_q$, $R^6$, $R^7$, X, Y, $Z^1$, $Z^2$, and $Z^3$ are as defined for Scheme (I) and leaving group is as defined for Scheme (IV). Referring to Scheme (V), protected-2-amino-4-chloropyrimidine A-29 is reacted with amine A-3 to yield 4N-substituted-2,4-pyrimidinediamine A-30, which, following deprotection and reaction with compound A-23, yields a N2,N4-2,4-pyrimidinediamine derivative A-6. Alternatively, 2-chloro-4-amino-pyrimidine A-31 can be reacted with compound A-28 to give compound A-32, which, on reaction with amine A-5, yields A-6.

A variety of pyrimidines A-29 and A-31 suitable for use as starting materials in Scheme (V) are commercially available from General Intermediates of Canada, Inc., Edmonton, CA, and/or Interchim, Cedex, France, or can be prepared using standard techniques. Myriad textbook references teaching suitable synthetic methods are provided infra.

Alternatively, 4-chloro-2-pyrimidineamines A-29 can be prepared as illustrated in Scheme (Va):

Scheme (Va)

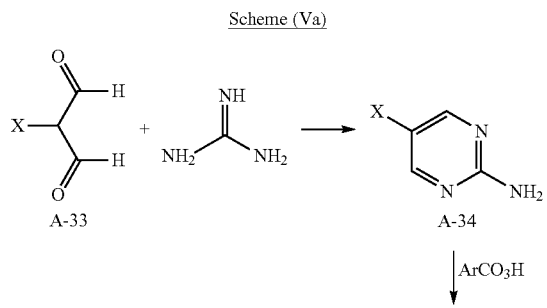

↓ ArCO₃H

-continued

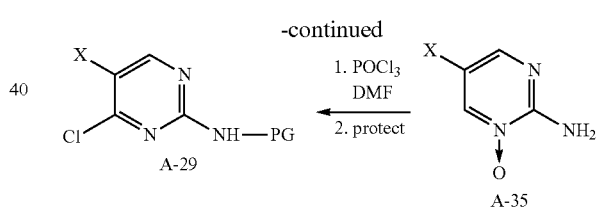

In Scheme (Va), X is as previously defined for Scheme I. In Scheme (Va), dialdehyde A-33 is reacted with guanidine to yield 2-pyrimidineamine A-34. Reaction with a peracid such as m-chloroperbenzoic acid, trifluoroperacetic acid, or urea hydrogen peroxide complex yields N-oxide A-35, which is then halogenated and the amine protected to give 4-chloro-2-pyrimidineamine A-29. Corresponding 4-halo-2-pyrimidineamines can be obtained by using suitable halogenation reagents.

In yet another exemplary embodiment, the 2,4-pyrimidinediamine compounds of the invention can be prepared from substituted or unsubstituted uridines as illustrated in Scheme (VI), below:

Scheme (VI)

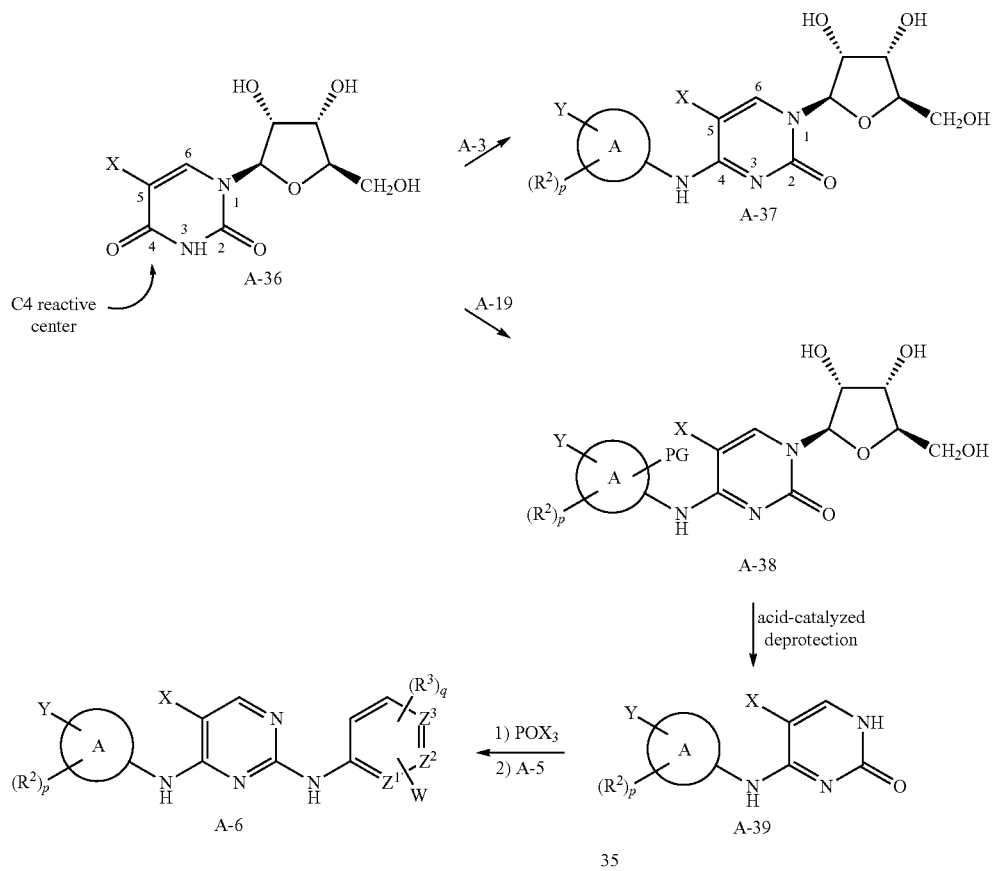

In Scheme (VI), ring A, $(R^2)_p$, $(R^3)_q$, $R^6$, $R^7$, X, Y, $Z^1$, $Z^2$, and $Z^3$ are as previously defined for Scheme (I) and PG represents a protecting group, as discussed in connection with Scheme (IIb). According to Scheme (VI), uridine A-36 has a C4 reactive center such that reaction with amine A-3 or protected amine A-19 yields N4-substituted cytidine A-37 or A-38, respectively. Acid-catalyzed deprotection of N4-substituted A-37 or A-38 (when "PG" represents an acid-labile protecting group) yields N4-substituted cytosine A-39, which can be subsequently halogenated at the C2-position and reacted with amine A-5 to yield a 2,4-pyrimidinediamine derivative A-6.

Cytidines may also be used as starting materials in an analogous manner, as illustrated in Scheme (VII), below:

Scheme (VII)

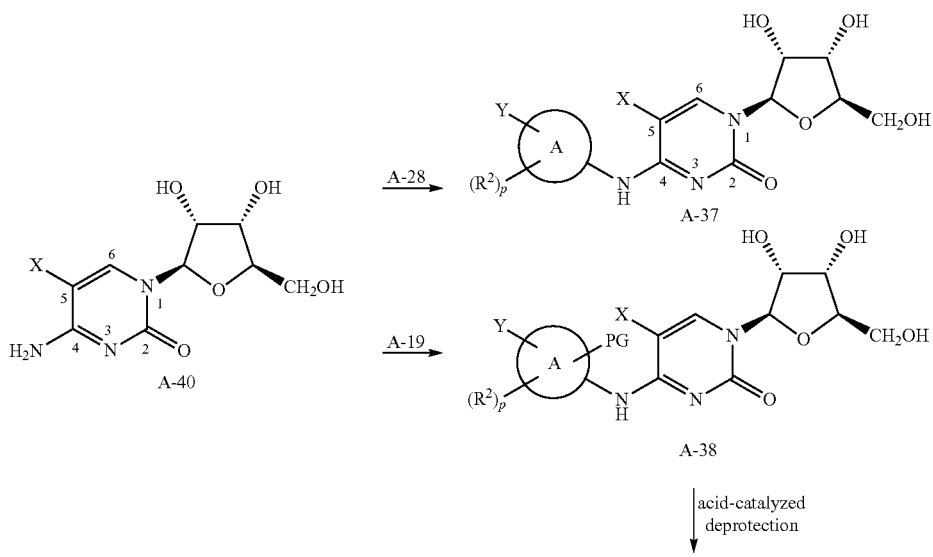

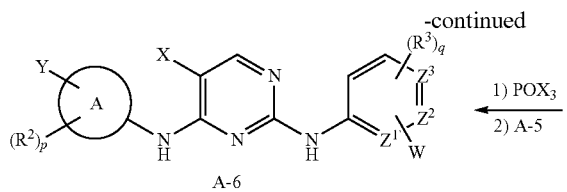
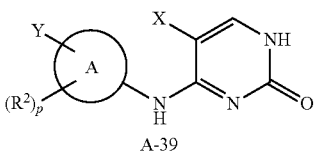

In Scheme (VII), ring A, $(R^2)_p$, $(R^3)_q$, $R^6$, $R^7$, X, Y, $Z^1$, $Z^2$, and $Z^3$ are as previously defined in Scheme (I) and PG represents a protecting group as discussed above. Referring to Scheme (VII), cytidine A-40 has a C4 reactive amine such that reaction with electrophile A-28 or A-19 yields N4-substituted cytidine A-37 or A-38, respectively. These cytidines A-37 and A-38 are then treated as previously described for Scheme (VI) to yield a 2,4-pyrimidinediamine derivative A-6.

Although Schemes (VI) and (VII) are exemplified with ribosylnucleosides, skilled artisans will appreciate that the corresponding 2'-deoxyribo and 2',3'-dideoxyribo nucleosides, as well as nucleosides including sugars or sugar analogs other than ribose would also work.

Numerous uridines and cytidines useful as starting materials in Schemes (VI) and (VII) are known in the art and include, by way of example and not limitation, 5-trifluoromethyl-2'-deoxycytidine (Chem. Sources #ABCR F07669; CAS Registry 66,384-66-5); 5-bromouridine (Chem. Sources Int'l 2000; CAS Registry 957-75-5); 5-iodo-2'-deoxyuridine (Aldrich #1-775-6; CAS Registry 54-42-2); 5-fluorouridine (Aldrich #32,937-1; CAS Registry 316-46-1); 5-iodouridine (Aldrich #85,259-7; CAS Registry 1024-99-3); 5-(trifluoromethyl)uridine (Chem. Sources Int'l 2000; CAS Registry 70-00-8); and 5-trifluoromethyl-2'-deoxyuridine (Chem. Sources Int'l 2000; CAS Registry 70-00-8). Additional uridines and cytidines that can be used as starting materials in Schemes (VI) and (VII) are available from General Intermediates of Canada, Inc., Edmonton, CA, and/or Interchim, Cedex, France, or can be prepared using standard techniques. Myriad textbook references teaching suitable synthetic methods are provided infra.

Although many of the synthetic schemes discussed above do not illustrate the use of protecting groups, skilled artisans will recognize that in some instances certain substituents, such as, for example, $R^2$ and/or $R^4$, may include functional groups requiring protection. The exact identity of the protecting group used will depend upon, among other things, the identity of the functional group being protected and the reaction conditions used in the particular synthetic scheme and will be apparent to those of skill in the art. Guidance for selecting protecting groups and their attachment and removal suitable for a particular application can be found, for example, in Greene & Wuts, supra.

Prodrugs as described herein can be prepared by routine modification of the above-described methods. Alternatively, such prodrugs can be prepared by reacting a suitably protected 2,4-pyrimidinediamine 6 with a suitable progroup. Conditions for carrying out such reactions and for deprotecting the product to yield a prodrugs as described herein are well-known.

Myriad references teaching methods useful for synthesizing pyrimidines generally, as well as starting materials described in Schemes (I)-(VII), are known in the art. For specific guidance, the reader is referred to Brown, D. J., "The Pyrimidines", in *The Chemistry of Heterocyclic Compounds*, Volume 16 (Weissberger, A., Ed.), 1962, Interscience Publishers, (A Division of John Wiley & Sons), New York ("Brown I"); Brown, D. J., "The Pyrimidines", in *The Chemistry of Heterocyclic Compounds*, Volume 16, Supplement I (Weissberger, A. and Taylor, E. C., Ed.), 1970, Wiley-Interscience, (A Division of John Wiley & Sons), New York ("Brown II"); Brown, D. J., "The Pyrimidines", in *The Chemistry of Heterocyclic Compounds*, Volume 16, Supplement II (Weissberger, A. and Taylor, E. C., Ed.), 1985, An Interscience Publication (John Wiley & Sons), New York ("Brown III"); Brown, D. J., "The Pyrimidines" in *The Chemistry of Heterocyclic Compounds*, Volume 52 (Weissberger, A. and Taylor, E. C., Ed.), 1994, John Wiley & Sons, Inc., New York, pp. 1-1509 ("Brown IV"); Kenner, G. W. and Todd, A., in *Heterocyclic Compounds*, Volume 6, (Elderfield, R. C., Ed.), 1957, John Wiley, New York, Chapter 7 (pyrimidines); Paquette, L. A., *Principles of Modern Heterocyclic Chemistry*, 1968, W. A. Benjamin, Inc., New York, pp. 1-401 (uracil synthesis pp. 313, 315; pyrimidinediamine synthesis pp. 313-316; amino pyrimidinediamine synthesis pp. 315); Joule, J. A., Mills, K. and Smith, G. F., *Heterocyclic Chemistry*, $3^{rd}$ Edition, 1995, Chapman and Hall, London, UK, pp. 1-516; Vorbrüggen, H. and Ruh-Pohlenz, C., *Handbook of Nucleoside Synthesis*, John Wiley & Sons, New York, 2001, pp. 1-631 (protection of pyrimidines by acylation pp. 90-91; silylation of pyrimidines pp. 91-93); Joule, J. A., Mills, K. and Smith, G. F., *Heterocyclic Chemistry*, $4^{th}$ Edition, 2000, Blackwell Science, Ltd, Oxford, UK, pp. 1-589; and *Comprehensive Organic Synthesis, Volumes* 1-9 (Trost, B. M. and Fleming, I., Ed.), 1991, Pergamon Press, Oxford, UK.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, triethylamine, ammonia, etc.).

The 2,4-pyrimidinediamine compounds and prodrugs thereof, as well as the salts thereof, may also be in the form of hydrates, solvates and N-oxides, as are well-known in the art.

In another embodiment, this invention provides a compound, or stereoisomer, tautomer, prodrug, solvate, or pharmaceutically acceptable salt thereof, selected from Tables I and II.

V. EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

In the examples below as well as throughout the application, the following abbreviations have the following meanings. If not defined, the terms have their generally accepted meanings.

TFA=trifluoroacetic acid
mL=milliliter
mmol=millimole
ng=nanogram
nM=nanomolar
DMSO=dimethylsulfoxie
s=singlet
d=doublet
t=triplet
q=quartet
m=multiplet
dd=double doublet
br=broad
MS=mass spectrum
LC=liquid chromatography
Pd/C=palladium over carbon
HCl=hydrochloric acid
uL=microliter
mg=milligram
psi=pound per square inch
$NH_4Cl$=ammonium chloride
N=normal
μM=micromolar
rpm=revolutions per minute
rt=room temperature
iPrOH=isopropanol
aq.=aqueous Example 1

(I-4): N2-(3-Aminosulfonylphenyl)-5-fluoro-N4-[4-(prop-2-ynylaminosulfonylmethyl)phenyl]-2,4-pyrimidinediamine To a cooled (0° C.) suspension of 4-nitrophenylmethanesulfonylchloride (0.510 g, 2.16 mmol) in ethyl acetate (3.0 mL) was added a solution of propargyl amine (1.0 mL, 14.5 mmol) in water (1.0 mL). The reaction mixture was stirred for 30 minutes and then diluted with ethyl acetate (30 mL) and washed with 1N HCl (10 mL), water (10 mL), and brine (10 mL). The organic layer was dried ($MgSO_4$), filtered, and concentrated in vacuo to provide 4-(prop-2-ynylaminosulfonylmethyl)nitrobenzene as a tan solid (0.437 g), which was used without further purification. $^1$HNMR ($CDCl_3$): δ 8.25 (d, J=8.7 Hz, 2H), 7.66 (d, J=8.7 Hz, 2H), 4.48 (s, 3H), 3.98 (dd, J=2.7 and 6.3 Hz, 2H), 2.48 (t, J=2.7 Hz, 1H); LCMS: purity: 99%; MS (m/e): 253 (M$^-$).

4-(Prop-2-ynylaminosulfonylmethyl)nitrobenzene (0.437 g, 1.72 mmol), iron (0.48 g, 8.6 mmol), and $NH_4Cl$ (0.24 g, 4.5 mmol) were vigorously stirred in ethanol:water (1:1, 40 mL) at 70° C. for 25 minutes. The reaction mixture was filtered hot through Celite and concentrated in vacuo. The residue was suspended in 10% 2N ammoniacal methanol in dichloromethane, sonicated, and filtered through Celite. Concentration gave 4-(Prop-2-ynylaminosulfonylmethyl) aniline as a brown oil which was purified by column chromatography (silica gel, dichloromethane ramped to methanol:dichloromethane (0.75:100)). $^1$H NMR (DMSO-$d_6$): δ 7.45 (t, J=5.4 Hz, 1H), 6.99 (d, J=8.1 Hz, 2H), 6.50 (d, J=8.1 Hz, 2H), 5.15 (s, 2H), 4.12 (s, 2H), 3.68 (dd, J=2.1 and 5.7 Hz, 2H), 3.31 (t, J=2.1 Hz, 1H); LCMS: purity: 97%; MS (m/e): 225 (MH$^+$).

4-(Prop-2-ynylaminosulfonylmethyl)aniline (0.353 g, 1.57 mmol) and 2,4-dichloro-5-fluoropyrimidine (0.471 g, 2.81 mmol) were stirred in methanol:water (4:1, 10 mL) at room temperature for 24 h. The reaction mixture was diluted

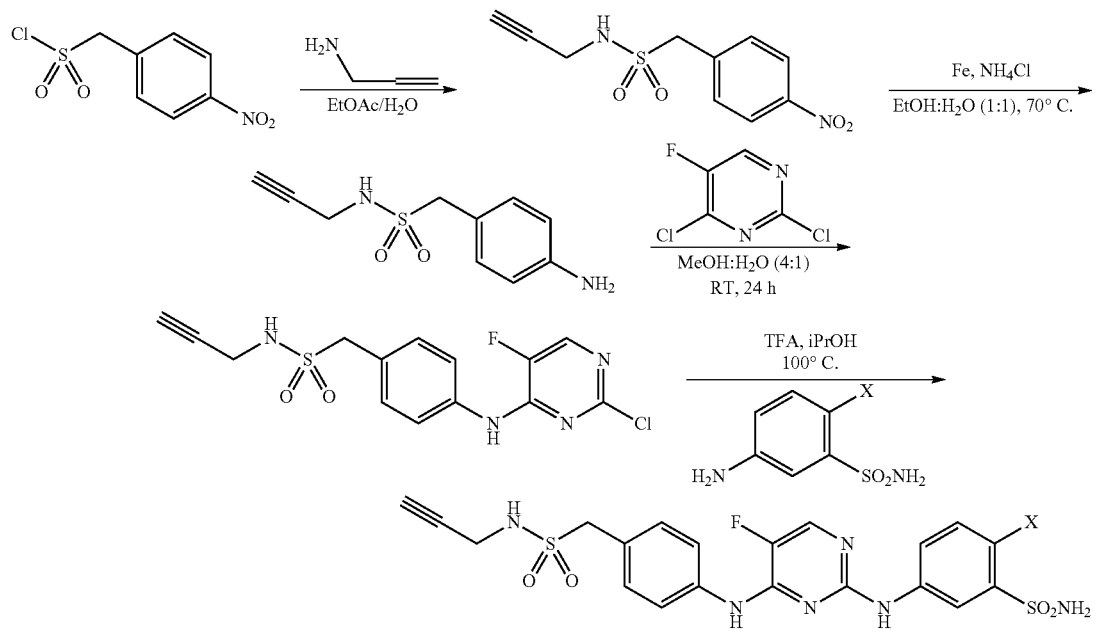

R932374 (X = H)
R932375 (X = Me)

with ethyl acetate (75 mL) and washed with 1N HCl (25 mL) and brine (10 mL). The organic layer was dried (MgSO$_4$), filtered, and concentrated in vacuo. The residue was purified by column chromatography (silica gel, dichloromethane ramped to methanol:dichloromethane (3:100)) to provide 2-chloro-5-fluoro-N4-[4-(prop-2-ynylaminosulfonylmethyl)phenyl]-4-pyrimidineamine as an off-white solid (0.255 g). $^1$H NMR (DMSO-d$_6$): δ 10.03 (s, 1H), 8.31 (d, J=3.0 Hz, 1H), 7.68-7.63 (m, 3H), 7.36 (d, J=8.4 Hz, 2H), 4.35 (s, 2H), 3.78 (dd, J=2.4 and 5.7 Hz, 2H), 3.34 (t, J=2.4 Hz, 1H); LCMS: purity: 90%; MS (m/e): 356 (MH$^+$).

2-Chloro-5-fluoro-N4-[4-(prop-2-ynylaminosulfonylmethyl)phenyl]-4-pyrimidineamine (34 mg, 0.096 mmol), 3-aminobenzenesulfonamide (33 mg, 0.19 mmol), and trifluoroacetic acid (11 µL, 0.14 mmol) were combined with iPrOH (0.40 mL) in a sealed vial and heated at 100° C. for 4 h. The reaction mixture was cooled to room temperature and diluted with 1N HCl (80 mL). The crude product was isolated by filtration. Further purified by column chromatography (silica gel, dichloromethane ramped to methanol:dichloromethane (3:100)) provided N2-(3-aminosulfonylphenyl)-5-fluoro-N4-[4-(prop-2-ynylaminosulfonylmethyl)phenyl]-2,4-pyrimidinediamine (I-4) as an off-white solid. $^1$H NMR (DMSO-d$_6$): δ 9.57 (s, 1H), 9.47 (s, 1H), 8.15-8.08 (m, 2H), 7.99-7.95 (m, 1H), 7.84 (d, J=8.4 Hz, 2H), 7.62 (t, J=5.7 Hz, 1H), 7.43-7.32 (m, 4H), 7.26 (s, 2H), 4.35 (s, 2H), 3.79-3.75 (m, 2H), 3.35 (t, J=2.4 Hz, 1H); LCMS: purity: 96%; MS (m/e): 492 (MH$^+$).

The following compounds were made in a similar fashion to the example 1 or by methods described herein or known to skilled artisans.

(I-2): N2-(4-Aminosulfonylphenyl)-5-fluoro-N4-[3-(prop-2-ynylaminosulfonylmethyl)phenyl]-2,4-pyrimidinediamine $^1$H NMR (DMSO-d$_6$): δ 9.61-9.54 (m, 2H), 8.16 (d, J=3.6 Hz, 1H), 7.86 (d, J=7.2 Hz, 1H), 7.79 (d, J=8.7 Hz, 2H), 7.75-7.59 (m, 5H), 7.63 (t, J=7.8 Hz, 1H), 7.18-7.09 (m, 3H), 4.37 (s, 2H), 3.77 (s, 2H), 3.28 (t, J=2.4 Hz, 1H); LCMS: purity: 95%; MS (m/e): 492 (MH$^+$).

(I-3): N2-(3-Aminosulfonylphenyl)-5-fluoro-N4-[3-(prop-2-ynylaminosulfonylmethyl)phenyl]-2,4-pyrimidinediamine $^1$H NMR (DMSO-d$_6$): δ 9.50 (s, 1H), 9.46 (s, 1H), 8.13 (d, J=3.3 Hz, 1H), 8.12-8.09 (m, 1H), 7.93 (t, J=8.7 Hz, 2H), 7.72-7.65 (m, 2H), 7.42-7.31 (m, 3H), 7.27 (s, 2H), 7.10 (d, J=7.5 Hz, 1H), 4.36 (s, 2H), 3.79-3.75 (m, 2H), 3.27 (t, J=2.4 Hz, 1H); LCMS: purity: 98%; MS (m/e): 492 (MH$^+$).

(I-5): N2-(3-Aminosulfonyl-4-methylphenyl)-5-fluoro-N4-[4-(prop-2-ynylaminosulfonylmethyl)phenyl]-2,4-pyrimidinediamine (X=Me)

$^1$H NMR (DMSO-d$_6$): δ 9.48 (s, 1H), 9.46 (s, 1H), 8.13-8.09 (m, 2H), 7.92 (dd, J=8.4 and 2.1 Hz, 1H), 7.83 (d, J=7.8 Hz, 2H), 7.63 (t, J=6.0 Hz, 1H), 7.33 (d, J=8.1 Hz, 2H), 7.24 (s, 2H), 7.20 (d, J=8.4 Hz, 1H), 4.35 (s, 2H), 3.80-3.74 (m, 2H), 3.36-3.33 (m, 1H); LCMS: purity: 97%; MS (m/e): 506 (MH$^+$).

(I-6): N2-(4-Aminosulfonylphenyl)-5-fluoro-N4-[4-(prop-2-ynylaminosulfonylmethyl)phenyl]-2,4-pyrimidinediamine $^1$H NMR (DMSO-d$_6$): δ 9.72 (s, 1H), 9.61 (s, 1H), 8.18 (d, J=3.6 Hz, 1H), 7.84-7.78 (m, 4H), 7.68-7.62 (m, 3H), 7.36 (d, J=8.4 Hz, 2H), 7.13 (s, 2H), 4.37 (s, 2H), 3.80-3.77 (m, 2H), 3.34 (t, J=2.4 Hz, 1H); LCMS: purity: 98%; MS (m/e): 492 (MH$^+$).

(I-7): 5-Fluoro-N4-[4-(cyclopropylsulfonylaminomethyl)phenyl]-N2-[3-(prop-2-ynylaminosulfonyl)phenyl]-2,4-pyrimidinediamine $^1$H NMR (DMSO-d$_6$): δ 9.69 (s, 1H), 9.61 (s, 1H), 8.16 (d, J=4.2 Hz, 1H), 8.07 (t, J=6.0 Hz, 1H), 8.03-7.98 (m, 2H), 7.74 (d, J=8.4 Hz, 2H), 7.63-7.56 (m, 1H), 7.42 (t, J=8.1 Hz, 1H), 7.35-7.28 (m, 3H), 4.16 (d, J=3.6 Hz, 2H), 3.66 (q, J=2.4 Hz, 2H), 3.06 (t, J=2.4 Hz, 1H), 2.44-2.41 (m, 1H), 0.92-0.84 (m, 4H); LCMS: purity: 90%; MS (m/e): 532 (MH$^+$).

(I-8): N2-(4-aminosulfonyl)phenyl-N4-(4-ethylsulfonylaminomethyl)phenyl-5-fluoro-2,4-pyrimidinediamine $^1$H NMR (DMSO-d$_6$): δ 1.16 (t, J=7.5 Hz, 3H), 2.93 (q, J=7.5 Hz, 2H), 4.12 (d, J=5.7 Hz, 2H), 7.13 (br, 2H), 7.31 (d, J=8.1 Hz, 2H), 7.58 (t, J=6.0 Hz, 1H), 7.64 (d, J=8.7 Hz, 2H), 7.74 (d, J=7.8 Hz, 2H), 7.80 (d, J=8.4 Hz, 2H), 8.17 (d, J=3.3 Hz, 1H), 9.60 (br, 1H), 9.74 (br, 1H); $^{19}$F NMR (282 MHz, DMSO-d$_6$): δ −200.98; LCMS: purity: 96.26%; MS (m/e): 481.05 (MH+).

(I-9): N2-(3-aminosulfonyl)phenyl-N4-(4-ethylsulfonylaminomethyl)phenyl-5-fluoro-2,4-pyrimidinediamine $^1$H NMR (DMSO-d$_6$): δ 1.16 (t, J=7.5 Hz, 3H), 2.92 (q, J=7.5 Hz, 2H), 4.11 (d, J=6.3 Hz, 2H), 7.28 (br, 2H), 7.29 (d, J=8.4 Hz, 2H), 7.38 (m, 2H), 7.56 (t, J=6.0 Hz, 1H), 7.75 (d, J=8.4 Hz, 2H), 7.93 (d, J=7.5 Hz, 1H), 8.04 (s, 1H), 8.14 (d, J=3.9 Hz, 1H), 9.57 (br, 1H), 9.66 (br, 1H); $^{19}$F NMR (282 MHz, DMSO-d$_6$): δ −201.39; LCMS: purity: 98.14%; MS (m/e): 481.09 (MH+).

(I-10): N2-(3-aminosulfonyl-4-methyl)phenyl-N4-(4-ethylsulfonylaminomethyl)phenyl-5-fluoro-2,4-pyrimidinediamine $^1$H NMR (DMSO-d$_6$): δ 1.15 (t, J=7.5 Hz, 3H), 2.51 (s, 3H), 2.92 (q, J=7.2 Hz, 2H), 4.11 (d, J=6.0 Hz, 2H), 7.21 (d, J=8.4 Hz, 1H), 7.28 (br, 2H), 7.30 (d, J=8.7 Hz, 2H), 7.57 (t, J=6.0 Hz, 1H), 7.72 (d, J=8.4 Hz, 2H), 7.83 (dd, J=2.4, 8.1 Hz, 1H), 7.99 (s, 1H), 8.15 (d, J=4.2 Hz, 1H), 9.76 (br, 2H); $^{19}$F NMR (282 MHz, DMSO-d$_6$): δ −201.27; LCMS: purity: 97.10%; MS (m/e): 495.01 (MH+).

(I-11): N2-(4-aminosulfonyl)phenyl-N4-(3-ethylsulfonylaminomethyl)phenyl-5-fluoro-2,4-pyrimidinediamine $^1$H NMR (DMSO-d$_6$): δ 1.16 (t, J=7.2 Hz, 3H), 2.94 (q, J=7.2 Hz, 2H), 4.14 (d, J=6.6 Hz, 2H), 7.11 (m, 3H), 7.33 (t, J=7.8 Hz, 1H), 7.62 (m, 4H), 7.73 (d, J=8.1 Hz, 1H), 7.79 (d, J=9.0 Hz, 2H), 8.15 (d, J=3.9 Hz, 1H), 9.52 (br, 1H), 9.54 (br, 1H); $^{19}$F NMR (282 MHz, DMSO-d$_6$): δ −201.39; LCMS: purity: 93.38%; MS (m/e): 481.11 (MH+).

(I-12): N2-(3-aminosulfonyl)phenyl-N4-(3-ethylsulfonylaminomethyl)phenyl-5-fluoro-2,4-pyrimidinediamine $^1$H NMR (DMSO-d$_6$): δ 1.16 (t, J=7.5 Hz, 3H), 2.95 (q, J=7.2 Hz, 2H), 4.13 (d, J=6.0 Hz, 2H), 7.07 (d, J=7.2 Hz, 1H), 7.28 (m, 2H), 7.38 (m, 3H), 7.60 (t, J=6.0 Hz, 1H), 7.70 (s, 1H), 7.75 (d, J=8.4 Hz, 1H), 7.92 (d, J=6.6 Hz, 1H), 8.04 (s, 1H), 8.16 (d, J=3.9 Hz, 1H), 9.60 (br, 1H), 9.66 (br, 1H); $^{19}$F NMR (282 MHz, DMSO-d$_6$): δ −201.14; LCMS: purity: 92.32%; MS (m/e): 481.11 (MH+).

(I-13): N2-(3-aminosulfonyl-4-methyl)phenyl-N4-(3-ethylsulfonylaminomethyl)phenyl-5-fluoro-2,4-pyrimidinediamine $^1$H NMR (DMSO-d$_6$): δ 1.17 (t, J=7.2 Hz, 3H), 2.48 (s, 3H), 2.95 (q, J=7.2 Hz, 2H), 4.12 (d, J=6.6 Hz, 2H), 7.07 (d, J=7.8 Hz, 1H), 7.19 (d, J=8.4 Hz, 1H), 7.25 (br, 2H), 7.30 (t, J=7.5 Hz, 1H), 7.59 (t, J=6.0 Hz, 1H), 7.70 (s, 1H), 7.75 (d, J=8.7 Hz, 1H), 7.86 (dd, J=2.1, 8.1 Hz, 1H), 8.04 (s, 1H), 8.12 (d, J=4.2 Hz, 1H), 9.47 (br, 1H), 9.59 (br, 1H); $^{19}$F NMR (282 MHz, DMSO-d$_6$): δ −201.73; LCMS: purity: 99.49%; MS (m/e): 495.41 (MH+).

(I-14): N2-(4-aminosulfonyl)phenyl-N4-[4-(2-ethylsulfonylamino)ethyl]phenyl-5-fluoro-2,4-pyrimidinediamine $^1$H NMR (DMSO-d$_6$): δ 1.14 (t, J=7.2 Hz, 3H), 2.75 (t, J=7.2 Hz, 2H), 2.94 (q, J=7.5 Hz, 2H), 3.15 (m, 2H), 7.12 (br, 3H), 7.21 (d, J=8.1 Hz, 2H), 7.61 (d, J=8.4 Hz, 2H), 7.64 (d, J=8.4 Hz, 2H), 7.77 (d, J=9.0 Hz, 2H), 8.12 (d, J=3.6 Hz, 1H), 9.51 (br, 1H), 9.63 (br, 1H); $^{19}$F NMR (282 MHz, DMSO-d$_6$): δ −201.27; LCMS: purity: 95.18%; MS (m/e): 495.09 (MH+).

(I-15): N2-(3-aminosulfonyl)phenyl-N4-[4-(2-ethylsulfonylamino)ethyl]phenyl-5-fluoro-2,4-pyrimidinediamine $^1$H NMR (DMSO-d$_6$): δ 1.14 (t, J=7.2 Hz, 3H), 2.74 (t, J=8.1 Hz, 2H), 2.95 (q, J=7.5 Hz, 2H), 7.10 (t, 1H), 7.19 (d, J=8.1 Hz, 2H), 7.27 (br, 2H), 7.38 (m, 2H), 7.70 (d, J=8.1 Hz, 2H), 7.94 (d, J=7.5 Hz, 1H), 8.06 (s, 1H), 8.12 (d, J=3.6 Hz, 1H), 9.49 (br, 1H), 9.62 (br, 1H); $^{19}$F NMR (282 MHz, DMSO-d$_6$): δ −201.65; LCMS: purity: 94.71%; MS (m/e): 495.44 (MH+).

(I-16): N2-(3-aminosulfonyl-4-methyl)phenyl-N4-[4-(2-ethylsulfonylamino)ethyl]phenyl-5-fluoro-2,4-pyrimidinediamine $^1$H NMR (DMSO-d$_6$): δ 1.13 (t, J=7.2 Hz, 3H), 2.52 (s, 3H), 2.74 (t, J=7.2 Hz, 2H), 2.94 (q, J=7.2 Hz, 2H), 3.14 (q, J=6.6 Hz, 2H), 7.10 (t, J=5.7 Hz, 1H), 7.20 (d, J=8.7 Hz, 2H), 7.22 (m, 1H), 7.27 (br, 2H), 7.65 (d, J=8.4 Hz, 2H), 7.81 (dd, J=2.1, 8.4 Hz, 1H), 7.98 (s, 1H), 8.14 (d, J=4.5 Hz, 1H), 9.77 (br, 2H); $^{19}$F NMR (282 MHz, DMSO-d$_6$): δ −201.30; LCMS: purity: 99.94%; MS (m/e): 509.47 (MH+).

(I-17): N2-(4-aminosulfonyl)phenyl-N4-[4-(N-ethylsulfonyl-N-propylamino)methyl]phenyl-5-fluoro-2,4-pyrimidinediamine $^1$H NMR (DMSO-d$_6$): δ 0.74 (t, J=7.2 Hz, 3H), 1.23 (t, J=7.2 Hz, 3H), 1.41 (q, J=7.5 Hz, 2H), 3.08 (m, 2H), 4.35 (s, 2H), 7.11 (br, 2H), 7.33 (d, J=8.1 Hz, 2H), 7.63 (d, J=8.4 Hz, 2H), 7.79 (d, J=8.7 Hz, 2H), 7.83 (d, J=8.7 Hz, 2H), 8.15 (d, J=3.6 Hz, 1H), 9.47 (br, 1H), 9.62 (br, 1H); $^{19}$F NMR (282 MHz, DMSO-d$_6$): δ −201.38; LCMS: purity: 89.49%; MS (m/e): 523.18 (MH+).

(I-18): N2-(3-aminosulfonyl)phenyl-N4-[4-(N-ethylsulfonyl-N-propylamino)methyl]phenyl-5-fluoro-2,4-pyrimidinediamine $^1$H NMR (DMSO-d$_6$): δ 0.74 (t, J=7.2 Hz, 3H), 1.23 (t, J=7.2 Hz, 3H), 1.41 (q, J=7.5 Hz, 2H), 3.04-3.17 (m, 4H), 4.34 (s, 2H), 7.26 (br, 2H), 7.35 (m, 4H), 7.83 (d, J=8.1 Hz, 2H), 7.96 (d, J=7.2 Hz, 1H), 8.12 (d, J=3.3 Hz, 2H), 9.42 (br, 1H), 9.53 (br, 1H); $^{19}$F NMR (282 MHz, DMSO-d$_6$): δ −201.84; LCMS: purity: 97.59%; MS (m/e): 523.36 (MH+).

(I-19): N2-(3-aminosulfonyl-4-methyl)phenyl-N4-[4-(N-ethylsulfonyl-N-propylamino)methyl]phenyl-5-fluoro-2,4-pyrimidinediamine $^1$H NMR (DMSO-d$_6$): δ 0.74 (t, J=7.2 Hz, 3H), 1.23 (t, J=7.2 Hz, 3H), 1.42 (q, J=7.5 Hz, 2H), 2.49 (s, 3H), 3.04-3.17 (m, 4H), 4.34 (s, 2H), 7.16 (d, J=8.4 Hz, 1H), 7.24 (br, 2H), 7.31 (d, J=8.4 Hz, 2H), 7.82 (d, J=8.4 Hz, 2H), 7.92 (dd, J=2.1, 8.1 Hz, 1H), 8.09 (d, J=3.6 Hz, 2H), 9.38 (br, 1H), 9.42 (br, 1H); $^{19}$F NMR (282 MHz, DMSO-d$_6$): δ −202.44; LCMS: purity: 98.54%; MS (m/e): 537.49 (MH+).

(I-20): N2-(4-aminosulfonyl)phenyl-N4-(4-ethylsulfonylaminomethyl)phenyl-5-methyl-2,4-pyrimidinediamine $^1$H NMR (DMSO-d$_6$): δ 1.16 (t, J=7.2 Hz, 3H), 2.17 (s, 3H), 2.95 (q, J=7.5 Hz, 2H), 4.17 (d, J=6.3 Hz, 2H), 7.24 (br, 2H), 7.38 (d, J=8.1 Hz, 2H), 7.53 (d, J=8.4 Hz, 2H), 7.57 (m, 1H), 7.62 (d, J=9.0 Hz, 2H), 7.64 (d, J=8.1 Hz, 2H), 7.93 (s, 1H), 9.67 (br, 1H), 10.50 (br, 1H); LCMS: purity: 90.57%; MS (m/e): 477.44 (MH+).

(I-21): N2-(3-aminosulfonyl)phenyl-N4-(4-ethylsulfonylaminomethyl)phenyl-5-methyl-2,4-pyrimidinediamine $^1$H NMR (DMSO-d$_6$): δ 1.16 (t, J=7.2 Hz, 3H), 2.17 (s, 3H), 2.94 (q, J=7.2 Hz, 2H), 4.15 (d, J=6.6 Hz, 2H), 7.36 (m, 5H), 7.50 (d, J=7.5 Hz, 3H), 7.66 (m, 2H), 7.80 (d, J=8.4 Hz, 1H), 7.91 (s, 1H), 9.71 (br, 1H), 10.46 (br, 1H); LCMS: purity: 99.29%; MS (m/e): 477.44 (MH+).

(I-22): N2-(3-aminosulfonyl-4-methyl)phenyl-N4-(4-ethylsulfonylaminomethyl)phenyl-5-methyl-2,4-pyrimidinediamine $^1$H NMR (DMSO-d$_6$): δ 1.16 (t, J=7.2 Hz, 3H), 2.16 (s, 3H), 2.52 (s, 3H), 2.94 (q, J=7.2 Hz, 2H), 4.15 (d, J=6.3 Hz, 2H), 7.19 (d, J=8.1 Hz, 1H), 7.35 (m, 4H), 7.50 (d, J=8.4 Hz, 2H), 7.64 (t, J=6.3 Hz, 1H), 7.70 (m, 2H), 7.86 (s, 1H), 9.67 (br, 1H), 10.32 (br, 1H); LCMS: purity: 99.67%; MS (m/e): 491.45 (MH+).

(I-23): N2-(4-aminosulfonyl)phenyl-N4-(4-cyclopropylsulfonylaminomethyl)phenyl-5-fluoro-2,4-pyrimidinediamine $^1$H NMR (DMSO-d$_6$): δ 0.90 (m, 4H), 4.18 (d, J=5.1 Hz, 2H), 7.15 (br, 2H), 7.33 (d, J=7.8 Hz, 2H), 7.64 (d, J=8.1 Hz, 3H), 7.72 (d, J=7.8 Hz, 2H), 7.78 (d, J=8.4 Hz, 2H), 8.18 (d, J=3.0 Hz, 1H), 9.69 (br, 1H), 9.83 (br, 1H); $^{19}$F NMR (282 MHz, DMSO-d$_6$): δ −200.76; LCMS: purity: 99.66%; MS (m/e): 493.37 (MH+).

(I-26): N2-(4-aminosulfonyl)phenyl-N4-[4-(1S-ethylsulfonylamino)ethyl]phenyl-5-fluoro-2,4-pyrimidinediamine $^1$H NMR (DMSO-d$_6$): δ 1.06 (t, J=7.2 Hz, 3H), 1.41 (d, J=7.2 Hz, 3H), 2.61-2.84 (m, 2H), 4.44 (t, J=7.5 Hz, 1H), 7.12 (br, 2H), 7.34 (d, J=8.4 Hz, 2H), 7.63 (d, J=8.4 Hz, 2H), 7.66 (m, 1H), 7.71 (d, J=9.0 Hz, 2H), 7.79 (d, J=8.7 Hz, 2H), 8.16 (d, J=3.9 Hz, 1H), 9.56 (br, 1H), 9.70 (br, 1H); $^{19}$F NMR (282 MHz, DMSO-d$_6$): δ −201.20; LCMS: purity: 97.32%; MS (m/e): 495.27 (MH+).

(I-29): N2-(4-aminosulfonyl)phenyl-N4-[4-(1R-ethylsulfonylamino)ethyl]phenyl-5-fluoro-2,4-pyrimidinediamine $^1$H NMR (DMSO-d$_6$): δ 1.06 (t, J=7.2 Hz, 3H), 1.41 (d, J=6.9 Hz, 3H), 2.61-2.86 (m, 2H), 4.44 (t, J=7.2 Hz, 1H), 7.13 (br, 2H), 7.35 (d, J=8.4 Hz, 2H), 7.63 (d, J=9.0 Hz, 2H), 7.66 (m, 1H), 7.70 (d, J=8.7 Hz, 2H), 7.79 (d, J=8.7 Hz, 2H), 8.16 (d, J=3.9 Hz, 1H), 9.58 (br, 1H), 9.73 (br, 1H); $^{19}$F NMR (282 MHz, DMSO-d$_6$): δ −201.13; LCMS: purity: 100%; MS (m/e): 495.37 (MH+).

(I-24): N2-(3-aminosulfonyl)phenyl-N4-(4-cyclopropylsulfonylaminomethyl)phenyl-5-fluoro-2,4-pyrimidinediamine $^1$H NMR (DMSO-d$_6$): δ 0.89 (m, 4H), 2.44 (m, 1H), 4.16 (d, J=5.7 Hz, 2H), 7.29 (br, 2H), 7.31 (d, J=8.7 Hz, 2H), 7.40 (m, 2H), 7.60 (t, 1H), 7.73 (d, J=8.7 Hz, 2H), 7.92 (dt, J=2.7, 6.6 Hz, 1H), 8.00 (s, 1H), 8.17 (d, J=3.9 Hz, 1H), 9.72 (br, 1H), 9.79 (br, 1H); $^{19}$F NMR (282 MHz, DMSO-d$_6$): δ −201.02; LCMS: purity: 98.59%; MS (m/e): 493.39 (MH+).

(I-25): N2-(3-aminosulfonyl-4-methyl)phenyl-N4-(4-cyclopropylsulfonylaminomethyl)phenyl-5-fluoro-2,4-pyrimidinediamine $^1$H NMR (DMSO-d$_6$): δ 0.89 (m, 4H), 2.51 (s, 3H), 4.16 (d, J=6.3 Hz, 2H), 7.21 (d, J=8.4 Hz, 1H), 7.27 (br, 2H), 7.31 (d, J=8.4 Hz, 2H), 7.60 (t, J=5.7 Hz, 1H), 7.72 (d, J=8.1 Hz, 2H), 7.84 (dd, J=8.4 Hz, 1H), 8.01 (s, 1H), 8.14 (d, J=4.2 Hz, 1H), 9.70 (br, 2H); $^{19}$F NMR (282 MHz, DMSO-d$_6$): δ −201.51; LCMS: purity: 100%; MS (m/e): 507.39 (MH+).

(I-27): N2-(3-aminosulfonyl)phenyl-N4-[4-(1S-ethylsulfonylamino)ethyl]phenyl-5-fluoro-2,4-pyrimidinediamine $^1$H NMR (DMSO-d$_6$): δ 1.06 (t, J=7.5 Hz, 3H), 1.40 (d, J=6.9 Hz, 3H), 2.60-2.82 (m, 2H), 4.42 (t, J=7.5 Hz, 1H), 7.26 (br, 2H), 7.32 (d, J=8.1 Hz, 3H), 7.38 (t, J=7.5 Hz, 1H), 7.65 (d, J=8.7 Hz, 1H), 7.76 (d, J=8.7 Hz, 2H), 7.96 (d, J=8.7 Hz, 1H), 8.11 (d, J=3.6 Hz, 2H), 9.38 (br, 1H), 9.52 (br, 1H); $^{19}$F NMR (282 MHz, DMSO-d$_6$): δ −201.99; LCMS: purity: 86.90%; MS (m/e): 495.39 (MH+).

(I-28): N2-(3-aminosulfonyl-4-methyl)phenyl-N4-[4-(1S-ethylsulfonylamino)ethyl]phenyl-5-fluoro-2,4-pyrimidinediamine $^1$H NMR (DMSO-d$_6$): δ 1.06 (t, J=7.2 Hz, 3H), 1.40 (d, J=6.9 Hz, 3H), 2.62-2.82 (m, 2H), 4.42 (t, J=6.9 Hz, 1H), 7.16 (d, J=8.7 Hz, 1H), 7.22 (br, 2H), 7.32 (d, J=8.7 Hz, 2H), 7.64 (d, J=8.4 Hz, 1H), 7.75 (d, J=8.7 Hz, 2H), 7.90 (dd, J=2.4, 8.4 Hz, 1H), 8.07 (d, J=3.6 Hz, 1H), 8.09 (s, 1H), 9.33 (br, 1H), 9.40 (br, 1H); $^{19}$F NMR (282 MHz, DMSO-d$_6$): δ −202.57; LCMS: purity: 93.70%; MS (m/e): 509.25 (MH+).

(I-30): N2-(3-aminosulfonyl)phenyl-N4-[4-(1R-ethylsulfonylamino)ethyl]phenyl-5-fluoro-2,4-pyrimidinediamine $^1$H NMR (DMSO-d$_6$): δ 1.06 (t, J=7.2 Hz, 3H), 1.40 (d, J=6.9 Hz, 3H), 2.60-2.82 (m, 2H), 4.42 (t, J=7.8 Hz, 1H), 7.26 (br, 2H), 7.32 (d, J=8.4 Hz, 3H), 7.38 (t, J=7.5 Hz, 1H), 7.65 (d, J=8.4 Hz, 1H), 7.76 (d, J=8.7 Hz, 2H), 7.96 (d, J=7.8 Hz, 1H), 8.11 (d, J=3.9 Hz, 2H), 9.38 (br, 1H), 9.52 (br, 1H); $^{19}$F NMR (282 MHz, DMSO-d$_6$): δ −201.97; LCMS: purity: 93.94%; MS (m/e): 495.39 (MH+).

(I-31): N2-(3-aminosulfonyl-4-methyl)phenyl-N4-[4-(1R-ethylsulfonylamino)ethyl]phenyl-5-fluoro-2,4-pyrimidinediamine $^1$H NMR (DMSO-d$_6$): δ 1.06 (t, J=7.5 Hz, 3H), 1.40 (d, J=6.6 Hz, 3H), 2.59-2.80 (m, 2H), 4.42 (t, J=6.9 Hz, 1H), 7.16 (d, J=8.1 Hz, 1H), 7.23 (br, 2H), 7.32 (d, J=7.8 Hz, 2H), 7.65 (d, J=8.4 Hz, 1H), 7.75 (d, J=8.1 Hz, 2H), 7.90 (d, J=6.0 Hz, 1H), 8.07 (d, J=3.9 Hz, 1H), 8.09 (s, 1H), 9.34 (br, 1H), 9.41 (br, 1H); $^{19}$F NMR (282 MHz, DMSO-d$_6$): δ −202.57; LCMS: purity: 89.86%; MS (m/e): 509.41 (MH+).

(I-32): N2-(4-aminosulfonyl)phenyl-N4-(3-cyclopropylsulfonylaminomethyl)phenyl-5-fluoro-2,4-pyrimidinediamine $^1$H NMR (DMSO-d$_6$): δ 0.88 (m, 4H), 4.20 (d, J=5.7 Hz, 2H), 7.12 (d, J=7.2 Hz, 1H), 7.13 (br, 2H), 7.34 (t, J=7.5 Hz, 1H), 7.62 (d, J=9.0 Hz, 2H), 7.65 (m, 2H), 7.72 (d, J=8.4 Hz, 1H), 7.78 (d, J=9.0 Hz, 2H), 8.17 (d, J=3.9 Hz, 1H), 9.63 (br, 1H), 9.66 (br, 1H); $^{19}$F NMR (282 MHz, DMSO-d$_6$): δ −201.11; LCMS: purity: 98.00%; MS (m/e): 493.42 (MH+).

(I-33): N2-(3-aminosulfonyl)phenyl-N4-(3-cyclopropylsulfonylaminomethyl)phenyl-5-fluoro-2,4-pyrimidinediamine $^1$H NMR (DMSO-d$_6$): δ 0.89 (m, 4H), 4.18 (d, J=6.3 Hz, 2H), 7.08 (d, J=7.5 Hz, 1H), 7.28 (br, 2H), 7.31 (t, J=7.8 Hz, 1H), 7.37 (m, 2H), 7.63 (t, 1H), 7.72 (s, 1H), 7.76 (d, J=7.2 Hz, 1H), 7.93 (d, J=7.8 Hz, 1H), 8.05 (s, 1H), 8.14 (d, J=3.9 Hz, 1H), 9.55 (br, 1H), 9.58 (br, 1H); $^{19}$F NMR (282 MHz, DMSO-d$_6$): δ −201.34; LCMS: purity: 98.59%; MS (m/e): 493.42 (MH+).

(I-34): N2-(3-aminosulfonyl-4-methyl)phenyl-N4-(3-cyclopropylsulfonylaminomethyl)phenyl-5-fluoro-2,4-pyrimidinediamine $^1$H NMR (DMSO-d$_6$): δ 0.89 (m, 4H), 4.18 (d, J=5.4 Hz, 2H), 7.10 (d, J=7.5 Hz, 1H), 7.21 (d, J=7.8 Hz, 1H), 7.27 (br, 2H), 7.32 (d, J=7.5 Hz, 1H), 7.62 (t, J=5.7 Hz, 1H), 7.70 (s, 1H), 7.74 (d, J=8.7 Hz, 1H), 7.85 (d, J=8.1 Hz, 1H), 8.02 (s, 1H), 8.13 (d, J=3.9 Hz, 1H), 9.56 (br, 1H), 9.68 (br, 1H); $^{19}$F NMR (282 MHz, DMSO-d$_6$): δ −201.50; LCMS: purity: 96.85%; MS (m/e): 507.43 (MH+).

(I-35): N2-(4-aminosulfonyl)phenyl-5-fluoro-N4-[4-(thiophen-2-yl)sulfonylaminomethyl]phenyl-2,4-pyrimidinediamine $^1$H NMR (DMSO-d$_6$): δ 4.04 (d, J=6.0 Hz, 2H), 7.15 (br, 2H), 7.16 (t, J=4.2 Hz, 1H), 7.22 (d, J=8.7 Hz, 2H), 7.59 (dd, J=1.2, 3.3 Hz, 1H), 7.64 (d, J=9.0 Hz, 2H), 7.70 (d, J=8.4 Hz, 2H), 7.80 (d, J=8.7 Hz, 2H), 7.90 (dd, J=1.2, 4.8 Hz, 1H), 8.16 (d, J=3.6 Hz, 1H), 8.34 (t, J=6.0 Hz, 1H), 9.55 (br, 1H), 9.70 (br, 1H); $^{19}$F NMR (282 MHz, DMSO-d$_6$): δ −201.05; LCMS: purity: 83.50%; MS (m/e): 535.35 (MH+).

(I-36): N2-(3-aminosulfonyl)phenyl-5-fluoro-N4-[4-(thiophen-2-yl)sulfonylaminomethyl]phenyl-2,4-pyrimidinediamine $^1$H NMR (DMSO-d$_6$): δ 4.03 (d, J=6.0 Hz, 2H), 7.16 (t, J=4.5 Hz, 1H), 7.21 (d, J=8.7 Hz, 2H), 7.28 (br, 2H), 7.38 (m, 2H), 7.59 (dd, J=1.5, 3.6 Hz, 1H), 7.71 (d, J=8.4 Hz, 2H), 7.92 (m, 2H), 8.03 (s, 1H), 8.14 (d, J=3.9 Hz, 1H), 8.33 (t, J=6.0 Hz, 1H), 9.59 (br, 1H), 9.68 (br, 1H); $^{19}$F NMR (282 MHz, DMSO-d$_6$): δ −201.37; LCMS: purity: 96.97%; MS (m/e): 535.34 (MH+).

(I-37): N2-(3-aminosulfonyl-4-methyl)phenyl-5-fluoro-N4-[4-(thiophen-2-yl)sulfonylaminomethyl]phenyl-2,4-pyrimidinediamine $^1$H NMR (DMSO-d$_6$): δ 2.48 (s, 3H), 4.03 (d, J=6.3 Hz, 2H), 7.15 (t, J=4.5 Hz, 1H), 7.21 (d, J=8.7 Hz, 2H), 7.21 (m, 1H), 7.26 (br, 2H), 7.58 (d, J=3.3 Hz, 1H), 7.70 (d, J=8.4 Hz, 2H), 7.85 (dd, J=8.4 Hz, 1H), 7.90 (dd, J=1.2, 4.8 Hz, 1H), 8.03 (s, 1H), 8.12 (d, J=3.6 Hz, 1H), 8.33 (t, J=6.0 Hz, 1H), 9.62 (br, 2H); $^{19}$F NMR (282 MHz, DMSO-d$_6$): δ −201.76; LCMS: purity: 92.93%; MS (m/e): 549.03 (MH+).

(I-38): N2-(4-aminosulfonyl)phenyl-N4-[4-(2-ethylsulfonylamino)ethyl]phenyl-5-methyl-2,4-pyrimidinediamine $^1$H NMR (DMSO-d$_6$): δ 1.15 (t, J=7.2 Hz, 3H), 2.17 (s, 3H), 2.80 (t, J=7.5 Hz, 2H), 2.96 (q, J=7.5 Hz, 2H), 3.18 (m, 2H), 7.15 (t, J=5.1 Hz, 1H), 7.23 (br, 2H), 7.28 (d, J=8.4 Hz, 2H), 7.46 (d, J=8.4 Hz, 2H), 7.58 (d, J=9.0 Hz, 2H), 7.62 (d, J=9.0 Hz, 2H), 7.92 (s, 1H), 9.66 (br, 1H), 10.45 (br, 1H); LCMS: purity: 99.70%; MS (m/e): 491.23 (MH+).

(I-39): N2-(3-aminosulfonyl)phenyl-N4-[4-(2-ethylsulfonylamino)ethyl]phenyl-5-methyl-2,4-pyrimidinediamine $^1$H NMR (DMSO-d$_6$): δ 1.15 (t, J=7.2 Hz, 3H), 2.11 (s, 3H), 2.74 (t, J=7.2 Hz, 2H), 2.95 (q, J=7.2 Hz, 2H), 3.15 (q, J=5.1 Hz, 2H), 7.10 (t, J=5.7 Hz, 1H), 7.18 (d, J=8.4 Hz, 2H), 7.22 (br, 2H), 7.29 (m, 2H), 7.65 (d, J=8.4 Hz, 2H), 7.88 (s, 1H), 8.01 (d, J=7.8 Hz, 1H), 8.06 (s, 1H), 8.24 (s, 1H), 9.28 (br, 1H); LCMS: purity: 98.77%; MS (m/e): 491.43 (MH+).

(I-40): N2-(3-aminosulfonyl-4-methyl)phenyl-N4-[4-(2-ethylsulfonylamino)ethyl]phenyl-5-methyl-2,4-pyrimidinediamine $^1$H NMR (DMSO-d$_6$): δ 1.14 (t, J=7.2 Hz, 3H), 2.09 (s, 3H), 2.48 (s, 3H), 2.74 (t, J=7.2 Hz, 2H), 2.95 (q, J=7.2 Hz, 2H), 3.15 (q, J=7.2 Hz, 2H), 7.10 (d, J=8.1 Hz, 1H), 7.11 (t, 1H), 7.17 (d, J=8.1 Hz, 2H), 7.18 (br, 2H), 7.64 (d, J=8.1 Hz, 2H), 7.85 (s, 1H), 7.93 (dd, J=2.1, 8.4 Hz, 1H), 8.07 (s, 1H), 8.21 (s, 1H), 9.16 (br, 1H); LCMS: purity: 99.54%; MS (m/e): 505.31 (MH+).

(I-41): N4-[4-(2-amino-4-methylthiazol-5-yl)sulfonylaminomethyl]phenyl-N2-(3-aminosulfonyl)phenyl-5-fluoro-2,4-pyrimidinediamine $^1$H NMR (DMSO-d$_6$): δ 2.26 (s, 3H), 3.99 (d, 2H), 7.26 (m, 2H), 7.36 (m, 2H), 7.43 (br, 2H), 7.65 (m, 2H), 7.75 (d, J=8.7 Hz, 1H), 7.82 (d, J=7.2 Hz, 1H), 8.10 (s, 1H), 8.19 (s, 1H), 9.37 (br, 1H), 9.52 (br, 1H), 11.52 (br, 1H); $^{19}$F NMR (282 MHz, DMSO-d$_6$): δ −201.89; LCMS: purity: 100%; MS (m/e): 565.24 (MH+).

(I-42): N4-[4-(2-acetylamino-4-methylthiazol-5-yl)sulfonylaminomethyl]phenyl-N2-(3-aminosulfonyl)phenyl-5-fluoro-2,4-pyrimidinediamine $^1$H NMR (DMSO-d$_6$): δ 2.14 (s, 3H), 2.41 (s, 3H), 4.02 (d, 2H), 7.19 (d, J=8.4 Hz, 2H), 7.26 (br, 2H), 7.36 (m, 2H), 7.74 (d, J=8.7 Hz, 2H), 7.95 (d, 1H), 8.10 (m, 2H), 8.36 (t, 1H), 9.36 (br, 1H), 9.52 (br, 1H), 12.44 (br, 1H); $^{19}$F NMR (282 MHz, DMSO-d$_6$): δ −201.84; LCMS: purity: 99.32%; MS (m/e): 607.32 (MH+).

(I-43): N4-[4-(2-amino-4-methylthiazol-5-yl)sulfonylaminomethyl]phenyl-N2-(3-aminosulfonyl-4-methyl)phenyl-5-fluoro-2,4-pyrimidinediamine $^1$H NMR (DMSO-d$_6$): δ 2.26 (s, 3H), 4.00 (d, J=5.4 Hz, 2H), 7.19 (m, 3H), 7.23 (br, 2H), 7.58 (br, 2H), 7.75 (d, J=8.7 Hz, 2H), 7.91 (d, J=6.0 Hz, 1H), 8.03 (t, 1H), 8.07 (d, J=3.0 Hz, 1H), 8.10 (s, 1H), 8.13 (s, 1H), 9.33 (br, 1H), 9.41 (br, 1H); $^{19}$F NMR (282 MHz, DMSO-d$_6$): δ −202.45; LCMS: purity: 100%; MS (m/e): 577.47 (MH+).

(I-44): N4-[4-(2-acetylamino-4-methylthiazol-5-yl)sulfonylaminomethyl]phenyl-N2-(3-aminosulfonyl-4-methyl)phenyl-5-fluoro-2,4-pyrimidinediamine $^1$H NMR (DMSO-d$_6$): δ 2.14 (s, 3H), 2.41 (s, 3H), 4.02 (d, 2H), 7.17 (m, 3H), 7.23 (br, 2H), 7.74 (d, J=8.4 Hz, 2H), 7.90 (d, 1H), 8.08 (d, J=3.6 Hz, 1H), 8.10 (s, 1H), 8.37 (t, 1H), 9.32 (br, 1H), 9.41 (br, 1H), 12.44 (br, 1H); $^{19}$F NMR (282 MHz, DMSO-d$_6$): δ −202.41; LCMS: purity: 99.77%; MS (m/e): 621.34 (MH+).

(I-45): N2-(4-aminosulfonyl)phenyl-N4-(4-cyclopropylsulfonylaminomethyl)phenyl-5-methyl-2,4-pyrimidinediamine $^1$H NMR (DMSO-d$_6$): δ 0.91 (m, 4H), 2.12 (s, 3H), 4.18 (d, J=6.3 Hz, 2H), 7.07 (br, 2H), 7.31 (d, J=8.4 Hz, 2H), 7.58 (d, J=8.7 Hz, 3H), 7.67 (d, J=8.4 Hz, 2H), 7.82 (d, J=9.0 Hz, 2H), 7.92 (s, 1H), 8.35 (br, 1H), 9.39 (br, 1H); LCMS: purity: 95.56%; MS (m/e): 489.19 (MH+).

(I-46): N2-(3-aminosulfonyl)phenyl-N4-(4-cyclopropylsulfonylaminomethyl)phenyl-5-methyl-2,4-pyrimidinediamine $^1$H NMR (DMSO-d$_6$): δ 0.90 (m, 4H), 2.11 (s, 3H), 2.44 (m, 1H), 4.16 (d, J=6.3 Hz, 2H), 7.23 (br, 2H), 7.30 (m, 4H), 7.58 (t, J=6.0 Hz, 1H), 7.71 (d, J=8.4 Hz, 2H), 7.89 (s, 1H), 8.01 (d, J=8.4 Hz, 1H), 8.06 (s, 1H), 8.29 (br, 1H), 9.29 (br, 1H); LCMS: purity: 96.15%; MS (m/e): 489.40 (MH+).

(I-47): N2-(3-aminosulfonyl-4-methyl)phenyl-N4-(4-cyclopropylsulfonylaminomethyl)phenyl-5-methyl-2,4-pyrimidinediamine $^1$H NMR (DMSO-d$_6$): δ 0.90 (m, 4H), 2.10 (s, 3H), 2.42 (m, 1H), 2.48 (s, 3H), 4.16 (d, J=6.3 Hz, 2H), 7.12 (d, J=8.1 Hz, 1H), 7.19 (br, 2H), 7.28 (d, J=8.4 Hz, 2H), 7.59 (t, J=6.3 Hz, 1H), 7.71 (d, J=9.0 Hz, 2H), 7.86 (s, 1H), 7.94 (dd, J=2.1, 8.4 Hz, 1H), 8.08 (s, 1H), 8.25 (br, 1H), 9.18 (br, 1H); LCMS: purity: 93.49%; MS (m/e): 503.42 (MH+).

(I-48): N2-(4-aminosulfonyl)phenyl-5-fluoro-N4-(4-trifluoroethylsulfonylaminomethyl)phenyl-2,4-pyrimidinediamine $^1$H NMR (DMSO-d$_6$): δ 4.20 (s, 2H), 4.40 (q, J=9.9 Hz, 2H), 7.12 (br, 2H), 7.30 (d, J=8.4 Hz, 2H), 7.64 (d, J=9.0 Hz, 2H), 7.77 (d, J=8.7 Hz, 2H), 7.83 (d, J=9.0 Hz, 2H), 8.15 (d, J=3.6 Hz, 1H), 8.29 (br, 1H), 9.46 (br, 1H), 9.61 (br, 1H); $^{19}$F NMR (282 MHz, DMSO-d$_6$): δ-201.35, −100.92; LCMS: purity: 78.79%; MS (m/e): 535.36 (MH+).

(I-49): N2-(3-aminosulfonyl)phenyl-5-fluoro-N4-(4-trifluoroethylsulfonylaminomethyl)phenyl-2,4-pyrimidinediamine $^1$H NMR (DMSO-d$_6$): δ 4.18 (d, J=6.6 Hz, 2H), 4.40 (q, J=9.9 Hz, 2H), 7.26 (br, 2H), 7.28 (d, 2H), 7.36 (m, 2H), 7.79 (d, J=8.4 Hz, 2H), 7.96 (d, J=8.1 Hz, 1H), 8.11 (m, 2H), 8.27 (t, J=6.0 Hz, 1H), 9.41 (br, 1H), 9.52 (br, 1H); $^{19}$F NMR (282 MHz, DMSO-d$_6$): δ −201.90, −100.93; LCMS: purity: 96.17%; MS (m/e): 535.27 (MH+).

(I-50): N2-(3-aminosulfonyl-4-methyl)phenyl-5-fluoro-N4-(4-trifluoroethylsulfonylaminomethyl)phenyl-2,4-pyrimidinediamine $^1$H NMR (DMSO-d$_6$): δ 4.18 (d, J=6.3 Hz, 2H), 4.40 (q, J=9.9 Hz, 2H), 7.17 (d, J=8.7 Hz, 1H), 7.23 (br, 2H), 7.28 (d, J=8.4 Hz, 2H), 7.79 (d, J=8.1 Hz, 2H), 7.90 (dd, J=2.7, 7.8 Hz, 1H), 8.08 (d, J=3.6 Hz, 1H), 8.10 (d, J=2.7 Hz, 1H), 8.27 (t, J=6.0 Hz, 1H), 9.36 (br, 1H), 9.40 (br, 1H); $^{19}$F NMR (282 MHz, DMSO-d$_6$): δ −202.47, −100.92; LCMS: purity: 86.53%; MS (m/e): 549.33 (MH+).

(I-1): N4-(4-Aminosulfonylmethylenephenyl)-N2-(3-aminosulfonyl-4-methyl-phenyl)-5-fluoro-2,4-pyrimidinediamine $^1$H NMR (DMSO-d$_6$): δ 9.43 (s, 1H), 9.41 (s, 1H), 8.09 (m, 2H), 7.92 (dd, 1H, J=2.4 and 8.4 Hz), 7.82 (d, 2H, J=8.4 Hz), 7.29 (d, 2H, J=8.4 Hz), 7.22 (s, 2H), 7.19 (d, 1H, J=7.2 Hz), 6.80 (s, 2H), 4.23 (s, 2H), 2.21 (s, 3H); LCMS: purity: 99%; MS (m/e): 468 (MH$^+$).

Example 2

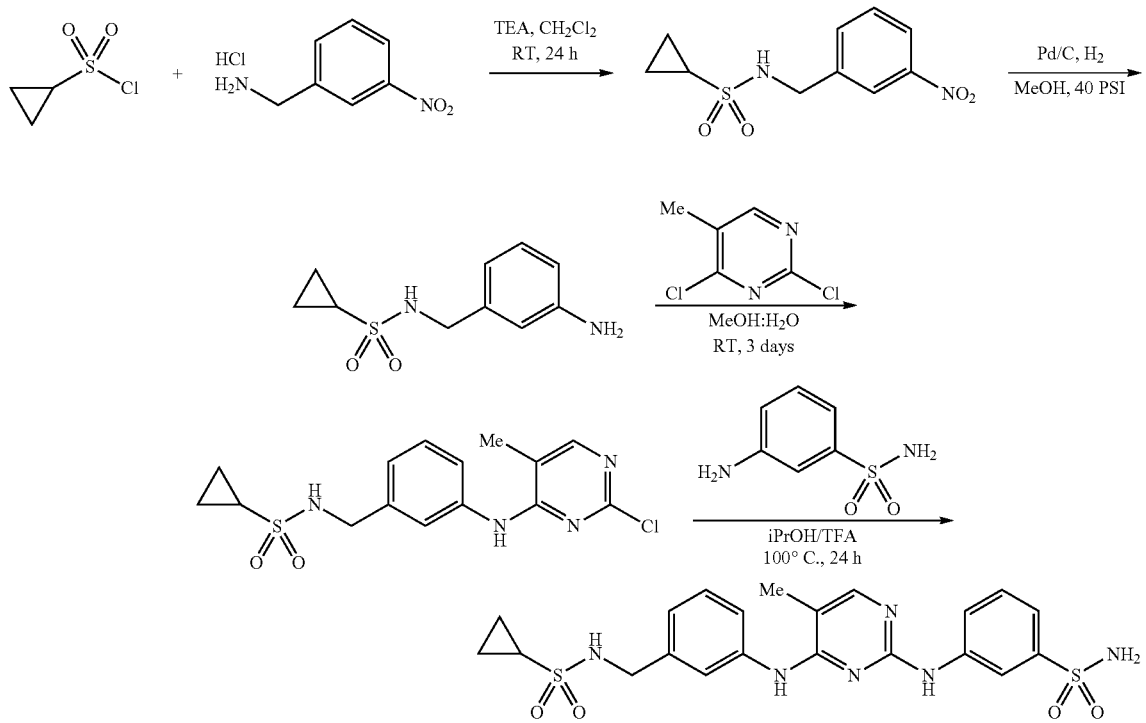

R946232

(I-51): N2-(3-aminosulfonyl)phenyl-N4-(3-cyclopropylsulfonylaminomethyl)phenyl-5-methyl-2,4-pyrimidinediamine 3-Nitrobenzylamine HCl (1.48 g), cyclopropanesulfonyl chloride (1 g) and triethylamine (2.98 mL) were dissolved in dichloromethane (20 mL). The reaction solution was stirred at rt overnight. The reaction mixture was diluted with 1N HCl aq. solution (50 mL) and water (100 mL). The solution was extracted with ethyl acetate (2×100 mL). The organic solution was evaporated to give N-cyclopropylsulfonyl-3-nitrobenzylamine.

N-Cyclopropylsulfonyl-3-nitrobenzylamine was dissolved in methanol (50 mL) and to the solution was added 10% Pd-C. The reaction mixture was reacted under hydrogen atmosphere (~40 psi) for 2 h. The catalyst was filtered off over celite and washed with methanol. The filtrate was evaporated to give N-cyclopropylsulfonyl-3-aminobenzylamine. $^1$H NMR (DMSO-$d_6$): δ 0.88 (d, J=6.6 Hz, 4H), 2.44 (m, 1H), 4.00 (d, J=6.3 Hz, 2H), 5.08 (br, 2H), 6.44 (t, J=9.0 Hz, 2H), 6.53 (s, 1H), 6.94 (t, J=7.8 Hz, 1H), 7.46 (t, J=6.6 Hz, 1H).

N-Cyclopropylsulfonyl-3-aminobenzylamine and 2,6-dichloro-5-methylpyrimidine (1.5 g) were dissolved in methanol (10 mL) and water (2 mL). The reaction solution was stirred at rt for 3 d. The reaction solution was diluted with water (150 mL) and extracted with ethyl acetate (2×150 mL). The organic layers were evaporated and purified by flash column chromatography (dichloromethane, EtOAc) to give 2-chloro-N4-(3-cyclopropylsulfonylaminomethyl)phenyl-5-methyl-4-pyrimidineamine. $^1$H NMR (DMSO-$d_6$): δ 0.83-0.89 (m, 4H), 2.16 (s, 3H), 4.17 (d, J=6.6 Hz, 2H), 7.09 (d, J=8.7 Hz, 1H), 7.32 (t, J=7.5 Hz, 1H), 7.53 (m, 2H), 7.64 (t, J=6.3 Hz, 1H), 8.02 (s, 1H), 8.87 (br, 1H).

2-Chloro-N4-(3-cyclopropylsulfonylaminomethyl)phenyl-5-methyl-4-pyrimidineamine (800 mg) and 3-aminobenzylsulfonamide (800 mg) were suspended in isopropanol (10 mL) and TFA (10 drops). The solution was heated at 100° C. overnight. The solution was diluted with methanol (100 mL), sonicated, and the precipitate was filtered off to give N2-(3-aminosulfonyl)phenyl-N4-(3-cyclopropylsulfonylaminomethyl)phenyl-5-methyl-2,4-pyrimidinediamine (I-51). $^1$H NMR (DMSO-$d_6$): δ 0.81-0.95 (m, 4H), 2.12 (s, 3H), 4.18 (d, J=6.0 Hz, 2H), 7.04 (d, J=7.2 Hz, 1H), 7.23 (br, 2H), 7.29 (m, 3H), 7.61 (t, J=6.3 Hz, 1H), 7.66 (s, 1H), 7.71 (d, J=8.1 Hz, 1H), 7.91 (s, 1H), 8.00 (d, J=7.5 Hz, 1H), 8.06 (s, 1H), 8.36 (s, 1H), 9.22 (br, 1H); LCMS: purity: 94.01%; MS (m/e): 489.01 (MH$^+$).

The following compounds were made in a similar fashion to the example 2 or by methods described herein or known to skilled artisans.

(I-52): N2-(3-aminosulfonyl-4-methyl)phenyl-N4-(3-cyclopropylsulfonylaminomethyl)phenyl-5-methyl-2,4-pyrimidinediamine $^1$H NMR (DMSO-$d_6$): δ 0.89 (m, 4H), 2.11 (s, 3H), 4.18 (d, J=6.0 Hz, 2H), 7.04 (d, J=7.8 Hz, 1H), 7.12 (d, J=7.8 Hz, 1H), 7.20 (br, 2H), 7.29 (t, J=7.8 Hz, 1H), 7.60 (t, J=6.0 Hz, 1H), 7.67 (s, 1H), 7.71 (d, J=8.1 Hz, 1H), 7.88 (s, 1H), 7.93 (d, J=6.9 Hz, 1H), 8.08 (s, 1H), 8.32 (s, 1H), 9.12 (br, 1H); LCMS: purity: 96.74%; MS (m/e): 503.40 (MH+).

(I-53): N2-(4-aminosulfonyl)phenyl-N4-[4-(2-cyclopropylsulfonylamino)ethyl]phenyl-5-methyl-2,4-pyrimidinediamine $^1$H NMR (DMSO-$d_6$): δ 0.90 (m, 4H), 2.17 (s, 3H), 2.54 (m, 1H), 2.83 (t, J=7.8 Hz, 2H), 3.22 (q, J=7.8 Hz, 2H), 7.18 (t, 1H), 7.23 (br, 2H), 7.28 (d, J=8.4 Hz, 2H), 7.46 (d, J=8.4 Hz, 2H), 7.61 (m, 4H), 7.92 (s, 1H), 9.63 (br, 1H), 10.42 (br, 1H); LCMS: purity: 92.94%; MS (m/e): 503.40 (MH+).

(I-54): N2-(3-aminosulfonyl)phenyl-N4-[4-(2-cyclopropylsulfonylamino)ethyl]phenyl-5-methyl-2,4-pyrimidinediamine $^1$H NMR (DMSO-$d_6$): δ 0.90 (m, 4H), 2.16 (s, 3H), 2.52 (m, 1H), 2.80 (t, J=7.5 Hz, 2H), 3.21 (q, J=6.9 Hz, 2H), 7.17 (t, J=5.4 Hz, 1H), 7.25 (d, J=8.1 Hz, 2H), 7.35 (br, 2H), 7.40 (d, J=8.1 Hz, 1H), 7.46 (d, J=8.4 Hz, 2H), 7.49 (d, J=7.5 Hz, 1H), 7.70 (s, 1H), 7.81 (d, J=7.8 Hz, 1H), 7.88 (s, 1H), 9.59 (br, 1H), 10.30 (br, 1H); LCMS: purity: 97.75%; MS (m/e): 503.39 (MH+).

(I-55): N2-(3-aminosulfonyl-4-methyl)phenyl-N4-[4-(2-cyclopropylsulfonylamino)ethyl]phenyl-5-methyl-2,4-pyrimidinediamine $^1$H NMR (DMSO-$d_6$): δ 0.90 (m, 4H), 2.15 (s, 3H), 2.53 (s, 3H), 2.80 (t, J=7.5 Hz, 2H), 3.21 (q, J=6.9 Hz, 2H), 7.19 (m, 2H), 7.25 (d, J=8.1 Hz, 2H), 7.35 (br, 2H), 7.44 (d, J=8.7 Hz, 2H), 7.67 (d, J=8.1 Hz, 1H), 7.72 (s, 1H), 7.85 (s, 1H), 9.60 (br, 1H), 10.27 (br, 1H); LCMS: purity: 98.96%; MS (m/e): 517.41 (MH+).

(I-56): N2-(4-aminosulfonyl)phenyl-N4-(3-cyclopropylsulfonylaminomethyl)phenyl-5-methyl-2,4-pyrimidinediamine $^1$H NMR (DMSO-$d_6$): δ 0.89 (m, 4H), 2.13 (s, 3H), 2.44 (m, 1H), 4.20 (d, J=6.0 Hz, 2H), 7.09 (br, 3H), 7.33 (t, J=7.8 Hz, 1H), 7.59 (m, 3H), 7.64 (m, 2H), 7.80 (d, J=8.7 Hz, 2H), 7.94 (s, 1H), 8.47 (s, 1H), 9.37 (br, 1H); LCMS: purity: 94.36%; MS (m/e): 489.39 (MH+).

(I-57): N4-(4-cyclopropylsulfonylaminomethyl)phenyl-5-fluoro-N2-(3-propionylaminosulfonyl)phenyl-2,4-pyrimidinediamine $^1$H NMR (DMSO-$d_6$): δ 0.88 (m, 7H), 2.22 (q, J=7.5 Hz, 2H), 2.46 (m, 1H), 4.16 (d, J=6.3 Hz, 2H), 7.30 (d, J=8.4 Hz, 2H), 7.41 (m, 2H), 7.58 (t, J=6.3 Hz, 1H), 7.77 (d, J=8.7 Hz, 2H), 8.07 (d, J=7.8 Hz, 1H), 8.11 (d, J=3.6 Hz, 1H), 8.20 (s, 1H), 9.40 (br, 1H), 9.59 (br, 1H), 11.95 (br, 1H); $^{19}$F NMR (282 MHz, DMSO-$d_6$): δ −201.64; LCMS: purity: 93.76%; MS (m/e): 549.39 (MH+).

(I-58): N4-[4-(N-cyclopropylsulfonyl-N-propionyl)aminomethyl]phenyl-5-fluoro-N2-(3-propionylaminosulfonyl)phenyl-2,4-pyrimidinediamine $^1$H NMR (DMSO-$d_6$): δ 0.88 (t, J=7.5 Hz, 3H), 1.00 (t, J=6.9 Hz, 3H), 1.10 (m, 4H), 2.21 (q, J=7.5 Hz, 2H), 2.66 (q, J=7.5 Hz, 2H), 4.89 (s, 2H), 7.24 (d, J=8.7 Hz, 2H), 7.38 (m, 2H), 7.80 (d, J=8.7 Hz, 2H), 8.05 (d, J=7.2 Hz, 1H), 8.11 (d, J=3.6 Hz, 1H), 8.21 (s, 1H), 9.44 (br, 1H), 9.59 (br, 1H), 11.95 (br, 1H); $^{19}$F NMR (282 MHz, DMSO-$d_6$): δ −201.64; LCMS: purity: 98.43%; MS (m/e): 605.39 (MH+).

(I-59): N4-(4-cyclopropylsulfonylaminomethyl)phenyl-5-fluoro-N2-(4-methyl-3-propionylaminosulfonyl)phenyl-2,4-pyrimidinediamine $^1$H NMR (DMSO-$d_6$): δ 0.88 (m, 7H), 2.24 (q, J=7.8 Hz, 2H), 4.16 (d, J=6.0 Hz, 2H), 7.21 (d, J=8.1 Hz, 1H), 7.30 (d, J=8.7 Hz, 2H), 7.59 (t, 1H), 7.78 (d, J=8.1 Hz, 2H), 8.02 (d, J=7.5 Hz, 1H), 8.09 (d, J=3.6 Hz, 1H), 8.16 (s, 1H), 9.37 (br, 1H), 9.50 (br, 1H), 12.03 (br, 1H); $^{19}$F NMR (282 MHz, DMSO-d$_6$): δ −202.22; LCMS: purity: 98.80%; MS (m/e): 563.31 (MH+).

(I-60): N4-[4-(N-cyclopropylsulfonyl-N-propionyl) aminomethyl]phenyl-5-fluoro-N2-(4-methyl-3-propionylaminosulfonyl)phenyl-2,4-pyrimidinediamine $^{1}$H NMR (DMSO-d$_6$): δ 0.88 (t, J=7.2 Hz, 3H), 1.00 (t, J=6.9 Hz, 3H), 1.10 (m, 4H), 2.24 (q, J=7.8 Hz, 2H), 2.67 (q, J=7.2 Hz, 2H), 4.89 (s, 2H), 7.18 (d, J=8.4 Hz, 1H), 7.23 (d, J=8.4 Hz, 2H), 7.79 (d, J=8.4 Hz, 2H), 8.02 (d, J=8.4 Hz, 1H), 8.10 (d, J=3.6 Hz, 1H), 8.14 (s, 1H), 9.42 (br, 1H), 9.50 (br, 1H), 12.02 (br, 1H); $^{19}$F NMR (282 MHz, DMSO-d$_6$): δ −202.28; LCMS: purity: 96.49%; MS (m/e): 619.42 (MH+).

(I-61): N4-(4-cyclopropylsulfonylaminomethyl)phenyl-5-fluoro-N2-(3-propionylaminosulfonyl)phenyl-2,4-pyrimidinediamine sodium salt $^{1}$H NMR (DMSO-d$_6$): δ 0.85 (m, 7H), 2.01 (q, 2H), 4.14 (d, 2H), 7.30 (d, J=8.7 Hz, 4H), 7.59 (t, 1H), 7.80 (d, J=8.7 Hz, 2H), 7.93 (m, 2H), 8.09 (d, J=3.6 Hz, 1H), 9.34 (br, 2H); $^{19}$F NMR (282 MHz, DMSO-d$_6$): δ −201.64; LCMS: purity: 88.05%; MS (m/e): 549.39 (MH+).

(I-62): N4-[4-(N-cyclopropylsulfonyl-N-propionyl) aminomethyl]phenyl-5-fluoro-N2-(3-propionylaminosulfonyl)phenyl-2,4-pyrimidinediamine sodium salt $^{1}$H NMR (DMSO-d$_6$): δ 0.84 (t, J=7.5 Hz, 3H), 1.01 (t, J=6.9 Hz, 3H), 1.09 (m, 4H), 1.93 (q, 2H), 2.67 (q, J=7.5 Hz, 2H), 4.89 (s, 2H), 7.23 (d, J=8.7 Hz, 4H), 7.82 (d, J=8.1 Hz, 2H), 7.90 (m, 2H), 8.08 (d, J=3.6 Hz, 1H), 9.36 (br, 2H); $^{19}$F NMR (282 MHz, DMSO-d$_6$): δ-201.64; LCMS: purity: 92.66%; MS (m/e): 605.40 (MH+).

(I-63): N4-(4-cyclopropylsulfonylaminomethyl)phenyl-5-fluoro-N2-(4-methyl-3-propionylaminosulfonyl)phenyl-2,4-pyrimidinediamine sodium salt $^{1}$H NMR (DMSO-d$_6$): δ 0.86 (m, 7H), 1.99 (m, 2H), 4.15 (d, J=5.7 Hz, 2H), 7.02 (d, 1H), 7.29 (d, J=8.7 Hz, 2H), 7.59 (t, 1H), 7.81 (d, J=9.0 Hz, 3H), 8.06 (d, J=3.9 Hz, 1H), 9.30 (br, 2H); LCMS: purity: 97.08%; MS (m/e): 563.40 (MH+).

(I-64): N4-[4-(N-cyclopropylsulfonyl-N-propionyl) aminomethyl]phenyl-5-fluoro-N2-(4-methyl-3-propionylaminosulfonyl)phenyl-2,4-pyrimidinediamine sodium salt $^{1}$H NMR (DMSO-d$_6$): δ 0.86 (t, J=7.2 Hz, 3H), 1.00 (t, J=7.2 Hz, 3H), 1.08 (m, 4H), 2.66 (q, J=6.6 Hz, 2H), 4.89 (s, 2H), 7.23 (d, J=8.4 Hz, 2H), 7.81 (d, J=8.4 Hz, 2H), 8.08 (d, 1H), 9.36 (br, 2H); LCMS: purity: 92.09%; MS (m/e): 619.41 (MH+).

(I-65): N2-(4-aminosulfonyl)phenyl-5-fluoro-N4-(4-isopropylsulfonylaminomethyl)phenyl-2,4-pyrimidinediamine $^{1}$H NMR (DMSO-d$_6$): δ 1.21 (d, J=6.6 Hz, 6H), 3.08 (m, J=6.9 Hz, 1H), 4.14 (d, J=6.3 Hz, 2H), 7.11 (br, 2H), 7.30 (d, J=8.7 Hz, 2H), 7.55 (t, 1H), 7.63 (d, J=9.0 Hz, 2H), 7.75 (d, J=8.7 Hz, 2H), 7.82 (d, J=9.0 Hz, 2H), 8.14 (d, J=3.3 Hz, 1H), 9.44 (br, 1H), 9.61 (br, 1H); $^{19}$F NMR (282 MHz, DMSO-d$_6$): δ −162.33; LCMS: purity: 87.52%; MS (m/e): 495.30 (MH+).

(I-66): N2-(3-aminosulfonyl)phenyl-5-fluoro-N4-(4-isopropylsulfonylaminomethyl)phenyl-2,4-pyrimidinediamine $^{1}$H NMR (DMSO-d$_6$): δ 1.20 (d, J=6.9 Hz, 6H), 3.06 (m, J=6.3 Hz, 1H), 4.13 (d, J=6.3 Hz, 2H), 7.26 (br, 2H), 7.28 (d, J=8.7 Hz, 2H), 7.36 (m, 2H), 7.54 (t, J=6.0 Hz, 1H), 7.78 (d, J=8.1 Hz, 2H), 7.97 (d, J=7.8 Hz, 1H), 8.11 (m, 2H), 9.39 (br, 1H), 9.52 (br, 1H); $^{19}$F NMR (282 MHz, DMSO-d$_6$): δ −162.84; LCMS: purity: 95.00%; MS (m/e): 495.30 (MH+).

(I-67): N2-(3-aminosulfonyl-4-methyl)phenyl-5-fluoro-N4-(4-isopropylsulfonylaminomethyl)phenyl-2,4-pyrimidinediamine $^{1}$H NMR (DMSO-d$_6$): δ 1.20 (d, J=6.6 Hz, 6H), 3.06 (m, J=6.3 Hz, 1H), 4.13 (d, J=5.7 Hz, 2H), 7.17 (d, J=8.1 Hz, 1H), 7.22 (br, 2H), 7.28 (d, J=7.5 Hz, 2H), 7.52 (t, J=6.0 Hz, 1H), 7.78 (d, J=7.8 Hz, 2H), 7.91 (d, J=7.5 Hz, 1H), 8.07 (d, J=3.6 Hz, 1H), 8.10 (s, 1H), 9.34 (br, 1H), 9.40 (br, 1H); $^{19}$F NMR (282 MHz, DMSO-d$_6$): δ −163.40; LCMS: purity: 94.12%; MS (m/e): 509.38 (MH+).

(I-68): N2-(4-aminosulfonyl)phenyl-N4-(4-cyclopentylsulfonylaminomethyl)phenyl-5-fluoro-2,4-pyrimidinediamine $^{1}$H NMR (DMSO-d$_6$): δ 1.51-1.63 (m, 4H), 1.84 (q, J=6.5 Hz, 4H), 3.42 (m, J=7.8 Hz, 1H), 4.15 (d, J=6.0 Hz, 2H), 7.11 (br, 2H), 7.30 (d, J=8.4 Hz, 2H), 7.57 (t, J=6.3 Hz, 1H), 7.63 (d, J=9.3 Hz, 2H), 7.75 (d, J=8.4 Hz, 2H), 7.82 (d, J=8.7 Hz, 2H), 8.14 (d, J=3.6 Hz, 1H), 9.44 (br, 1H), 9.61 (br, 1H); $^{19}$F NMR (282 MHz, DMSO-d$_6$): δ −201.00; LCMS: purity: 94.73%; MS (m/e): 521.36 (MH+).

(I-69): N2-(3-aminosulfonyl)phenyl-N4-(4-cyclopentylsulfonylaminomethyl)phenyl-5-fluoro-2,4-pyrimidinediamine $^{1}$H NMR (DMSO-d$_6$): δ 1.52 (q, J=7.5 Hz, 2H), 1.62 (q, J=6.6 Hz, 2H), 1.84 (q, J=6.9 Hz, 4H), 3.41 (m, J=7.5 Hz, 1H), 4.13 (d, J=6.0 Hz, 2H), 7.26 (br, 2H), 7.28 (d, J=8.4 Hz, 2H), 7.37 (m, 2H), 7.55 (t, J=6.0 Hz, 1H), 7.78 (d, J=8.7 Hz, 2H), 7.96 (d, J=7.8 Hz, 1H), 8.11 (m, 2H), 9.39 (br, 1H), 9.52 (br, 1H); $^{19}$F NMR (282 MHz, DMSO-d$_6$): δ −201.91; LCMS: purity: 98.85%; MS (m/e): 521.38 (MH+).

(I-70): N2-(3-aminosulfonyl-4-methyl)phenyl-N4-(4-cyclopentylsulfonylaminomethyl)phenyl-5-fluoro-2,4-pyrimidinediamine $^{1}$H NMR (DMSO-d$_6$): δ 1.52 (q, J=6.6 Hz, 2H), 1.62 (q, J=7.2 Hz, 2H), 1.84 (q, J=6.9 Hz, 4H), 3.41 (m, J=7.8 Hz, 1H), 4.13 (d, J=6.3 Hz, 2H), 7.18 (d, J=8.4 Hz, 1H), 7.23 (br, 2H), 7.28 (d, J=8.4 Hz, 2H), 7.55 (t, J=6.3 Hz, 1H), 7.78 (d, J=8.4 Hz, 2H), 7.91 (dd, J=2.4, 8.4 Hz, 1H), 8.08 (d, J=3.0 Hz, 1H), 8.10 (d, J=2.1 Hz, 1H), 9.35 (br, 1H), 9.41 (br, 1H); $^{19}$F NMR (282 MHz, DMSO-d$_6$): δ −202.46; LCMS: purity: 97.24%; MS (m/e): 535.05 (MH+).

(I-71): N2-(4-aminosulfonyl)phenyl-N4-(4-cyclohexylsulfonylaminomethyl)phenyl-5-fluoro-2,4-pyrimidinediamine $^1$H NMR (DMSO-d$_6$): δ 1.14 (m, 3H), 1.30 (m, 2H), 1.57 (m, 1H), 1.73 (m, 2H), 2.00 (m, 2H), 2.72 (m 1H), 4.13 (d, J=7.2 Hz, 2H), 7.11 (br, 2H), 7.30 (d, J=8.7 Hz, 2H), 7.54 (t, 1H), 7.63 (d, J=8.7 Hz, 2H), 7.75 (d, J=8.4 Hz, 2H), 7.82 (d, J=9.0 Hz, 2H), 8.14 (d, J=3.0 Hz, 1H), 9.44 (br, 1H), 9.61 (br, 1H); $^{19}$F NMR (282 MHz, DMSO-d$_6$): δ −162.32; LCMS: purity: 86.73%; MS (m/e): 535.24 (MH+).

(I-72): N2-(3-aminosulfonyl)phenyl-N4-(4-cyclohexylsulfonylaminomethyl)phenyl-5-fluoro-2,4-pyrimidinediamine $^1$H NMR (DMSO-d$_6$): δ 1.14 (m, 3H), 1.30 (m, 2H), 1.60 (m, 1H), 1.73 (m, 2H), 2.00 (m, 2H), 2.76 (m 1H), 4.11 (d, J=6.3 Hz, 2H), 7.26 (br, 2H), 7.28 (d, J=8.4 Hz, 2H), 7.36 (m, 2H), 7.52 (t, J=6.6 Hz, 1H), 7.78 (d, J=8.7 Hz, 2H), 7.97 (d, J=8.4 Hz, 1H), 8.10 (m, 2H), 9.39 (br, 1H), 9.52 (br, 1H); $^{19}$F NMR (282 MHz, DMSO-d$_6$): δ −162.84; LCMS: purity: 97.80%; MS (m/e): 535.38 (MH+).

(I-73): N2-(3-aminosulfonyl-4-methyl)phenyl-N4-(4-cyclohexylsulfonylaminomethyl)phenyl-5-fluoro-2,4-pyrimidinediamine $^1$H NMR (DMSO-d$_6$): δ 1.14 (m, 3H), 1.30 (m, 2H), 1.60 (m, 1H), 1.72 (m, 2H), 2.00 (m, 2H), 2.76 (m 1H), 4.11 (d, J=6.0 Hz, 2H), 7.18 (d, J=8.7 Hz, 1H), 7.23 (br, 2H), 7.28 (d, J=8.4 Hz, 2H), 7.52 (t, J=6.0 Hz, 1H), 7.77 (d, J=8.4 Hz, 2H), 7.91 (dd, J=2.1, 8.4 Hz, 1H), 8.08 (m, 2H), 9.35 (br, 1H), 9.41 (br, 1H); $^{19}$F NMR (282 MHz, DMSO-d$_6$): δ −163.40; LCMS: purity: 94.72%; MS (m/e): 549.41 (MH+).

(I-74): N2-(4-aminosulfonyl)phenyl-N4-(3-chloro-4-ethylsulfonylaminomethyl)phenyl-5-fluoro-2,4-pyrimidinediamine $^1$H NMR (DMSO-d$_6$): δ 1.20 (t, J=7.2 Hz, 3H), 3.05 (q, J=7.2 Hz, 2H), 4.22 (d, J=5.7 Hz, 2H), 7.14 (br, 2H), 7.38 (d, J=8.7 Hz, 1H), 7.64 (d, J=8.7 Hz, 2H), 7.67 (t, 1H), 7.80 (d, J=8.7 Hz, 2H), 7.85 (d, J=8.7 Hz, 1H), 7.96 (s, 1H), 8.18 (d, J=3.3 Hz, 1H), 9.47 (br, 1H), 9.71 (br, 1H); $^{19}$F NMR (282 MHz, DMSO-d$_6$): δ −161.97; LCMS: purity: 89.12%; MS (m/e): 515.29 (MH+).

(I-75): N2-(3-aminosulfonyl)phenyl-N4-(3-chloro-4-ethylsulfonylaminomethyl)phenyl-5-fluoro-2,4-pyrimidinediamine $^1$H NMR (DMSO-d$_6$): δ 1.20 (t, J=7.2 Hz, 3H), 3.05 (q, J=7.2 Hz, 2H), 4.21 (d, J=6.0 Hz, 2H), 7.26 (br, 2H), 7.37 (m, 3H), 7.63 (t, J=6.3 Hz, 1H), 7.88 (t, J=6.6 Hz, 2H), 8.00 (s, 1H), 8.15 (d, J=3.3 Hz, 2H), 9.33 (br, 1H), 9.65 (br, 1H); $^{19}$F NMR (282 MHz, DMSO-d$_6$): δ −162.34; LCMS: purity: 97.03%; MS (m/e): 515.30 (MH+).

(I-76): N2-(3-aminosulfonyl-4-methyl)phenyl-N4-(3-chloro-4-ethylsulfonylaminomethyl)phenyl-5-fluoro-2,4-pyrimidinediamine $^1$H NMR (DMSO-d$_6$): δ 1.20 (t, J=7.5 Hz, 3H), 3.04 (q, J=7.5 Hz, 2H), 4.21 (d, J=6.0 Hz, 2H), 7.20 (d, J=8.1 Hz, 1H), 7.25 (br, 2H), 7.35 (d, J=9.0 Hz, 2H), 7.63 (t, J=6.0 Hz, 1H), 7.83 (dd, J=2.1, 8.4 Hz, 1H), 7.90 (dd, J=2.1, 8.4 Hz, 1H), 8.01 (s, 1H), 8.12 (d, J=3.0 Hz, 1H), 8.15 (d, J=2.1 Hz, 1H), 9.23 (br, 1H), 9.62 (br, 1H); $^{19}$F NMR (282 MHz, DMSO-d$_6$): 8-162.88; LCMS: purity: 100%; MS (m/e): 529.35 (MH+).

(I-77): N4-[4-(N-cyclopropylsulfonyl-N-propionyl)aminomethyl]phenyl-5-methyl-N2-(4-propionylaminosulfonyl)phenyl-2,4-pyrimidinediamine $^1$H NMR (DMSO-d$_6$): δ 0.88 (t, J=7.2 Hz, 3H), 1.02 (t, J=7.2 Hz, 3H), 1.10 (m, 4H), 2.13 (s, 3H), 2.18 (q, J=7.2 Hz, 2H), 2.69 (q, J=6.6 Hz, 2H), 4.91 (s, 2H), 7.25 (d, J=8.7 Hz, 2H), 7.67 (d, J=9.0 Hz, 2H), 7.71 (d, J=8.7 Hz, 2H), 7.87 (d, J=8.7 Hz, 2H), 7.94 (s, 1H), 8.11 (s, 1H), 8.41 (s, 1H), 9.54 (br, 1H); LCMS: purity: 89.06%; MS (m/e): 601.64 (MH+).

(I-78): N4-[4-(N-cyclopropylsulfonyl-N-propionyl)aminomethyl]phenyl-5-methyl-N2-(4-propionylaminosulfonyl)phenyl-2,4-pyrimidinediamine sodium salt $^1$H NMR (DMSO-d$_6$): δ 0.84 (t, J=7.5 Hz, 3H), 1.02 (t, J=7.2 Hz, 3H), 1.07 (d, J=6.3 Hz, 4H), 1.91 (q, J=7.5 Hz, 2H), 2.11 (s, 3H), 2.69 (q, J=7.2 Hz, 2H), 4.91 (s, 2H), 7.23 (d, J=8.4 Hz, 2H), 7.52 (d, J=8.7 Hz, 2H), 7.65 (d, J=9.3 Hz, 2H), 7.73 (d, J=8.7 Hz, 2H), 7.90 (s, 1H), 8.30 (s, 1H), 9.16 (br, 1H); LCMS: purity: 89.53%; MS (m/e): 601.55 (MH+).

(I-79): N2-(4-aminosulfonyl)phenyl-N4-[4-(N-cyclopropylsulfonyl-N-propylamino)methyl]phenyl-5-methyl-2,4-pyrimidinediamine $^1$H NMR (DMSO-d$_6$): δ 0.73 (t, J=7.5 Hz, 3H), 1.00 (m, 4H), 1.44 (q, J=7.5 Hz, 2H), 2.17 (s, 3H), 2.69 (m, 1H), 3.76 (t, J=6.0 Hz, 2H), 4.41 (s, 2H), 7.22 (br, 2H), 7.41 (d, J=8.4 Hz, 2H), 7.55 (d, J=8.7 Hz, 2H), 7.61 (m, 4H), 7.94 (s, 1H), 9.67 (br, 1H), 10.48 (br, 1H); LCMS: purity: 96.85%; MS (m/e): 531.47 (MH+).

(I-80): N2-(3-aminosulfonyl)phenyl-N4-[4-(N-cyclopropylsulfonyl-N-propylamino)methyl]phenyl-5-methyl-2,4-pyrimidinediamine $^1$H NMR (DMSO-d$_6$): δ 0.75 (t, J=7.2 Hz, 3H), 1.00 (m, 4H), 1.45 (q, J=7.5 Hz, 2H), 2.12 (s, 3H), 2.66 (p, J=6.3 Hz, 1H), 3.08 (t, J=7.5 Hz, 2H), 4.35 (s, 2H), 7.24 (br, 2H), 7.32 (m, 4H), 7.74 (d, J=8.1 Hz, 2H), 7.90 (s, 1H), 8.01 (d, J=6.9 Hz, 1H), 8.05 (s, 1H), 8.36 (br, 1H), 9.34 (br, 1H); LCMS: purity: 92.07%; MS (m/e): 531.33 (MH+).

(I-81): N2-(3-aminosulfonyl-4-methyl)phenyl-N4-[4-(N-cyclopropylsulfonyl-N-propylamino)methyl]phenyl-5-methyl-2,4-pyrimidinediamine $^1$H NMR (DMSO-d$_6$): δ 0.75 (t, J=7.2 Hz, 3H), 0.99 (m, 4H), 1.46 (q, J=7.5 Hz, 2H), 2.10 (s, 3H), 2.66 (p, J=6.6 Hz, 1H), 3.09 (t, J=7.8 Hz, 2H), 4.35 (s, 2H), 7.10 (d, J=8.4 Hz, 1H), 7.20 (br, 2H), 7.31 (d, J=8.7 Hz, 2H), 7.74 (d, J=8.7 Hz, 2H), 7.87 (s, 1H), 7.95 (d, 1H), 8.06 (s, 1H), 8.28 (br, 1H), 9.20 (br, 1H); LCMS: purity: 98.54%; MS (m/e): 545.22 (MH+).

(I-82): N4-(4-cyclopropylsulfonylaminomethyl)phenyl-N2-(3,5-diaminosulfonyl)phenyl-5-fluoro-2,4-pyrimidinediamine $^1$H NMR (DMSO-d$_6$): δ 0.90 (m, 4H), 2.44 (m, 1H), 4.15 (d, J=6.0 Hz, 2H), 7.30 (d, J=8.7 Hz, 2H), 7.50 (br, 4H), 7.58

(t, J=6.3 Hz, 1H), 7.80 (s, 1H), 7.86 (d, J=8.4 Hz, 2H), 8.15 (d, J=3.6 Hz, 1H), 8.41 (s, 2H), 9.47 (br, 1H), 9.87 (br, 1H); $^{19}$F NMR (282 MHz, DMSO-$d_6$): 8-161.39; LCMS: purity: 95.79%; MS (m/e): 572.29 (MH+).

(I-83): N4-(4-cyclopropylsulfonylaminomethyl)phenyl-5-methyl-N2-(4-propionylaminosulfonyl)phenyl-2,4-pyrimidinediamine $^1$H NMR (DMSO-$d_6$): δ 0.87 (t, J=7.5 Hz, 3H), 0.90 (m, 4H), 2.12 (s, 3H), 2.18 (q, J=7.2 Hz, 2H), 4.18 (d, J=6.0 Hz, 2H), 7.31 (d, J=8.1 Hz, 2H), 7.60 (t, J=6.0 Hz, 1H), 7.67 (m, 4H), 7.85 (d, J=8.7 Hz, 2H), 7.93 (s, 1H), 8.11 (s, 1H), 8.39 (s, 1H), 9.53 (br, 1H); LCMS: purity: 98.27%; MS (m/e): 545.12 (MH+).

(I-84): N4-(4-cyclopropylsulfonylaminomethyl)phenyl-N2-(3,5-diaminosulfonyl)phenyl-5-methyl-2,4-pyrimidinediamine $^1$H NMR (DMSO-$d_6$): δ 0.91 (m, 4H), 2.14 (s, 3H), 4.14 (d, J=6.0 Hz, 2H), 7.28 (d, J=8.7 Hz, 2H), 7.48 (br, 4H), 7.57 (t, 1H), 7.76 (s, 1H), 7.82 (d, J=8.4 Hz, 2H), 7.94 (s, 1H), 8.31 (br, 1H), 8.44 (s, 2H), 9.64 (br, 1H); $^{19}$F NMR (282 MHz, DMSO-$d_6$): δ −161.39; LCMS: purity: 88.07%; MS (m/e): 568.08 (MH+).

(I-85): N2-(4-aminosulfonyl)phenyl-5-fluoro-N4-[4-(methylsulfonylmethylsulfonylamino)methyl]phenyl-2,4-pyrimidinediamine $^1$H NMR (DMSO-$d_6$): δ 3.19 (s, 3H), 4.21 (d, J=6.0 Hz, 2H), 5.13 (s, 2H), 7.13 (br, 2H), 7.31 (d, J=8.1 Hz, 2H), 7.64 (d, J=8.7 Hz, 2H), 7.75 (d, J=8.7 Hz, 2H), 7.81 (d, J=8.7 Hz, 2H), 8.17 (d, J=3.6 Hz, 1H), 8.25 (t, J=6.0 Hz, 1H), 9.60 (br, 1H), 9.72 (br, 1H); $^{19}$F NMR (282 MHz, DMSO-$d_6$): δ −161.95; LCMS: purity: 87.84%; MS (m/e): 545.01 (MH+).

(I-86): N2-(3-aminosulfonyl)phenyl-5-fluoro-N4-[4-(methylsulfonylmethylsulfonylamino)methyl]phenyl-2,4-pyrimidinediamine $^1$H NMR (DMSO-$d_6$): δ 3.18 (s, 3H), 4.20 (d, J=5.7 Hz, 2H), 5.12 (s, 2H), 7.28 (br, 2H), 7.30 (d, J=9.0 Hz, 2H), 7.38 (m, 2H), 7.76 (d, J=9.0 Hz, 2H), 7.94 (d, J=7.8 Hz, 1H), 8.05 (s, 1H), 8.14 (d, J=3.9 Hz, 1H), 8.22 (t, J=6.0 Hz, 1H), 9.58 (br, 1H), 9.64 (br, 1H); $^{19}$F NMR (282 MHz, DMSO-$d_6$): δ −162.38; LCMS: purity: 88.57%; MS (m/e): 545.00 (MH+).

(I-87): N2-(3-aminosulfonyl-4-methyl)phenyl-5-fluoro-N4-[4-(methylsulfonylmethylsulfonylamino)methyl]phenyl-2,4-pyrimidinediamine $^1$H NMR (DMSO-$d_6$): δ 3.18 (s, 3H), 4.20 (d, J=5.4 Hz, 2H), 5.13 (s, 2H), 7.19 (d, J=8.1 Hz, 1H), 7.25 (br, 2H), 7.29 (d, J=8.4 Hz, 2H), 7.76 (d, J=8.4 Hz, 2H), 7.88 (d, J=8.4 Hz, 1H), 8.06 (s, 1H), 8.11 (d, J=3.9 Hz, 1H), 8.23 (t, J=6.3 Hz, 1H), 9.55 (br, 2H); LCMS: purity: 89.56%; MS (m/e): 559.04 (MH+).

(I-88): N4-(4-cyclopropylsulfonylaminomethyl)phenyl-5-methyl-N2-(4-propionylaminosulfonyl)phenyl-2,4-pyrimidinediamine sodium salt LCMS: purity: 82.56%; MS (m/e): 545.22 (MH+).

(I-89): N2-(4-aminosulfonyl)phenyl-5-fluoro-N4-[4-(pyrid-3-yl)sulfonylaminomethyl]phenyl-2,4-pyrimidinediamine $^1$H NMR (DMSO-$d_6$): δ 4.05 (d, J=5.7 Hz, 2H), 7.11 (br, 2H), 7.18 (d, J=8.4 Hz, 2H), 7.57 (dd, J=4.8, 7.8 Hz, 1H), 7.63 (d, J=8.7 Hz, 2H), 7.68 (d, J=8.7 Hz, 2H), 7.81 (d, J=9.0 Hz, 2H), 8.13 (m, 2H), 8.39 (t, J=5.7 Hz, 1H), 8.76 (d, J=3.3 Hz, 1H), 8.91 (d, J=1.5 Hz, 1H), 9.40 (br, 1H), 9.59 (br, 1H); $^{19}$F NMR (282 MHz, DMSO-$d_6$): δ −162.26; LCMS: purity: 99.68%; MS (m/e): 530.00 (MH+).

(I-90): N2-(3-aminosulfonyl-4-methyl)phenyl-5-fluoro-N4-[4-(pyrid-3-yl)sulfonylaminomethyl]phenyl-2,4-pyrimidinediamine $^1$H NMR (DMSO-$d_6$): δ 4.03 (d, J=6.3 Hz, 2H), 7.16 (d, J=8.4 Hz, 2H), 7.18 (d, J=8.4 Hz, 1H), 7.23 (br, 2H), 7.57 (dd, J=5.4, 7.8 Hz, 1H), 7.71 (d, J=8.4 Hz, 2H), 7.90 (dd, J=1.8, 7.8 Hz, 1H), 8.07 (d, J=3.9 Hz, 1H), 8.10 (m, 2H), 8.38 (t, J=6.3 Hz, 1H), 8.76 (dd, J=1.5, 5.1 Hz, 1H), 8.91 (d, J=2.1 Hz, 1H), 9.32 (br, 1H), 9.40 (br, 1H); $^{19}$F NMR (282 MHz, DMSO-$d_6$): δ −163.35; LCMS: purity: 98.98%; MS (m/e): 544.03 (MH+).

(I-91): N4-[4-(N-ethylsulfonyl-N-propionyl)aminomethyl]phenyl-5-methyl-N2-(4-propionylaminosulfonyl)phenyl-2,4-pyrimidinediamine $^1$H NMR (DMSO-$d_6$): δ 0.88 (t, J=7.5 Hz, 3H), 0.98 (t, J=6.9 Hz, 3H), 1.24 (t, J=7.2 Hz, 3H), 2.13 (s, 3H), 2.18 (q, J=7.5 Hz, 2H), 2.61 (q, J=6.9 Hz, 2H), 3.59 (q, J=7.5 Hz, 2H), 4.91 (s, 2H), 7.27 (d, J=8.4 Hz, 2H), 7.67 (d, J=9.0 Hz, 2H), 7.71 (d, J=8.4 Hz, 2H), 7.87 (d, J=9.3 Hz, 2H), 7.94 (s, 1H), 8.42 (br, 1H), 9.55 (br, 1H), 11.75 (br, 1H); LCMS: purity: 100%; MS (m/e): 589.13 (MH+).

(I-92): N4-[4-(N-ethylsulfonyl-N-propionyl)aminomethyl]phenyl-5-methyl-N2-(4-propionylaminosulfonyl)phenyl-2,4-pyrimidinediamine sodium salt $^1$H NMR (DMSO-$d_6$): δ 0.84 (t, J=7.5 Hz, 3H), 0.98 (t, J=7.2 Hz, 3H), 1.24 (t, J=7.2 Hz, 3H), 1.94 (q, J=6.9 Hz, 2H), 2.11 (s, 3H), 2.62 (q, J=7.5 Hz, 2H), 3.58 (q, J=7.5 Hz, 2H), 4.92 (s, 2H), 7.26 (d, J=8.4 Hz, 2H), 7.54 (d, J=8.1 Hz, 2H), 7.67 (d, J=8.1 Hz, 2H), 7.74 (d, J=9.0 Hz, 2H), 7.90 (s, 1H), 8.30 (br, 1H), 9.18 (br, 1H); LCMS: purity: 81.98%; MS (m/e): 589.20 (MH+).

(I-93): N4-[3-(N-cyclopropylsulfonyl-N-propionyl)aminomethyl]phenyl-5-methyl-N2-(3-propionylaminosulfonyl)phenyl-2,4-pyrimidinediamine $^1$H NMR (DMSO-$d_6$): δ 0.88 (t, J=7.2 Hz, 3H), 0.97 (t, J=7.2 Hz, 3H), 1.10 (m, 4H), 2.13 (s, 3H), 2.21 (q, J=7.2 Hz, 2H), 2.64 (q, J=7.2 Hz, 2H), 4.92 (s, 2H), 6.95 (d, J=7.8 Hz, 1H), 7.34 (m, 3H), 7.62 (s, 1H), 7.67 (d, J=8.4 Hz, 1H), 7.92 (s, 1H), 8.07 (m, 1H), 8.20 (s, 1H), 8.41 (s, 1H), 9.20 (br, 1H), 11.95 (br, 1H); LCMS: purity: 95.88%; MS (m/e): 601.13 (MH+).

(I-94): N4-[3-(N-cyclopropylsulfonyl-N-propionyl)aminomethyl]phenyl-5-methyl-N2-(3-propionylaminosulfonyl)phenyl-2,4-pyrimidinediamine sodium salt $^1$H NMR (DMSO-$d_6$): δ 0.84 (t, J=7.5 Hz, 3H), 0.98 (t, J=6.9 Hz, 3H), 1.10 (m, 4H), 1.90 (q, J=7.5 Hz, 2H), 2.11 (s, 3H), 2.63 (q, J=6.9 Hz, 2H), 4.92 (s, 2H), 6.91 (d, J=7.2 Hz, 1H), 7.12 (d, J=8.7 Hz, 1H), 7.21 (d, J=7.8 Hz, 1H), 7.30 (t, J=7.8 Hz, 1H), 7.68 (d, J=7.8 Hz, 1H), 7.72 (s, 1H), 7.84 (m, 2H), 7.88 (s, 1H), 8.28 (s, 1H), 8.86 (s, 1H); LCMS: purity: 90.93%; MS (m/e): 601.06 (MH+).

(I-95): N2-(3-aminosulfonyl)phenyl-5-fluoro-N4-[4-(pyrid-3-yl)sulfonylaminomethyl]phenyl-2,4-pyrimidinediamine $^1$H NMR (DMSO-d$_6$): δ 4.04 (d, J=6.3 Hz, 2H), 7.17 (d, J=8.4 Hz, 2H), 7.25 (br, 2H), 7.36 (m, 1H), 7.57 (dd, J=5.4, 7.5 Hz, 1H), 7.71 (d, J=8.4 Hz, 2H), 7.96 (d, J=7.8 Hz, 1H), 8.11 (m, 3H), 8.37 (t, J=7.2 Hz, 1H), 8.76 (dd, J=1.5, 5.1 Hz, 1H), 8.91 (d, J=1.8 Hz, 1H), 9.35 (br, 1H), 9.50 (br, 1H); $^{19}$F NMR (282 MHz, DMSO-d$_6$): δ −162.78; LCMS: purity: 99.56%; MS (m/e): 530.09 (MH+).

(I-96): N2-(4-aminosulfonyl)phenyl-5-methyl-N4-(4-trifluoroethylsulfonylaminomethyl)phenyl-2,4-pyrimidinediamine $^1$H NMR (DMSO-d$_6$): δ 2.12 (s, 3H), 4.20 (d, J=6.3 Hz, 2H), 4.39 (q, J=10.2 Hz, 2H), 7.08 (br, 2H), 7.29 (d, J=8.1 Hz, 2H), 7.59 (d, J=9.0 Hz, 2H), 7.70 (d, J=8.7 Hz, 2H), 7.83 (d, J=8.7 Hz, 2H), 7.92 (s, 1H), 8.28 (t, 1H), 8.37 (br, 1H), 9.39 (br, 1H); $^{19}$F NMR (282 MHz, DMSO-d$_6$): δ −61.83; LCMS: purity: 98.02%; MS (m/e): 530.83 (MH+).

(I-97): N2-(3-aminosulfonyl)phenyl-5-methyl-N4-(4-trifluoroethylsulfonylaminomethyl)phenyl-2,4-pyrimidinediamine $^1$H NMR (DMSO-d$_6$): δ 2.12 (s, 3H), 4.18 (d, J=5.4 Hz, 2H), 4.39 (q, J=10.2 Hz, 2H), 7.23 (br, 2H), 7.29 (m, 4H), 7.72 (d, J=8.4 Hz, 2H), 7.90 (s, 1H), 8.01 (d, J=8.4 Hz, 1H), 8.07 (s, 1H), 8.27 (t, J=6.3 Hz, 1H), 8.31 (br, 1H), 9.30 (br, 1H); $^{19}$F NMR (282 MHz, DMSO-d$_6$): 8-61.84; LCMS: purity: 99.53%; MS (m/e): 531.39 (MH+).

(I-98): N2-(3-aminosulfonyl-4-methyl)phenyl-5-methyl-N4-(4-trifluoroethylsulfonylaminomethyl)phenyl-2,4-pyrimidinediamine $^1$H NMR (DMSO-d$_6$): δ 2.10 (s, 3H), 4.18 (d, J=6.0 Hz, 2H), 4.40 (q, J=9.9 Hz, 2H), 7.12 (d, J=8.7 Hz, 1H), 7.20 (br, 2H), 7.27 (d, J=8.4 Hz, 2H), 7.72 (d, J=8.4 Hz, 2H), 7.87 (s, 1H), 7.94 (d, J=8.7 Hz, 1H), 8.08 (s, 1H), 8.27 (m, 2H), 9.19 (br, 1H); $^{19}$F NMR (282 MHz, DMSO-d$_6$): δ −61.84; LCMS: purity: 99.71%; MS (m/e): 545.02 (MH+).

(I-99): N2-(4-aminosulfonyl)phenyl-5-methyl-N4-[4-(pyrid-3-yl)sulfonylaminomethyl]phenyl-2,4-pyrimidinediamine $^1$H NMR (DMSO-d$_6$): δ 2.11 (s, 3H), 4.05 (d, J=6.0 Hz, 2H), 7.09 (br, 2H), 7.18 (d, J=8.4 Hz, 2H), 7.57 (m, 1H), 7.58 (d, J=9.3 Hz, 2H), 7.61 (d, J=9.0 Hz, 2H), 7.81 (d, J=8.4 Hz, 2H), 7.92 (s, 1H), 8.14 (dt, J=8.1 Hz, 1H), 8.33 (s, 1H), 8.40 (t, J=6.3 Hz, 1H), 8.76 (d, J=6.6 Hz, 1H), 8.92 (d, J=3.0 Hz, 1H), 9.39 (br, 1H); LCMS: purity: 86.90%; MS (m/e): 526.04 (MH+).

(I-100): N2-(3-aminosulfonyl)phenyl-5-methyl-N4-[4-(pyrid-3-yl)sulfonylaminomethyl]phenyl-2,4-pyrimidinediamine $^1$H NMR (DMSO-d$_6$): δ 2.11 (s, 3H), 4.01 (d, J=6.9 Hz, 2H), 7.16 (d, J=8.4 Hz, 2H), 7.24 (br, 2H), 7.30 (m, 2H), 7.58 (dd, J=4.8, 7.8 Hz, 1H), 7.65 (d, J=8.4 Hz, 2H), 7.89 (s, 1H), 8.01 (d, J=7.5 Hz, 1H), 8.06 (s, 1H), 8.14 (dt, J=1.8, 7.8 Hz, 1H), 8.27 (s, 1H), 8.38 (t, J=6.0 Hz, 1H), 8.77 (dd, J=1.5, 4.8 Hz, 1H), 8.92 (d, J=2.4 Hz, 1H), 9.30 (br, 1H); LCMS: purity: 96.15%; MS (m/e): 526.12 (MH+).

(I-101): N2-(3-aminosulfonyl-4-methyl)phenyl-5-methyl-N4-[4-(pyrid-3-yl)sulfonylaminomethyl]phenyl-2,4-pyrimidinediamine $^1$H NMR (DMSO-d$_6$): δ 2.10 (s, 3H), 4.03 (s, 2H), 7.13 (m, 1H), 7.16 (d, J=8.4 Hz, 1H), 7.20 (br, 2H), 7.58 (dd, J=5.1, 7.8 Hz, 1H), 7.65 (d, J=8.7 Hz, 2H), 7.86 (s, 1H), 7.94 (d, J=5.7 Hz, 1H), 8.08 (s, 1H), 8.14 (d, J=8.7 Hz, 1H), 8.23 (s, 1H), 8.76 (dd, J=3.3 Hz, 1H), 8.92 (d, J=1.8 Hz, 1H), 9.18 (br, 1H); LCMS: purity: 93.15%; MS (m/e): 540.14 (MH+).

(I-106): N2-(3-Aminosulfonylphenyl)-5-fluoro-N4-[4-(N-methylaminosulfonylmethylene)phenyl]-2,4-pyrimidinediamine $^1$H NMR (DMSO-d$_6$): δ 9.56 (s, 1H), 9.46 (s, 1H), 8.13 (m, 2H), 7.99 (d, 1H, J=8.7 Hz), 7.85 (d, 2H, J=8.4 Hz), 7.35 (m, 6H), 6.89 (s, 1H), 4.29 (s, 2H), 2.56 (s, 3H): LCMS: purity: 90%; MS (m/e): 467 (MH$^+$).

(I-102): N2-(3-Aminosulfonylphenyl)-5-fluoro-N4-[3-(N-methylaminosulfonylmethylene)phenyl]-2,4-pyrimidinediamine $^1$H NMR (DMSO-d$_6$): δ 8.13 (d, 2H, J=10.5 Hz), 7.73 (s, 1H), 7.35 (m, 4H), 7.08 (d, 1H, J=6.9 Hz), 6.93 (s, 1H), 4.30 (s, 2H), 2.55 (s, 3H): LCMS: purity: 92%; MS (m/e): 467 (MH$^+$).

(I-103): N2-(3-Aminosulfonyl-4-methylphenyl)-5-fluoro-N4-[3-(N-methylaminosulfonylmethylene)phenyl]-2,4-pyrimidinediamine $^1$HNMR (DMSO-d$_6$): δ 8.11 (d, 2H, J=3.6 Hz), 7.90 (d, 2H, J=8.1 Hz), 7.73 (s, 1H), 7.20 (m, 2H,), 7.05 (d, 1H, J=7.2 Hz), 6.93 (d, 1H, J=4.8 Hz), 4.29 (s, 2H), 2.56 (s, 3H), 2.50 (s, 3H): LCMS: purity: 91%; MS (m/e): 481 (MH$^+$).

(I-104): N2-(3-Aminosulfonylphenyl)-5-fluoro-N4-[3-(N,N-dimethylaminosulfonylmethylene)phenyl]-2,4-pyrimidinediamine $^1$HNMR (DMSO-d$_6$): δ 8.15 (d, 1H, J=3.6 Hz), 8.08 (s, 1H), 7.94 (d, 2H, J=7.8 Hz), 7.75 (s, 1H), 7.34 (m, 3H), 7.27 (s, 1H), 7.13 (d, 1H, J=8.7 Hz), 4.38 (s, 2H), 2.70 (s, 6H): LCMS: purity: 94%; MS (m/e): 481 (MH$^+$).

(I-105): N2-(3-Aminosulfonyl-4-methylphenyl)-5-fluoro-N4-[3-(N,N-dimethylaminosulfonylmethylene)phenyl]-2,4-pyrimidinediamine $^1$HNMR (DMSO-d$_6$): δ 8.11 (d, 2H, J=3.9 Hz), 7.95 (d, 1H, J=7.8 Hz), 7.89 (d, 1H, J=7.8 Hz), 7.76 (s, 1H), 7.33 (t, 1H, J=8.1 Hz), 7.24 (s, 1H), 7.19 (d, 1H, J=8.1 Hz), 7.11 (d, 1H, J=7.5 Hz), 4.37 (s, 2H), 2.69 (s, 6H), 2.45 (s, 3H): LCMS: purity: 93%; MS (m/e): 495 (MH$^+$).

(I-107): N2-(3-Aminosulfonyl-4-methylphenyl)-5-fluoro-N4-[3-(1-methylpiperdin-4-ylaminosulfonylmethylene)phenyl]-2,4-pyrimidinediamine $^1$HNMR (DMSO-d$_6$): δ 9.55 (d, 1H, J=8.1 Hz), 9.46 (s, 1H), 8.38 (s, 2H), 8.17 (s, 2H), 7.92 (m, 3H), 7.38 (m, 4H), 7.16 (d, 1H, J=6.9 Hz), 4.36 (s, 2H), 2.6 (m, 1H), 2.5 (s, 3H), 2.10 (s, 3H), 2.03 (bm, 4H), 1.86 (m, 4H): LCMS: purity: 95%; MS (m/e): 564 (MH+).

(I-108): N2-(3-Aminosulfonylphenyl)-5-fluoro-N4-[3-(1-methylpiperdin-4-ylaminosulfonylmethylene)phenyl]-2,4-pyrimidinediamine $^1$HNMR (DMSO-d$_6$): δ 9.59 (s, 1H), 9.53 (s, 1H), 8.40 (s, 1H), 8.21 (m, 1H), 8.02 (m, 1H), 7.90 (m, 2H), 7.43 (m, 5H), 7.14 (m, 2H), 4.37 (s, 2H), 2.6 (m, 1H), 2.09 (s, 3H), 2.03 (bm, 4H), 1.85 (m, 4H): LCMS: purity: 83%; MS (m/e): 550 (MH+).

(I-109): N2-(3-Aminosulfonyl-4-methylphenyl)-5-fluoro-N4-[4-(N-methylaminosulfonylmethylene)phenyl]-2,4-pyrimidinediamine $^1$HNMR (DMSO-d$_6$): δ 9.45 (d, 2H, J=9.9 Hz), 8.10 (d, 2H, J=4.2 Hz), 7.93 (m, 1H), 7.85 (d, 2H, J=8.4 Hz), 7.32 (d, 2H, J=8.7 Hz), 7.21 (t, 3H, J=7.8 Hz), 6.89 (d, 1H, J=4.8 Hz), 4.29 (s, 2H), 2.57 (s, 3H), 2.50 (s, 3H): LCMS: purity: 96%; MS (m/e): 481 (MH+)

(I-110): N2-(3-Aminosulfonyl-4-methylphenyl)-5-fluoro-N4-[4-(N,N-dimethylaminosulfonylmethylene)phenyl]-2,4-pyrimidinediamine $^1$HNMR (DMSO-d$_6$): δ 9.45 (d, 2H, J=9.9 Hz), 8.10 (d, 2H, J=4.2 Hz), 7.93 (m, 1H), 7.85 (d, 2H, J=8.4 Hz), 7.32 (d, 2H, J=8.7 Hz), 7.21 (t, 3H, J=7.8 Hz), 6.89 (d, 1H, J=4.8 Hz), 4.29 (s, 2H), 2.57 (s, 6H), 2.50 (s, 3H): LCMS: purity: 92%; MS (m/e): 495 (MH+).

(I-111): N2-(3-Aminosulfonylphenyl)-5-fluoro-N4-[3-(N-cyclopropylaminosulfonylmethylene)phenyl]-2,4-pyrimidinediamine $^1$HNMR (DMSO-d$_6$): δ 9.50 (s, 1H), 9.46 (s, 1H), 8.14 (d, 1H, J=3.6 Hz), 8.10 (s, 1H), 7.95 (d, 1H, J=7.8 Hz), 7.89 (d, 1H, J=8.1 Hz), 7.75 (s, 2H), 7.47 (s, 1H), 7.36 (m, 2H), 7.27 (s, 2H), 7.09 (d, 1H, J=7.5 Hz), 4.34 (s, 2H), 2.49 (s, 1H), 0.56 (m, 4H): LCMS: purity: 99%; MS (m/e): 493 (MH+).

(I-112): N2-(3-Aminosulfonyl-4-methylphenyl)-5-fluoro-N4-[3-(N-cyclopropylaminosulfonylmethylene)phenyl]-2,4-pyrimidinediamine $^1$HNMR (DMSO-d$_6$): δ 9.35 (s, 1H), 8.10 (d, 2H, J=3.0 Hz), 7.89 (d, 2H, J=8.4 Hz), 7.75 (s, 1H), 7.33 (t, 2H, J=8.1 Hz), 7.20 (d, 1H, J=8.1 Hz), 7.09 (d, 1H, J=7.2 Hz), 4.33 (s, 2H), 2.50 (s, 3H), 2.49 (s, 1H), 0.53 (m, 4H): LCMS: purity: 97%; MS (m/e): 507 (MH+).

(I-149): N4-(4-cyclopropylsulfonylaminomethyl)phenyl-5-methyl-N2-(4-phenylaminosulfonyl)phenyl-2,4-pyrimidinediamine $^1$H NMR (DMSO-d$_6$): δ 0.90 (m, 4H), 2.10 (s, 3H), 4.17 (d, J=6.3 Hz, 2H), 6.96 (t, J=6.6 Hz, 1H), 7.05 (d, J=8.4 Hz, 2H), 7.18 (t, J=7.5 Hz, 2H), 7.26 (d, J=8.4 Hz, 2H), 7.50 (d, J=9.0 Hz, 2H), 7.62 (d, J=8.7 Hz, 3H), 7.76 (d, J=8.7 Hz, 2H), 7.89 (s, 1H), 8.37 (s, 1H), 9.44 (s, 1H), 10.00 (s, 1H); LCMS: purity: 94.71%; MS (m/e): 565.12 (MH+).

(I-150): N4-(4-cyclopropylsulfonylaminomethyl)phenyl-5-methyl-N2-(3-phenylaminosulfonyl)phenyl-2,4-pyrimidinediamine $^1$H NMR (DMSO-d$_6$): δ 0.89 (m, 4H), 2.12 (s, 3H), 2.43 (m, 1H), 4.16 (d, J=6.0 Hz, 2H), 6.97 (t, J=7.8 Hz, 1H), 7.07 (d, J=8.4 Hz, 2H), 7.19 (m, 3H), 7.30 (m, 3H), 7.58 (t, J=6.0 Hz, 1H), 7.66 (d, J=8.4 Hz, 2H), 7.88 (s, 1H), 7.99 (d, J=7.2 Hz, 1H), 8.07 (s, 1H), 8.38 (br, 1H), 9.35 (br, 1H), 10.21 (s, 1H); LCMS: purity: 92.55%; MS (m/e): 565.19 (MH+).

(I-151): N4-(4-cyclopropylsulfonylaminomethyl)phenyl-5-methyl-N2-[4-(1-methylpiperidin-4-yl)aminosulfonyl]phenyl-2,4-pyrimidinediamine $^1$H NMR (DMSO-d$_6$): δ 0.90 (m, 4H), 1.34 (m, 2H), 1.50 (m, 2H), 1.81 (m, 2H), 2.06 (s, 3H), 2.12 (s, 3H), 2.56 (m, 2H), 2.81 (m, 1H), 4.18 (d, J=6.0 Hz, 2H), 7.31 (d, J=8.4 Hz, 2H), 7.39 (d, J=7.2 Hz, 1H), 7.56 (d, J=8.7 Hz, 2H), 7.62 (t, J=6.0 Hz, 1H), 7.66 (d, J=8.4 Hz, 2H), 7.83 (d, J=8.7 Hz, 2H), 7.92 (s, 1H), 8.37 (s, 1H), 9.44 (s, 1H); LCMS: purity: 99.16%; MS (m/e): 586.15 (MH+).

(I-152): N4-(4-cyclopropylsulfonylaminomethyl)phenyl-5-methyl-N2-[3-(1-methylpiperidin-4-yl)aminosulfonyl]phenyl-2,4-pyrimidinediamine $^1$H NMR (DMSO-d$_6$): δ 0.90 (m, 4H), 1.37 (m, 2H), 1.54 (m, 2H), 1.83 (m, 2H), 2.08 (s, 3H), 2.12 (s, 3H), 2.61 (m, 2H), 2.89 (m, 1H), 4.16 (d, J=5.7 Hz, 2H), 7.23-7.37 (m, 4H), 7.58 (m, 2H), 7.70 (d, J=7.5 Hz, 2H), 7.90 (s, 1H), 8.04 (d, J=9.0 Hz, 1H), 8.07 (s, 1H), 8.31 (s, 1H), 9.30 (s, 1H); LCMS: purity: 96.63%; MS (m/e): 586.33 (MH+).

(I-153): N2-(4-benzylaminosulfonyl)phenyl-N4-(4-cyclopropylsulfonylaminomethyl)phenyl-5-methyl-2,4-pyrimidinediamine $^1$H NMR (DMSO-d$_6$): δ 0.89 (m, 4H), 2.14 (s, 3H), 3.92 (d, J=6.0 Hz, 2H), 4.17 (d, J=6.6 Hz, 2H), 7.24 (m, 5H), 7.32 (d, J=8.4 Hz, 2H), 7.59 (m, 3H), 7.68 (d, J=7.8 Hz, 2H), 7.84 (m, 3H), 7.94 (s, 1H), 8.38 (s, 1H), 9.45 (s, 1H); LCMS: purity: 96.62%; MS (m/e): 579.19 (MH+).

(I-154): N2-(3-benzylaminosulfonyl)phenyl-N4-(4-cyclopropylsulfonylaminomethyl)phenyl-5-methyl-2,4-pyrimidinediamine $^1$H NMR (DMSO-d$_6$): δ 0.90 (m, 4H), 2.12 (s, 3H), 3.97 (d, J=6.0 Hz, 2H), 4.16 (d, J=6.0 Hz, 2H), 7.24 (m, 6H), 7.30 (d, J=9.0 Hz, 2H), 7.36 (t, J=8.1 Hz, 1H), 7.59 (t, J=6.3 Hz, 1H), 7.70 (d, J=8.4 Hz, 2H), 7.90 (s, 1H), 8.06 (m, 3H), 8.38 (br, 1H), 9.35 (s, 1H); LCMS: purity: 95.05%; MS (m/e): 579.19 (MH+).

(I-155): N4-(3-cyclopropylsulfonylaminomethyl)phenyl-5-methyl-N2-(4-phenylaminosulfonyl)phenyl-2,4-pyrimidinediamine $^1$H NMR (DMSO-d$_6$): δ 0.86 (m, 4H), 2.11 (s, 3H), 2.46 (m, 1H), 4.17 (d, J=6.3 Hz, 2H), 6.96 (t, J=6.9 Hz, 1H), 7.06 (t, 3H), 7.18 (t, 2H), 7.26 (t, J=8.4 Hz, 1H), 7.47 (d, J=8.7 Hz, 2H), 7.53 (s, 1H), 7.62 (m, 2H), 7.73 (d, J=8.7 Hz, 2H), 7.91 (s, 1H), 8.47 (s, 1H), 9.42 (s, 1H), 10.01 (s, 1H); LCMS: purity: 85.09%; MS (m/e): 565.18 (MH+).

(I-156): N4-(3-cyclopropylsulfonylaminomethyl)phenyl-5-methyl-N2-(3-phenylaminosulfonyl)phenyl-2,4-pyrimidinediamine $^1$H NMR (DMSO-d$_6$): δ 0.87 (m, 4H), 2.12 (s, 3H), 4.17 (d, J=6.6 Hz, 2H), 6.97 (t, J=7.2 Hz, 1H), 7.06 (m, 3H), 7.19 (m, 3H), 7.28 (t, J=8.1 Hz, 2H), 7.60 (t, J=6.9 Hz, 1H), 7.64 (s, 1H), 7.68 (d, J=8.1 Hz, 1H), 7.90 (s, 1H), 7.99 (d, J=8.4 Hz, 1H), 8.09 (s, 1H), 8.37 (s, 1H), 9.23 (s, 1H), 10.22 (s, 1H); LCMS: purity: 83.10%; MS (m/e): 565.19 (MH+).

(I-157): N2-(4-benzylaminosulfonyl)phenyl-N4-(3-cyclopropylsulfonylaminomethyl)phenyl-5-methyl-2,4-pyrimidinediamine $^1$H NMR (DMSO-d$_6$): δ 0.86 (m, 4H), 2.13 (s, 3H), 3.90 (d, J=6.6 Hz, 2H), 4.19 (d, J=6.0 Hz, 2H), 7.09 (d, J=7.2 Hz, 1H), 7.23 (m, 5H), 7.32 (t, J=8.1 Hz, 1H), 7.54 (d, J=8.7 Hz, 2H), 7.59 (s, 1H), 7.62 (m, 2H), 7.82 (d, J=8.7 Hz, 3H), 7.94 (s, 1H), 8.47 (s, 1H), 9.41 (s, 1H); LCMS: purity: 87.95%; MS (m/e): 579.22 (MH+).

(I-158): N2-(3-benzylaminosulfonyl)phenyl-N4-(3-cyclopropylsulfonylaminomethyl)phenyl-5-methyl-2,4-pyrimidinediamine $^1$H NMR (DMSO-d$_6$): δ 0.88 (m, 4H), 2.13 (s, 3H), 3.97 (d, J=5.7 Hz, 2H), 4.18 (d, J=6.0 Hz, 2H), 7.04 (d, J=7.5 Hz, 1H), 7.24 (m, 7H), 7.34 (t, J=8.1 Hz, 1H), 7.60 (t, J=5.7 Hz, 1H), 7.69 (m, 2H), 7.92 (s, 1H), 8.07 (m, 3H), 8.36 (s, 1H), 9.22 (s, 1H); LCMS: purity: 98.59%; MS (m/e): 579.42 (MH+).

(I-159): N4-(3-cyclopropylsulfonylaminomethyl)phenyl-5-methyl-N2-[4-(1-methylpiperidin-4-yl)aminosulfonyl]phenyl-2,4-pyrimidinediamine $^1$H NMR (DMSO-d$_6$): δ 0.82 (m, 4H), 1.29 (m, 2H), 1.46 (m, 2H), 1.80 (m, 2H), 2.05 (s, 3H), 2.12 (s, 3H), 2.55 (m, 2H), 2.78 (m, 1H), 4.18 (d, J=5.4 Hz, 2H), 7.08 (d, J=7.2 Hz, 1H), 7.31 (t, J=7.8 Hz, 1H), 7.39 (d, J=5.7 Hz, 1H), 7.52 (d, J=8.7 Hz, 2H), 7.57 (s, 1H), 7.62 (d, 2H), 7.79 (d, J=8.4 Hz, 2H), 7.92 (s, 1H), 8.47 (s, 1H), 9.40 (s, 1H); LCMS: purity: 99.55%; MS (m/e): 586.20 (MH+).

(I-160): N4-(3-cyclopropylsulfonylaminomethyl)phenyl-5-methyl-N2-[3-(1-methylpiperidin-4-yl)aminosulfonyl]phenyl-2,4-pyrimidinediamine $^1$H NMR (DMSO-d$_6$): δ 0.88 (m, 4H), 1.38 (m, 2H), 1.53 (m, 2H), 1.81 (m, 2H), 2.06 (s, 3H), 2.12 (s, 3H), 2.57 (m, 2H), 2.88 (m, 1H), 4.18 (d, J=6.0 Hz, 2H), 7.04 (d, J=7.2 Hz, 1H), 7.23-7.35 (m, 3H), 7.58 (m, 2H), 7.68 (m, 2H), 7.90 (s, 1H), 8.01 (d, J=8.1 Hz, 1H), 8.05 (s, 1H), 8.36 (s, 1H), 9.22 (s, 1H); LCMS: purity: 98.17%; MS (m/e): 586.44 (MH+).

(I-161): N4-(4-cyclopropylsulfonylaminomethyl)phenyl-5-methyl-N2-(3-methylaminosulfonyl)phenyl-2,4-pyrimidinediamine $^1$H NMR (DMSO-d$_6$): δ 0.89 (m, 4H), 2.11 (s, 3H), 2.40 (d, J=4.8 Hz, 3H), 4.15 (d, J=5.7 Hz, 2H), 7.19 (d, J=6.9 Hz, 1H), 7.30 (m, 3H), 7.36 (t, J=7.8 Hz, 1H), 7.58 (t, J=6.3 Hz, 1H), 7.69 (d, J=8.4 Hz, 2H), 7.89 (s, 1H), 8.02 (s, 1H), 8.07 (d, J=8.1 Hz, 1H), 8.30 (s, 1H), 9.31 (s, 1H); LCMS: purity: 98.90%; MS (m/e): 503.16 (MH+).

(I-162): N4-(3-cyclopropylsulfonylaminomethyl)phenyl-5-methyl-N2-(3-methylaminosulfonyl)phenyl-2,4-pyrimidinediamine $^1$H NMR (DMSO-d$_6$): δ 0.88 (m, 4H), 2.12 (s, 3H), 2.40 (d, J=4.8 Hz, 3H), 4.18 (d, J=5.4 Hz, 2H), 7.04 (d, J=8.1 Hz, 1H), 7.20 (d, J=7.8 Hz, 1H), 7.27-7.38 (m, 3H), 7.61 (t, J=6.0 Hz, 1H), 7.66 (s, 1H), 7.70 (d, J=7.5 Hz, 1H), 7.91 (s, 1H), 8.01 (s, 1H), 8.06 (d, J=9.0 Hz, 1H), 8.37 (s, 1H), 9.25 (s, 1H); LCMS: purity: 84.33%; MS (m/e): 503.08 (MH+).

(I-163): N4-(4-cyclopropylsulfonylaminomethyl)phenyl-5-methyl-N2-(4-methylaminosulfonyl)phenyl-2,4-pyrimidinediamine $^1$H NMR (DMSO-d$_6$): δ 0.90 (m, 4H), 2.12 (s, 3H), 2.36 (d, J=4.8 Hz, 3H), 4.17 (d, J=6.3 Hz, 2H), 7.11 (q, J=5.1 Hz, 1H), 7.31 (d, J=8.4 Hz, 2H), 7.53 (d, J=8.7 Hz, 2H), 7.60 (t, J=5.7 Hz, 1H), 7.66 (d, J=8.7 Hz, 2H), 7.85 (d, J=8.7 Hz, 2H), 7.92 (s, 1H), 8.37 (s, 1H), 9.44 (s, 1H); LCMS: purity: 98.28%; MS (m/e): 503.15 (MH+).

(I-164): N4-(4-cyclopropylsulfonylaminomethyl)phenyl-5-methyl-N2-(4-propargylaminosulfonyl)phenyl-2,4-pyrimidinediamine $^1$H NMR (DMSO-d$_6$): δ 0.91 (m, 4H), 2.12 (s, 3H), 3.05 (t, J=2.4 Hz, 1H), 3.61 (dd, J=2.4, 6.0 Hz, 2H), 4.18 (d, J=6.0 Hz, 2H), 7.31 (d, J=8.4 Hz, 2H), 7.55 (d, J=9.0 Hz, 2H), 7.60 (t, J=6.3 Hz, 1H), 7.66 (d, J=8.4 Hz, 2H), 7.80 (t, J=6.0 Hz, 1H), 7.85 (d, J=9.3 Hz, 2H), 7.93 (s, 1H), 8.38 (s, 1H), 9.46 (s, 1H); LCMS: purity: 96.96%; MS (m/e): 527.16 (MH+).

(I-165): N4-(4-cyclopropylsulfonylaminomethyl)phenyl-5-methyl-N2-(3-propargylaminosulfonyl)phenyl-2,4-pyrimidinediamine $^1$H NMR (DMSO-d$_6$): δ 0.90 (m, 4H), 2.12 (s, 3H), 3.07 (t, 1H), 3.65 (dd, J=2.4, 6.0 Hz, 2H), 4.16 (d, J=6.3 Hz, 2H), 7.24 (d, J=6.9 Hz, 1H), 7.29 (d, J=8.1 Hz, 2H), 7.35 (t, J=7.8 Hz, 1H), 7.59 (t, J=6.6 Hz, 1H), 7.70 (d, J=8.1 Hz, 2H), 7.90 (s, 1H), 8.01 (m, 2H), 8.09 (d, J=8.4 Hz, 1H), 8.31 (s, 1H), 9.30 (s, 1H); LCMS: purity: 95.54%; MS (m/e): 527.17 (MH+).

(I-166): N2-(4-cyclopentylaminosulfonyl)phenyl-N4-(4-cyclopropylsulfonylaminomethyl)phenyl-5-methyl-2,4-pyrimidinediamine $^1$H NMR (DMSO-d$_6$): δ 0.91 (m, 4H), 1.31 (m, 4H), 1.54 (m, 4H), 2.13 (s, 3H), 4.18 (d, J=6.0 Hz, 2H), 7.31 (d, J=8.1 Hz, 2H), 7.32 (m, 1H), 7.55 (d, J=8.4 Hz, 2H), 7.61 (t, J=6.6 Hz, 1H), 7.67 (d, J=8.1 Hz, 2H), 7.84 (d, J=8.4 Hz, 2H), 7.93 (s, 1H), 8.37 (s, 1H), 9.44 (s, 1H); LCMS: purity: 95.61%; MS (m/e): 557.18 (MH+).

(I-167): N2-(4-aminosulfonyl)phenyl-N4-[4-(N-cyclopropylsulfonyl-N-propionyl)aminomethyl]phenyl-5-methyl-2,4-pyrimidinediamine $^1$H NMR (DMSO-d$_6$): δ 1.01 (t, J=7.2 Hz, 3H), 1.10 (m, 4H), 2.12 (s, 3H), 2.67 (q, J=7.2 Hz, 2H), 4.90 (s, 2H), 7.06 (s, 2H), 7.24 (d, J=8.4 Hz, 2H), 7.58 (d, J=8.7 Hz, 2H), 7.70 (d, J=8.7 Hz, 2H), 7.82 (d, J=8.7 Hz, 2H), 7.93 (s, 1H), 8.37 (s, 1H), 9.39 (s, 1H); LCMS: purity: 82.58%; MS (m/e): 545.16 (MH+).

(I-168): N4-(4-cyclopropylsulfonylaminomethyl)phenyl-5-methyl-N2-[4-(4-pyridylmethyl)aminosulfonyl]phenyl-2,4-pyrimidinediamine LCMS: purity: 99.67%; MS (m/e): 580.15 (MH+).

(I-169): N4-(4-cyclopropylsulfonylaminomethyl)phenyl-5-methyl-N2-[3-(4-pyridylmethyl)aminosulfonyl]phenyl-2,4-pyrimidinediamine LCMS: purity: 99.17%; MS (m/e): 580.16 (MH+).

(I-170): N2-(3-cyclopentylaminosulfonyl)phenyl-N4-(4-cyclopropylsulfonylaminomethyl)phenyl-5-methyl-2,4-pyrimidinediamine $^1$H NMR (DMSO-$d_6$): δ 0.90 (m, 4H), 1.33 (m, 4H), 1.53 (m, 4H), 2.12 (s, 3H), 3.38 (m, J=7.2 Hz, 1H), 4.16 (d, J=6.3 Hz, 2H), 7.24 (d, J=8.1 Hz, 1H), 7.30 (d, J=8.7 Hz, 2H), 7.35 (t, J=8.4 Hz, 1H), 7.51 (d, J=7.2 Hz, 1H), 7.60 (t, J=6.3 Hz, 1H), 7.70 (d, J=8.7 Hz, 2H), 7.90 (s, 1H), 8.06 (m, 2H), 8.31 (s, 1H), 9.30 (s, 1H); LCMS: purity: 95.61%; MS (m/e): 557.18 (MH+).

(I-171): N4-(4-cyclopropylsulfonylaminomethyl)phenyl-5-methyl-N2-[4-(3-pyridyl)aminosulfonyl]phenyl-2,4-pyrimidinediamine $^1$H NMR (DMSO-$d_6$): δ 0.90 (m, 4H), 2.30 (s, 3H), 4.19 (d, J=6.0 Hz, 2H), 5.51 (br, 1H), 6.42 (d, J=9.0 Hz, 2H), 7.37 (d, J=7.8 Hz, 2H), 7.41 (d, J=8.4 Hz, 2H), 7.64 (d, J=7.5 Hz, 6H), 8.35 (s, 1H), 8.71 (br, 1H), 9.03 (br, 1H), 9.24 (s, 1H); LCMS: purity: 84.84%; MS (m/e): 566.14 (MH+).

(I-172): N4-(4-cyclopropylsulfonylaminomethyl)phenyl-N2-(4-isopropylaminosulfonyl)phenyl-5-methyl-2,4-pyrimidinediamine $^1$H NMR (DMSO-$d_6$): δ 0.92 (m, 4H), 0.93 (d, J=6.6 Hz, 6H), 2.12 (s, 3H), 4.17 (d, J=6.0 Hz, 2H), 7.24 (d, J=7.5 Hz, 1H), 7.30 (d, J=8.4 Hz, 2H), 7.55 (d, J=8.7 Hz, 2H), 7.59 (t, J=6.0 Hz, 1H), 7.66 (d, J=7.8 Hz, 2H), 7.83 (d, J=8.7 Hz, 2H), 7.92 (s, 1H), 8.36 (s, 1H), 9.42 (s, 1H); LCMS: purity: 98.62%; MS (m/e): 531.17 (MH+).

(I-173): N4-(4-cyclopropylsulfonylaminomethyl)phenyl-N2-(3-isopropylaminosulfonyl)phenyl-5-methyl-2,4-pyrimidinediamine $^1$H NMR (DMSO-$d_6$): δ 0.90 (m, 4H), 0.93 (d, J=6.6 Hz, 6H), 2.12 (s, 3H), 3.25 (m, J=6.6 Hz, 1H), 4.16 (d, J=5.7 Hz, 2H), 7.24 (d, J=8.1 Hz, 1H), 7.30 (d, J=8.1 Hz, 2H), 7.35 (t, J=7.8 Hz, 1H), 7.45 (d, J=6.9 Hz, 1H), 7.59 (t, J=6.3 Hz, 1H), 7.70 (d, J=8.4 Hz, 2H), 7.90 (s, 1H), 8.05 (d, J=9.3 Hz, 1H), 8.06 (s, 1H), 8.31 (s, 1H), 9.30 (s, 1H); LCMS: purity: 100%; MS (m/e): 531.17 (MH+).

(I-174): N4-(4-cyclopropylsulfonylaminomethyl)phenyl-5-methyl-N2-[3-(3-pyridyl)aminosulfonyl]phenyl-2,4-pyrimidinediamine $^1$H NMR (DMSO-$d_6$): δ 0.90 (m, 4H), 2.30 (s, 3H), 4.19 (d, J=5.7 Hz, 2H), 5.24 (br, 1H), 6.53 (d, J=8.4 Hz, 1H), 6.85 (d, J=7.8 Hz, 1H), 6.96 (m, 2H), 7.40 (d, J=8.1 Hz, 2H), 7.65 (m, 4H), 7.82 (d, J=9.9 Hz, 1H), 8.35 (d, 2H), 8.73 (d, 1H), 9.04 (br, 1H), 9.24 (s, 1H); LCMS: purity: 98.43%; MS (m/e): 566.05 (MH+).

(I-175): N4-(4-cyclopropylsulfonylaminomethyl)phenyl-N2-(4-ethylaminosulfonyl)phenyl-5-methyl-2,4-pyrimidinediamine $^1$H NMR (DMSO-$d_6$): δ 0.91 (m, 4H), 0.95 (t, J=7.2 Hz, 3H), 2.12 (s, 3H), 2.72 (p, J=6.9 Hz, 2H), 4.17 (d, J=6.3 Hz, 2H), 7.22 (t, J=5.7 Hz, 1H), 7.30 (d, J=8.4 Hz, 2H), 7.54 (d, J=8.7 Hz, 2H), 7.60 (t, 1H), 7.66 (d, J=8.4 Hz, 2H), 7.84 (d, J=8.7 Hz, 2H), 7.92 (s, 1H), 8.37 (s, 1H), 9.44 (s, 1H); LCMS: purity: 94.97%; MS (m/e): 517.13 (MH+).

(I-176): N4-(4-cyclopropylsulfonylaminomethyl)phenyl-N2-(3-ethylaminosulfonyl)phenyl-5-methyl-2,4-pyrimidinediamine $^1$H NMR (DMSO-$d_6$): δ 0.90 (m, 4H), 0.98 (t, J=7.2 Hz, 3H), 2.12 (s, 3H), 2.79 (p, J=5.7 Hz, 2H), 4.16 (d, J=5.1 Hz, 2H), 7.22 (d, J=7.2 Hz, 1H), 7.29 (d, J=8.1 Hz, 2H), 7.36 (t, J=7.8 Hz, 1H), 7.42 (t, 1H), 7.59 (t, 1H), 7.70 (d, J=7.8 Hz, 2H), 7.90 (s, 1H), 8.04 (s, 1H), 8.07 (d, J=9.0 Hz, 1H), 8.31 (s, 1H), 9.30 (s, 1H); LCMS: purity: 98.72%; MS (m/e): 517.14 (MH+).

(I-177): N4-(4-cyclopropylsulfonylaminomethyl)phenyl-5-methyl-N2-(4-propylaminosulfonyl)phenyl-2,4-pyrimidinediamine $^1$H NMR (DMSO-$d_6$): δ 0.78 (t, J=7.2 Hz, 3H), 0.91 (m, 4H), 1.35 (q, J=7.2 Hz, 2H), 2.12 (s, 3H), 2.68 (q, J=6.6 Hz, 2H), 4.17 (d, J=6.3 Hz, 2H), 7.26 (t, J=5.7 Hz, 1H), 7.30 (d, J=7.8 Hz, 2H), 7.54 (d, J=8.1 Hz, 2H), 7.60 (t, J=6.0 Hz, 1H), 7.66 (d, J=8.4 Hz, 2H), 7.84 (d, J=8.4 Hz, 2H), 7.92 (s, 1H), 8.37 (s, 1H), 9.44 (s, 1H); LCMS: purity: 98.73%; MS (m/e): 531.12 (MH+).

(I-178): N4-(4-cyclopropylsulfonylaminomethyl)phenyl-5-methyl-N2-(3-propylaminosulfonyl)phenyl-2,4-pyrimidinediamine $^1$H NMR (DMSO-$d_6$): δ 0.78 (t, J=7.2 Hz, 3H), 0.90 (m, 4H), 1.37 (q, J=7.2 Hz, 2H), 2.12 (s, 3H), 2.70 (q, J=6.6 Hz, 2H), 4.16 (d, J=5.7 Hz, 2H), 7.21 (d, J=7.8 Hz, 1H), 7.29 (d, J=7.8 Hz, 2H), 7.35 (t, J=7.8 Hz, 1H), 7.44 (t, J=6.0 Hz, 1H), 7.58 (t, J=5.7 Hz, 1H), 7.70 (d, J=8.1 Hz, 2H), 7.90 (s, 1H), 8.03 (s, 1H), 8.06 (d, J=9.0 Hz, 1H), 8.30 (s, 1H), 9.30 (s, 1H); LCMS: purity: 96.70%; MS (m/e): 531.15 (MH+).

(I-179): N2-(4-cyclopropylmethylaminosulfonyl)phenyl-N4-(4-cyclopropylsulfonylaminomethyl)phenyl-5-methyl-2,4-pyrimidinediamine $^1$H NMR (DMSO-$d_6$): δ 0.066 (q, J=5.1 Hz, 2H), 0.34 (q, J=7.8 Hz, 2H), 0.78 (m, 1H), 0.91 (m, 4H), 2.13 (s, 3H), 2.59 (t, J=6.3 Hz, 2H), 4.18 (d, J=5.7 Hz, 2H), 7.31 (d, J=8.7 Hz, 2H), 7.40 (t, J=5.7 Hz, 1H), 7.54 (d, J=8.1 Hz, 2H), 7.61 (t, J=6.3 Hz, 1H), 7.67 (d, J=8.1 Hz, 2H), 7.84 (d, J=9.0 Hz, 2H), 7.92 (s, 1H), 8.37 (s, 1H), 9.43 (s, 1H); LCMS: purity: 86.70%; MS (m/e): 543.19 (MH+).

(I-180): N2-(3-cyclopropylmethylaminosulfonyl)phenyl-N4-(4-cyclopropylsulfonylaminomethyl)phenyl-5-methyl-2,4-pyrimidinediamine $^1$H NMR (DMSO-$d_6$): δ 0.084 (q, J=5.1 Hz, 2H), 0.35 (q, J=7.8 Hz, 2H), 0.81 (m, 1H), 0.90 (m, 4H), 2.12 (s, 3H), 2.65 (t, J=6.0 Hz, 2H), 4.16 (d, J=6.3 Hz, 2H), 7.23 (d, J=7.5 Hz, 1H), 7.30 (d, J=8.4 Hz, 2H), 7.35 (t, J=7.8 Hz, 1H), 7.60 (t, J=5.7 Hz, 2H), 7.70 (d, J=7.8 Hz, 2H), 7.90 (s, 1H), 8.02 (s, 1H), 8.06 (d, J=9.0 Hz, 1H), 8.33 (s, 1H), 9.30 (s, 1H); LCMS: purity: 98.70%; MS (m/e): 543.20 (MH+).

(I-181): N4-(4-cyclopropylsulfonylaminomethyl)phenyl-N2-[4-(3-methoxypropyl)aminosulfonyl]phenyl-5-methyl-2,4-pyrimidinediamine $^1$H NMR (DMSO-d$_6$): δ 0.91 (m, 4H), 1.57 (p, J=6.6 Hz, 2H), 2.13 (s, 3H), 2.72 (q, J=6.6 Hz, 2H), 3.25 (t, J=6.0 Hz, 2H), 4.18 (d, J=6.0 Hz, 2H), 7.27 (t, J=5.7 Hz, 1H), 7.31 (d, J=8.7 Hz, 2H), 7.54 (d, J=8.7 Hz, 2H), 7.61 (t, J=6.3 Hz, 1H), 7.67 (d, J=8.4 Hz, 2H), 7.85 (d, J=8.7 Hz, 2H), 7.93 (s, 1H), 8.37 (s, 1H), 9.45 (s, 1H); LCMS: purity: 97.46%; MS (m/e): 561.16 (MH+).

(I-182): N4-(4-cyclopropylsulfonylaminomethyl)phenyl-N2-[3-(3-methoxypropyl)aminosulfonyl]phenyl-5-methyl-2,4-pyrimidinediamine $^1$H NMR (DMSO-d$_6$): δ 0.90 (m, 4H), 1.58 (p, J=6.6 Hz, 2H), 2.12 (s, 3H), 2.79 (t, J=6.9 Hz, 2H), 3.26 (t, J=5.7 Hz, 2H), 4.16 (s, 2H), 7.21 (d, J=7.5 Hz, 1H), 7.30 (d, J=8.4 Hz, 2H), 7.36 (t, J=7.8 Hz, 1H), 7.61 (br, 1H), 7.70 (d, J=8.4 Hz, 2H), 7.90 (s, 1H), 8.04 (s, 1H), 8.07 (d, J=9.3 Hz, 1H), 8.31 (s, 1H), 9.31 (s, 1H); LCMS: purity: 98.02%; MS (m/e): 561.19 (MH+).

(I-183): N4-(4-cyclopropylsulfonylaminomethyl)phenyl-N2-[4-(2-methoxyethyl)aminosulfonyl]phenyl-5-methyl-2,4-pyrimidinediamine $^1$H NMR (DMSO-d$_6$): δ 0.91 (m, 4H), 2.12 (s, 3H), 2.84 (q, J=5.7 Hz, 2H), 3.15 (s, 3H), 3.26 (m, 2H), 4.17 (d, J=6.0 Hz, 2H), 7.31 (d, J=8.7 Hz, 2H), 7.38 (t, J=6.0 Hz, 1H), 7.55 (d, J=8.4 Hz, 2H), 7.60 (t, J=6.0 Hz, 1H), 7.66 (d, J=8.1 Hz, 2H), 7.84 (d, J=8.7 Hz, 2H), 7.92 (s, 1H), 8.37 (s, 1H), 9.44 (s, 1H); LCMS: purity: 97.78%; MS (m/e): 547.15 (MH+).

(I-184): N4-(4-cyclopropylsulfonylaminomethyl)phenyl-N2-[3-(2-methoxyethyl)aminosulfonyl]phenyl-5-methyl-2,4-pyrimidinediamine $^1$H NMR (DMSO-d$_6$): δ 0.90 (m, 4H), 2.12 (s, 3H), 2.89 (m, 2H), 3.15 (s, 3H), 3.29 (m, 2H), 4.16 (d, J=6.0 Hz, 2H), 7.23 (d, J=6.9 Hz, 1H), 7.29 (d, J=8.4 Hz, 2H), 7.35 (t, J=8.1 Hz, 1H), 7.58 (t, 2H), 7.70 (d, J=8.4 Hz, 2H), 7.90 (s, 1H), 8.03 (s, 1H), 8.07 (d, J=9.0 Hz, 1H), 8.30 (s, 1H), 9.29 (s, 1H); LCMS: purity: 99.10%; MS (m/e): 547.12 (MH+).

(I-185): N4-(4-cyclopropylsulfonylaminomethyl)phenyl-5-methyl-N2-(4-methyl-3-methylaminosulfonyl)phenyl)-2,4-pyrimidinediamine $^1$H NMR (DMSO-d$_6$): δ 0.90 (m, 4H), 2.11 (s, 3H), 2.42 (d, 3H), 2.45 (s, 3H), 4.17 (d, J=4.5 Hz, 2H), 7.16 (d, J=9.3 Hz, 1H), 7.29 (d, J=8.1 Hz, 3H), 7.60 (t, J=6.3 Hz, 1H), 7.70 (d, J=8.1 Hz, 2H), 7.88 (s, 1H), 8.00 (m, 2H), 8.27 (s, 1H), 9.19 (s, 1H); LCMS: purity: 91.76%; MS (m/e): 517.15 (MH+).

(I-186): N4-(4-cyclopropylsulfonylaminomethyl)phenyl-N2-(3-ethylaminosulfonyl-4-methyl)phenyl-5-methyl-2,4-pyrimidinediamine $^1$H NMR (DMSO-d$_6$): δ 0.90 (m, 4H), 0.97 (t, J=7.2 Hz, 3H), 2.11 (s, 3H), 2.46 (s, 3H), 2.81 (m, 2H), 4.16 (d, J=5.1 Hz, 2H), 7.16 (d, J=8.1 Hz, 1H), 7.29 (d, J=8.4 Hz, 2H), 7.46 (t, 1H), 7.60 (t, J=6.6 Hz, 1H), 7.70 (d, J=8.4 Hz, 2H), 7.87 (s, 1H), 7.99 (d, J=8.1 Hz, 1H), 8.03 (s, 1H), 8.27 (s, 1H), 9.19 (s, 1H); LCMS: purity: 97.35%; MS (m/e): 531.21 (MH+).

(I-187): N4-(4-cyclopropylsulfonylaminomethyl)phenyl-5-methyl-N2-(4-methyl-3-propylaminosulfonyl)phenyl-2,4-pyrimidinediamine $^1$H NMR (DMSO-d$_6$): δ 0.77 (t, J=7.5 Hz, 3H), 0.90 (m, 4H), 1.36 (q, J=7.2 Hz, 2H), 2.10 (s, 3H), 2.46 (s, 3H), 2.73 (q, J=6.6 Hz, 2H), 4.16 (d, J=6.0 Hz, 2H), 7.15 (d, J=7.8 Hz, 1H), 7.29 (d, J=8.7 Hz, 2H), 7.49 (t, J=5.7 Hz, 1H), 7.59 (t, J=6.3 Hz, 1H), 7.70 (d, J=8.4 Hz, 2H), 7.87 (s, 1H), 7.99 (d, J=8.1 Hz, 1H), 8.00 (s, 1H), 8.27 (s, 1H), 9.18 (s, 1H); LCMS: purity: 89.69%; MS (m/e): 545.20 (MH+).

(I-188): N4-(4-cyclopropylsulfonylaminomethyl)phenyl-5-methyl-N2-(4-methyl-3-propargylaminosulfonyl)phenyl-2,4-pyrimidinediamine $^1$H NMR (DMSO-d$_6$): δ 0.90 (m, 4H), 2.10 (s, 3H), 2.46 (s, 3H), 3.02 (t, 1H), 3.66 (dd, J=2.7, 6.0 Hz, 2H), 4.16 (d, J=6.3 Hz, 2H), 7.14 (d, J=9.0 Hz, 1H), 7.29 (d, J=8.4 Hz, 2H), 7.59 (t, J=6.6 Hz, 1H), 7.70 (d, J=8.4 Hz, 2H), 7.87 (s, 1H), 8.00 (s, 2H), 8.01 (d, J=6.6 Hz, 1H), 8.28 (s, 1H), 9.18 (s, 1H); LCMS: purity: 97.36%; MS (m/e): 541.13 (MH+).

(I-189): N4-(4-cyclopropylsulfonylaminomethyl)phenyl-N2-(3-isopropylaminosulfonyl-4-methyl)phenyl-5-methyl-2,4-pyrimidinediamine $^1$H NMR (DMSO-d$_6$): δ 0.90 (m, 4H), 0.96 (d, J=6.6 Hz, 6H), 2.11 (s, 3H), 2.47 (s, 3H), 3.08 (m, 1H), 4.16 (d, J=6.3 Hz, 2H), 7.15 (d, J=8.1 Hz, 1H), 7.29 (d, J=8.7 Hz, 2H), 7.43 (d, J=8.4 Hz, 1H), 7.59 (t, 1H), 7.71 (d, J=8.4 Hz, 2H), 7.87 (s, 1H), 7.98 (d, J=8.1 Hz, 1H), 8.08 (s, 1H), 8.26 (s, 1H), 9.17 (s, 1H); LCMS: purity: 99.96%; MS (m/e): 545.46 (MH+).

(I-190): N4-(4-cyclopropylsulfonylaminomethyl)phenyl-N2-[3-(2-methoxyethyl)aminosulfonyl-4-methyl]phenyl-5-methyl-2,4-pyrimidinediamine $^1$H NMR (DMSO-d$_6$): δ 0.88 (m, 4H), 2.16 (s, 3H), 2.89 (q, J=5.4 Hz, 2H), 3.08 (s, 3H), 3.21 (t, J=5.7 Hz, 2H), 4.20 (d, J=6.0 Hz, 2H), 7.22 (d, J=8.7 Hz, 1H), 7.36 (d, J=8.4 Hz, 2H), 7.49 (d, J=8.1 Hz, 2H), 7.66 (t, J=6.0 Hz, 1H), 7.69 (m, 2H), 7.78 (t, J=5.7 Hz, 1H), 7.86 (s, 1H), 9.65 (br, 1H), 10.27 (br, 1H); LCMS: purity: 95.71%; MS (m/e): 561.19 (MH+).

(I-191): N4-(4-cyclopropylsulfonylaminomethyl)phenyl-N2-[3-(3-methoxypropyl)aminosulfonyl-4-methyl]phenyl-5-methyl-2,4-pyrimidinediamine $^1$H NMR (DMSO-d$_6$): δ 0.89 (m, 4H), 1.55 (p, J=6.6 Hz, 2H), 2.16 (s, 3H), 2.76 (q, J=6.6 Hz, 2H), 3.09 (s, 3H), 3.21 (t, J=6.0 Hz, 2H), 4.20 (d, J=6.0 Hz, 2H), 7.22 (d, J=8.1 Hz, 1H), 7.36 (d, J=8.1 Hz, 2H), 7.49 (d, J=8.1 Hz, 2H), 7.62-7.73 (m, 4H), 7.87 (s, 1H), 9.67 (br, 1H), 10.30 (br, 1H); LCMS: purity: 94.11%; MS (m/e): 575.30 (MH+).

(I-192): N2-(3-cyclopropylmethylaminosulfonyl-4-methyl)phenyl-N4-(4-cyclopropylsulfonylaminomethyl)phenyl-5-methyl-2,4-pyrimidinediamine $^1$H NMR (DMSO-d$_6$): δ 0.024 (q, J=4.8 Hz, 2H), 0.29 (q, J=5.7 Hz, 2H), 0.73 (m, 1H), 0.89 (m, 4H), 2.16 (s, 3H), 2.53

(s, 3H), 2.64 (t, J=6.3 Hz, 2H), 4.20 (d, J=6.3 Hz, 2H), 7.22 (d, J=9.0 Hz, 1H), 7.35 (d, J=8.1 Hz, 2H), 7.49 (d, J=8.1 Hz, 2H), 7.66 (t, J=5.7 Hz, 1H), 7.69 (m, 2H), 7.80 (t, J=5.7 Hz, 1H), 7.87 (s, 1H), 9.65 (br, 1H), 10.26 (br, 1H); LCMS: purity: 97.33%; MS (m/e): 557.16 (MH+).

(I-193): N2-(3-acetamidosulfonyl)phenyl-N4-[3-(N-acetyl-N-cyclopropylsulfonyl)aminomethyl]phenyl-5-methyl-2,4-pyrimidinediamine $^1$H NMR (DMSO-d$_6$): δ 1.10 (m, 4H), 1.90 (s, 3H), 1.92 (s, 3H), 2.13 (s, 3H), 4.91 (s, 2H), 6.95 (d, J=7.2 Hz, 1H), 7.35 (m, 3H), 7.61 (s, 1H), 7.71 (d, J=8.1 Hz, 1H), 7.92 (s, 1H), 8.08 (d, J=6.9 Hz, 1H), 8.19 (s, 1H), 8.41 (s, 1H), 9.22 (s, 1H), 11.92 (s, 1H); LCMS: purity: 94.91%; MS (m/e): 573.14 (MH+).

(I-194): N2-(4-acetamidosulfonyl)phenyl-N4-[4-(N-acetyl-N-cyclopropylsulfonyl)aminomethyl]phenyl-5-methyl-2,4-pyrimidinediamine $^1$H NMR (DMSO-d$_6$): δ 1.10 (m, 4H), 1.89 (s, 3H), 1.90 (s, 3H), 2.13 (s, 3H), 4.90 (s, 2H), 7.25 (d, J=8.7 Hz, 2H), 7.66 (d, J=8.7 Hz, 2H), 7.68 (d, J=8.1 Hz, 2H), 7.86 (d, J=8.7 Hz, 2H), 7.94 (s, 1H), 8.42 (s, 1H), 9.55 (s, 1H), 11.80 (s, 1H); LCMS: purity: 93.76%; MS (m/e): 573.08 (MH+).

(I-195): N2-(3-benzylaminosulfonyl-4-methyl-phenyl-N4-(4-cyclopropylsulfonylaminomethyl)phenyl-5-methyl-2,4-pyrimidinediamine $^1$H NMR (DMSO-d$_6$): δ 0.88 (m, 4H), 2.16 (s, 3H), 3.96 (d, J=6.0 Hz, 2H), 4.20 (d, J=6.3 Hz, 2H), 7.17 (m, 6H), 7.36 (d, J=8.1 Hz, 2H), 7.50 (d, J=8.4 Hz, 2H), 7.66 (m, 3H), 7.86 (s, 1H), 8.22 (t, J=6.0 Hz, 1H), 9.64 (br, 1H), 10.20 (br, 1H); LCMS: purity: 95.32%; MS (m/e): 593.11 (MH+).

(I-196): N2-(3-acetamidosulfonyl)phenyl-N4-[3-(N-acetyl-N-cyclopropylsulfonyl)aminomethyl]phenyl-5-methyl-2,4-pyrimidinediamine sodium salt $^1$H NMR (DMSO-d$_6$): δ 1.10 (m, 4H), 1.62 (s, 3H), 2.11 (s, 3H), 2.33 (s, 3H), 4.90 (s, 2H), 6.92 (d, J=8.4 Hz, 1H), 7.11 (t, J=9.0 Hz, 1H), 7.19 (d, J=6.9 Hz, 1H), 7.30 (t, J=8.1 Hz, 1H), 7.70 (m, 2H), 7.81 (s, 1H), 7.87 (d, 1H), 7.89 (s, 1H), 8.30 (s, 1H), 8.89 (s, 1H); LCMS: purity: 98.55%; MS (m/e): 573.32 (MH+).

(I-197): N2-(4-acetamidosulfonyl)phenyl-N4-[4-(N-acetyl-N-cyclopropylsulfonyl)aminomethyl]phenyl-5-methyl-2,4-pyrimidinediamine sodium salt $^1$H NMR (DMSO-d$_6$): δ 1.06 (d, J=6.6 Hz, 4H), 1.56 (s, 3H), 1.59 (s, 3H), 2.11 (s, 3H), 4.90 (s, 2H), 7.24 (d, J=8.4 Hz, 2H), 7.48 (d, J=9.0 Hz, 2H), 7.62 (d, J=8.4 Hz, 2H), 7.71 (d, J=7.8 Hz, 2H), 7.89 (s, 1H), 8.31 (s, 1H), 9.12 (s, 1H); LCMS: purity: 87.22%; MS (m/e): 573.12 (MH+).

(I-198): N4-[3-(N-cyclopropylsulfonyl-N-isobutyryl)aminomethyl]phenyl-N2-(3-isobutyrylaminosulfonyl)phenyl-5-methyl-2,4-pyrimidinediamine $^1$H NMR (DMSO-d$_6$): δ 0.94 (d, J=6.9 Hz, 6H), 1.03 (d, J=6.6 Hz, 6H), 1.08 (d, J=6.0 Hz, 4H), 2.13 (s, 3H), 3.06 (p, J=6.3 Hz, 1H), 3.25 (t, J=6.3 Hz, 1H), 4.94 (s, 2H), 6.93 (d, J=7.8 Hz, 1H), 7.34 (m, 3H), 7.64 (d, J=8.1 Hz, 1H), 7.70 (s, 1H), 7.92 (s, 1H), 8.05 (d, J=7.2 Hz, 1H), 8.24 (s, 1H), 8.42 (s, 1H), 9.16 (s, 1H), 11.95 (s, 1H); LCMS: purity: 91.71%; MS (m/e): 629.28 (MH+).

(I-199): N4-[4-(N-cyclopropylsulfonyl-N-isobutyryl)aminomethyl]phenyl-N2-(4-isobutyrylaminosulfonyl)phenyl-5-methyl-2,4-pyrimidinediamine $^1$H NMR (DMSO-d$_6$): δ 0.92 (d, J=6.9 Hz, 6H), 1.08 (m, 10H), 2.13 (s, 3H), 2.43 (m, J=6.9 Hz, 1H), 3.16 (m, J=6.6 Hz, 1H), 4.92 (s, 2H), 7.24 (d, J=8.1 Hz, 2H), 7.66 (d, J=9.3 Hz, 2H), 7.72 (d, J=8.7 Hz, 2H), 7.87 (d, J=9.0 Hz, 2H), 7.94 (s, 1H), 8.41 (s, 1H), 9.56 (s, 1H), 11.75 (s, 1H); LCMS: purity: 96.23%; MS (m/e): 629.24 (MH+).

(I-200): N4-[3-(N-cyclopropylsulfonyl-N-isobutyryl)aminomethyl]phenyl-N2-(3-isobutyrylaminosulfonyl)phenyl-5-methyl-2,4-pyrimidinediamine sodium salt $^1$H NMR (DMSO-d$_6$): δ 0.88 (d, J=6.9 Hz, 6H), 1.03 (d, J=6.6 Hz, 6H), 1.08 (d, J=6.3 Hz, 4H), 2.11 (s, 3H), 3.05 (p, J=6.3 Hz, 1H), 3.24 (t, J=6.0 Hz, 1H), 4.94 (s, 2H), 6.89 (d, J=7.5 Hz, 1H), 7.09 (t, J=7.8 Hz, 1H), 7.18 (d, J=8.1 Hz, 1H), 7.30 (t, J=7.8 Hz, 1H), 7.63 (d, J=9.0 Hz, 1H), 7.78 (s, 1H), 7.82 (d, J=8.4 Hz, 1H), 7.86 (s, 1H), 7.88 (s, 1H), 8.30 (s, 1H), 8.82 (s, 1H); LCMS: purity: 95.01%; MS (m/e): 629.25 (MH+).

(I-201): N4-[4-(N-cyclopropylsulfonyl-N-isobutyryl)aminomethyl]phenyl-N2-(4-isobutyrylaminosulfonyl)phenyl-5-methyl-2,4-pyrimidinediamine sodium salt $^1$H NMR (DMSO-d$_6$): δ 0.87 (d, J=6.9 Hz, 6H), 1.07 (m, 10H), 2.11 (s, 3H), 3.15 (m, 1H), 4.92 (s, 2H), 7.22 (d, J=9.3 Hz, 2H), 7.48 (d, J=8.4 Hz, 2H), 7.61 (d, J=9.3 Hz, 2H), 7.74 (d, J=7.8 Hz, 2H), 7.89 (s, 1H), 8.28 (s, 1H), 9.11 (s, 1H); LCMS: purity: 97.71%; MS (m/e): 629.24 (MH+).

(I-202): N4-(4-cyclopropylsulfonylaminomethyl)phenyl-5-methyl-N2-(4-methyl-3-phenylaminosulfonyl)phenyl-2,4-pyrimidinediamine $^1$H NMR (DMSO-d$_6$): δ 0.89 (m, 4H), 2.10 (s, 3H), 4.16 (d, J=6.0 Hz, 2H), 6.92 (t, J=7.8 Hz, 1H), 7.04 (d, J=8.4 Hz, 2H), 7.09-7.19 (m, 3H), 7.28 (d, J=8.4 Hz, 2H), 7.59 (t, J=6.0 Hz, 1H), 7.68 (d, J=8.7 Hz, 2H), 7.86 (s, 1H), 7.98 (d, J=8.4 Hz, 1H), 8.17 (s, 1H), 8.28 (s, 1H), 9.20 (s, 1H), 10.29 (s, 1H); LCMS: purity: 91.37%; MS (m/e): 579.19 (MH+).

(I-203): N2-(3-butyrylaminosulfonyl)phenyl-N4-[3-(N-butyryl-N-cyclopropylsulfonyl)aminomethyl]phenyl-5-methyl-2,4-pyrimidinediamine $^1$H NMR (DMSO-d$_6$): δ 0.75 (t, J=7.2 Hz, 3H), 0.81 (t, J=7.2 Hz, 3H), 1.10 (m, 4H), 1.42 (q, J=7.2 Hz, 2H), 1.52 (q, J=7.2 Hz, 2H), 2.13 (s, 3H), 2.17 (t, J=7.2 Hz, 2H), 2.61 (t, J=6.9 Hz, 2H), 4.92 (s, 2H), 6.95 (d, J=7.8 Hz, 1H), 7.34 (m, 3H), 7.66 (m, 2H), 7.92 (s, 1H), 8.06 (d, J=6.6 Hz, 1H), 8.21 (s, 1H), 8.42 (s, 1H), 9.21 (s, 1H), 11.96 (s, 1H); LCMS: purity: 94.32%; MS (m/e): 629.67 (MH+).

(I-204): N2-(4-butyrylaminosulfonyl)phenyl-N4-[4-(N-butyryl-N-cyclopropylsulfonyl)aminomethyl]phenyl-5-methyl-2,4-pyrimidinediamine $^1$H NMR (DMSO-d$_6$): δ 0.74 (t, J=7.5 Hz, 3H), 0.85 (t, J=7.2 Hz, 3H), 1.08 (d, J=6.0 Hz, 4H), 1.41 (q, J=6.9 Hz, 2H), 1.56 (q, J=7.2 Hz, 2H), 2.13 (s, 3H), 2.14 (t, J=6.9 Hz, 2H), 2.65 (t, J=6.9 Hz, 2H), 4.91 (s, 2H), 7.24 (d, J=9.0 Hz, 2H), 7.67 (d, J=8.7 Hz, 2H), 7.71 (d, J=9.0 Hz, 2H), 7.87 (d, J=9.0 Hz, 2H), 7.94 (s, 1H), 8.42 (s, 1H), 9.55 (s, 1H), 11.76 (s, 1H); LCMS: purity: 95.92%; MS (m/e): 629.23 (MH+).

(I-205): N2-(3-butyrylaminosulfonyl)phenyl-N4-[3-(N-butyryl-N-cyclopropylsulfonyl)aminomethyl] phenyl-5-methyl-2,4-pyrimidinediamine sodium salt $^1$H NMR (DMSO-d$_6$): δ 0.77 (t, J=7.5 Hz, 3H), 0.82 (t, J=7.8 Hz, 3H), 1.11 (m, 4H), 1.37 (q, J=7.2 Hz, 2H), 1.53 (q, J=7.2 Hz, 2H), 1.86 (t, J=7.5 Hz, 2H), 2.12 (s, 3H), 2.60 (t, J=6.9 Hz, 2H), 4.92 (s, 2H), 6.91 (d, J=8.1 Hz, 1H), 7.11 (d, J=8.1 Hz, 1H), 7.19 (d, J=6.9 Hz, 1H), 7.30 (t, J=8.1 Hz, 1H), 7.67 (d, J=8.1 Hz, 1H), 7.75 (s, 1H), 7.83 (br, 2H), 7.89 (s, 1H), 8.29 (s, 1H), 8.87 (s, 1H); LCMS: purity: 91.88%; MS (m/e): 629.27 (MH+).

(I-206): N2-(4-butyrylaminosulfonyl)phenyl-N4-[4-(N-butyryl-N-cyclopropylsulfonyl)aminomethyl] phenyl-5-methyl-2,4-pyrimidinediamine sodium salt $^1$H NMR (DMSO-d$_6$): δ 0.76 (t, J=7.2 Hz, 3H), 0.85 (t, J=7.5 Hz, 3H), 1.08 (d, J=6.3 Hz, 4H), 1.37 (q, J=7.2 Hz, 2H), 1.56 (q, J=7.2 Hz, 2H), 1.84 (t, J=7.2 Hz, 2H), 2.11 (s, 3H), 2.67 (t, J=6.9 Hz, 2H), 4.91 (s, 2H), 7.23 (d, J=8.1 Hz, 2H), 7.49 (d, J=8.1 Hz, 2H), 7.62 (d, J=8.4 Hz, 2H), 7.74 (d, J=8.4 Hz, 2H), 7.90 (s, 1H), 8.28 (s, 1H), 9.11 (s, 1H); LCMS: purity: 93.45%; MS (m/e): 629.27 (MH+).

(I-207): N4-(3-cyclopropylsulfonylaminomethyl) phenyl-5-methyl-N2-(4-methylaminosulfonyl)phenyl-2,4-pyrimidinediamine $^1$H NMR (DMSO-d$_6$): δ 0.87 (m, 4H), 2.13 (s, 3H), 2.35 (d, J=4.8 Hz, 3H), 4.19 (d, J=6.6 Hz, 2H), 7.09-7.15 (m, 2H), 7.32 (t, J=7.8 Hz, 1H), 7.50 (d, J=8.7 Hz, 2H), 7.62 (m, 3H), 7.83 (d, J=8.4 Hz, 2H), 7.94 (s, 1H), 8.48 (s, 1H), 9.43 (s, 1H); LCMS: purity: 96.09%; MS (m/e): 503.18 (MH+).

(I-208): N4-(3-cyclopropylsulfonylaminomethyl) phenyl-N2-(3-ethylaminosulfonyl)phenyl-5-methyl-2,4-pyrimidinediamine $^1$H NMR (DMSO-d$_6$): δ 0.87 (m, 4H), 0.96 (t, J=6.9 Hz, 3H), 2.17 (s, 3H), 2.75 (p, J=6.3 Hz, 2H), 4.16 (d, J=6.3 Hz, 2H), 7.18 (d, J=7.5 Hz, 1H), 7.40 (m, 3H), 7.48 (s, 1H), 7.55 (m, 2H), 7.64 (t, J=6.0 Hz, 1H), 7.72 (s, 1H), 7.85 (d, 1H), 7.91 (s, 1H), 9.47 (br, 1H), 10.11 (br, 1H); LCMS: purity: 93.59%; MS (m/e): 517.25 (MH+).

(I-209): N4-(3-cyclopropylsulfonylaminomethyl) phenyl-N2-(3-isopropylaminosulfonyl-4-methyl) phenyl-5-methyl-2,4-pyrimidinediamine $^1$H NMR (DMSO-d$_6$): δ 0.86 (m, 4H), 0.92 (d, J=6.6 Hz, 6H), 2.16 (s, 3H), 4.16 (d, J=6.0 Hz, 2H), 7.19 (d, J=8.4 Hz, 2H), 7.34 (t, J=7.5 Hz, 1H), 7.46 (s, 1H), 7.51 (d, J=7.5 Hz, 1H), 7.59-7.65 (m, 2H), 7.71 (d, J=9.0 Hz, 1H), 7.76 (s, 1H), 7.87 (s, 1H), 9.55 (br, 1H), 10.13 (br, 1H); LCMS: purity: 98.47%; MS (m/e): 545.18 (MH+).

(I-210): N4-(3-cyclopropylsulfonylaminomethyl) phenyl-N2-[3-(2-methoxyethyl)aminosulfonyl-4-methyl]phenyl-5-methyl-2,4-pyrimidinediamine $^1$H NMR (DMSO-d$_6$): δ 0.87 (m, 4H), 2.16 (s, 3H), 2.89 (q, J=5.7 Hz, 2H), 3.08 (s, 3H), 3.21 (t, J=5.7 Hz, 2H), 4.16 (d, J=6.3 Hz, 2H), 7.19 (m, 2H), 7.34 (t, J=7.8 Hz, 1H), 7.49 (s, 1H), 7.54 (d, J=8.4 Hz, 1H), 7.63 (t, J=6.3 Hz, 1H), 7.76 (m, 3H), 7.86 (s, 1H), 9.39 (br, 1H), 9.96 (br, 1H); LCMS: purity: 100%; MS (m/e): 561.17 (MH+).

(I-211): N4-(3-cyclopropylsulfonylaminomethyl) phenyl-5-methyl-N2-(4-methyl-3-methylaminosulfonyl)phenyl-2,4-pyrimidinediamine $^1$H NMR (DMSO-d$_6$): δ 0.88 (m, 4H), 2.11 (s, 3H), 2.41 (d, J=5.1 Hz, 3H), 2.44 (s, 3H), 4.18 (d, J=6.0 Hz, 2H), 7.04 (d, J=7.8 Hz, 1H), 7.15 (d, J=9.0 Hz, 1H), 7.28 (m, 2H), 7.60 (t, J=6.3 Hz, 1H), 7.66 (m, 2H), 7.88 (s, 1H), 7.98 (m, 2H), 8.33 (s, 1H), 9.12 (s, 1H); LCMS: purity: 99.46%; MS (m/e): 517.14 (MH+).

(I-212): N4-(3-cyclopropylsulfonylaminomethyl) phenyl-N2-(4-ethylaminosulfonyl)phenyl-5-methyl-2,4-pyrimidinediamine $^1$H NMR (DMSO-d$_6$): δ 0.87 (m, 4H), 0.95 (t, J=7.2 Hz, 3H), 2.15 (s, 3H), 2.72 (p, J=6.6 Hz, 2H), 4.19 (d, J=6.3 Hz, 2H), 7.14 (d, J=7.2 Hz, 1H), 7.28 (s, 1H), 7.34 (t, J=7.5 Hz, 1H), 7.51 (s, 1H), 7.54 (s, 2H), 7.60 (d, J=7.5 Hz, 2H), 7.76 (d, J=8.7 Hz, 2H), 7.93 (s, 1H), 8.78 (br, 1H), 9.61 (br, 1H); LCMS: purity: 79.55%; MS (m/e): 517.05 (MH+).

(I-213): N4-(3-cyclopropylsulfonylaminomethyl) phenyl-N2-(3-ethylaminosulfonyl-4-methyl)phenyl-5-methyl-2,4-pyrimidinediamine $^1$H NMR (DMSO-d$_6$): δ 0.88 (m, 4H), 0.95 (t, J=7.2 Hz, 3H), 2.15 (s, 3H), 2.78 (m, J=6.3 Hz, 2H), 4.17 (d, J=6.6 Hz, 2H), 7.16 (m, 2H), 7.32 (t, J=7.8 Hz, 1H), 7.55-7.61 (m, 4H), 7.87 (m, 3H); LCMS: purity: 93.18%; MS (m/e): 531.20 (MH+).

(I-214): N4-(3-cyclopropylsulfonylaminomethyl) phenyl-5-methyl-N2-(4-methyl-3-propargylaminosulfonyl)phenyl-2,4-pyrimidinediamine $^1$H NMR (DMSO-d$_6$): δ 0.88 (m, 4H), 2.14 (s, 3H), 2.99 (t, 1H), 3.64 (dd, J=1.8, 5.1 Hz, 2H), 4.17 (d, J=6.6 Hz, 2H), 7.13 (d, J=7.5 Hz, 1H), 7.17 (d, J=9.6 Hz, 1H), 7.32 (t, J=7.8 Hz, 1H), 7.60 (m, 3H), 7.88 (s, 3H), 8.10 (d, J=4.5 Hz, 1H), 8.96 (br, 1H), 9.60 (br, 1H); LCMS: purity: 90.90%; MS (m/e): 541.14 (MH+).

(I-215): N4-(3-cyclopropylsulfonylaminomethyl) phenyl-5-methyl-N2-(4-methyl-3-propylaminosulfonyl)phenyl-2,4-pyrimidinediamine $^1$H NMR (DMSO-d$_6$): δ 0.74 (t, J=7.5 Hz, 3H), 0.87 (m, 4H), 1.34 (q, J=7.2 Hz, 2H), 2.15 (s, 3H), 2.69 (q, J=6.6 Hz, 2H), 4.16 (d, J=6.3 Hz, 2H), 7.17 (m, 2H), 7.33 (t, J=7.5 Hz, 1H), 7.52-7.65 (m, 4H), 7.79 (m, 2H), 7.87 (s, 1H), 9.21 (br, 1H), 9.84 (br, 1H); LCMS: purity: 95.70%; MS (m/e): 545.16 (MH+).

(I-216): N2-(3-cyclopropylmethylaminosulfonyl-4-methyl)phenyl-N4-(3-cyclopropylsulfonylaminomethyl)phenyl-5-methyl-2,4-pyrimidinediamine $^1$H NMR (DMSO-d$_6$): δ 0.023 (q, J=5.1 Hz, 2H), 0.29 (q, J=6.3 Hz, 2H), 0.73 (m, 1H), 0.87 (m, 4H), 2.15 (s, 3H), 2.64 (t, J=6.3 Hz, 2H), 4.16 (d, J=6.0 Hz, 2H), 7.16 (m, 2H), 7.33

(t, J=7.5 Hz, 1H), 7.54 (m, 2H), 7.62 (t, J=6.6 Hz, 1H), 7.75 (m, 3H), 7.86 (s, 1H), 9.79 (br, 1H); LCMS: purity: 91.73%; MS (m/e): 557.14 (MH+).

(I-217): N4-(3-cyclopropylsulfonylaminomethyl) phenyl-N2-[3-(3-methoxypropyl)aminosulfonyl-4-methyl]phenyl-5-methyl-2,4-pyrimidinediamine $^1$H NMR (DMSO-d$_6$): δ 0.87 (m, 4H), 1.56 (p, J=6.3 Hz, 2H), 2.14 (s, 3H), 2.78 (q, J=6.3 Hz, 2H), 3.10 (s, 3H), 3.22 (t, J=5.7 Hz, 2H), 4.17 (d, J=6.3 Hz, 2H), 7.13 (d, J=7.2 Hz, 1H), 7.17 (d, J=9.0 Hz, 1H), 7.32 (t, J=7.8 Hz, 1H), 7.55-7.64 (m, 4H), 7.84 (m, 3H), 8.99 (br, 1H), 9.64 (br, 1H); LCMS: purity: 93.24%; MS (m/e): 575.15 (MH+).

(I-218): N4-[3-(N-cyclopropylsulfonyl-N-hexanoyl) aminomethyl]phenyl-N2-(3-hexanoylaminosulfonyl) phenyl-5-methyl-2,4-pyrimidinediamine $^1$H NMR (DMSO-d$_6$): δ 0.76 (m, 6H), 1.10 (m, 4H), 1.16 (m, 8H), 1.39 (p, J=7.2 Hz, 2H), 1.49 (t, 2H), 2.13 (s, 3H), 2.17 (t, J=6.9 Hz, 2H), 2.60 (t, J=6.6 Hz, 2H), 4.92 (s, 2H), 6.94 (d, J=7.2 Hz, 1H), 7.33 (m, 3H), 7.64 (d, J=7.8 Hz, 1H), 7.69 (s, 1H), 7.92 (s, 1H), 8.05 (d, J=7.5 Hz, 1H), 8.22 (s, 1H), 8.40 (s, 1H), 9.16 (s, 1H), 11.94 (s, 1H); LCMS: purity: 94.19%; MS (m/e): 685.27 (MH+).

(I-219): N4-[3-(N-cyclopropylsulfonyl-N-hexanoyl) aminomethyl]phenyl-N2-(3-hexanoylaminosulfonyl) phenyl-5-methyl-2,4-pyrimidinediamine sodium salt $^1$H NMR (DMSO-d$_6$): δ 0.78 (m, 6H), 1.11 (m, 4H), 1.17 (m, 8H), 1.36 (p, J=7.2 Hz, 2H), 1.50 (t, 2H), 1.94 (t, J=7.5 Hz, 2H), 2.12 (s, 3H), 2.60 (t, J=7.2 Hz, 2H), 4.92 (s, 2H), 6.91 (d, J=7.5 Hz, 1H), 7.15 (t, J=7.5 Hz, 1H), 7.22 (d, J=8.1 Hz, 1H), 7.30 (t, J=7.8 Hz, 1H), 7.66 (d, J=8.4 Hz, 1H), 7.75 (s, 1H), 7.89 (m, 2H), 7.93 (s, 1H), 8.32 (s, 1H), 8.92 (s, 1H); LCMS: purity: 97.48%; MS (m/e): 685.26 (MH+).

(I-220): N4-[3-(N-cyclopropylsulfonyl-N-valeryl) aminomethyl]phenyl-5-methyl-N2-(3-valerylaminosulfonyl)phenyl-2,4-pyrimidinediamine $^1$H NMR (DMSO-d$_6$): δ 0.77 (t, J=7.2 Hz, 6H), 1.10 (m, 4H), 1.13-1.24 (m, 4H), 1.37 (p, J=7.2 Hz, 2H), 1.48 (p, J=7.2 Hz, 2H), 2.13 (s, 3H), 2.18 (t, J=7.2 Hz, 2H), 2.61 (t, J=6.9 Hz, 2H), 4.92 (s, 2H), 6.94 (d, J=7.5 Hz, 1H), 7.33 (m, 3H), 7.67 (m, 2H), 7.91 (s, 1H), 8.05 (d, J=7.5 Hz, 1H), 8.21 (s, 1H), 8.40 (s, 1H), 9.17 (s, 1H), 11.93 (s, 1H); LCMS: purity: 92.83%; MS (m/e): 657.49 (MH+).

(I-221): N4-[3-(N-cyclopropylsulfonyl-N-valeryl) aminomethyl]phenyl-5-methyl-N2-(3-valerylaminosulfonyl)phenyl-2,4-pyrimidinediamine sodium salt $^1$H NMR (DMSO-d$_6$): δ 0.78 (m, 6H), 1.10 (m, 4H), 1.14-1.25 (m, 4H), 1.34 (p, J=7.2 Hz, 2H), 1.49 (p, J=7.2 Hz, 2H), 1.87 (t, J=7.5 Hz, 2H), 2.11 (s, 3H), 2.61 (t, J=7.2 Hz, 2H), 4.92 (s, 2H), 6.90 (d, J=8.1 Hz, 1H), 7.09 (t, J=7.8 Hz, 1H), 7.19 (d, J=7.5 Hz, 1H), 7.29 (t, J=7.8 Hz, 1H), 7.66 (d, J=9.0 Hz, 1H), 7.84 (m, 2H), 7.88 (s, 1H), 8.28 (s, 1H), 8.85 (s, 1H); LCMS: purity: 94.42%; MS (m/e): 657.73 (MH+).

(I-222): N2-(3-butyrylaminosulfonyl)phenyl-N4-[3-(N-butyryl-N-cyclopropylsulfonyl)aminomethyl] phenyl-5-methyl-2,4-pyrimidinediamine Choline salt $^1$H NMR (DMSO-d$_6$): δ 0.76 (t, J=8.1 Hz, 3H), 0.82 (t, J=7.2 Hz, 3H), 1.10 (m, 4H), 1.37 (q, J=7.2 Hz, 2H), 1.53 (q, J=6.9 Hz, 2H), 1.85 (t, J=7.2 Hz, 2H), 2.11 (s, 3H), 2.60 (t, J=7.2 Hz, 2H), 3.08 (s, 9H), 3.37 (t, J=4.8 Hz, 2H), 3.81 (m, 2H), 4.92 (s, 2H), 5.30 (m, 1H), 6.90 (d, J=6.6 Hz, 1H), 7.09 (t, J=8.1 Hz, 1H), 7.18 (d, J=6.9 Hz, 1H), 7.29 (t, J=7.5 Hz, 1H), 7.66 (d, J=8.1 Hz, 1H), 7.75 (s, 1H), 7.82 (m, 2H), 7.88 (s, 1H), 8.28 (s, 1H), 8.85 (s, 1H); LCMS: purity: 93.44%; MS (m/e): 629.10 (MH+).

(I-223): N2-(3-butyrylaminosulfonyl)phenyl-N4-(3-cyclopropylsulfonylaminomethyl)phenyl-5-methyl-2,4-pyrimidinediamine $^1$H NMR (DMSO-d$_6$): δ 0.75 (t, J=7.2 Hz, 3H), 1.24 (m, 4H), 1.41 (q, J=7.5 Hz, 2H), 2.13 (s, 3H), 2.18 (t, J=6.9 Hz, 2H), 4.18 (d, J=6.3 Hz, 2H), 7.05 (d, J=7.5 Hz, 1H), 7.33 (m, 3H), 7.60 (t, J=6.3 Hz, 1H), 7.65 (s, 1H), 7.71 (d, J=8.7 Hz, 1H), 7.91 (s, 1H), 8.09 (d, J=8.1 Hz, 1H), 8.17 (s, 1H), 8.38 (s, 1H), 9.32 (s, 1H), 11.96 (br, 1H); LCMS: purity: 97.11%; MS (m/e): 559.20 (MH+).

(I-224): N2-(3-aminosulfonyl)phenyl-N4-[3-(N-butyryl-N-cyclopropylsulfonyl)aminomethyl]phenyl-5-methyl-2,4-pyrimidinediamine $^1$H NMR (DMSO-d$_6$): δ 0.83 (t, 3H), 1.10 (m, 4H), 1.53 (q, J=6.9 Hz, 2H), 2.12 (s, 3H), 2.61 (t, J=6.9 Hz, 2H), 4.92 (s, 2H), 6.93 (d, J=8.4 Hz, 1H), 7.24 (s, 2H), 7.30 (m, 3H), 7.68 (m, 2H), 7.92 (s, 1H), 7.98 (d, 1H), 8.10 (d, J=4.8 Hz, 1H), 8.37 (s, 1H), 9.08 (s, 1H); LCMS: purity: 90.92%; MS (m/e): 559.34 (MH+).

(I-225): N2-[3-(N-acetoxymethyl-N-butyryl)aminosulfonyl]phenyl-N4-(3-cyclopropylsulfonylaminomethyl)phenyl-5-methyl-2,4-pyrimidinediamine $^1$H NMR (DMSO-d$_6$): δ 0.78 (t, J=7.2 Hz, 3H), 0.88 (m, 4H), 1.42 (q, J=7.2 Hz, 2H), 2.06 (s, 3H), 2.13 (s, 3H), 2.58 (t, J=6.9 Hz, 2H), 3.16 (s, 2H), 4.18 (d, J=6.0 Hz, 2H), 7.06 (d, J=6.3 Hz, 1H), 7.30 (t, J=7.8 Hz, 1H), 7.38 (m, 2H), 7.62 (m, 2H), 7.70 (d, J=8.1 Hz, 1H), 7.93 (s, 1H), 8.14 (d, 1H), 8.22 (s, 1H), 8.40 (s, 1H), 9.33 (s, 1H); LCMS: purity: 86.49%; MS (m/e): 631.09 (MH+).

(I-226): N4-[3-(N-cyclopropylsulfonyl-N-propionyl) aminomethyl]phenyl-5-methyl-N2-(3-propionylaminosulfonyl)phenyl-2,4-pyrimidinediamine Choline salt $^1$H NMR (DMSO-d$_6$): δ 0.83 (t, J=7.5 Hz, 3H), 0.98 (t, J=7.5 Hz, 3H), 1.10 (m, 4H), 1.88 (q, J=7.5 Hz, 2H), 2.11 (s, 3H), 3.08 (s, 9H), 3.38 (t, J=6.0 Hz, 2H), 3.81 (m, 2H), 4.92 (s, 2H), 5.31 (m, 1H), 6.91 (d, J=6.9 Hz, 1H), 7.09 (t, J=7.5 Hz, 1H), 7.20 (d, J=7.5 Hz, 1H), 7.30 (t, J=7.8 Hz, 1H), 7.67 (d, J=8.4 Hz, 1H), 7.72 (s, 1H), 7.82 (m, 2H), 7.88 (s, 1H), 8.29 (s, 1H), 8.86 (s, 1H); LCMS: purity: 96.43%; MS (m/e): 601.09 (MH+).

Example 3

Assay for Ramos B-Cell Line Stimulated with IL-4

B-cells stimulated with cytokine Interleukin-4 (IL-4) activate the JAK/Stat pathway through phosphorylation of the JAK family kinases, JAK-1 and JAK-3, which in turn phosphorylate and activate the transcription factor Stat-6. One of the genes upregulated by activated Stat-6 is the low affinity IgE receptor, CD23. To study the effect of inhibitors on the JAK family kinases, human Ramos B cells are stimulated with human IL-4.

The Ramos B-cell line was acquired from ATCC (ATCC Catalog No. CRL-1596). The cells were cultured in RPMI 1640 (Cellgro, MediaTech, Inc., Herndon, Va., Cat No. 10-040-CM) with 10% fetal bovine serum (FBS), heat inactivated (JRH Biosciences, Inc, Lenexa, Kans., Cat No. 12106-500M) according to ATCC propagation protocol. Cells were maintained at a density of $3.5\times10^5$. The day before the experiment, Ramos B-cells were diluted to $3.5\times10^5$ cells/mL to ensure that they were in a logarithmic growth phase.

Cells were spun down and suspended in RPMI with 5% serum. $5\times10^4$ cells were used per point in a 96-well tissue culture plate. Cells were pre-incubated with compound or DMSO (Sigma-Aldrich, St. Louis, Mo., Cat No. D2650) vehicle control for 1 hour in a 37° C. incubator. Cells were then stimulated with IL-4 (Peprotech Inc., Rocky Hill, N.J., Cat No. 200-04) for a final concentration of 50 units/mL for 20-24 hours. Cells were then spun down and stained with anti-CD23-PE(BD Pharmingen, San Diego, Calif., Cat No. 555711) and analyzed by FACS. Detection was performed using a BD LSR I System Flow Cytometer, purchased from Becton Dickinson Biosciences of San Jose, Calif. The $IC_{50}$ calculated based on the results of this assay are provided in Table III.

Example 4

Primary Human T-Cell Proliferation Assay Stimulated with IL-2

Primary human T-cells derived from peripheral blood and pre-activated through stimulation of the T-cell receptor and CD28 proliferate in vitro in response to the cytokine Interleukin-2 (IL-2). This proliferative response is dependent on the activation of JAK-1 and JAK-3 tyrosine kinases, which phosphorylate and activate the transcription factor Stat-5.

Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 min at 4° C. at 1750 rpm. The lymphocytes at the serum: ficoll interface were recovered and washed twice with 5 volumes of PBS. The cells were resuspended in Yssel's medium (Gemini Bio-products, Woodland, Calif., Catalog #400-103) containing 40 U/mL recombinant IL2 (R and D Systems, Minneapolis, Minn., Catalog #202-IL (20 µg)) and seeded into a flask pre-coated with 1 µg/mL anti-CD3 (BD Pharmingen, San Diego, Calif., Catalog #555336) and 5 µg/mL anti-CD28 (Immunotech, Beckman Coulter of Brea Calif., Catalog #IM1376). The primary T-cells were stimulated for 3 to 4 days, then transferred to a fresh flask and maintained in RPMI with 10% FBS and 40 U/mL IL-2.

Primary T-cells were washed twice with PBS to remove the IL-2 and resuspended in Yssel's medium at $2\times10^6$ cells/mL. 50 µL of cell suspension containing 80 U/mL IL-2 was added to each well of a flat bottom 96 well black plate. For the unstimulated control, IL-2 was omitted from the last column on the plate. Compounds were serially diluted in dimethyl sulfoxide (DMSO, 99.7% pure, cell culture tested, Sigma-Aldrich, St. Louis, Mo., Catalog No. D2650) from 5 mM in 3-fold dilutions and then diluted 1:250 in Yssel's medium. 50 µL of 2× compound was added per well in duplicate and the cells were allowed to proliferate for 72 hours at 37° C.

Proliferation was measured using CellTiter-Glo® Luminescent Cell Viability Assay (Promega), which determines the number of viable cells in culture based on quantitation of the ATP present, as an indicator of metabolically active cells. The substrate was thawed and allowed to come to room temperature. After mixing the Cell Titer-Glo reagent and diluent together, 100 µL was added to each well. The plates were mixed on an orbital shaker for two minutes to induce lysis and incubated at room temperature for an additional ten minutes to allow the signal to equilibrate. Detection was performed using a Wallac Victor2 1420 multilabel counter purchased from Perkin Elmer, Shelton, Conn. The $IC_{50}$ calculated based on the results of this assay are provided in Table III.

Example 5

A549 Epithelial Line Stimulated with IFNγ

A549 lung epithelial cells up-regulate ICAM-1 (CD54) surface expression in response to a variety of different stimuli. Therefore, using ICAM-1 expression as readout, compound effects on different signaling pathways can be assessed in the same cell type. IFNγ up-regulates ICAM-1 through activation of the JAK/Stat pathway. In this example, the up-regulation of ICAM-1 by IFNγ was assessed.

The A549 lung epithelial carcinoma cell line originated from the American Type Culture Collection. Routine culturing was with F12K media (Mediatech Inc., Lenexa, Kans., Cat. No. 10-025-CV) with 10% fetal bovine serum, 100 I.U. penicillin and 100 ng/mL streptomycin (complete F12k media). Cells were incubated in a humidified atmosphere of 5% $CO_2$ at 37° C. Prior to use in the assay, A549 cells were washed with PBS and trypsinized (Mediatech Inc., Cat. No. 25-052-CI) to lift the cells. The trypsin cell suspension was neutralized with complete F12K media and centrifuged to pellet the cells. The cell pellet was resuspended in complete F12K media at a concentration of $2.0\times10^5$/mL. Cells were seeded at 20,000 per well, 100 µL total volume, in a flat bottom tissue culture plate and allowed to adhere overnight.

On day two, A549 cells were pre-incubated with a 2,4-pyrimidinediamine test compound or DMSO (control) (Sigma-Aldrich, St. Louis, Mo., Catalog No. D2650) for 1 hour. The cells were then stimulated with IFNγ (75 ng/mL) (Peprotech Inc., Rocky Hill, N.J., Cat. No. 300-02) and allowed to incubate for 24 hours. The final test compound dose range was 30 µM to 14 nM in 200 µL F12K media containing 5% FBS, 0.3% DMSO.

On day three, the cell media was removed and the cells were washed with 200 µL PBS (phosphate buffered saline). Each well was trypsinized to dissociate the cells, then neutralized by addition of 200 µL complete F12K media. Cells were pelleted and stained with an APC conjugated mouse anti-human ICAM-1 (CD54) (BD Pharmingen, San Diego, Calif., Catalog #559771) antibody for 20 minutes at 4° C. Cells were washed with ice cold FACS buffer (PBS+ 2% FBS) and surface ICAM-1 expression was analyzed by flow cytometry. Detection was performed using a BD LSR I System Flow Cytometer, purchased from BD Biosciences of San Jose, Calif. Events were gated for live scatter and the geometric mean was calculated (Becton-Dickinson Cell-Quest software version 3.3, Franklin Lakes, N.J.). Geometric means were plotted against the compound concentration to generate a dose response curve. The $IC_{50}$ calculated based on the results of this assay are provided in Table III.

Example 6

U937 IFNγ ICAM1 FACS Assay

U937 human monocytic cells up-regulate ICAM-1 (CD54) surface expression in response to a variety of different stimuli. Therefore, using ICAM-1 expression as readout, compound effects on different signaling pathways can be assessed in the same cell type. IFNγ up-regulates ICAM-1 through activation of the JAK/Stat pathway. In this example, the up-regulation of ICAM-1 by IFNγ was assessed.

The U937 human monocytic cell line was obtained from ATCC of Rockville, Md., catalog number CRL-1593.2, and cultured in RPM1-1640 medium containing 10% (v/v) FCS. U937 cells were grown in 10% RPMI. The cells were then plated at a concentration of 100,000 cells per 160 µL in 96 well flat bottom plates. The test compounds were then diluted as follows: 10 mM test compound was diluted 1:5 in DMSO (3 µL 10 mM test compound in 12 µL DMSO), followed by a 1:3 serial dilution of test compound in DMSO (6 µL test compound serially diluted into 12 µL DMSO to give 3-fold dilutions). Then 4 µL of test compound was transferred to 76 µL of 10% RPMI resulting in a 10× solution (100 µM test compound, 5% DMSO). For control wells, 4 µL of DMSO was diluted into 76 µL 10% RPMI.

The assay was performed in duplicate with 8 points (8 3-fold dilution concentrations from 10 µl) and with 4 wells of DMSO only (control wells) under stimulated conditions and 4 wells of DMSO only under unstimulated conditions.

The diluted compound plate was mixed 2× using a multimek (Beckman Coulter of Brea, Calif.) and then 20 µL of the diluted compounds was transferred to the 96 well plate containing 160 µL of cells, which were then mixed again twice at low speeds. The cells and compounds were then pre-incubated for 30 minutes at 37° C. with 5% $CO_2$.

The 10× stimulation mix was made by preparing a 100 ng/mL solution of human IFNγ in 10% RPMI. The cells and compound were then stimulated with 20 µL of IFNγ stimulation mix to give a final concentration of 10 ng/mL IFNγ, 10 µM test compound, and 0.5% DMSO. The cells were kept under conditions for stimulation for 18-24 hours at 37° C. with 5% $CO_2$.

The cells were transferred to a 96 well round bottom plate for staining and then kept on ice for the duration of the staining procedure. Cells were spun down at 1000 rpm for 5 minutes at 4° C., following which the supernatant was removed. Following removal of the supernatant, 1 µL APC conjugated mouse anti-human ICAM-1 antibody was added per 100 µL FACS buffer. The cells were then incubated on ice in the dark for 30 minutes. Following incubation, 150 µL of FACS buffer was added and the cells were centrifuged at 1000 rpm for 5 minutes at 4° C., following which the supernatant was removed. After removal of the supernatant, 200 µL of FACS buffer was added and the cells were resuspended. After suspension, the cells were centrifuged at 1000 rpm for 5 min at 4° C. Supernatant was then removed prior to resuspension of the cells in 150 µL FACS buffer.

Detection was performed using a BD LSR I System Flow Cytometer, purchased from BD Biosciences of San Jose, Calif. The live cells were gated for live scatter and the geometric mean of ICAM-APC was measured (Becton-Dickinson CellQuest software version 3.3, Franklin Lakes, N.J.). Both % live cells and ICAM-1 expression was analyzed. The assays for the test compounds were carried out in parallel with a control compound of known activity. The $EC_{50}$ for the control compound is typically 40-100 nM. The $IC_{50}$ calculated based on the results of this assay are provided in Table III.

TABLE III

| Compound # | Example 3 | Example 4 | Example 5 | Example 6 |
|---|---|---|---|---|
| I-1 | 0.3568 | 0.4179 | 9999 | |
| I-2 | 0.6472 | 3.7263 | | |
| I-3 | 0.2272 | 0.4583 | | 4.5317 |
| I-4 | 0.1414 | 0.1088 | 18.221 | 0.9084 |
| I-5 | 0.1302 | 0.1195 | 56.614 | 0.7104 |
| I-6 | 0.5588 | 0.5363 | | |
| I-102 | 0.0901 | 0.5188 | 20.484 | 3.4725 |
| I-103 | 0.1819 | 1.0683 | | |
| I-104 | 0.0988 | 0.679 | 4.5841 | |
| I-105 | 0.1239 | 0.7979 | 5.8194 | |
| I-106 | 0.2072 | 0.1158 | | 3.8242 |
| I-107 | 2.9344 | 18.139 | | |
| I-108 | 5.1572 | 25.752 | | |
| I-109 | 0.1188 | 0.1389 | 16.866 | 1.1926 |
| I-110 | 0.089 | 0.1481 | | 1.0277 |
| I-111 | 0.1536 | 0.2927 | | 2.2677 |
| I-112 | 0.2626 | 0.614 | | |
| I-7 | 0.0735 | 0.1127 | | |
| I-8 | 0.2349 | 0.2754 | 9999 | 3.25 |
| I-9 | 0.0801 | 0.0702 | 9999 | 0.9926 |
| I-10 | 0.094 | 0.0606 | 29.498 | 0.477 |
| I-11 | 0.25 | 0.5878 | | 2.7856 |
| I-12 | 0.17 | 0.1581 | 4.5746 | 1.5761 |
| I-13 | 0.1355 | 0.1974 | 3.6295 | 0.5356 |
| I-14 | 0.1436 | 0.8349 | 9999 | 5.2671 |
| I-15 | 0.0658 | 0.1841 | 9999 | 3.1141 |
| I-16 | 0.1483 | 0.5363 | 9.0101 | 2.2827 |
| I-17 | 0.1641 | 1.0689 | 8.2383 | 4445.3 |
| I-18 | 0.107 | 0.2716 | 9999 | 1.2939 |
| I-19 | 0.1479 | 0.4941 | | 1.6447 |
| I-20 | 0.0736 | 0.0461 | 9999 | 0.6208 |
| I-21 | 0.0812 | 0.0589 | 2.4946 | 0.3623 |
| I-22 | 0.0259 | 0.0822 | 9999 | 0.2069 |
| I-23 | 0.1262 | 0.1977 | 9999 | 3.8494 |
| I-24 | 0.0592 | 0.032 | 9999 | 0.5077 |
| I-25 | 0.069 | 0.0639 | 8888 | 0.3628 |
| I-26 | 0.2521 | 1.1606 | 9999 | |
| I-27 | 0.1177 | 0.1443 | 5.8424 | 1.2427 |
| I-28 | 0.1154 | 0.3764 | | 1.1085 |
| I-29 | 0.2028 | 0.8823 | 9999 | |
| I-30 | 0.0743 | 0.153 | 6.0966 | 1.1578 |
| I-31 | 0.1041 | 0.2828 | | 1.0219 |
| I-32 | 0.3642 | 1.5602 | 9999 | |
| I-33 | 0.1018 | 0.3145 | 9999 | 1.4093 |
| I-34 | 0.1838 | 0.4838 | 5.7035 | 1.1871 |
| I-35 | 0.1333 | 0.4358 | 9999 | 8888 |
| I-36 | 0.0408 | 0.0639 | 9999 | 0.3259 |
| I-37 | 0.0462 | 0.1524 | 27.71 | 0.3751 |
| I-38 | 0.1219 | 0.1895 | 9999 | 0.8548 |
| I-39 | 0.0462 | 0.058 | 3.7509 | 0.6036 |
| I-40 | 0.0681 | 0.0924 | 3.4902 | 0.3411 |
| I-41 | 1.0179 | 2.122 | | |
| I-42 | 1.1463 | 3.2246 | | |
| I-43 | 0.5367 | 1.7932 | | 37.805 |
| I-44 | 1.2177 | 4.1555 | | 9999 |
| I-45 | 0.0598 | 0.0293 | 7777 | 0.2835 |
| I-46 | 0.0268 | 0.0249 | 9999 | 0.1878 |
| I-47 | 0.028 | 0.0362 | 2.8935 | 0.104 |
| I-48 | 0.2633 | 0.7577 | 29.86 | 3.757 |
| I-49 | 0.0468 | 0.0383 | 78.902 | 0.8359 |
| I-50 | 0.0343 | 0.0627 | 9.3473 | 0.5475 |
| I-51 | 0.0622 | 0.0297 | 2.8041 | 0.3238 |
| I-52 | 0.0685 | 0.0662 | 2.5463 | 0.2029 |
| I-53 | 0.1309 | 0.1749 | 9999 | 0.6045 |
| I-54 | 0.0943 | 0.047 | 4.6916 | 0.3888 |
| I-55 | 0.0788 | 0.0845 | 3.8786 | 0.3596 |
| I-56 | 0.1622 | 0.3102 | | 0.7255 |
| I-57 | 12.299 | | | |

TABLE III-continued

| Compound # | Example 3 | Example 4 | Example 5 | Example 6 |
|---|---|---|---|---|
| I-58 | 11.095 | | | |
| I-59 | 6.5002 | | | |
| I-60 | 7.08 | | | |
| I-61 | 18.945 | | | |
| I-62 | 10.695 | | | |
| I-63 | 9.4529 | | | |
| I-64 | 4.2742 | | | |
| I-65 | 0.2113 | 0.634 | 10.39 | |
| I-66 | 0.0694 | 0.065 | 8888 | 0.4718 |
| I-67 | 0.0824 | 0.0845 | 3.2855 | 0.3209 |
| I-68 | 0.094 | 0.1024 | 4.9488 | 0.2892 |
| I-69 | 0.0515 | 0.05 | 7.7628 | 0.1756 |
| I-70 | 0.043 | 0.1495 | 2.5836 | 0.1586 |
| I-71 | 0.1197 | 0.1316 | 10.52 | 0.4006 |
| I-72 | 0.0569 | 0.0251 | 2.6645 | 0.2044 |
| I-73 | 0.0899 | 0.071 | 3.5675 | 0.3115 |
| I-74 | 0.362 | 2.2463 | 9999 | |
| I-75 | 0.1811 | 0.2461 | | 1.2019 |
| I-76 | 0.1691 | 0.4626 | | |
| I-77 | 1.2345 | | | |
| I-78 | 1.0832 | | | |
| I-79 | 0.098 | 0.0923 | 8888 | 0.3449 |
| I-80 | 0.0371 | 0.0463 | 4.1337 | 0.1431 |
| I-81 | 0.0736 | 0.0892 | | 0.2148 |
| I-83 | 0.1809 | 0.1516 | | 0.266 |
| I-85 | 3.0981 | 3.9016 | | |
| I-86 | 0.5055 | 0.224 | | 9999 |
| I-87 | 0.2508 | 0.3086 | | 5006.6 |
| I-88 | 0.0599 | | | |
| I-89 | 0.4476 | 1.5026 | | |
| I-90 | 0.1521 | 0.3487 | | 2.4322 |
| I-91 | 1.2891 | | | |
| I-92 | 0.9596 | | | |
| I-93 | 2.8128 | | | |
| I-94 | 2.4973 | | | |
| I-95 | 0.1595 | 0.2862 | | 2.6894 |
| I-96 | 0.0744 | 0.1054 | 9999 | 3.6709 |
| I-97 | 0.0347 | 0.0488 | 13.281 | 0.2573 |
| I-98 | 0.0253 | 0.0521 | 9999 | 0.1518 |
| I-99 | 0.5654 | 0.9544 | | |
| I-100 | 0.1015 | 0.1527 | | 0.4886 |
| I-101 | 0.0624 | 0.2242 | | 0.4327 |
| I-140 | 3.936 | | | |
| I-141 | 4.7053 | | | |
| I-142 | 5.6204 | | | |
| I-143 | 7.2875 | | | |
| I-136 | 1.6287 | | | |
| I-116 | 0.0367 | 0.0299 | 1.8338 | 0.1778 |
| I-137 | 1.9061 | | | |
| I-123 | 0.0836 | 0.0429 | 18.954 | 0.1639 |
| I-118 | 0.0398 | 0.0158 | 2.4784 | 0.2176 |
| I-117 | 0.0388 | 0.0179 | 2.169 | 0.0601 |
| I-131 | 0.5567 | | | |
| I-133 | 0.7152 | 1.2075 | | |
| I-129 | 0.1609 | 0.4322 | 7777 | 2.5064 |
| I-119 | 0.0535 | 0.0954 | 4.4177 | 0.5349 |
| I-125 | 0.0949 | 0.1381 | 4.0251 | 0.3886 |
| I-127 | 0.126 | 0.2328 | 9999 | 0.6158 |
| I-121 | 0.0736 | 0.0465 | 36.461 | 0.2308 |
| I-126 | 0.104 | 0.0742 | 5.5599 | 0.2244 |
| I-124 | 0.0898 | 0.1321 | 5.7164 | 0.3727 |
| I-120 | 0.0671 | 0.0473 | 2.5396 | 0.0984 |
| I-122 | 0.0816 | 0.0883 | | 0.1548 |
| I-139 | 3.3234 | | | |
| I-144 | 7.7204 | | | |
| I-135 | 1.0002 | | | |
| I-134 | 0.7506 | | | |
| I-132 | 0.5938 | | | |
| I-138 | 2.3815 | | | |
| I-148 | 16.189 | | | |
| I-146 | 12.328 | | | |
| I-145 | 8.5439 | | | |
| I-147 | 13.799 | 25.074 | | |
| I-130 | 0.5445 | | | |
| I-128 | 0.1567 | 0.0622 | | 0.7066 |
| I-115 | 0.0233 | 0.0192 | 2.7217 | 0.1051 |
| I-114 | 0.0206 | 0.0092 | 5.649 | 0.0517 |
| I-113 | 0.0186 | 0.017 | 0.8877 | 0.0471 |
| I-82 | 1.0986 | 0.9638 | | |
| I-84 | 0.3551 | 0.237 | 9.5335 | 0.9277 |
| II-1 | 0.04227 | 0.1081 | 18.2992 | 0.22889 |
| II-2 | 0.00775 | 0.03044 | 9999 | 0.10747 |
| II-3 | 0.01942 | 0.0475 | 12.3592 | 0.08789 |
| II-4 | 0.72032 | | | |
| II-5 | 0.69778 | | | |
| II-6 | 0.63985 | | | |
| II-7 | 0.13044 | 0.15526 | | 0.65181 |
| II-8 | 0.09794 | 0.1473 | 17.826 | 0.77531 |
| II-9 | 0.11794 | 0.27658 | | 1.11 |
| I-149 | 0.08223 | 0.19 | | |
| I-150 | 0.08859 | 0.12729 | | 0.56492 |
| I-151 | 0.3526 | 1.07925 | | |
| I-152 | 0.16558 | 0.71664 | | |
| I-153 | 0.08001 | 0.11814 | 9999 | 8888 |
| I-154 | 0.08456 | 0.06193 | 6.35464 | 0.18447 |
| I-155 | 0.25031 | 1.42812 | | |
| I-156 | 0.26615 | 1.07878 | | |
| I-157 | 0.24988 | 1.1013 | | |
| I-158 | 0.29998 | 0.5314 | | |
| I-159 | 0.53933 | 7.96064 | | |
| I-160 | 0.24186 | 3.96195 | | |
| I-161 | 0.01669 | 0.0112 | 24.353 | 0.05105 |
| I-162 | 0.05789 | 0.04627 | 1.9181 | 0.15506 |
| I-163 | 0.04674 | 0.05271 | 9999 | 0.14323 |
| I-164 | 0.06134 | 0.03283 | 13.7775 | 0.16011 |
| I-165 | 0.03484 | 0.01989 | 8.9726 | 0.15016 |
| I-166 | 0.08255 | 0.21212 | | 0.28021 |
| I-167 | 0.13214 | 0.11573 | | 0.5872 |
| I-168 | 0.27815 | 0.34717 | | |
| I-169 | 0.13978 | 0.20625 | | 0.47831 |
| I-170 | 0.13602 | 0.17191 | | 0.23802 |
| I-171 | 19.4799 | 42.2553 | | |
| I-172 | 0.05211 | 0.08102 | 9999 | 0.12251 |
| I-173 | 0.03481 | 0.04242 | 1.88491 | 0.10871 |
| I-174 | 1.12317 | | | |
| I-175 | 0.04612 | 0.10203 | 2.37086 | 0.07226 |
| I-176 | 0.00798 | 0.06454 | 10.3863 | 0.04841 |
| I-177 | 0.01773 | 0.16024 | 9999 | 0.10674 |
| I-178 | 0.02304 | 0.12232 | 5.45019 | 0.05772 |
| I-179 | 0.04592 | 0.28969 | 9999 | 0.36528 |
| I-180 | 0.0257 | 0.14837 | 2.22102 | 0.06217 |
| I-181 | 0.07306 | 0.12129 | 2.34967 | 0.24262 |
| I-182 | 0.02568 | 0.05509 | 2.24926 | 0.1029 |
| I-183 | 0.06672 | 0.15526 | 8888 | 0.20722 |
| I-184 | 0.01412 | 0.05172 | 1.40643 | 0.09775 |
| I-185 | 0.0225 | 0.04105 | 4.09804 | 0.08531 |
| I-186 | 0.01949 | 0.04001 | 1.76155 | 0.07296 |
| I-187 | 0.07236 | 0.10105 | 2.41861 | 0.17385 |
| I-188 | 0.04362 | 0.57253 | 5.07933 | 0.19338 |
| I-189 | 0.03518 | 0.03437 | 1.71662 | 0.15322 |
| I-190 | 0.07257 | 0.10123 | 1.36072 | 0.18699 |
| I-191 | 0.0512 | 0.07994 | 3.06433 | 0.24747 |
| I-192 | 0.05468 | 0.04335 | 2.30116 | 0.25971 |
| I-193 | 1.88972 | | | |
| I-194 | 1.64595 | | | |
| I-195 | 0.06642 | 0.10434 | 3.54496 | 0.22978 |
| I-196 | 2.04693 | | | |
| I-197 | 1.549 | | | |
| I-198 | 2.05231 | | | |
| I-199 | 1.27294 | | | |
| I-200 | 2.31342 | | | |
| I-201 | 1.20917 | | | |
| I-202 | 0.08648 | 0.18399 | 6.05207 | 0.48216 |
| I-203 | 3.0177 | | | |
| I-204 | 1.04089 | | | |
| I-205 | 3.44129 | | | |
| I-206 | 0.94595 | | | |
| I-207 | 0.0865 | 0.15751 | 6.10888 | 0.31234 |
| I-208 | 0.07431 | 0.04575 | 1.30281 | 0.25743 |
| I-209 | 0.11289 | 0.13127 | | 0.52909 |
| I-210 | 0.12814 | 0.14312 | 2.469 | 0.17492 |
| I-211 | 0.10317 | 0.04819 | | 0.17654 |
| I-212 | 0.23555 | 0.1605 | | 0.21505 |
| I-213 | 0.08816 | 0.09177 | | 0.12471 |

TABLE III-continued

| Compound # | Example 3 | Example 4 | Example 5 | Example 6 |
|---|---|---|---|---|
| I-214 | 0.16177 | 0.13597 | | 0.19002 |
| I-215 | 0.13209 | 0.11638 | | 0.38537 |
| I-216 | 0.16058 | 0.15417 | | 0.58956 |
| I-217 | 0.08025 | 0.12875 | | 0.49595 |
| I-218 | 3.80438 | | | |
| I-219 | 2.60437 | | | |
| I-220 | 2.01592 | | | |
| I-221 | 1.87849 | | | |
| I-222 | 3.0337 | | | |
| I-223 | 3.69204 | | | |
| I-224 | 0.02181 | | | |
| I-225 | 0.11489 | | | |
| I-226 | 5.49011 | | | |

What is claimed is:

1. A compound having a formula

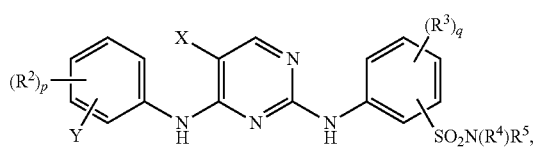

or a pharmaceutically acceptable salt thereof, wherein:
p is 0, 1, 2 or 3;
q is 0, 1, 2 or 3;
X is selected from the group consisting of hydrogen, alkyl, substituted alkyl, hydroxy, alkoxy, substituted alkoxy, amino, substituted amino, carboxyl, carboxyl ester, cyano, halo, nitro, alkenyl, substituted alkenyl, alkynyl, substituted alkynyl, cycloalkynyl, and substituted cycloalkynyl;
Y is alk-$SO_2N(R^4)R^5$ or alk-$N(R^4)SO_2R^5$;
alk is selected from the group consisting of straight or branched chain $C_{1-6}$ alkylene group, cycloalkylene and substituted cycloalkylene;
each $R^2$ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, and halo;
or $R^4$ and one of $R^2$ together with the intervening atoms bound thereto form a heterocyclic or a substituted heterocyclic fused to the phenyl ring;
or $R^5$ and one of $R^2$ together with the intervening atoms bound thereto form a heterocyclic or a substituted heterocyclic fused to the phenyl ring;
each $R^3$ independently is selected from the group consisting of alkyl, substituted alkyl, alkoxy, substituted alkoxy, alkynyl, substituted alkynyl, cycloalkynyl, substituted cycloalkynyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, halo, and aminosulfonyl;
$R^4$ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, acyl and $M^+$, wherein $M^+$ is a counterion selected from the group consisting of $K^+$, $Na^+$, $Li^+$ and $^+N(R^8)_4$, wherein $R^8$ is hydrogen or alkyl, and the nitrogen of —$SO_2N(R^4)R^5$ or —$N(R^4)SO_2R^5$ is $N^-$; and
$R^5$ is selected from the group consisting of hydrogen, alkyl, substituted alkyl, amine, cycloalkyl, substituted cycloalkyl, heterocyclic, substituted heterocyclic, aryl, substituted aryl, heteroaryl, substituted heteroaryl, and acyl; or
$R^4$ and $R^5$ together with the intervening atom or atoms bound thereto form a heterocyclic or a substituted heterocyclic group.

2. The compound of claim 1 wherein the compound has a formula

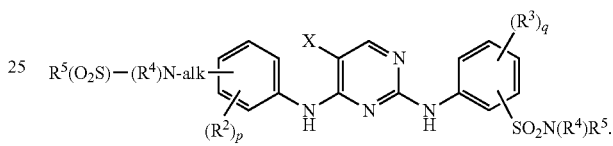

3. The compound of claim 2, wherein alk is $C_{1-2}$ alkyl.
4. The compound of claim 3, wherein X is halo, alkyl or haloalkyl.
5. The compound of claim 4, wherein p is 0, 1, or 2 and $R^2$ is halo.
6. The compound of claim 5, wherein q is 0, 1, or 2 and $R^3$ is alkyl.
7. The compound of claim 6, wherein each of $R^4$ and $R^5$ independently is selected from the group consisting of hydrogen, alkyl, substituted alkyl, alkynyl, substituted alkynyl, acyl, and carboxyl ester; or $R^4$ and $R^5$ together with the nitrogen atom bound thereto optionally form —N=C$(OR^9)_2$ wherein each $R^9$ is independently an alkyl group.
8. The compound of claim 7, wherein each of $R^4$ and $R^5$ is independently selected from the group consisting of hydrogen and acyl.
9. The compound of claim 2, wherein the compound has a formula

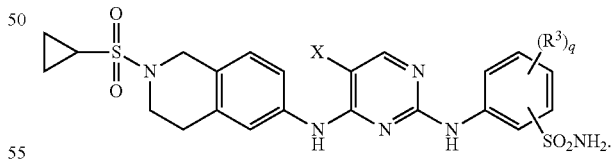

10. The compound of claim 1 wherein the compound has a formula

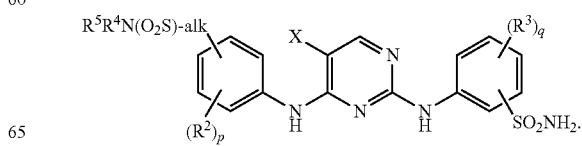

11. The compound of claim 10, wherein X is halo.

12. The compound of claim 11, wherein X is fluoro.

13. The compound of claim 12, wherein p is 0 and q is 0 or 1.

14. The compound of claim 12, wherein q is 1 or 2 and $R^3$ is alkyl.

15. The compound of claim 12, wherein alk is —$CH_2$— and each of $R^4$ and $R^5$ independently is selected from the group consisting of hydrogen, alkyl, alkynyl, cycloalkyl and heterocyclic.

16. A method of inhibiting an activity of a JAK kinase, comprising contacting the JAK kinase with an amount of a compound according to claim 1 effective to inhibit an activity of the JAK kinase.

17. The method according to claim 16 comprising contacting in vitro a JAK3 kinase with an amount of a compound according to claim 1 effective to inhibit an activity of the JAK3 kinase.

18. A method of treating or preventing rheumatoid arthritis, comprising administering to a subject an effective amount of a compound according to claim 1.

19. The method of claim 18 in which the compound is administered in combination with, or adjunctively to, a compound that inhibits Syk kinase with an $IC_{50}$ in the range of at least 10 μM.

* * * * *